US011168124B2

(12) United States Patent
Anguela et al.

(10) Patent No.: US 11,168,124 B2

(45) Date of Patent: Nov. 9, 2021

(54) CPG REDUCED FACTOR VIII VARIANTS, COMPOSITIONS AND METHODS AND USES FOR TREATMENT OF HEMOSTASIS DISORDERS

(71) Applicant: SPARK THERAPEUTICS, INC., Philadelphia, PA (US)

(72) Inventors: Xavier Anguela, Philadelphia, PA (US); Sam Hsien-I Shen, Iowa City, IA (US)

(73) Assignee: SPARK THERAPEUTICS, INC., Philadelphia, PA (US)

( * ) Notice: Subject to any disclaimer, the term of this patent is extended or adjusted under 35 U.S.C. 154(b) by 0 days.

(21) Appl. No.: 15/462,660

(22) Filed: Mar. 17, 2017

(65) Prior Publication Data

US 2017/0216408 A1 Aug. 3, 2017

Related U.S. Application Data

(63) Continuation of application No. PCT/US2016/059793, filed on Oct. 31, 2016.

(60) Provisional application No. 62/249,001, filed on Oct. 30, 2015, provisional application No. 62/331,872, filed on May 4, 2016, provisional application No. 62/349,532, filed on Jun. 13, 2016, provisional application No. 62/357,874, filed on Jul. 1, 2016.

(51) Int. Cl.

| | |
|---|---|
| ***C12N 15/86*** | (2006.01) |
| ***C07K 14/755*** | (2006.01) |
| ***A61K 38/37*** | (2006.01) |
| ***A61K 45/06*** | (2006.01) |
| ***A61K 48/00*** | (2006.01) |
| ***C12N 7/00*** | (2006.01) |

(52) U.S. Cl.

CPC ............ *C07K 14/755* (2013.01); *A61K 38/37* (2013.01); *A61K 45/06* (2013.01); *A61K 48/0066* (2013.01); *C12N 7/00* (2013.01); *C12N 15/86* (2013.01); *A61K 48/00* (2013.01); *C12N 2710/10342* (2013.01); *C12N 2710/10343* (2013.01); *C12N 2750/14122* (2013.01); *C12N 2750/14143* (2013.01); *C12N 2750/14145* (2013.01)

(58) Field of Classification Search

CPC ...... C07K 14/755; A61K 38/37; A61K 45/06; A61K 48/0066; A61K 48/00; C12N 7/00; C12N 15/86; C12N 2750/14143; C12N 2750/14122; C12N 2750/14145; C12N 2710/10342; C12N 2710/10343; C12N 15/8645; C12N 2750/14141; A61P 7/04; A61P 43/00; A61P 37/06; C12P 21/00

See application file for complete search history.

(56) References Cited

U.S. PATENT DOCUMENTS

| | | | |
|---|---|---|---|
| 6,818,439 | B1 | 11/2004 | Jolly et al. |
| 2006/0099685 | A1 | 5/2006 | Yallop et al. |
| 2013/0024960 | A1 | 1/2013 | Nathwani et al. |
| 2014/0271550 | A1 | 9/2014 | Rabinowitz et al. |
| 2015/0071883 | A1 | 3/2015 | Colosi |
| 2015/0273082 | A1 | 10/2015 | Nathwani et al. |
| 2017/0119906 | A1 | 5/2017 | Riley |

FOREIGN PATENT DOCUMENTS

| | | | |
|---|---|---|---|
| CL | 201102893 | | 11/2011 |
| CL | 201400024 | | 1/2014 |
| DE | 60042171 | | 6/2009 |
| KR | 20030033074 | A | 4/2003 |
| WO | 2001/75092 | A2 | 10/2001 |
| WO | 2010133834 | A2 | 11/2010 |
| WO | 2013009627 | A2 | 1/2013 |
| WO | 2013123457 | A1 | 8/2013 |
| WO | 2015/038625 | A1 | 3/2015 |
| WO | 2015/054439 | A2 | 4/2015 |
| WO | 2019/028192 | A1 | 2/2019 |

OTHER PUBLICATIONS

Choi et al. "AAV Hybrid Serotypes: Improved Vectors for Gene Delivery." Curr Gene Ther. Jun. 2005 ; 5(3): 299-310. (Year: 2005).*

Chua et al. "Gene therapy for hemophilia." J Thromb Haemost 2013; 11 (Suppl. 1): 99-110. (Year: 2013).*

Collela et al. "Emerging Issues in AAV-Mediated In Vivo Gene Therapy." Mol Ther Methods Clin Dev. Mar. 16, 2018; 8: 87-104. (Year: 2018).*

Driessche et al. "Hemophilia Gene Therapy: Ready for Prime Time?" Hum Gene Ther. Nov. 2017;28(11):1013-1023. (Year: 2017).*

Pierce et al. "Past, present and future of haemophilia gene therapy: From vectors and transgenes to known and unknown outcomes." Haemophilia. May 2018;24 Suppl 6:60-67 (Year: 2018).*

Nathwani et al. "Prospects for gene therapy of haemophilia." Haemophilia. Jul. 2004;10(4):309-18. (Year: 2004).*

Colella et al. "Emerging Issues in AAV-Mediated In Vivo Gene Therapy." Mol Ther Methods Clin Dev. Dec. 1, 2017,8:87-104. (Year: 2017).*

Matsui et al. "Ex vivo gene therapy for hemophilia A that enhances safe delivery and sustained in vivo factor VIII expression from lentivirally engineered endothelial progenitors." Stem Cells. Oct. 2007;25(10):2660-9. Epub Jul. 5, 2007. (Year: 2007).*

(Continued)

*Primary Examiner* — Titilayo Moloye

(74) *Attorney, Agent, or Firm* — Pillsbury Winthrop Shaw Pittman LLP; Robert M. Bedgood

(57) ABSTRACT

CpG reduced nucleic acid variants encoding FVIII protein and methods of use thereof are disclosed. In particular embodiments, CpG reduced nucleic acid variants encoding FVIII are expressed more efficiently by cells, are secreted at increased levels by cells over wild-type Factor VIII proteins, exhibit enhanced expression and/or activity over wild-type Factor VIII proteins or are packaged more efficiently into viral vectors.

41 Claims, 16 Drawing Sheets

Specification includes a Sequence Listing.

(56) References Cited

OTHER PUBLICATIONS

Markusic et al. "688. Supplemental Immune Suppression Is Required for AAV-F8 ITI in Hemophilia A Mice with Pre-Existing Inhibitors" Hematologic & Immunologic Diseases II| vol. 24, Supplement 1, S272-S273, May 1, 2016 (Year: 2016).*

Gollomp et al. "Gene therapy for hemophilia: Progress to date and challenges moving forward." Transfus Apher Sci. Oct. 2019;58(5):602-612. (Year: 2019).*

Swystun et al. "Gene Therapy for Coagulation Disorders." Circulation Research. 2016;118:1443-1452 (Year: 2016).*

Lisowski et al. "Adeno-associated virus serotypes for gene therapeutics." Curr Opin Pharmacol. Oct. 2015;24:59-67. (Year: 2015).*

High et al. "Adeno-associated viral vectors for the treatment of hemophilia." Hum Mol Genet. Apr. 15, 2016; 25(R1): R36-R41. (Year: 2016).*

Chua et al. "Gene therapy for hemophilia." J Thromb Haemost. Jun. 2013; 11 Suppl 1:99-110. (Year: 2013).*

Sabatino et al. "Muscle Gene Therapy for Hemophilia." J Genet Syndr Gene Ther. May 7, 2012; Suppl 1: S1-010. (Year: 2012).*

Agenda from Jul. 21 Interview. (Year: 2020).*

Clancy, S."Genetic Mutation." Nature Education 1(1):187 (2008) (Year: 2008).*

Rudinger et al. "Characteristics of the amino acids as components of a peptide hormone sequence.". In: Parsons J.A. (eds) Peptide Hormones.1976, pp. 1-7. (Year: 1976).*

Halbert, C.L., et al., Adeno-associated virus type 6 (AAV6) vectors mediate efficient transduction of airway epithelial cells in mouse lungs compared to that of AAV2 vectors, Journal of Virology, 2001, 75(14):6615-6624.

Hodges, B.L. et al., Long-term transgene expression from plasmid DNA gene therapy vectors is negatively affected by CpG dinucleotides, Molecular Therapy, 2004, 10(2):269-278.

McIntosh, J., et al., Therapeutic levels of FVIII following a since peripheral vein administration of rAAV vector encoding a novel human factor VIII variant, Blood, 2013, 121(17):3335-3344.

NCBI, GenBank accession No. AAS99242.1 (Jun. 24, 2004).

Rogers, G.L. et al., Role of the vector genome and underlying factor IX mutation in immune responses to AAV gene therapy for hemophilia B., Journal of Translational Medicine, 2014, 12(1):e25 (inner pp. 1-10).

Yew, N.S., et al., CpG-Depleted Plasmid DNA Vectors with Enhanced Safety and Long-Term Gene Expression in vivo. Molecular Therapy, 2002, 5(6):731-738.

International Application No. PCT/US2016/039075, PCT International Search Report and Written Opinion dated Sep. 30, 2016.

Nair, A.R., et al., Effect of different UCOE-promoter combinations in creation of engineered cell lines for the production of Factor VIII, BMC Research Notes, 2011, 4:178.

NCBI, GenBank accession No. EU159410.1 (Jul. 23, 2009) See the whole sequence.

NCBI, GenBank accession No. NM_000132.3 (Sep. 11, 2015) See the who sequence.

International Application No. PCT/US2016/059793, International Search Report and Written Opinion dated Feb. 10, 2017.

High, K.A., et a., A Phase 1/2 Trial of Investigational Spk-8011 in Hemophilia a Demonstrates Durable Expression and Prevention of Bleeds, Blood (2018) 132 (Supplement 1): 487.

Hyde, S.C., et al., CpG-free Plasmids Confer Reduced Inflammation and Sustained Pulmonary Gene Expression, Nat. Biotechnol., 2008, 26(5):549-551.

Faulkner, F.G., et al., "Development of SHP654, a highly efficient AAV8-based BDD-FVIII gene therapy vector for treatment of hemophilia a," Research and Practice in Thrombosis and Haemostasis, Jul. 1, 2017, Wiley-Blackwell Publishing Ltd NLD, vol. 1, No. Supplement 1, pp. 145-146.

Mannully, S.T., et al., "Perspectives on progressive strategies and recent trends in the production of recombinant human factor VIII", International Journal of Biological Macromolecules, Elsevier BV, NL, vol. 119, Jul. 29, 2018, pp. 496-504.

"Sequence 45 from Patent W02015038625", XP002788427, retrieved from EBI accession No. EM PAT:LP633674 Database accession No. LP633674, Feb. 19, 2016.

* cited by examiner hFVIII levels 24 hour following HTV injection of 50 μg of plasmid, for 18 different clones (X01-X18) and CO3

*HTV = Hydrodynamic Tail Vein Injection*

*hFVIII normalized to 1 relative unit for CO3 plasmid*

Human FVIII levels in mice after
AAV administration

TTRmutFVIII CO3
TTRmutFVIII X09
TTRmutFVIII X12
TTRmutFVIII X16
Plasma hFVIII (ng/ml)
800
600
400
200
0
0
4
8
Week Post Treatment TTRmutFVIII CO3
TTRmutFVIII X07
TTRmutFVIII X10
Plasma hFVIII (ng/ml)
800
600
400
200
0
0
4
8
Week Post Treatment TTRmutFVIII CO3
TTRmutFVIII X01
TTRmutFVIII X11
Plasma hFVIII (ng/ml)
800
600
400
200
0
0
4
8
Week Post Treatment
Dose: 4x10^12 vg/kg
Mouse model: HA/CD4-/-

Levels of hFVIII in ng/ml (B) or % total antigen (C) in plasma of NOD/SCID mice

Levels of D-dimers in plasma of NOD/SCID mice following intravenous administration of AAV-SPK-8005-hFVIII

FIG. 4

Non-Human Primate (NHP) Study design

| Species | Cynomolgus monkeys (*Macaca fascicularis*) |
|---|---|
| Test article | SPK-8005 or SPK-8011 (LK03 capsid) |
| Age | 2 to 3 years |
| Weight | 2 to 4 kg |
| Duration | 8 weeks |

| AAV-SPK-8005 | | |
|---|---|---|
| GROUP | # of NHPs | DOSE LEVEL |
| | Male | vg/kg |
| 1 (Control) | 2 | 0 |
| 2 (Low) | 3 | $2x10^{12}$ |
| 3 (Medium) | 3 | $5x10^{12}$ |
| 4 (High) | 3 | $1x10^{13}$ |

| AAV-SPK-8011 (LK03 capsid) | | |
|---|---|---|
| GROUP | # of NHPs | DOSE LEVEL |
| | Male | vg/kg |
| 1 (Control) | 2 | 0 |
| 2 (Low) | 3 | $2x10^{12}$ |
| 3 (Medium) | 3 | $6x10^{12}$ |
| 4 (High) | 3 | $2x10^{13}$ |

hFVIII antigen levels in NHPs
FIG. 5A
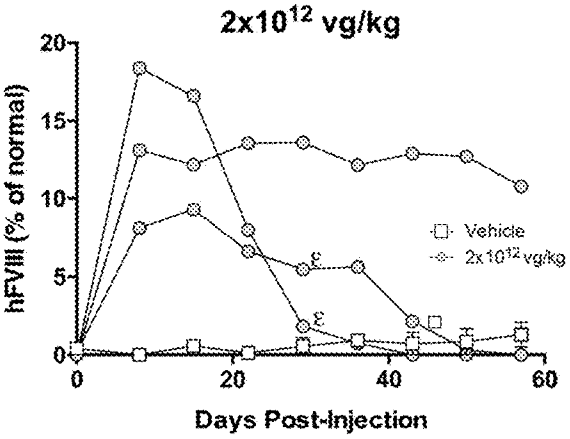
FIG. 5B
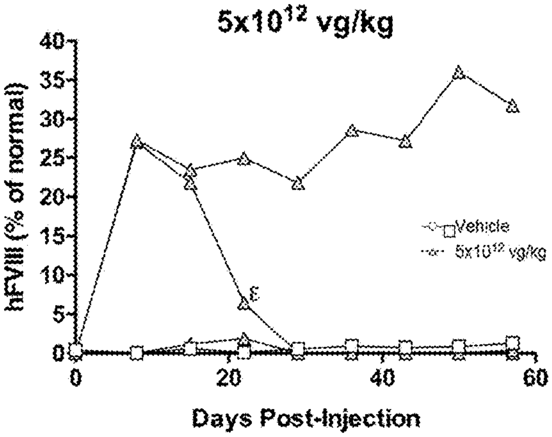
FIG. 5C
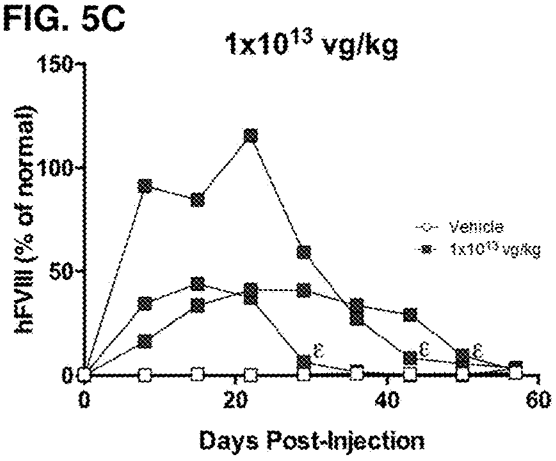
e-inhibitor antibodies
FIG. 5D
| AAV-SPK-8005 | | |
|---|---|---|
| GROUP | vg/kg | AVERAGE hFVIII at PEAK |
| 1 (Control) | 0 | |
| 2 (Low) | $2x10^{12}$ | 12.7 ± 2.1 |
| 3 (Medium) | $5x10^{12}$ | 22.6 ± 0.8 |
| 4 (High) | $1x10^{13}$ | 54.1 ± 15.6 |

ALT levels in NHPs

D-Dimer levels in NHPs

FIG. 8

Summary

- Therapeutic levels of hFVIII achieved in all three doses of SPK-8005

| Dose | Average peak hFVIII in ALL animals (% of normal) | Average "stable" hFVIII in NHPs w/o Inh. (% of normal) |
|---|---|---|
| $2x10^{12}$ vg/kg | 13.2 | 10.8 |
| $5x10^{12}$ vg/kg | 27.1 | 31.8 |
| $1x10^{13}$ vg/kg | 54.1 | N/A |

- Neutralizing Abs against human FVIII observed in 6/8 animals, as expected
- No safety issues

AAV-SPK-8011 (LK03): hFVIII antigen levels in cynomolgus macaques
FIG. 9A
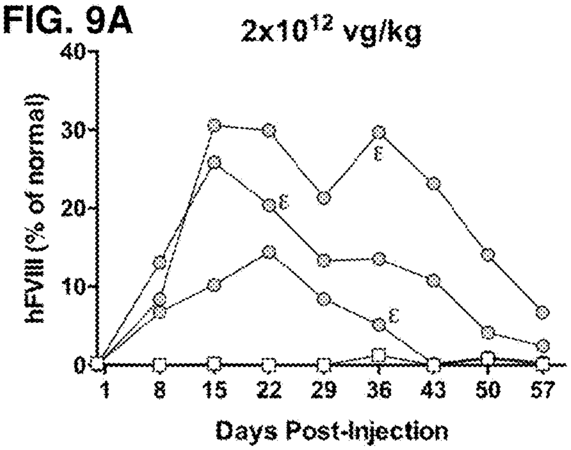
FIG. 9B
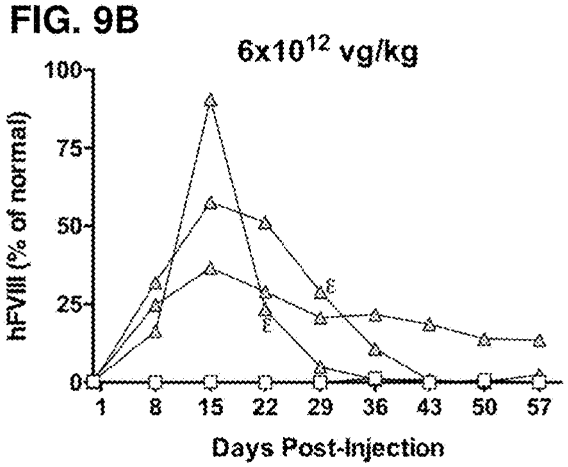
FIG. 9C
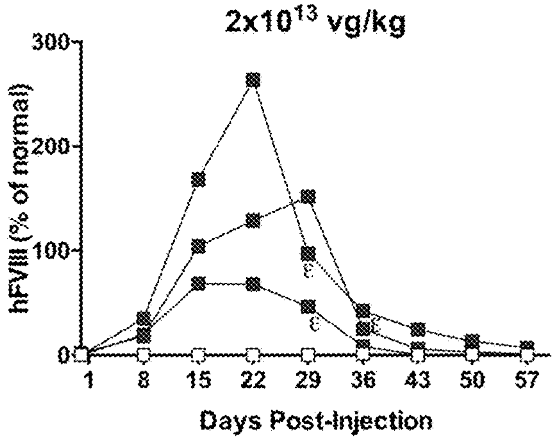
FIG. 9D
ε FVIII inhibitors
| AAV-SPK-8011 (LK03 capsid) | | |
|---|---|---|
| GROUP | vg/kg | AVERAGE hFVIII at PEAK |
| 1 (Control) | 0 | |
| 2 (Low) | $2x10^{12}$ | 22.3 ± 6.1 |
| 3 (Medium) | $6x10^{12}$ | 61.6 ± 15.7 |
| 4 (High) | $2x10^{13}$ | 153.3 ± 58 |

AAV-SPK-8011 (LK03 capsid) vs AAV5 vs AAV8: hFVIII antigen levels in macaques

| | AAV-SPK-8011 (LK03) | AAV5 | AAV8 |
|---|---|---|---|
| vg/kg | MAXIMUM hFVIII at PEAK (% of normal) | | |
| $2x10^{12}$ | 31 | | |
| $6x10^{12}$ | 91 | | |
| $1x10^{13}$ | | ~3 | |
| $2x10^{13}$ | 264 | | ~120 |
| $2.4x10^{13}$ | | ~15 | |
| $3.6x10^{13}$ | | ~23 | |
| $6.3x10^{13}$ | | ~45 | |

| AAV-SPK-8011 (LK03 capsid) | AAV5 |
|---|---|
| Predicted dose to achieve 50% of normal hFVIII | |
| $3.2x10^{12}$ vg/kg | $69.5x10^{12}$ vg/kg |

Plasma concentration of hFIX in rabbits after AAV administration

Time course of antibody formation to human FIX

SEQUENCE LISTING

```
<160> NUMBER OF SEQ ID NOS: 29

<210> SEQ ID NO 1
<211> LENGTH: 4374
<212> TYPE: DNA
<213> ORGANISM: Artificial Sequence
<220> FEATURE:
<223> OTHER INFORMATION: Description of Artificial Sequence: FVIII
      Nucleic Acid

<400> SEQUENCE: 1

atgcagattg agctgtctac ctgcttcttc ctgtgcctgc tgaggttctg cttctctgct     60

accaggaggt actacctggg ggctgtggag ctgagctggg attacatgca gtctgacctg    120

ggggagctgc ctgtggatgc caggtttccc cccagggtgc ccaagagctt ccccttcaat    180

acctctgtgg tgtataagaa gaccctgttt gtggagttca ctgatcatct gttcaacatt    240

gctaaaccca ggcccccctg gatggggctg ctgggcccta ccatccaggc tgaggtgtat    300

gacactgtgg tgatcactct gaagaacatg gctagccatc ctgtgtctct gcatgctgtg    360

ggggtgagct actggaaggc ttctgagggg gctgagtatg atgatcagac tagccagagg    420

gagaaggagg atgacaaggt gttccctggg ggctctcaca cctatgtctg gcaggtgctg    480

aaggagaatg gccccatggc ctctgatcct ctgtgtctga cctatagcta cctgagccat    540
```

-continued

```
gtggacctgg tgaaggacct gaactctggc ctgattgggg ccctgctggt gtgtagggag    600
gggagcctgg ccaaggagaa gacccagacc ctgcacaagt tcattctgct gtttgctgtg    660
tttgatgagg gcaagagctg gcattctgaa accaagaaca gcctgatgca ggacagggat    720
gctgcctctg ctagggcctg gcccaagatg cacactgtga atgggtatgt caataggtct    780
ctgcctggcc tgattggctg ccacaggaag tctgtgtact ggcatgtgat tgggatgggc    840
accacccctg aggtgcacag catctttctg gagggccaca ccttcctggt gaggaatcac    900
agacaggcca gcctggagat cagccccatc accttcctga ctgcccagac cctgctgatg    960
gacctgggcc agtttctgct gttctgccac atctctagcc accagcatga tggcatggag   1020
gcctatgtga aggtggactc ctgccctgag gagccccagc tgaggatgaa gaataatgag   1080
gaggctgagg actatgatga tgacctgact gactctgaga tggatgtggt gagatttgat   1140
gatgacaatt ctcccagctt cattcagatc aggtctgtgg ccaagaagca tcccaagacc   1200
tgggtgcact acattgctgc tgaggaggag gactgggact atgccccccct ggtgctggcc   1260
cctgatgaca ggagctataa gagccagtac ctgaataatg gcccccagag gattgggagg   1320
aagtataaga aggtgaggtt catggcctat actgatgaaa ccttcaagac cagagaggcc   1380
atccagcatg agtctgggat cctggggccc ctgctgtatg gggaggtggg ggacaccctg   1440
ctgatcatct tcaagaacca ggccagcagg ccctacaaca tctaccctca tggcatcact   1500
gatgtgaggc ctctgtacag cagaaggctg cccaaggggg tgaagcatct gaaggacttc   1560
cccattctgc ctggggagat tttcaagtac aagtggactg tgactgtgga ggatggccca   1620
accaagtctg accctaggtg cctgactagg tactacagca gctttgtgaa tatggagagg   1680
gacctggcct ctggcctgat tggcccccctg ctgatctgct acaaggagtc tgtggatcag   1740
aggggcaacc agatcatgtc tgacaagagg aatgtgatcc tgttctctgt gtttgatgag   1800
aacaggagct ggtacctgac tgagaacatt cagaggtttc tgcccaaccc tgctggggtg   1860
cagctggagg accctgaatt ccaggcctct aacatcatgc acagcattaa tggctatgtg   1920
tttgacagcc tgcagctgtc tgtgtgcctg catgaggtgg cctactggta cattctgagc   1980
attggggccc agactgactt cctgtctgtg ttcttctctg gctacacctt taagcacaag   2040
atggtgtatg aggataccct gaccctgttt cctttctctg ggagactgt gttcatgagc   2100
atggagaacc ctggcctgtg gatcctgggc tgccacaact ctgacttcag gaacaggggg   2160
atgactgctc tgctgaaggt gagcagctgt gataagaaca ctggggacta ctatgaggac   2220
agctatgagg acatctctgc ctatctgctg agcaagaata atgctattga gcccaggagc   2280
ttctctcaga acccccctgt gctgaagagg caccagaggg agatcaccag aactactctg   2340
cagtctgacc aggaggagat tgactatgat gacaccatct ctgtggagat gaagaaggag   2400
gattttgata tttatgatga ggatgaaaac cagagcccca ggagctttca gaagaagact   2460
aggcactatt tcattgctgc tgtggagagg ctgtgggact atggcatgtc ttctagcccc   2520
catgtgctga ggaacagggc ccagtctggc tctgtgcccc agttcaagaa ggtggtgttc   2580
caggagttca ctgatggcag cttcactcag cccctgtaca ggggggagct gaatgagcac   2640
ctggggctgc tgggccctta tatcagggct gaggtggagg ataacatcat ggtgaccttc   2700
aggaaccagg ccagcaggcc ctacagcttc tactctagcc tgatcagcta tgaggaggac   2760
cagaggcagg gggctgagcc caggaagaac tttgtgaagc ccaatgagac caagacttat   2820
ttctggaagg tgcagcacca tatggccccc accaaggatg agtttgattg caaagcctgg   2880
gcctacttct ctgatgtgga cctggagaag gatgtgcact ctgggctgat tggcccccctg   2940
```

```
ctggtgtgcc acaccaacac tctgaaccct gcccatggca ggcaggtgac tgtgcaggag   3000

tttgccctgt tcttcaccat ctttgatgag actaagagct ggtacttcac tgagaacatg   3060

gagaggaact gcagggcccc ctgcaatatc cagatggagg accccacctt taaggaaaat   3120

tataggtttc atgccattaa tggctacatc atggacaccc tgcctggcct ggtgatggcc   3180

caggaccaga ggatcaggtg gtacctgctg agcatgggca gcaatgagaa cattcacagc   3240

atccacttct ctggccatgt gttcactgtg aggaagaagg aggagtacaa gatggccctg   3300

tataatctgt accctggggt gtttgagact gtggagatgc tgcccagcaa ggctggcatc   3360

tggagggtgg agtgcctgat tggggagcac ctgcatgctg gcatgagcac cctgttcctg   3420

gtgtattcta acaagtgtca gaccccccctg ggcatggcct ctggccatat cagggacttc   3480

cagatcactg cctctggcca gtatgggcag tgggccccca agctggccag gctgcattac   3540

tctggcagca tcaatgcctg gagcaccaag gagccattca gctggattaa ggtggacctg   3600

ctggctccaa tgattatcca tggcatcaag acccaggggg ccaggcagaa gtttagcagc   3660

ctgtacatct ctcagtttat catcatgtac tctctggatg gcaaaaagtg gcagacctac   3720

aggggcaatt ctactggcac tctgatggtg ttctttggca atgtggacag ctctgggatc   3780

aagcacaaca tctttaaccc ccctatcatt gccaggtaca ttaggctgca ccccacccat   3840

tacagcatca ggagcaccct gaggatggag ctgatgggct gtgatctgaa cagctgcagc   3900

atgcccctgg gcatggagag caaggctatc tctgatgccc agattactgc cagcagctac   3960

ttcaccaata tgtttgccac ctggagcccc agcaaggcca ggctgcacct gcagggcagg   4020

tctaatgcct ggaggcccca ggtgaacaac cccaaggagt ggctgcaggt ggacttccag   4080

aagaccatga aggtgactgg ggtgaccacc caggggggtga agagcctgct gactagcatg   4140

tatgtgaagg agttcctgat cagcagcagc caggatggcc atcagtggac cctgttcttc   4200

cagaatggca aggtgaaggt gttccagggc aatcaggaca gcttcacccc tgtggtgaac   4260

agcctggacc ccccccctgct gaccagatac ctgaggatcc acccccagag ctgggtgcat   4320

cagattgccc tgaggatgga ggtgctgggg tgtgaggccc aggacctgta ctga         4374
```

<210> SEQ ID NO 2
<211> LENGTH: 4374
<212> TYPE: DNA
<213> ORGANISM: Artificial Sequence
<220> FEATURE:
<223> OTHER INFORMATION: Description of Artificial Sequence: FVIII Nucleic Acid

<400> SEQUENCE: 2

```
atgcagattg agctgtctac ctgctttttc ctgtgtctgc tgaggttctg cttctctgcc     60

actaggaggt actacctggg ggctgtggag ctgtcttggg attacatgca gtctgatctg    120

ggggagctgc ctgtggatgc caggtttcct cccagggtgc ccaagtcttt ccccttcaat    180

acctctgtgg tgtataagaa gaccctgttt gtggagttta ctgatcacct gttcaacatt    240

gccaagccca ggcccccttg gatgggcctg ctggggccca ccatccaggc tgaggtgtat    300

gacactgtgg tgatcaccct gaagaacatg gcctctcacc ctgtgagcct gcatgctgtg    360

ggggtgagct actggaaggc ctctgagggg gctgagtatg atgaccagac cagccagagg    420

gagaaggagg atgataaggt gttccctggg gggagccaca cttatgtgtg gcaggtgctg    480

aaggagaatg gcccaatggc ctctgatccc ctgtgcctga cctattctta cctgagccat    540

gtggacctgg tgaaggacct gaactctggc ctgattgggg ccctgctggt gtgcagggag    600
```

-continued

```
ggctctctgg ctaaggagaa gacccagacc ctgcacaagt tcatcctgct gtttgctgtg     660
tttgatgagg ggaagagctg gcactctgag accaagaaca gcctgatgca ggacagggat     720
gctgcctctg ccagggcctg gcccaaaatg cacactgtga atggctatgt gaataggagc     780
ctgcctggcc tgattggctg ccacaggaag tctgtgtatt ggcatgtgat tggcatgggc     840
accacccctg aggtgcactc tatcttcctg gagggccata ctttcctggt gaggaatcat     900
aggcaggcca gcctggagat tagccccatt acctttctga ctgcccagac cctgctgatg     960
gacctgggcc agttcctgct gttttgccac atcagctctc accagcatga tggcatggag    1020
gcctatgtga aggtggatag ctgccctgag gagccccagc tgaggatgaa gaacaatgag    1080
gaggctgagg attatgatga tgatctgact gattctgaaa tggatgtggt gaggtttgat    1140
gatgacaata gcccctcttt catccagatc aggtctgtgg ccaagaagca tcctaagacc    1200
tgggtgcact acattgctgc tgaggaggag gactgggact atgctcccct ggtgctggcc    1260
cctgatgaca ggtcttacaa gagccagtac ctgaacaatg gcccccagag aattgggagg    1320
aagtataaga aggtgagatt catggcttac actgatgaga ccttcaagac tagggaggcc    1380
atccagcatg agtctggcat tctgggcccc ctgctgtatg gggaggtggg ggacaccctg    1440
ctgatcatct tcaagaacca ggcctctagg ccctacaata tttacccccca tgggatcact    1500
gatgtgaggc ccctgtacag caggaggctg cctaaggggg tgaagcatct gaaggacttc    1560
cccatcctgc ctggggagat cttcaagtat aagtggactg tgactgtgga agatggcccc    1620
accaagtctg accctaggtg cctgaccagg tactactctt cttttgtgaa catggagagg    1680
gacctggcct ctggcctgat tggcccccctg ctgatctgct acaaggagtc tgtggaccag    1740
agggggaacc agattatgtc tgacaagagg aatgtgattc tgttctctgt gtttgatgag    1800
aacaggagct ggtatctgac tgagaacatc cagaggttcc tgcccaatcc tgctggggtg    1860
cagctggagg accctgagtt ccaggccagc aacatcatgc acagcatcaa tgggtatgtg    1920
tttgattctc tgcagctgtc tgtgtgcctg catgaggtgg cctactggta catcctgagc    1980
attggggctc agactgattt cctgtctgtg ttcttttctg gctacacctt taagcataag    2040
atggtgtatg aggacactct gaccctgttt cccttctctg ggagactgt gtttatgagc     2100
atggagaacc ctggcctgtg gatcctgggc tgccacaact ctgatttcag gaacaggggc    2160
atgactgctc tgctgaaggt gtcttcttgt gacaagaaca ctggggacta ttatgaggac    2220
agctatgagg acatctctgc ctacctgctg agcaagaaca atgctattga gcccagatct    2280
ttcagccaga accccccctgt gctgaagagg caccagaggg agatcactag gaccaccctg    2340
cagtctgacc aggaggagat tgactatgat gacactatct ctgtggagat gaagaaggag    2400
gactttgata tctatgatga ggatgagaac cagtctccca ggagcttcca gaaaaagacc    2460
aggcactact tcattgctgc tgtggagagg ctgtgggact atggcatgtc ttctagcccc    2520
catgtgctga ggaacagggc ccagtctggg tctgtgcccc agttcaagaa ggtggtgttc    2580
caggagttca ctgatgggag cttcacccag cctctgtaca ggggggagct gaatgagcac    2640
ctggggctgc tgggcccctta tattagggct gaggtggagg acaacatcat ggtgactttc    2700
aggaatcagg cctctaggcc ctatagcttc tacagctctc tgatcagcta tgaggaggat    2760
cagaggcagg gggctgagcc caggaagaac tttgtgaagc ccaatgagac caagacctac    2820
ttctggaagg tgcagcacca catggctcct accaaggatg agtttgactg caaggcctgg    2880
gcctactttt ctgatgtgga cctggagaag gatgtgcact ctggcctgat tggccccctg    2940
```

-continued

```
ctggtgtgtc ataccaacac cctgaaccct gcccatggca ggcaggtgac tgtgcaggag   3000

tttgccctgt tcttcaccat ctttgatgag accaagagct ggtactttac tgagaacatg   3060

gagaggaatt gcagagcccc ttgcaacatc cagatggagg acccaacctt caaagagaac   3120

tacaggttcc atgccatcaa tgggtacatc atggacaccc tgcctggcct ggtgatggct   3180

caggaccaga ggatcaggtg gtatctgctg agcatgggca gcaatgagaa tatccatagc   3240

attcacttct ctggccatgt gttcactgtg aggaagaagg aggagtacaa gatggccctg   3300

tataacctgt accctggggt gtttgagact gtggagatgc tgccaagcaa ggctgggatt   3360

tggagggtgg agtgcctgat tggggagcac ctgcatgctg gcatgtctac cctgttcctg   3420

gtgtactcca ataagtgcca gacccccctg ggcatggcct ctggccacat cagggacttc   3480

cagatcactg cctctggcca gtatgggcag tgggccccaa agctggccag gctgcactat   3540

tctgggagca tcaatgcttg gagcaccaag gagcctttca gctggattaa ggtggatctg   3600

ctggccccca tgatcattca tggcatcaaa acccaggggg ctagacagaa gttttctagc   3660

ctgtacatca gccagttcat catcatgtac agcctggatg gcaagaagtg gcagacttac   3720

aggggcaata gcactggcac cctgatggtg tttttggca atgtggacag ctctggcatc   3780

aagcacaaca tctttaaccc cccattatt gccaggtata tcaggctgca tcccacccac   3840

tattctatta ggtctactct gagaatggag ctgatgggct gtgacctgaa cagctgtagc   3900

atgcccctgg ggatggagag caaggctatc tctgatgccc agatcactgc cagctcttat   3960

ttcaccaata tgtttgccac ctggtctccc tctaaggcca ggctgcacct gcagggcagg   4020

agcaatgctt ggaggcccca ggtgaataac cccaaggagt ggctgcaggt ggacttccag   4080

aagaccatga aggtgactgg ggtgactacc caggggggtga agtctctgct gactagcatg   4140

tatgtgaagg agttcctgat cagcagcagc caggatgggc atcagtggac tctgttcttc   4200

cagaatggca aggtgaaggt cttccagggg aaccaggata gcttcactcc tgtggtgaac   4260

tctctggacc cccccctgct gactaggtat ctgaggatcc acccccagag ctgggtgcac   4320

cagattgccc tgaggatgga ggtgctgggc tgtgaggccc aggacctgta ttga         4374
```

<210> SEQ ID NO 3
<211> LENGTH: 4374
<212> TYPE: DNA
<213> ORGANISM: Artificial Sequence
<220> FEATURE:
<223> OTHER INFORMATION: Description of Artificial Sequence: FVIII
      Nucleic Acid

<400> SEQUENCE: 3

```
atgcagattg aactgtctac ttgtttcttc ctgtgcctgc tgaggttttg cttctctgct     60

actaggaggt actatctggg ggctgtggag ctgtcttggg actatatgca gtctgacctg    120

ggggagctgc ctgtggatgc taggtttccc cccagggtgc ccaagagctt cccctttaac    180

acctctgtgg tgtataagaa gactctgttt gtggagttca ctgaccatct gttcaacatt    240

gccaagccaa ggcccccctg gatgggcctg ctgggcccca ccatccaggc tgaggtgtat    300

gacactgtgg tgattactct gaagaacatg gccagccatc ctgtgagcct gcatgctgtg    360

ggggtgtctt actggaaggc ctctgagggg gctgagtatg atgaccagac ctctcagagg    420

gagaaggagg atgacaaggt gttccctggg ggctctcata cctatgtgtg gcaggtcctg    480

aaggagaatg ggcccatggc ctctgacccc ctgtgcctga cctactctta tctgtctcat    540

gtggacctgg tgaaggacct gaactctggc ctgattgggg ccctgctggt gtgcagggag    600
```

-continued

```
ggcagcctgg ctaaggagaa gacccagact ctgcacaagt tcatcctgct gtttgctgtg    660
tttgatgagg gcaagagctg gcactctgag accaagaaca gcctgatgca ggacagggat    720
gctgcctctg ctagggcctg gcccaagatg cacactgtga atgggtatgt gaacaggagc    780
ctgccaggcc tgattggctg ccataggaag tctgtgtatt ggcatgtgat tgggatgggg    840
actacccctg aggtccacag cattttcctg gaggggcata cctttctggt gaggaaccac    900
aggcaggcct ctctggagat ctctcccatt actttcctga ctgcccagac cctgctgatg    960
gacctgggcc agttcctgct gttctgccac atcagcagcc accagcatga tggcatggag   1020
gcctatgtga aggtggatag ctgccctgag gagccccagc tgaggatgaa aaacaatgag   1080
gaggctgagg attatgatga tgacctgact gattctgaga tggatgtggt gaggtttgat   1140
gatgataaca gccccagctt catccagatt aggtctgtgg ccaagaagca tcccaagacc   1200
tgggtgcact acattgctgc tgaggaggag gattgggact atgctcctct ggtgctggcc   1260
cctgatgaca ggagctacaa gagccagtac ctgaataatg gcccccagag gattggcagg   1320
aagtataaga aggtgaggtt catggcctac actgatgaga cctttaagac cagggaggcc   1380
atccagcatg aatctgggat cctgggcccc ctgctgtatg gggaggtggg ggacaccctg   1440
ctgattatct ttaagaacca ggctagcagg ccctacaaca tttaccccca tggcattact   1500
gatgtgaggc ccctgtacag caggaggctg cccaaggggg tgaagcacct gaaggatttc   1560
cccattctgc ctggggagat ctttaagtac aaatggactg tgactgtgga ggatggccct   1620
actaagtctg atcccaggtg tctgaccaga tactacagca gctttgtgaa tatggagagg   1680
gacctggctt ctggcctgat tggcccccctg ctgatctgct acaaggagtc tgtggaccag   1740
aggggcaatc agattatgtc tgacaagagg aatgtgatcc tgttctctgt gtttgatgag   1800
aacagaagct ggtacctgac tgagaacatc cagaggttcc tgcccaaccc tgctggggtg   1860
cagctggagg accctgagtt ccaggctagc aatatcatgc acagcattaa tggctatgtg   1920
tttgacagcc tgcagctgtc tgtgtgcctg catgaggtgg cctattggta cattctgagc   1980
attggggccc agactgattt cctgtctgtg ttcttttctg gctacacctt caagcacaag   2040
atggtgtatg aggatactct gaccctgttt cccttctctg ggagactgt gttcatgagc    2100
atggagaacc ctggcctgtg gatcctgggc tgtcacaact ctgacttcag gaacaggggc   2160
atgactgccc tgctgaaggt gagctcttgt gataagaaca ctggggacta ctatgaggac   2220
tcttatgagg acatctctgc ctacctgctg agcaagaaca atgctattga gcccaggagc   2280
ttctctcaga atccccctgt gctgaagagg catcagaggg agatcactag gactaccctg   2340
cagtctgacc aggaagagat tgactatgat gacaccatct ctgtggaaat gaagaaggag   2400
gactttgata tctatgatga ggatgaaaac cagagcccca ggagcttcca gaagaagacc   2460
aggcattact tcattgctgc tgtggagagg ctgtgggact atgggatgag ctcttctccc   2520
catgtgctga ggaatagggc tcagtctggc tctgtcccac agttcaagaa ggtggtgttt   2580
caggagttca ctgatggcag cttcactcag cccctgtaca ggggggagct gaatgagcat   2640
ctgggcctgc tggggcccta catcagggct gaggtggagg ataacattat ggtgactttc   2700
aggaaccagg cctctaggcc ctacagcttc tacagcagcc tgatcagcta tgaggaggac   2760
cagaggcagg gggctgagcc caggaagaac tttgtgaagc ccaatgagac taagacctat   2820
ttctggaagg tgcagcatca catggctccc actaaagatg agtttgactg caaggcctgg   2880
gcctacttct ctgatgtgga tctggagaag gatgtgcatt ctgggctgat tggccctctg   2940
ctggtctgcc atactaacac cctgaatcct gcccatggca ggcaggtgac tgtgcaggag   3000
```

tttgccctgt tctttaccat ctttgatgag accaagtctt ggtacttcac tgagaacatg 3060
gagaggaact gcagggcccc ctgtaacatc cagatggagg accccacctt taaggagaac 3120
tacaggttcc atgccatcaa tggctacatc atggacactc tgcctggcct ggtgatggcc 3180
caggaccaga ggatcaggtg gtacctgctg tctatgggct ctaatgagaa cattcattct 3240
atccacttct ctggccatgt gtttactgtg aggaagaagg aggagtacaa gatggccctg 3300
tacaatctgt accctggggt gtttgaaact gtggagatgc tgccctctaa ggctggcatc 3360
tggagggtgg agtgcctgat tggggaacac ctgcatgctg gcatgagcac cctgttcctg 3420
gtctatagca ataagtgcca gaccccccctg gggatggcct ctgggcatat cagagacttc 3480
cagatcactg cctctggcca gtatggccag tgggccccca agctggccag gctgcactac 3540
tctggcagca ttaatgcctg gagcaccaag gagcccttct cttggatcaa ggtggacctg 3600
ctggctccca tgatcatcca tgggatcaag acccaggggg ccaggcagaa gttcagcagc 3660
ctgtacatct ctcagttcat catcatgtac tctctggatg gcaagaagtg gcagacctac 3720
aggggcaata gcactgggac cctgatggtg ttctttggga atgtggacag ctctggcatc 3780
aagcacaata tcttcaaccc ccccatcatt gccaggtaca tcagactgca ccccactcat 3840
tacagcatca ggagcactct gaggatggag ctgatgggct gtgacctgaa tagctgctct 3900
atgcccctgg gcatggagag caaggccatt tctgatgccc agattactgc ctcttcttac 3960
ttcactaata tgtttgccac ctggagcccc agcaaggcca ggctgcatct gcaggggagg 4020
agcaatgcct ggaggcccca ggtgaacaac cccaaggagt ggctgcaggt ggacttccag 4080
aagactatga aggtgactgg ggtgaccact caggggggtga agagcctgct gaccagcatg 4140
tatgtgaagg agttcctgat ctcttctagc caggatgggc accagtggac cctgtttttc 4200
cagaatggga aggtgaaggt gtttcagggc aatcaggaca gctttactcc tgtggtgaac 4260
agcctggacc cccccctgct gactaggtac ctgaggattc acccccagag ctgggtgcac 4320
cagattgccc tgaggatgga ggtgctgggc tgtgaggccc aggatctgta ctga 4374

<210> SEQ ID NO 4
<211> LENGTH: 4374
<212> TYPE: DNA
<213> ORGANISM: Artificial Sequence
<220> FEATURE:
<223> OTHER INFORMATION: Description of Artificial Sequence: FVIII
Nucleic Acid

<400> SEQUENCE: 4
atgcagattg agctgtctac ctgcttcttt ctgtgcctgc tgaggttctg tttctctgcc 60
actaggaggt attatctggg ggctgtggag ctgtcctggg actacatgca gtctgatctg 120
ggggagctgc ctgtggatgc caggttccct cccagggtgc ccaagtcttt ccctttcaat 180
acctctgtgg tgtacaagaa gactctgttt gtggagttta ctgatcacct gtttaacatt 240
gccaagccca ggccccccctg gatggggctg ctgggcccca ccatccaggc tgaggtgtat 300
gacactgtgg tgattactct gaagaatatg gcttctcacc ctgtgagcct gcatgctgtg 360
ggggtgagct actggaaggc ctctgagggg gctgagtatg atgaccagac cagccagagg 420
gagaaggagg atgacaaggt gttccctggg ggcagccaca cttatgtgtg gcaggtgctg 480
aaggagaatg gcccaatggc ctctgacccc ctgtgcctga cctacagcta tctgagccat 540
gtggatctgg tgaaggatct gaactctggc ctgattgggg ccctgctggt gtgcagggag 600
ggctctctgg ccaaggagaa gactcagact ctgcacaagt tcatcctgct gtttgctgtg 660

-continued

```
tttgatgagg gcaagagctg gcactctgag accaagaact ctctgatgca ggatagggat    720
gctgcttctg ccagggcctg gcccaagatg cacactgtga atgggtatgt gaataggagc    780
ctgcctgggc tgattgggtg tcacaggaag tctgtgtact ggcatgtgat tggcatgggc    840
accactcctg aggtgcacag catctttctg gagggccaca cttttctggt gaggaatcac    900
aggcaggcca gcctggagat cagccccatc accttcctga ctgcccagac cctgctgatg    960
gatctgggcc agttcctgct gttttgccat atcagcagcc atcagcatga tgggatggag   1020
gcttatgtga aggtggactc ttgccctgag gagcctcagc tgaggatgaa gaataatgaa   1080
gaggctgagg actatgatga tgatctgact gactctgaga tggatgtggt gaggtttgat   1140
gatgacaaca gccccagctt tatccagatt aggtctgtgg ccaagaagca ccccaagacc   1200
tgggtgcatt acattgctgc tgaggaagag gattgggact atgcccccct ggtgctggcc   1260
cctgatgaca ggagctacaa gtctcagtac ctgaacaatg gccctcagag gattggcagg   1320
aagtacaaga aggtgaggtt catggcttac actgatgaga ccttcaagac cagggaggcc   1380
attcagcatg aatctgggat cctgggcccc ctgctgtatg gggaggtggg ggacaccctg   1440
ctgattattt tcaagaacca ggccagcagg ccctacaaca tttatcctca tggcattact   1500
gatgtgagac ccctgtacag caggaggctg cctaaggggg tgaagcacct gaaggacttc   1560
cccatcctgc ctggggagat cttcaagtac aagtggactg tgactgtgga ggatggcccc   1620
actaagtctg accccaggtg cctgactagg tactactcca gctttgtgaa catggagagg   1680
gacctggcct ctggcctgat tggcccccctg ctgatctgct acaaggagtc tgtggatcag   1740
aggggcaacc agatcatgtc tgacaagaga aatgtgatcc tgttctctgt gtttgatgag   1800
aataggtctt ggtacctgac tgagaacatc cagaggtttc tgcctaatcc tgctggggtg   1860
cagctggagg atcctgagtt ccaggcctct aacattatgc acagcatcaa tgggtatgtg   1920
tttgacagcc tgcagctgtc tgtgtgcctg catgaggtgg cctactggta catcctgagc   1980
attggggccc agactgactt tctgtctgtg ttcttctctg gctacacctt taagcataag   2040
atggtgtatg aggacaccct gactctgttc cccttctctg ggagactgt gttcatgagc   2100
atggagaacc caggcctgtg gatcctgggc tgccacaact ctgatttcag gaataggggc   2160
atgactgccc tgctgaaggt gagcagctgt gataagaaca ctggggacta ttatgaggat   2220
agctatgagg acatctctgc ctacctgctg agcaagaaca atgccattga gcccaggagc   2280
ttcagccaga atcctcctgt gctgaagagg caccagaggg agatcaccag gaccaccctg   2340
cagtctgatc aggaggagat tgactatgat gacactatct ctgtggagat gaagaaggag   2400
gactttgaca tctatgatga ggatgagaat cagagcccca ggagcttcca gaagaagact   2460
agacactact ttattgctgc tgtggagagg ctgtgggact atggcatgag ctcttctccc   2520
catgtgctga gaaacagggc ccagtctggc tctgtgcccc agttcaagaa ggtggtcttc   2580
caggagttca ctgatggctc tttcacccag cctctgtata gaggggagct gaatgagcac   2640
ctgggcctgc tgggcccctta catcagggct gaggtggagg acaatatcat ggtgaccttc   2700
aggaaccagg ctagcaggcc ctactctttc tacagcagcc tgatcagcta tgaggaggac   2760
cagaggcagg gggctgagcc taggaagaat tttgtgaagc ccaatgagac caagacctac   2820
ttctggaagg tgcagcacca catggctccc actaaggatg agtttgactg caaggcctgg   2880
gcctactttt ctgatgtgga cctggagaag gatgtgcatt ctggcctgat tggcccccctg   2940
ctggtctgcc acaccaatac tctgaaccct gctcatggga gacaggtgac tgtgcaggag   3000
```

```
tttgccctgt tcttcaccat ctttgatgag accaagtcct ggtactttac tgagaacatg   3060

gagaggaatt gcagggcccc ttgcaacatc cagatggagg accccacctt caaggaaaat   3120

tataggttcc atgccatcaa tggctacatc atggacaccc tgcctggcct ggtgatggcc   3180

caggaccaga ggatcaggtg gtatctgctg tctatgggct ctaatgagaa catccacagc   3240

atccatttct ctggccatgt gttcactgtg aggaagaagg aggagtataa gatggctctg   3300

tacaacctgt accctggggt ctttgagact gtggagatgc tgcccagcaa ggctggcatt   3360

tggagggtgg agtgcctgat tggggaacac ctgcatgctg ggatgagcac cctgttcctg   3420

gtgtactcta acaagtgcca gaccccactg ggcatggctt ctggccacat cagggatttc   3480

cagattactg cctctggcca gtatggccag tgggctccca agctggctag gctgcactac   3540

tctgggagca tcaatgcctg gtctactaag gagcctttct cttggatcaa agtggacctg   3600

ctggccccta tgatcatcca tgggatcaag actcaggggg ccaggcagaa gttcagcagc   3660

ctgtacatct ctcagttcat cattatgtac agcctggatg gcaagaagtg gcagacctac   3720

aggggcaaca gcactggcac cctgatggtg ttctttggga atgtggacag ctctgggatt   3780

aagcacaaca tctttaaccc ccccatcatt gccaggtata tcaggctgca ccctacccac   3840

tacagcatta ggagcaccct gaggatggag ctgatgggct gtgacctgaa cagctgcagc   3900

atgcccctgg ggatggagag caaggccatt tctgatgctc agatcactgc ttctagctac   3960

ttcactaaca tgtttgccac ctggtctccc agcaaggcta gactgcacct gcaggggagg   4020

agcaatgcct ggaggcccca ggtgaataat cccaaggagt ggctgcaggt ggatttccag   4080

aaaaccatga aggtgactgg ggtgactacc caggggggtga agtctctgct gaccagcatg   4140

tatgtgaagg agttcctgat cagcagcagc caggatgggc atcagtggac cctgttcttt   4200

cagaatggga aggtgaaggt gtttcagggc aatcaggaca gcttcacccc tgtggtgaac   4260

agcctggacc ccccccctgct gaccaggtac ctgaggatcc acccccagag ctgggtgcat   4320

cagattgccc tgaggatgga ggtgctgggc tgtgaggccc aggacctgta ctga         4374
```

<210> SEQ ID NO 5
<211> LENGTH: 4374
<212> TYPE: DNA
<213> ORGANISM: Artificial Sequence
<220> FEATURE:
<223> OTHER INFORMATION: Description of Artificial Sequence: FVIII Nucleic Acid

<400> SEQUENCE: 5

```
atgcagattg agctgtctac ttgcttcttc ctgtgcctgc tgaggttctg cttctctgcc     60

actaggaggt attacctggg ggctgtggag ctgagctggg actatatgca gtctgacctg    120

ggggagctgc ctgtggatgc caggtttcct cccagggtgc ctaagagctt ccccttcaac    180

acctctgtgg tgtacaagaa gactctgttt gtggagttta ctgatcatct gttcaacatt    240

gccaagccca ggcctccttg gatggggctg ctgggcccca ccatccaggc tgaggtgtat    300

gacactgtgg tgattaccct gaagaatatg gccagccatc ctgtgagcct gcatgctgtg    360

ggggtgagct attggaaggc ctctgagggg gctgagtatg atgatcagac tagccagagg    420

gagaaggagg atgacaaggt gttccctggg gggagccata cctatgtgtg gcaggtgctg    480

aaggagaatg gccccatggc ctctgaccct ctgtgcctga cttatagcta cctgagccat    540

gtggatctgg tgaaggacct gaactctggc ctgattgggg ccctgctggt gtgcagggag    600

ggcagcctgg ccaaggagaa gactcagacc ctgcacaagt tcatcctgct gtttgctgtg    660
```

-continued

```
tttgatgagg ggaagtcctg gcactctgag actaagaaca gcctgatgca ggatagggat    720
gctgcttctg ccagggcctg gcctaagatg cacactgtga atggctatgt gaataggagc    780
ctgcctggcc tgattggctg ccataggaag tctgtgtact ggcatgtgat tgggatgggc    840
accacccctg aggtgcactc tattttcctg gagggccata ctttcctggt gaggaaccat    900
aggcaggcca gcctggagat cagccccatc actttcctga ctgcccagac tctgctgatg    960
gacctgggcc agttcctgct gttctgccac atcagcagcc atcagcatga tggcatggag   1020
gcttatgtga aggtggacag ctgccctgag gagcctcagc tgaggatgaa gaataatgag   1080
gaggctgagg actatgatga tgacctgact gactctgaga tggatgtggt gaggtttgat   1140
gatgacaact ctccctcttt catccagatc aggtctgtgg ccaagaagca ccctaagacc   1200
tgggtgcact acattgctgc tgaggaggag gattgggact atgccccccct ggtgctggcc   1260
ccagatgaca ggagctacaa gtcccagtac ctgaacaatg gcccccagag gattggcagg   1320
aagtacaaga aggtgaggtt catggcttat actgatgaga ctttcaagac cagggaggcc   1380
atccagcatg agtctggcat cctgggccct ctgctgtatg gggaggtggg ggacaccctg   1440
ctgattatct tcaagaacca ggcttctagg ccctacaata tctaccctca tggcatcact   1500
gatgtgaggc ccctgtacag caggaggctg cccaaggggg tgaagcatct gaaggatttc   1560
cccatcctgc ctggggagat ctttaagtat aagtggactg tgactgtgga ggatggcccc   1620
actaagtctg accccaggtg cctgaccagg tattacagca gctttgtgaa catggagagg   1680
gatctggctt ctgggctgat tggcccccctg ctgatctgct acaaggagtc tgtggaccag   1740
aggggcaacc agatcatgtc tgacaagagg aatgtgatcc tgttctctgt gtttgatgag   1800
aataggagct ggtacctgac tgagaacatc cagaggtttc tgcccaatcc tgctggggtg   1860
cagctggagg atcctgagtt tcaggcctct aatatcatgc acagcatcaa tggctatgtg   1920
tttgactctc tgcagctgtc tgtgtgcctg catgaggtgg cctattggta catcctgagc   1980
attggggccc agactgactt tctgtctgtg tttttttctg gctacacctt caagcacaag   2040
atggtgtatg aggatactct gactctgttc cctttttctg ggagactgt gttcatgtct   2100
atggagaacc ctgggctgtg gattctgggc tgccacaatt ctgacttcag gaacagaggc   2160
atgactgctc tgctgaaggt gagcagctgt gacaagaaca ctggggacta ctatgaggac   2220
tcttatgagg acatttctgc ctacctgctg agcaagaaca atgccattga gcccagaagc   2280
ttttctcaga acccccctgt gctgaagagg caccagaggg agatcaccag gaccaccctg   2340
cagtctgacc aggaggagat tgactatgat gatactattt ctgtggagat gaagaaggag   2400
gactttgaca tctatgatga ggatgagaac cagagcccca ggtctttcca gaagaagact   2460
aggcactact ttattgctgc tgtggagagg ctgtgggact atgggatgtc tagctctcct   2520
catgtgctga ggaacagggc ccagtctggc tctgtgcccc agtttaaaaa ggtggtgttc   2580
caggaattca ctgatggcag ctttacccag cctctgtaca ggggggagct gaatgagcac   2640
ctggggctgc tggggcctta cattagggct gaggtggagg acaacatcat ggtgaccttc   2700
aggaatcagg ccagcaggcc ctactctttc tacagcagcc tgatctctta tgaggaggac   2760
cagaggcagg gggctgaacc caggaagaac tttgtgaagc ccaatgagac caagacctac   2820
ttctggaagg tgcagcacca catggctccc accaaggatg agtttgattg caaggcctgg   2880
gcttacttct ctgatgtgga tctggagaag gatgtgcact ctgggctgat tggccccctg   2940
ctggtgtgcc acaccaacac tctgaaccct gcccatggca gacaggtgac tgtgcaggag   3000
tttgccctgt tcttcactat ctttgatgag actaagagct ggtacttcac tgagaacatg   3060
```

gagaggaatt gcagggcccc ttgcaacatc cagatggagg accccacctt taaggagaac 3120
tacaggtttc atgccattaa tggctacatc atggacaccc tgcctggcct ggtgatggcc 3180
caggaccaga ggatcaggtg gtacctgctg tctatgggga gcaatgagaa catccacagc 3240
attcacttct ctggccatgt gttcactgtg aggaagaagg aggagtacaa gatggccctg 3300
tacaacctgt accctggggt gtttgagact gtggagatgc tgcccagcaa ggctgggatc 3360
tggagggtgg agtgcctgat tggggagcac ctgcatgctg ggatgagcac cctgttcctg 3420
gtgtatagca acaagtgcca gacccccctg ggcatggcct ctggccacat cagagacttt 3480
cagattactg cctctggcca gtatgggcag tgggccccca agctggccag gctgcactat 3540
tctggctcta ttaatgcctg gagcactaag gagcccttca gctggattaa ggtggacctg 3600
ctggctccca tgatcatcca tggcatcaag actcaggggg ccaggcagaa gttctcttct 3660
ctgtacatca gccagttcat tatcatgtac tccctggatg gcaagaagtg gcagacctat 3720
aggggcaaca gcactggcac cctgatggtg ttctttggga atgtggacag ctctggcatc 3780
aagcataata tcttcaatcc ccccatcatt gctaggtaca tcaggctgca ccccacccac 3840
tactctatta ggtctaccct gaggatggag ctgatgggct gtgacctgaa cagctgcagc 3900
atgcctctgg gcatggagag caaagccatc tctgatgccc agatcactgc cagcagctac 3960
tttaccaaca tgtttgctac ttggagcccc agcaaggcca ggctgcacct gcaggggagg 4020
tctaatgcct ggaggcccca ggtgaacaac cccaaggagt ggctgcaggt ggacttccag 4080
aagactatga aggtgactgg ggtgaccacc caggggggtga agagcctgct gacctctatg 4140
tatgtgaagg agttcctgat tagcagcagc caggatggcc accagtggac cctgtttttc 4200
cagaatggga aggtgaaggt gtttcagggg aaccaggaca gcttcactcc tgtggtgaac 4260
tctctggacc ccccccctgct gaccaggtat ctgaggatcc accctcagag ctgggtgcac 4320
cagattgccc tgaggatgga ggtgctgggc tgtgaggccc aggacctgta ctga 4374

<210> SEQ ID NO 6
<211> LENGTH: 4374
<212> TYPE: DNA
<213> ORGANISM: Artificial Sequence
<220> FEATURE:
<223> OTHER INFORMATION: Description of Artificial Sequence: FVIII Nucleic Acid

<400> SEQUENCE: 6
atgcagattg agctgagcac ctgcttcttc ctgtgcctgc tgaggttttg cttctctgcc 60
accaggaggt actacctggg ggctgtggag ctgagctggg attacatgca gtctgacctg 120
ggggagctgc ctgtggatgc caggttccct cccagggtgc ccaagtcttt ccccttcaac 180
acttctgtgg tgtacaagaa gaccctgttt gtggagttta ctgaccacct gttcaacatt 240
gccaagccca ggcctccctg gatgggcctg ctgggcccca ccattcaggc tgaggtgtat 300
gacactgtgg tcatcaccct gaaaaatatg gctagccacc ctgtgtctct gcatgctgtg 360
ggggtgagct actggaaggc ctctgagggg gctgagtatg atgaccagac tagccagagg 420
gagaaggagg atgacaaggt gttccctggg ggcagccaca cttatgtgtg gcaggtgctg 480
aaagagaatg gccccatggc ttctgatccc ctgtgtctga cctatagcta cctgagccat 540
gtggatctgg tgaaggacct gaactctggc ctgattgggg ccctgctggt gtgcagggag 600
ggcagcctgg ctaaggagaa gacccagacc ctgcataagt tcatcctgct gtttgctgtg 660
tttgatgagg gcaagagctg gcactctgag actaagaaca gcctgatgca ggatagggat 720
gctgcttctg ccagggcctg gcccaagatg cacactgtga atgggtatgt gaacaggagc 780
ctgcctggcc tgattggctg ccataggaag tctgtctatt ggcatgtgat tggcatgggc 840
actactcctg aggtgcacag catctttctg gagggccaca ccttcctggt gaggaaccac 900
aggcaggcca gcctggagat ctctcccatc actttcctga ctgctcagac cctgctgatg 960
gacctgggcc agttcctgct gttctgtcac atctctagcc accagcatga tggcatggag 1020
gcctatgtga aggtggatag ctgccctgag gaaccccagc tgaggatgaa gaacaatgag 1080
gaggctgagg attatgatga tgatctgact gattctgaga tggatgtggt gaggtttgat 1140
gatgacaatt ctcctagctt cattcagatc agatctgtgg ccaaaaagca tcctaagact 1200
tgggtgcatt atattgctgc tgaggaggag gattgggatt atgcccccct ggtgctggct 1260
cctgatgata ggagctacaa gtctcagtac ctgaataatg gccccagag gattggcagg 1320
aagtacaaga aggtgaggtt catggcctac actgatgaga ccttcaagac cagggaggcc 1380
attcagcatg agtctgggat tctggggccc ctgctgtatg ggaggtggg ggataccctg 1440
ctgatcattt tcaagaacca ggccagcagg ccctacaaca tctaccccca tgggattact 1500
gatgtgaggc ccctgtactc taggaggctg cctaaggggg tgaagcacct gaaggatttt 1560
cctatcctgc ctggggaaat cttcaagtac aagtggactg tgactgtgga ggatggcccc 1620
actaagtctg atcccaggtg tctgaccagg tattatagct cttttgtgaa catggagagg 1680
gatctggcct ctgggctgat tggccctctg ctgatctgct acaaggagtc tgtggaccag 1740
aggggcaacc agatcatgtc tgacaagagg aatgtgatcc tgttctctgt gtttgatgag 1800
aacaggagct ggtatctgac tgagaacatc cagaggtttc tgcccaatcc tgctggggtg 1860
cagctggagg atcctgagtt ccaggctagc aacatcatgc acagcatcaa tgggtatgtg 1920
tttgacagcc tgcagctgtc tgtgtgtctg catgaggtgg cctactggta tatcctgtct 1980
attggggccc agactgactt cctgtctgtg tttttttctg ggtatacttt taagcacaag 2040
atggtgtatg aggacaccct gactctgttc cccttctctg ggagactgt gtttatgagc 2100
atggagaacc ctggcctgtg gatcctgggc tgccacaatt ctgacttcag gaataggggg 2160
atgactgccc tgctgaaggt gagcagctgt gataagaata ctggggacta ctatgaggac 2220
tcttatgagg acatttctgc ctatctgctg tctaagaaca atgccattga acccaggagc 2280
ttctctcaga acccccctgt gctgaagagg caccagaggg aaatcaccag aactactctg 2340
cagtctgatc aggaggaaat tgactatgat gacactattt ctgtggagat gaagaaggag 2400
gactttgaca tctatgatga ggatgagaac cagagcccaa ggagcttcca gaagaagact 2460
aggcactact tcattgctgc tgtggagagg ctgtgggact atggcatgag cagcagcccc 2520
catgtgctga gaaacagggc ccagtctggg tctgtgcccc agttcaagaa ggtggtgttc 2580
caggagttca ctgatgggag cttcacccag cccctgtata gggggagct gaatgagcac 2640
ctgggcctgc tgggccccta tattagggct gaggtggagg acaacatcat ggtgaccttc 2700
aggaatcagg cctctaggcc ctacagcttc tacagcagcc tgattagcta tgaggaggat 2760
cagaggcagg gggctgaacc caggaagaac tttgtgaagc ccaatgagac caagacctat 2820
ttctggaagg tgcagcatca catggccccc accaaggatg agtttgactg caaggcctgg 2880
gcctacttct ctgatgtgga tctggagaag gatgtgcact ctggcctgat tggcccctg 2940
ctggtgtgcc acaccaacac cctgaaccct gctcatggca ggcaggtgac tgtgcaggag 3000
tttgccctgt tcttcaccat ctttgatgag actaagtctt ggtacttcac tgagaatatg 3060

-continued gagaggaatt gcagggcccc ctgcaatatt cagatggaag accccacctt caaggagaat 3120
tacaggttcc atgccattaa tggctacatc atggataccc tgcctggcct ggtgatggcc 3180
caggatcaga ggatcaggtg gtacctgctg agcatgggca gcaatgagaa catccactct 3240
atccacttct ctggccatgt gtttactgtg aggaagaagg aggagtataa gatggccctg 3300
tacaacctgt accctggggt ctttgagact gtggagatgc tgccttctaa ggctggcatt 3360
tggagggtgg agtgcctgat tggggaacac ctgcatgctg gcatgtctac cctgttcctg 3420
gtgtacagca ataagtgcca gaccccccctg ggcatggcct ctgggcatat cagggatttc 3480
cagatcactg cctctggcca gtatggccag tgggccccaa agctggctag gctgcactac 3540
tctgggagca tcaatgcctg gagcactaag gagcccttca gctggatcaa ggtggacctg 3600
ctggccccca tgattatcca tggattaag actcaggggg ccaggcagaa gttcagcagc 3660
ctgtacatca gccagttcat tatcatgtac agcctggatg gcaagaagtg gcagacctat 3720
aggggcaact ctactgggac cctgatggtg ttctttggga atgtggatag ctctgggatc 3780
aagcacaata tcttcaaccc ccccatcatt gccaggtata tcaggctgca ccccacccac 3840
tacagcatta ggtctaccct gaggatggag ctgatgggct gtgatctgaa cagctgtagc 3900
atgcctctgg gcatggagtc taaggccatt tctgatgccc agattactgc tagcagctac 3960
ttcaccaaca tgtttgccac ctggtctccc agcaaggcca ggctgcatct gcagggcagg 4020
tctaatgctt ggaggcccca ggtgaacaac ccaaaggagt ggctgcaggt ggatttccag 4080
aagactatga aggtgactgg ggtgaccact caggggggtga agtctctgct gacctctatg 4140
tatgtgaagg agttcctgat ctctagcagc caggatggcc atcagtggac cctgttcttc 4200
cagaatggca aggtgaaagt gttccagggc aatcaggata gcttcactcc agtggtgaac 4260
agcctggatc cccctctgct gactaggtac ctgaggatcc acccccagag ctgggtgcac 4320
cagattgccc tgaggatgga ggtgctgggc tgtgaggccc aggacctgta ctga 4374

<210> SEQ ID NO 7
<211> LENGTH: 4374
<212> TYPE: DNA
<213> ORGANISM: Artificial Sequence
<220> FEATURE:
<223> OTHER INFORMATION: Description of Artificial Sequence: FVIII
Nucleic Acid

<400> SEQUENCE: 7
atgcagattg agctgagcac ctgcttcttc ctgtgtctgc tgaggttctg cttctctgcc 60
accaggaggt attacctggg ggctgtggag ctgagctggg actatatgca gtctgacctg 120
ggggagctgc ctgtggatgc taggttcccc cccagggtgc ccaagagctt cccctttaac 180
acttctgtgg tgtacaagaa gaccctgttt gtggagttca ctgaccacct gttcaacatt 240
gccaagccca ggccccccctg gatggggctg ctggggccca ccatccaggc tgaggtgtat 300
gacactgtgg tgatcaccct gaagaacatg gccagccacc ctgtgagcct gcatgctgtg 360
ggggtgagct actggaaggc ttctgagggg gctgagtatg atgaccagac tagccagagg 420
gagaaggagg atgacaaggt gtttcctggg ggcagccata cctatgtgtg gcaggtgctg 480
aaggagaatg gccccatggc ctctgacccc ctgtgcctga cctacagcta cctgtctcat 540
gtggacctgg tgaaggacct gaactctggc ctgattgggg ctctgctggt gtgtagggag 600
ggcagcctgg ctaaggaaaa gacccagacc ctgcataagt ttatcctgct gtttgctgtg 660
tttgatgagg gcaagagctg gcactctgag accaagaaca gcctgatgca ggatagggat 720

```
gctgcctctg ccagggcttg gcctaagatg cacactgtga atgggtatgt gaataggagc    780
ctgcctggcc tgattggctg ccacaggaag tctgtgtact ggcatgtgat tgggatgggc    840
accacccctg aggtccatag catcttcctg gagggccaca ctttcctggt gaggaaccac    900
agacaggcct ctctggagat ctctcccatc accttcctga ctgctcagac tctgctgatg    960
gacctgggcc agttcctgct gttttgccat attagcagcc accagcatga tgggatggag   1020
gcctatgtga aggtggatag ctgccctgag gagcctcagc tgaggatgaa gaacaatgag   1080
gaggctgaag actatgatga tgacctgact gattctgaga tggatgtggt gaggtttgat   1140
gatgacaata gccccagctt cattcagatc aggtctgtgg ccaagaaaca ccccaagacc   1200
tgggtgcact acattgctgc tgaggaagag gactgggact atgctcccct ggtgctggcc   1260
cctgatgata ggtcttataa gagccagtac ctgaacaatg ggccccagag gattggcagg   1320
aagtacaaga aggtgaggtt catggcctac actgatgaaa ccttcaaaac cagggaggcc   1380
attcagcatg agtctggcat cctgggccct ctgctgtatg gggaggtggg ggacaccctg   1440
ctgatcatct tcaagaacca ggccagcagg ccctacaaca tctatcctca tggcatcact   1500
gatgtgaggc ccctgtacag caggaggctg cccaaggggg tgaagcacct gaaagacttc   1560
cccatcctgc ctggggagat ctttaagtat aagtggactg tgactgtgga ggatggccct   1620
accaagtctg accccaggtg tctgaccagg tactattcta gctttgtgaa catggagagg   1680
gacctggcct ctggcctgat tggccccctg ctgatctgct acaaggagtc tgtggaccag   1740
aggggcaacc agatcatgtc tgacaagagg aatgtgatcc tgttttctgt gtttgatgag   1800
aataggagct ggtacctgac tgagaacatc cagaggtttc tgcccaatcc tgctggggtg   1860
cagctggagg atcctgagtt ccaggccagc aatatcatgc atagcatcaa tggctatgtg   1920
tttgacagcc tgcagctgtc tgtgtgcctg catgaggtgg cctactggta catcctgagc   1980
attggggccc agactgactt tctgtctgtg ttcttttctg gctatacctt caagcacaag   2040
atggtgtatg aggataccct gaccctgttc cccttctctg ggagactgt gttcatgagc    2100
atggagaatc ctgggctgtg gatcctgggg tgccacaact ctgattttag gaacaggggg   2160
atgactgccc tgctgaaggt gtctagctgt gataagaaca ctggggacta ctatgaggac   2220
agctatgagg acatttctgc ttatctgctg tctaagaata atgccattga gcccagaagc   2280
ttcagccaga atcccctgt gctgaagaga catcagaggg agatcaccag aactaccctg    2340
cagtctgatc aggaggagat tgactatgat gacactatct ctgtggagat gaagaaggag   2400
gactttgaca tctatgatga ggatgagaat cagtctccca ggagctttca gaagaagacc   2460
agacattact tcattgctgc tgtggagagg ctgtgggact atggcatgag ctctagccct   2520
catgtgctga ggaacagggc ccagtctggc tctgtgcccc agttcaagaa ggtggtgttc   2580
caggaattca ctgatggcag cttcacccag cccctgtaca ggggggagct gaatgagcac   2640
ctgggcctgc tggggcctta tatcagggct gaggtggagg ataatattat ggtgactttc   2700
aggaaccagg ccagcaggcc ctactctttc tatagcagcc tgatctctta tgaggaggat   2760
cagaggcagg gggctgagcc taggaagaac tttgtgaagc ccaatgagac taagacctac   2820
ttctggaagg tccagcacca catggcccct accaaggatg agtttgactg caaggcctgg   2880
gcctatttct ctgatgtgga tctggagaag gatgtccatt ctgggctgat tggcccccctg  2940
ctggtgtgcc acactaacac tctgaatcct gcccatggca ggcaggtgac tgtccaggag   3000
tttgccctgt tcttcactat ctttgatgag accaagagct ggtactttac tgagaacatg   3060
gagaggaact gcagagctcc ttgcaatatt cagatggagg accccacctt caaggagaat   3120
```

```
tacaggttcc atgccattaa tgggtacatc atggacaccc tgcctggcct ggtgatggct   3180
caggaccaga ggatcaggtg gtacctgctg agcatgggct ctaatgagaa tatccacagc   3240
atccacttct ctgggcatgt gttcactgtg aggaagaagg aggagtacaa gatggctctg   3300
tataatctgt accctggggt gtttgaaact gtggagatgc tgccctctaa ggctggcatc   3360
tggagggtgg agtgcctgat tggggagcac ctgcatgctg gcatgagcac cctgttcctg   3420
gtgtacagca acaagtgcca gacccccctg ggcatggcct ctggccacat cagggacttc   3480
cagatcactg cctctggcca gtatggccag tgggccccca agctggccag gctgcactat   3540
tctggcagca tcaatgcctg gagcaccaag gagcccttca gctggatcaa ggtggacctg   3600
ctggccccca tgatcattca tggcatcaag acccaggggg ccaggcagaa gttcagctct   3660
ctgtacatct ctcagttcat catcatgtac tctctggatg ggaagaagtg gcagacctac   3720
aggggcaaca gcactggcac cctgatggtg ttctttggga atgtggactc ttctggcatc   3780
aagcacaaca tcttcaatcc ccccatcatt gctaggtata ttaggctgca tcccacccac   3840
tacagcatca ggtctaccct gaggatggag ctgatgggct gtgacctgaa ctcttgcagc   3900
atgcccctgg gcatggagtc taaggccatc tctgatgccc agattactgc cagcagctac   3960
ttcaccaaca tgtttgccac ctggagcccc tctaaggcca ggctgcatct gcaggggagg   4020
agcaatgcct ggaggcctca ggtgaacaac cccaaggagt ggctgcaggt ggatttccag   4080
aagaccatga aggtgactgg ggtgaccacc caggggggtca agagcctgct gaccagcatg  4140
tatgtgaagg agttcctgat cagcagcagc caggatggcc accagtggac tctgttcttt   4200
cagaatggga aggtgaaggt gtttcagggc aatcaggact ctttcacccc tgtggtgaac   4260
agcctggacc ccccctgct gaccagatac ctgaggatcc acccccagtc ttgggtgcat   4320
cagattgccc tgaggatgga ggtgctgggc tgtgaggctc aggatctgta ctga         4374
```

```
<210> SEQ ID NO 8
<211> LENGTH: 4374
<212> TYPE: DNA
<213> ORGANISM: Artificial Sequence
<220> FEATURE:
<223> OTHER INFORMATION: Description of Artificial Sequence: FVIII
      Nucleic Acid

<400> SEQUENCE: 8

atgcagattg agctgagcac ttgctttttt ctgtgcctgc tgaggttttg tttttctgcc     60
accaggaggt actacctggg ggctgtggag ctgagctggg actatatgca gtctgatctg    120
ggggagctgc ctgtggatgc caggttcccc cccagggtgc ccaagtcttt tcccttcaac    180
acctctgtgg tgtataagaa gaccctgttt gtggagttca ctgaccacct gttcaacatt    240
gctaagccta ggccccccctg gatgggcctg ctgggcccta ccattcaggc tgaggtgtat   300
gacactgtgg tgatcaccct gaagaacatg gccagccatc ctgtgagcct gcatgctgtg    360
ggggtctctt actggaaggc ctctgagggg gctgagtatg atgaccagac cagccagaga    420
gagaaggagg atgacaaggt cttccctggg ggctctcaca cctatgtgtg gcaggtgctg    480
aaggaaaatg gccccatggc ctctgacccc ctgtgcctga cctacagcta tctgagccat    540
gtggatctgg tgaaggacct gaattctggc ctgattgggg ccctgctggt gtgcagggag    600
ggcagcctgg ccaaggagaa gacccagacc ctgcacaagt ttatcctgct gtttgctgtg    660
tttgatgagg gcaagtcttg gcactctgag actaagaaca gcctgatgca ggacagggat    720
gctgcctctg ccagggcctg gcccaagatg cacactgtga atggctatgt gaacaggagc    780
```

```
ctgcctgggc tgattggctg ccacaggaag tctgtgtact ggcatgtgat tggcatgggc    840
accacccctg aggtgcacag catcttcctg gaaggccaca ctttcctggt gaggaaccat    900
aggcaggcca gcctggagat cagccctatc accttcctga ctgcccagac cctgctgatg    960
gatctggggc agttcctgct gttctgccac atctctagcc accagcatga tgggatggag   1020
gcctatgtga aggtggacag ctgcccagag gagcctcagc tgaggatgaa aaacaatgaa   1080
gaggctgagg attatgatga tgatctgact gactctgaga tggatgtggt gagatttgat   1140
gatgacaata gccctagctt tattcagatc aggtctgtgg ctaagaagca ccccaagacc   1200
tgggtgcatt acattgctgc tgaggaggag gactgggatt atgctcctct ggtgctggcc   1260
cctgatgata ggagctacaa gagccagtac ctgaataatg gccctcagag gattggcagg   1320
aagtacaaga aggtgaggtt catggcttac actgatgaga ccttcaagac tagggaggcc   1380
atccagcatg agtctgggat cctggggccc ctgctgtatg gggaggtggg ggacaccctg   1440
ctgatcatct tcaagaacca ggctagcagg ccttacaaca tctatcccca tgggatcact   1500
gatgtgagac ctctgtacag caggaggctg cccaaggggg tcaagcatct gaaagacttc   1560
cccatcctgc ctggggagat ctttaagtat aagtggactg tgactgtgga ggatgggccc   1620
accaagtctg accccaggtg cctgaccagg tattacagca gctttgtgaa catggagagg   1680
gatctggcct ctgggctgat tggcccccctg ctgatctgtt acaaggaatc tgtggatcag   1740
aggggcaatc agatcatgtc tgacaagagg aatgtgatcc tgttctctgt gtttgatgag   1800
aataggtctt ggtacctgac tgaaaacatc cagaggttcc tgcccaaccc tgctggggtc   1860
cagctggagg atcctgagtt ccaggctagc aacatcatgc acagcatcaa tgggtatgtg   1920
tttgatagcc tgcagctgtc tgtgtgcctg catgaggtgg cctactggta catcctgtct   1980
attggggccc agactgactt cctgtctgtg ttcttttctg gctacacctt caagcacaag   2040
atggtgtatg aggacaccct gaccctgttc cccttctctg ggagactgt ctttatgagc   2100
atggagaacc ctgggctgtg gatcctgggc tgccacaact ctgatttcag gaataggggc   2160
atgactgctc tgctgaaggt gagctcttgt gacaagaaca ctggggatta ctatgaggac   2220
agctatgagg acatttctgc ctacctgctg agcaagaaca atgccattga gcctaggagc   2280
tttagccaga atcctcctgt cctgaagagg caccagaggg agatcaccag gaccaccctg   2340
cagtctgacc aggaggagat tgactatgat gataccatct ctgtggagat gaagaaggag   2400
gactttgaca tctatgatga ggatgagaat cagtctccca ggagcttcca gaagaagacc   2460
aggcactatt tcattgctgc tgtggagagg ctgtgggact atggcatgag cagctctcct   2520
catgtgctga ggaatagggc tcagtctggc tctgtgcccc agttcaagaa agtggtgttt   2580
caggagttca ctgatggctc tttcacccag cctctgtata ggggggagct gaatgagcac   2640
ctggggctgc tgggccccta tatcagggct gaggtggagg ataacatcat ggtgaccttc   2700
aggaaccagg cctctaggcc ctacagcttc tatagcagcc tgatcagcta tgaggaggac   2760
cagaggcagg gggctgagcc caggaagaac tttgtgaagc ccaatgagac caagacttac   2820
ttctggaagg tgcagcatca catggccccc accaaggatg agtttgactg taaggcctgg   2880
gcctacttct ctgatgtgga tctggagaag gatgtgcact ctggcctgat tggcccccctg   2940
ctggtgtgcc ataccaatac tctgaaccct gctcatggca ggcaggtgac tgtgcaggag   3000
tttgctctgt tcttcactat ctttgatgag accaagtctt ggtatttcac tgagaatatg   3060
gagaggaact gcagggcccc ctgcaacatc cagatggagg accccacctt taaggagaac   3120
```

```
tataggtttc atgccatcaa tggctacatc atggacaccc tgcctggcct ggtgatggcc   3180
caggatcaga ggatcaggtg gtacctgctg agcatggggt ctaatgagaa catccacagc   3240
atccacttct ctggccatgt gtttactgtg agaaagaagg aggagtacaa gatggctctg   3300
tacaatctgt accctggggt ctttgagact gtggagatgc tgcctagcaa ggctgggatc   3360
tggagggtgg agtgcctgat tggggaacat ctgcatgctg ggatgtctac tctgttcctg   3420
gtgtacagca acaagtgcca gaccccctg ggcatggctt ctggccatat cagggacttt   3480
cagattactg cctctgggca gtatggccag tgggccccca agctggctag gctgcattat   3540
tctggcagca tcaatgcctg gtctactaag gagcccttca gctggatcaa ggtggatctg   3600
ctggccccca tgatcatcca tggcatcaag acccaggggg ccaggcagaa gtttagctct   3660
ctgtacatta gccagttcat catcatgtac agcctggatg ggaagaagtg gcagacctac   3720
aggggcaatt ctactggcac cctgatggtg ttctttggca atgtggacag ctctggcatc   3780
aagcacaaca tctttaaccc ccctatcatt gctaggtaca tcaggctgca tcccacccat   3840
tacagcatca ggagcaccct gaggatggag ctgatgggct gtgacctgaa ctcttgcagc   3900
atgcccctgg gcatggagag caaggccatt tctgatgccc agattactgc cagcagctac   3960
ttcactaaca tgtttgccac ctggtctccc agcaaggcca ggctgcacct gcagggcagg   4020
agcaatgcct ggaggcccca ggtgaacaac cccaaggagt ggctgcaggt ggatttccag   4080
aagaccatga aggtgactgg ggtgaccacc caggggggtga agagcctgct gactagcatg   4140
tatgtgaagg agttcctgat cagctctagc caggatggcc accagtggac tctgtttttc   4200
cagaatggca aggtgaaggt gttccagggc aaccaggact ctttcactcc tgtggtgaac   4260
agcctggacc ccccctgct gaccaggtat ctgaggattc acccccagtc ttgggtgcat   4320
cagattgccc tgaggatgga ggtgctgggc tgtgaggccc aggatctgta ctga         4374
```

<210> SEQ ID NO 9
<211> LENGTH: 4374
<212> TYPE: DNA
<213> ORGANISM: Artificial Sequence
<220> FEATURE:
<223> OTHER INFORMATION: Description of Artificial Sequence: FVIII
      Nucleic Acid

<400> SEQUENCE: 9

```
atgcagattg agctgagcac ctgcttcttc ctgtgtctgc tgagattttg cttttctgcc     60
actaggaggt attacctggg ggctgtggag ctgtcttggg actacatgca gtctgatctg    120
ggggagctgc ctgtggatgc caggttccca cctagggtgc ctaagagctt tcccttcaat    180
acctctgtgg tgtacaagaa gaccctgttt gtggagttca ctgaccacct gttcaacatt    240
gccaagccta ggccccctg gatgggcctg ctgggcccta ccatccaggc tgaagtgtat    300
gacactgtgg tgatcaccct gaagaacatg gccagccacc ctgtgagcct gcatgctgtg    360
ggggtgtctt actggaaggc ctctgagggg gctgagtatg atgatcagac cagccagagg    420
gagaaggaag atgacaaggt gttccctggg ggcagccaca cctatgtctg gcaggtgctg    480
aaggagaatg gccccatggc ctctgatccc ctgtgcctga cctactctta cctgagccat    540
gtggacctgg tgaaggatct gaattctggc ctgattgggg ccctgctggt gtgcagggag    600
ggcagcctgg ccaaggagaa gacccagacc ctgcataagt tcatcctgct gtttgctgtg    660
tttgatgaag ggaagagctg gcactctgag actaagaaca gcctgatgca ggacagggat    720
gctgcttctg ccagggcctg gcccaagatg cacactgtga atggctatgt gaatagaagc    780
```

-continued

```
ctgcctggcc tgattgggtg ccacaggaag tctgtgtact ggcatgtgat tgggatgggc    840
actaccccctg aggtgcatag catcttcctg gaaggccata ccttcctggt gaggaatcat    900
aggcaggctt ctctggaaat ttctcccatc actttcctga ctgctcagac cctgctgatg    960
gacctgggcc agttcctgct gttctgccac atcagctctc accagcatga tgggatggag   1020
gcctatgtga aggtggacag ctgtcctgag gagccccagc tgaggatgaa gaacaatgag   1080
gaggctgagg actatgatga tgacctgact gactctgaga tggatgtggt caggtttgat   1140
gatgacaata gcccctcttt catccagatc aggtctgtgg ccaagaagca ccccaagact   1200
tgggtgcact acattgctgc tgaggaggag gattgggatt atgcccctct ggtgctggcc   1260
cctgatgaca ggagctataa gtctcagtac ctgaataatg gcccccagag gattgggagg   1320
aagtataaga aggtgaggtt tatggcctac actgatgaga ccttcaagac cagggaggcc   1380
atccagcatg agtctggcat cctgggcccc ctgctgtatg gggaggtggg ggataccctg   1440
ctgatcatct tcaagaacca ggcctctagg ccctacaata tctaccctca tggcatcact   1500
gatgtgagac ccctgtatag caggaggctg cctaaggggg tgaagcacct gaaggacttc   1560
cccatcctgc ctggggagat cttcaagtat aagtggactg tgactgtgga ggatggcccc   1620
accaagtctg accccaggtg cctgaccagg tattacagct cttttgtgaa catggagagg   1680
gatctggcct ctgggctgat tggcccactg ctgatctgct acaaggagtc tgtggatcag   1740
aggggcaatc agatcatgtc tgacaagagg aatgtgatcc tgttttctgt gtttgatgaa   1800
aataggtctt ggtatctgac tgagaacatc cagaggtttc tgcccaatcc tgctggggtg   1860
cagctggagg atcctgagtt tcaggcctct aatatcatgc attctatcaa tggctatgtg   1920
tttgacagcc tgcagctgtc tgtgtgcctg catgaggtgg cctactggta catcctgagc   1980
attggggctc agactgactt cctgtctgtg ttcttttctg gctatacttt caagcacaag   2040
atggtgtatg aggacactct gaccctgttc cccttctctg ggagagactgt gttcatgtct   2100
atggaaaatc ctgggctgtg gattctgggc tgccacaatt ctgacttcag gaataggggg   2160
atgactgccc tgctgaaggt gtctagctgt gataagaaca ctggggatta ctatgaggac   2220
tcttatgaag atatctctgc ctatctgctg agcaagaaca atgccattga gcccaggagc   2280
ttcagccaga acccccctgt gctgaagagg caccagaggg agatcaccag gaccactctg   2340
cagtctgatc aggaggagat tgactatgat gacactatct ctgtggagat gaagaaggag   2400
gattttgaca tttatgatga ggatgagaac cagtctccca ggagcttcca gaagaagacc   2460
aggcattact ttattgctgc tgtggagagg ctgtgggact atgggatgag cagctctcct   2520
catgtgctga ggaacagggc ccagtctggg tctgtgcccc agttcaagaa ggtggtgttc   2580
caggagttca ctgatgggag cttcacccag cccctgtata ggggggagct gaatgagcac   2640
ctgggcctgc tgggccccta catcagggct gaggtggagg ataatatcat ggtgaccttc   2700
aggaaccagg ctagcaggcc ttacagcttt tacagcagcc tgatctctta tgaagaagac   2760
cagaggcagg gggctgagcc caggaagaat tttgtgaagc ctaatgagac caagacttat   2820
ttttggaagg tgcagcatca catggctcct accaaggatg agtttgactg caaggcctgg   2880
gcctactttt ctgatgtgga tctggagaag gatgtgcact ctggcctgat tggccctctg   2940
ctggtgtgcc atactaacac tctgaaccct gcccatggga ggcaggtgac tgtgcaggag   3000
tttgccctgt tcttcactat ttttgatgag accaagtctt ggtatttcac tgagaacatg   3060
gagaggaact gcagggctcc ctgcaacatc cagatggaag accccacctt caaggagaac   3120
tataggttcc atgccatcaa tgggtacatc atggataccc tgcctggcct ggtgatggcc   3180
```

-continued

```
caggatcaga ggattaggtg gtatctgctg agcatgggct ctaatgagaa catccacagc   3240

atccatttct ctggccatgt gttcactgtg aggaagaagg aggagtacaa gatggctctg   3300

tacaacctgt atcctggggt gtttgagact gtggagatgc tgcccagcaa ggctggcatc   3360

tggagggtgg aatgcctgat tggggagcac ctgcatgctg gcatgagcac tctgttcctg   3420

gtgtatagca acaagtgcca gaccccccctg ggcatggcct ctggccatat cagggatttc   3480

cagatcactg cttctggcca gtatggccag tgggcccccca agctggccag gctgcactat   3540

tctggcagca tcaatgcctg gagcactaag gagccttttt cttggatcaa ggtggacctg   3600

ctggccccta tgattattca tggcatcaag acccaggggg ccaggcagaa gttctctagc   3660

ctgtacatct ctcagttcat cattatgtat agcctggatg gcaagaagtg gcagacctac   3720

aggggcaata gcactggcac cctgatggtg ttttttggga atgtggactc ttctgggatc   3780

aagcacaaca tctttaaccc cccatcatt gccaggtata ttaggctgca ccccacccac   3840

tacagcatca ggagcaccct gaggatggag ctgatgggct gtgatctgaa ttcttgctct   3900

atgcccctgg gcatggagag caaggccatc tctgatgccc agatcactgc cagctcttac   3960

ttcaccaaca tgtttgccac ctggtctcct agcaaggcca ggctgcatct gcagggcagg   4020

agcaatgcct ggaggcccca ggtgaacaac cccaaggagt ggctgcaggt ggacttccag   4080

aagaccatga aggtgactgg ggtgaccact caggggggtga agagcctgct gacctctatg   4140

tatgtgaagg agttcctgat cagcagcagc caggatggcc accagtggac tctgttcttc   4200

cagaatggga aggtgaaggt gttccagggc aaccaggata gctttacccc tgtggtgaac   4260

agcctggacc ctcctctgct gaccagatac ctgaggatcc atcctcagag ctgggtgcac   4320

cagattgccc tgaggatgga ggtgctgggc tgtgaggccc aggatctgta ctga         4374
```

<210> SEQ ID NO 10
<211> LENGTH: 4374
<212> TYPE: DNA
<213> ORGANISM: Artificial Sequence
<220> FEATURE:
<223> OTHER INFORMATION: Description of Artificial Sequence: FVIII
Nucleic Acid

<400> SEQUENCE: 10

```
atgcagattg agctgagcac ttgcttcttc ctgtgcctgc tgaggttctg cttttctgct     60

actaggaggt actacctggg ggctgtggag ctgagctggg attacatgca gtctgacctg    120

ggggagctgc cagtggatgc caggttcccc cccagggtgc ccaagtcttt tcctttcaac    180

acctctgtgg tgtacaagaa gaccctgttt gtggagttca ctgaccacct gttcaacatt    240

gccaagccca ggccccccctg gatggggctg ctggggccca ccatccaggc tgaggtgtat    300

gacactgtgg tgattaccct gaagaacatg gctagccacc ctgtgagcct gcatgctgtg    360

ggggtgagct attggaaggc ctctgagggg gctgagtatg atgatcagac cagccagagg    420

gaaaaggagg atgacaaggt gttccctggg ggcagccata cttatgtgtg gcaggtgctg    480

aaggagaatg ggcccatggc ctctgacccc ctgtgcctga cttacagcta tctgagccat    540

gtggacctgg tgaaggatct gaactctggc ctgattgggg ctctgctggt gtgcagggag    600

ggcagcctgg ctaaggagaa gactcagact ctgcataagt tcatcctgct gtttgctgtg    660

tttgatgaag gcaagagctg gcactctgag accaagaact ctctgatgca ggatagggat    720

gctgcctctg ccagggcttg gcccaagatg cacactgtga atggctatgt gaacaggagc    780

ctgcctggcc tgattgggtg ccacaggaag tctgtgtact ggcatgtgat tggcatgggc    840
```

-continued

```
accaccccctg aggtgcacag cattttcctg gagggccaca ccttcctggt gaggaatcac    900
aggcaggcca gcctggagat cagccccatc accttcctga ctgcccagac cctgctgatg    960
gacctggggc agtttctgct gttctgccac atcagcagcc atcagcatga tggcatggag   1020
gcctatgtga aggtggactc ttgccctgag gagccccagc tgaggatgaa gaacaatgag   1080
gaggctgagg attatgatga tgacctgact gactctgaga tggatgtggt gaggtttgat   1140
gatgacaata gccccagctt catccagatt aggtctgtgg ccaagaagca ccctaagacc   1200
tgggtgcact acattgctgc tgaggaggag gattgggatt atgccccccct ggtgctggct   1260
cctgatgaca ggtcttataa gagccagtac ctgaacaatg ggccccagag gattggcagg   1320
aagtacaaga aggtgaggtt catggcttac actgatgaga ccttcaagac tagggaggcc   1380
atccagcatg agtctggcat cctgggcccc ctgctgtatg gggaggtggg ggataccctg   1440
ctgatcatct tcaagaacca ggccagcagg ccctacaaca tttaccctca tggcatcact   1500
gatgtgaggc ccctgtacag caggagactg cccaaggggg tgaagcacct gaaggatttt   1560
cccattctgc ctggggagat cttcaagtac aagtggactg tgactgtgga ggatggcccc   1620
accaagtctg atcccaggtg cctgactagg tactactctt cttttgtgaa tatggagagg   1680
gatctggcct ctggcctgat tggccccctg ctgatctgct acaaggagtc tgtggaccag   1740
aggggcaacc agatcatgtc tgacaagagg aatgtgatcc tgttctctgt gtttgatgag   1800
aataggagct ggtacctgac tgagaatatc cagaggttcc tgcctaatcc tgctggggtc   1860
cagctggagg atcctgagtt ccaggctagc aacattatgc acagcatcaa tggctatgtg   1920
tttgattctc tgcagctgtc tgtgtgcctg catgaggtgg cttactggta catcctgtct   1980
attggggccc agactgattt cctgtctgtg ttcttctctg gctacacttt caagcataag   2040
atggtgtatg aggataccct gaccctgttc cccttctctg ggagactgt gttcatgtct    2100
atggagaacc ctggcctgtg gatcctgggc tgtcataact ctgacttcag aaacaggggc   2160
atgactgccc tgctgaaggt gagcagctgt gacaagaaca ctggggacta ctatgaggac   2220
agctatgagg atatctctgc ttatctgctg agcaagaata atgccattga gcccaggagc   2280
ttcagccaga accccccctgt gctgaagagg caccagaggg agatcactag gactaccctg   2340
cagtctgatc aggaggagat tgactatgat gacaccatct ctgtggagat gaagaaggag   2400
gactttgaca tctatgatga ggatgagaac cagtccccca ggtctttcca gaagaagacc   2460
aggcactact tcattgctgc tgtggagagg ctgtgggact atggcatgag ctctagcccc   2520
catgtgctga ggaacagggc tcagtctggc tctgtgcccc agttcaagaa ggtggtcttc   2580
caggagttca ctgatggctc ttttacccag cctctgtaca gaggggagct gaatgagcac   2640
ctgggcctgc tgggccccta catcagggct gaggtggagg ataatatcat ggtgaccttc   2700
agaaaccagg cctctaggcc ctacagcttc tacagcagcc tgatctctta tgaggaggat   2760
cagaggcagg gggctgagcc caggaagaac tttgtgaagc ccaatgagac caagacctac   2820
ttctggaagg tgcagcacca tatggcccct actaaggatg agtttgactg caaggcctgg   2880
gcttattttt ctgatgtgga cctggagaag gatgtgcact ctgggctgat tggccccctg   2940
ctggtgtgcc acaccaacac cctgaaccct gcccatggca ggcaggtgac tgtgcaggag   3000
tttgccctgt tcttcactat ctttgatgag accaagagct ggtacttcac tgagaacatg   3060
gagagaaatt gtagggctcc ctgcaatatc cagatggagg accccacctt caaagaaaat   3120
tacagattcc atgccatcaa tgggtacatc atggataccc tgcctgggct ggtgatggct   3180
```

caggaccaga ggatcaggtg gtacctgctg agcatggggt ctaatgagaa catccactct 3240
atccatttct ctggccatgt gttcactgtg agaaagaagg aggagtataa gatggctctg 3300
tacaacctgt acccaggggt gtttgagact gtggaaatgc tgcccagcaa agctgggatc 3360
tggagggtgg agtgcctgat tggggagcac ctgcatgctg gcatgtctac cctgttcctg 3420
gtgtacagca acaagtgcca gactcccctg ggcatggcct ctgggcacat cagggatttt 3480
cagatcactg cctctggcca gtatggccag tgggccccca agctggccag gctgcactac 3540
tctggcagca ttaatgcttg gagcactaag gagcccttca gctggatcaa ggtggatctg 3600
ctggccccca tgatcatcca tggcatcaag acccaggggg ccaggcagaa gttctctagc 3660
ctgtacattt ctcagttcat catcatgtac agcctggatg ggaagaagtg gcagacctac 3720
agggggaaca gcactgggac cctgatggtg ttctttggca atgtggatag ctctggcatc 3780
aagcacaata tcttcaatcc ccccattatt gccaggtaca ttaggctgca tcctactcac 3840
tactctatta ggagcaccct gaggatggag ctgatggggt gtgacctgaa cagctgttct 3900
atgcccctgg gcatggagtc taaggctatc tctgatgccc agatcactgc cagcagctac 3960
ttcactaata tgtttgccac ctggagccct agcaaggcca gactgcacct gcagggcagg 4020
agcaatgcct ggaggcccca ggtgaacaac cccaaggagt ggctgcaggt ggacttccag 4080
aagaccatga aggtgactgg ggtgaccact caggggggtga agagcctgct gaccagcatg 4140
tatgtgaagg agttcctgat cagcagcagc caggatggcc accagtggac cctgttcttc 4200
cagaatggga aggtgaaggt gttccagggc aaccaggact ctttcacccc tgtggtgaac 4260
agcctggatc ctcccctgct gaccaggtac ctgaggatcc acccccagag ctgggtgcac 4320
cagattgctc tgaggatgga agtgctgggc tgtgaggccc aggatctgta ctga 4374

<210> SEQ ID NO 11
<211> LENGTH: 4374
<212> TYPE: DNA
<213> ORGANISM: Artificial Sequence
<220> FEATURE:
<223> OTHER INFORMATION: Description of Artificial Sequence: FVIII
Nucleic Acid

<400> SEQUENCE: 11
atgcagattg agctgagcac ctgcttcttc ctgtgcctgc tgaggttttg cttctctgct 60
accaggaggt actacctggg ggctgtggag ctgagctggg actatatgca gtctgacctg 120
ggggagctgc ctgtggatgc taggttccct cccagggtgc ccaagagctt cccctttaat 180
acctctgtgg tgtacaagaa aaccctgttt gtggagttca ctgaccatct gttcaacatt 240
gccaagccca ggccccttg gatgggcctg ctgggcccca ccattcaggc tgaggtgtat 300
gacactgtgg tcattaccct gaagaacatg gcttctcacc ctgtgagcct gcatgctgtg 360
ggggtgagct actggaaggc ctctgagggg gctgagtatg atgaccagac cagccagagg 420
gagaaggagg atgataaggt gttccctggg ggcagccaca cctatgtgtg gcaggtgctg 480
aaggagaatg gccccatggc ctctgatccc ctgtgcctga cctactctta tctgtctcat 540
gtggacctgg tgaaggacct gaactctggc ctgattgggg ctctgctggt gtgcagggag 600
ggctctctgg ccaaggagaa gacccagacc ctgcacaagt ttattctgct gtttgctgtc 660
tttgatgagg gcaagagctg gcattctgag accaagaaca gcctgatgca ggacagggat 720
gctgcctctg ccagggcctg gcccaaaatg cacactgtga atggctatgt gaacaggagc 780
ctgcctggcc tgattggctg ccacaggaag tctgtgtact ggcatgtgat tggcatgggc 840
accacccctg aggtgcacag catcttcctg gagggccaca cctttctggt gaggaatcac 900
aggcaggcca gcctggagat tagccccatc accttcctga ctgcccagac cctgctgatg 960
gacctgggcc agttcctgct gttctgccac atcagcagcc accagcatga tggcatggag 1020
gcctatgtga aggtggatag ctgccctgag gagccccagc tgaggatgaa aaacaatgag 1080
gaggctgagg attatgatga tgacctgact gactctgaga tggatgtggt gaggtttgat 1140
gatgacaata gccccagctt tattcagatt aggtctgtgg ctaagaagca ccccaagact 1200
tgggtgcact acattgctgc tgaggaggag gattgggact atgcccctct ggtcctggcc 1260
cctgatgata ggtcttacaa gagccagtat ctgaacaatg gcccccagag gattggcagg 1320
aagtacaaga aggtgaggtt catggcctac actgatgaga cctttaagac cagggaggcc 1380
attcagcatg agtctgggat cctgggcccc ctgctgtatg ggaggtggg ggacactctg 1440
ctgatcatct tcaagaacca ggccagcagg ccttataaca tctaccctca tgggatcact 1500
gatgtgaggc ccctgtactc tagaaggctg cccaaggggg tcaagcacct gaaggatttt 1560
cccatcctgc ctggggagat tttcaagtac aagtggactg tgactgtgga ggatggcccc 1620
accaagtctg accctaggtg cctgaccagg tactacagct cttttgtgaa catggagagg 1680
gacctggcct ctggcctgat tggccctctg ctgatttgct acaaggagtc tgtggaccag 1740
aggggcaacc agatcatgtc tgacaagagg aatgtgatcc tgttttctgt gtttgatgag 1800
aacaggtctt ggtacctgac tgagaacatc cagaggttcc tgcctaaccc agctggggtg 1860
cagctggagg atcctgagtt ccaggccagc aatattatgc atagcattaa tggctatgtg 1920
tttgatagcc tgcagctgtc tgtgtgcctg catgaggtgg cctactggta catcctgagc 1980
attggggccc agactgactt tctgtctgtg ttcttctctg gctacacctt caagcataag 2040
atggtgtatg aggacaccct gactctgttc ccttttctg gggagactgt gtttatgagc 2100
atggagaatc ctggcctgtg gatcctgggc tgccataatt ctgacttcag gaacaggggc 2160
atgactgccc tgctgaaagt gagcagctgt gacaagaata ctggggacta ctatgaagac 2220
agctatgagg acatctctgc ctacctgctg agcaagaaca atgccattga gcccaggagc 2280
ttcagccaga accccccagt gctgaagagg caccagagag agatcaccag gactaccctg 2340
cagtctgacc aggaggagat tgactatgat gacaccattt ctgtggagat gaagaaggag 2400
gactttgaca tttatgatga ggatgagaat cagagcccca ggagcttcca gaagaagact 2460
aggcactatt ttattgctgc tgtggagagg ctgtgggact atggcatgag cagctctccc 2520
catgtgctga ggaatagggc ccagtctggc tctgtgcctc agttcaagaa ggtggtgttc 2580
caggagttca ctgatggcag ctttacccag cccctgtata ggggggagct gaatgagcac 2640
ctgggcctgc tgggccccta tatcagggct gaggtggagg acaatattat ggtgaccttt 2700
aggaaccagg ccagcaggcc ctactctttc tatagcagcc tgatcagcta tgaggaggac 2760
cagaggcagg gggctgagcc caggaagaat tttgtgaagc ctaatgagac caagacctac 2820
ttctggaagg tgcagcatca catggccccc accaaggatg agtttgactg caaggcttgg 2880
gcctatttct ctgatgtgga cctggagaag gatgtgcact ctggcctgat tggccccctg 2940
ctggtgtgcc acactaacac tctgaatcct gcccatggca ggcaggtgac tgtgcaggag 3000
tttgccctgt tcttcaccat ctttgatgag accaagagct ggtacttcac tgagaacatg 3060
gagaggaact gcagggcccc ctgcaacatc cagatggagg atcccacctt caaggagaac 3120
tacaggtttc atgccatcaa tggctacatc atggacactc tgcctggcct ggtgatggcc 3180
caggatcaga ggatcaggtg gtacctgctg agcatgggct ctaatgagaa tatccatagc 3240
atccacttct ctggccatgt gttcactgtc aggaagaagg aggagtacaa gatggctctg 3300
tataatctgt accctggggt gtttgagact gtggagatgc tgcccagcaa ggctggcatc 3360
tggagggtgg agtgcctgat tggggagcac ctgcatgctg ggatgagcac cctgtttctg 3420
gtgtactcta acaagtgcca gacccccctg ggcatggcct ctgggcacat cagggatttc 3480
cagatcactg cttctggcca gtatggccag tgggccccca agctggccag gctgcactac 3540
tctggcagca tcaatgcctg gtctaccaag gagccctttt cttggattaa ggtggacctg 3600
ctggccccca tgatcatcca tggcatcaag acccaggggg ccaggcagaa gttcagcagc 3660
ctgtacatca gccagttcat catcatgtac agcctggatg gcaaaaagtg gcagacctac 3720
aggggcaata gcactgggac tctgatggtg ttctttggca atgtggacag ctctgggatc 3780
aagcacaata tcttcaaccc tcccatcatt gctaggtaca tcaggctgca ccccacccac 3840
tatagcatca ggtctaccct gaggatggag ctgatgggct gtgacctgaa ctcttgcagc 3900
atgcccctgg gcatggagtc caaagctatc tctgatgccc agattactgc cagcagctac 3960
ttcaccaaca tgtttgccac ctggtctccc tctaaggcca ggctgcacct gcagggcagg 4020
agcaatgcct ggaggcccca ggtgaacaat cccaaggagt ggctgcaggt ggatttccag 4080
aaaactatga aggtgactgg ggtgaccacc cagggggtga agtctctgct gaccagcatg 4140
tatgtgaagg agttcctgat ctcttctagc caggatggcc accagtggac tctgttcttc 4200
cagaatggca aggtgaaggt gttccagggc aaccaggaca gcttcacccc tgtggtgaac 4260
tctctggatc cccccctgct gaccaggtac ctgaggattc atccccagag ctgggtgcac 4320
cagattgctc tgagaatgga ggtgctgggg tgtgaggctc aggacctgta ttga 4374

<210> SEQ ID NO 12
<211> LENGTH: 4374
<212> TYPE: DNA
<213> ORGANISM: Artificial Sequence
<220> FEATURE:
<223> OTHER INFORMATION: Description of Artificial Sequence: FVIII Nucleic Acid

<400> SEQUENCE: 12
atgcagattg agctgtctac ttgttttttt ctgtgcctgc tgaggttctg cttctctgcc 60
accaggaggt attacctggg ggctgtggag ctgagctggg attacatgca gtctgatctg 120
ggggagctgc ctgtggatgc caggttcccc cccagggtgc ccaagagctt ccccttcaac 180
acctctgtgg tgtataagaa gaccctgttt gtggagttca ctgatcatct gtttaacatt 240
gccaagccca ggcccccctg gatgggcctg ctgggcccaa ctatccaggc tgaggtgtat 300
gacactgtgg tcatcaccct gaagaatatg gccagccatc ctgtgagcct gcatgctgtg 360
ggggtgagct actggaaggc ctctgagggg gctgagtatg atgaccagac cagccagagg 420
gagaaggagg atgacaaggt gttccctggg ggcagccaca cctatgtgtg gcaggtgctg 480
aaggagaatg gccccatggc ctctgacccc ctgtgcctga cttatagcta cctgtctcat 540
gtggacctgg tgaaggacct gaactctggc ctgattgggg ccctgctggt ctgtagggaa 600
ggcagcctgg ccaaggagaa gacccagacc ctgcacaagt ttattctgct gtttgctgtg 660
tttgatgaag gcaagagctg gcactctgag accaagaatt ctctgatgca ggatagggat 720
gctgcctctg ccagggcctg gcccaagatg catactgtga atggctatgt gaacagaagc 780
ctgcctggcc tgattggctg ccataggaag tctgtgtatt ggcatgtgat tgggatgggc 840
actacccctg aagtgcacag cattttcctg gagggccaca ctttcctggt gaggaaccac 900

```
aggcaggcct ctctggagat cagccccatt actttcctga ctgcccagac cctgctgatg    960
gatctgggcc agttcctgct gttctgccac atctctagcc accagcatga tggcatggag   1020
gcctatgtga aggtggacag ctgccctgag gagccccagc tgaggatgaa gaataatgag   1080
gaggctgagg attatgatga tgacctgact gactctgaga tggatgtggt gaggtttgat   1140
gatgataata gccccagctt catccagatc aggtctgtgg ccaagaagca tcccaagacc   1200
tgggtgcact atattgctgc tgaagaggag gactgggact atgcccctct ggtgctggct   1260
cctgatgaca ggagctataa gagccagtat ctgaacaatg ggccccagag gattgggagg   1320
aagtacaaga aggtgaggtt catggcctac actgatgaga cctttaagac cagggaggcc   1380
atccagcatg agtctggcat tctggggccc ctgctgtatg gggaggtggg ggacactctg   1440
ctgatcattt tcaagaacca ggccagcagg ccctacaata tttacccccca tggcatcact  1500
gatgtgaggc ccctgtacag caggaggctg cccaaggggg tgaagcacct gaaggacttc   1560
cccatcctgc ctggggagat cttcaagtac aagtggactg tgactgtgga ggatggccct   1620
accaagtctg accctaggtg tctgactagg tactacagca gctttgtgaa catggagaga   1680
gacctggctt ctggcctgat tggcccccctg ctgatctgct acaaggagtc tgtggatcag  1740
aggggcaacc agattatgtc tgataagagg aatgtcatcc tgttctctgt gtttgatgag   1800
aacaggagct ggtatctgac tgagaacatt cagaggttcc tgcccaaccc tgctggggtg   1860
cagctggagg accctgagtt ccaggccagc aacatcatgc attctattaa tggctatgtg   1920
tttgacagcc tgcagctgtc tgtgtgcctg catgaggtgg cctactggta catcctgagc   1980
attggggccc agactgactt tctgtctgtg tttttctctg ggtacacctt caagcacaag   2040
atggtctatg aggacaccct gaccctgttc cccttttctg ggaaaactgt gtttatgagc   2100
atggagaacc ctgggctgtg gatcctgggc tgccacaact ctgactttag gaataggggc   2160
atgactgccc tgctgaaggt gagcagctgt gacaagaata ctggggatta ctatgaggac   2220
agctatgagg atatctctgc ctacctgctg agcaagaaca atgccattga gcctaggagc   2280
ttcagccaga accccccctgt gctgaagagg caccagaggg agatcaccag gaccaccctg  2340
cagtctgatc aggaggagat tgactatgat gacaccatct ctgtggagat gaagaaggag   2400
gactttgata tttatgatga ggatgagaac cagagcccca ggagcttcca gaagaagacc   2460
aggcactatt tcattgctgc tgtggagagg ctgtgggact atggcatgag ctctagcccc   2520
catgtgctga ggaacagggc ccagtctggc tctgtgcccc agttcaagaa ggtggtgttc   2580
caggaattta ctgatggcag ctttacccag cccctgtaca gaggggagct gaatgagcac   2640
ctgggcctgc tgggccccta catcagggct gaggtggagg ataatatcat ggtgaccttt   2700
aggaaccagg cctctaggcc ctattctttt tacagcagcc tgatcagcta tgaggaggac   2760
cagaggcagg gggctgagcc taggaagaac tttgtgaagc ccaatgagac caagacctac   2820
ttttggaaag tgcagcacca catggccccc actaaggatg agtttgattg caaggcctgg   2880
gcctatttct ctgatgtgga cctggagaag gatgtgcact ctggcctgat tggcccccctg  2940
ctggtgtgcc acaccaacac tctgaaccct gcccatggca ggcaggtgac tgtgcaggag   3000
tttgccctgt tctttaccat ctttgatgag actaagagct ggtatttcac tgagaacatg   3060
gagaggaact gcagagcccc ttgcaacatc cagatggagg accctacctt caaggagaac   3120
tataggttcc atgccatcaa tgggtacatc atggataccc tgcctggcct ggtgatggct   3180
caggaccaga ggatcaggtg gtacctgctg agcatgggga gcaatgagaa cattcatagc   3240
```

atccacttct ctgggcatgt gttcactgtg aggaagaagg aggagtataa gatggccctg 3300
tacaacctgt accctggggt gtttgagact gtggagatgc tgcccagcaa ggctggcatc 3360
tggagggtgg agtgcctgat tggggagcac ctgcatgctg gcatgagcac tctgttcctg 3420
gtgtacagca acaagtgcca gaccccccctg ggcatggcct ctggccacat cagggacttc 3480
cagattactg cctctgggca gtatgggcag tgggccccca agctggccag gctgcactac 3540
tctgggtcta tcaatgcttg gagcaccaag gagcctttca gctggatcaa ggtggatctg 3600
ctggccccca tgatcattca tgggatcaag acccaggggg ccaggcagaa gttcagcagc 3660
ctgtatattt ctcagttcat catcatgtat tctctggatg gcaaaaagtg gcagacctat 3720
agagggaaca gcactgggac cctgatggtg ttttttggca atgtggatag ctctggcatc 3780
aagcacaata tcttcaaccc ccccattatt gccaggtaca tcaggctgca ccccacccac 3840
tactctatca ggagcaccct gaggatggag ctgatgggct gtgatctgaa cagctgctct 3900
atgcctctgg ggatggaaag caaggccatc tctgatgccc agatcactgc cagcagctat 3960
ttcaccaata tgtttgccac ttggagccct agcaaggcta ggctgcatct gcagggcagg 4020
tctaatgcct ggaggcccca ggtgaacaac cccaaggagt ggctgcaggt ggacttccag 4080
aagactatga aagtgactgg ggtgaccacc caggggggtga aaagcctgct gaccagcatg 4140
tatgtgaagg agttcctgat tagcagcagc caggatggcc accagtggac cctgttcttc 4200
cagaatggga aggtgaaggt gtttcagggc aatcaggata gcttcacccc agtggtgaac 4260
agcctggacc ccccccctgct gaccaggtac ctgaggatcc acccccagag ctgggtgcac 4320
cagattgccc tgaggatgga ggtgctgggc tgtgaggccc aggatctgta ctga 4374

<210> SEQ ID NO 13
<211> LENGTH: 4374
<212> TYPE: DNA
<213> ORGANISM: Artificial Sequence
<220> FEATURE:
<223> OTHER INFORMATION: Description of Artificial Sequence: FVIII Nucleic Acid

<400> SEQUENCE: 13
atgcagattg agctgagcac ctgctttttc ctgtgcctgc tgaggttctg cttctctgct 60
accaggaggt actacctggg ggctgtggag ctgtcttggg attacatgca gtctgacctg 120
ggggagctgc ctgtggatgc caggtttccc cccagggtgc ccaagtcttt cccctttaac 180
acctctgtgg tgtataagaa gactctgttt gtggagttca ctgatcacct gttcaatatt 240
gccaagccca ggcccccttg gatgggcctg ctgggcccca ctatccaggc tgaggtgtat 300
gacactgtgg tcatcaccct gaagaacatg gccagccacc ctgtgagcct gcatgctgtg 360
ggggtgagct actggaaggc ctctgagggg gctgagtatg atgaccagac cagccagagg 420
gagaaggagg atgacaaggt gttcccaggg gggtctcaca cttatgtgtg gcaggtgctg 480
aaggagaatg ggcccatggc ctctgaccct ctgtgcctga cttatagcta cctgtctcat 540
gtggatctgg tgaaggacct gaactctggc ctgattgggg ccctgctggt gtgcagggag 600
gggagcctgg ccaaggagaa gacccagacc ctgcacaagt tcatcctgct gtttgctgtg 660
tttgatgagg ggaagagctg gcactctgag accaagaata gcctgatgca ggacagggat 720
gctgcttctg ctagggcctg gcctaagatg cacactgtga atggctatgt gaacaggagc 780
ctgcctggcc tgattgggtg tcacaggaag tctgtgtact ggcatgtgat tggcatgggg 840
actactccag aagtgcacag catcttcctg gaggggcaca ccttcctggt gaggaatcac 900

-continued aggcaggcca gcctggagat ttctcccatc actttcctga ctgcccagac cctgctgatg 960
gatctggggc agttcctgct gttctgccac atcagcagcc atcagcatga tgggatggag 1020
gcctatgtga aggtggacag ctgccctgag gagcctcagc tgaggatgaa gaacaatgag 1080
gaggctgagg actatgatga tgatctgact gactctgaga tggatgtggt gaggtttgat 1140
gatgacaact ctcccagctt catccagatc aggtctgtgg ccaagaagca ccccaagacc 1200
tgggtgcact acattgctgc tgaggaggag gattgggatt atgctcccct ggtgctggct 1260
cctgatgata ggagctacaa gagccagtat ctgaataatg ggccccagag gattggcagg 1320
aagtataaga aggtgaggtt catggcctac actgatgaga cctttaagac cagggaggct 1380
attcagcatg agtctggcat cctgggcccc ctgctgtatg gggaggtggg ggacaccctg 1440
ctgatcattt tcaagaacca ggccagcagg ccctataaca tctatcccca tgggatcact 1500
gatgtgaggc ccctgtactc taggaggctg cccaaggggg tcaagcacct gaaggacttc 1560
cccatcctgc ctggggagat cttcaagtac aagtggactg tgactgtgga ggatggcccc 1620
actaagtctg accccaggtg cctgactagg tactacagca gctttgtgaa catggagaga 1680
gatctggcct ctggcctgat tggcccccctg ctgatctgct acaaagagtc tgtggatcag 1740
aggggcaacc agatcatgtc tgacaagagg aatgtgatcc tgttctctgt gtttgatgag 1800
aacagaagct ggtacctgac tgagaacatt cagaggtttc tgcccaaccc tgctggggtc 1860
cagctggagg accctgagtt tcaggccagc aacatcatgc acagcatcaa tgggtatgtg 1920
tttgacagcc tgcagctgtc tgtgtgcctg catgaggtgg cctactggta tatcctgagc 1980
attggggccc agactgattt cctgtctgtg ttcttctctg gctacacttt caagcacaag 2040
atggtgtatg aggataccct gaccctgttc cctttctctg ggaaaactgt gttcatgagc 2100
atggagaacc ctgggctgtg gatcctgggg tgccacaatt ctgatttcag gaacagaggc 2160
atgactgctc tgctgaaggt gtctagctgt gacaagaaca ctggggacta ctatgaggac 2220
agctatgagg acatctctgc ctacctgctg agcaagaaca atgctattga acccaggtct 2280
ttcagccaga accccccctgt gctgaagagg caccagaggg agatcactag gaccaccctg 2340
cagtctgatc aggaggagat tgactatgat gacaccatct ctgtggagat gaagaaggag 2400
gactttgaca tctatgatga ggatgagaat cagtctccca ggagcttcca gaagaagact 2460
aggcattact tcattgctgc tgtggagagg ctgtgggact atggcatgag ctctagccct 2520
catgtgctga ggaacagggc ccagtctggc tctgtgcccc agttcaagaa ggtggtgttt 2580
caggagttca ctgatggcag cttcacccag cccctgtaca gggggggagct gaatgagcat 2640
ctgggcctgc tgggccccta catcagggct gaggtggagg acaacatcat ggtgaccttc 2700
agaaatcagg ctagcaggcc ctacagcttc tacagcagcc tgatctctta tgaggaggac 2760
cagaggcagg gggctgagcc caggaagaac tttgtgaagc ccaatgagac caagacctat 2820
ttctggaagg tgcagcacca catggccccc accaaggatg agtttgattg caaggcctgg 2880
gcctacttct ctgatgtgga cctggagaag gatgtgcatt ctgggctgat tggccctctg 2940
ctggtgtgcc acaccaacac cctgaatcct gcccatggca ggcaggtgac tgtgcaggag 3000
tttgccctgt tctttactat ctttgatgag accaagtctt ggtattttac tgagaacatg 3060
gagaggaact gcagggcccc ctgcaacatc cagatggagg accccacctt caaggagaac 3120
tacagattcc atgccatcaa tggctacatt atggacactc tgcctggcct ggtgatggcc 3180
caggaccaga ggatcaggtg gtacctgctg tctatgggca gcaatgagaa cattcactct 3240
atccacttct ctgggcatgt gttcactgtg aggaagaagg aggagtacaa gatggccctg 3300

```
tacaacctgt accctggggt gtttgagact gtggagatgc tgcctagcaa ggctgggatc   3360
tggagggtgg agtgcctgat tggggagcac ctgcatgctg gcatgtctac cctgttcctg   3420
gtgtacagca acaagtgcca gacccccctg ggcatggcct ctggccacat cagagatttt   3480
cagatcactg cctctggcca gtatggccag tgggctccta agctggccag gctgcactac   3540
tctggcagca tcaatgcctg gagcaccaag gagcccttta gctggatcaa ggtggacctg   3600
ctggccccca tgatcatcca tggcatcaag actcaggggg ccaggcagaa gttctctagc   3660
ctgtacatta gccagttcat catcatgtat agcctggatg gcaagaagtg gcagacctac   3720
aggggcaaca gcactgggac cctgatggtg ttctttggga atgtggacag ctctgggatc   3780
aagcacaata tcttcaaccc ccccattatt gccaggtata ttaggctgca ccccactcac   3840
tacagcatta ggagcaccct gaggatggag ctgatgggct gtgatctgaa cagctgcagc   3900
atgcccctgg gcatggagtc taaggccatc tctgatgccc agatcactgc cagctcttac   3960
ttcaccaaca tgtttgccac ttggagcccc agcaaggcca ggctgcacct gcagggcagg   4020
agcaatgcct ggaggcccca ggtgaacaac cccaaggagt ggctgcaggt ggatttccag   4080
aagactatga aggtgactgg ggtgaccact caggggggtga agagcctgct gactagcatg   4140
tatgtgaagg agttcctgat cagctctagc caggatggcc accagtggac cctgttcttt   4200
cagaatggca aggtgaaggt gttccagggc aaccaggact ctttcacccc tgtggtgaat   4260
tctctggacc ctcccctgct gactaggtat ctgaggattc atccccagag ctgggtgcat   4320
cagattgccc tgaggatgga ggtgctgggc tgtgaggccc aggacctgta ttga         4374
```

<210> SEQ ID NO 14
<211> LENGTH: 4374
<212> TYPE: DNA
<213> ORGANISM: Artificial Sequence
<220> FEATURE:
<223> OTHER INFORMATION: Description of Artificial Sequence: FVIII
Nucleic Acid

<400> SEQUENCE: 14

```
atgcagattg agctgagcac ctgcttcttc ctgtgcctgc tgaggttttg cttttctgcc     60
actaggaggt actacctggg ggctgtggag ctgtcttggg attacatgca gtctgacctg    120
ggggagctgc cagtggatgc caggttcccc ccaagggtgc ccaagtcttt tcccttcaat    180
acctctgtgg tgtacaagaa gaccctgttt gtggagttta ctgatcatct gtttaacatt    240
gccaagccca ggcccccctg gatggggctg ctgggcccca ccatccaggc tgaggtgtat    300
gatactgtgg tgattaccct gaagaatatg gccagccatc ctgtgtctct gcatgctgtg    360
ggggtgtctt attggaaggc ctctgagggg gctgagtatg atgatcagac cagccagagg    420
gagaaggagg atgataaggt gttccctggg ggctctcaca cctatgtgtg gcaggtgctg    480
aaggagaatg ggcctatggc ctctgaccca ctgtgcctga cttacagcta tctgagccat    540
gtggacctgg tgaaggacct gaactctggg ctgattgggg ccctgctggt gtgcagggag    600
ggcagcctgg ccaaggagaa gactcagacc ctgcacaagt tcatcctgct gtttgctgtg    660
tttgatgagg gcaagtcttg gcactctgag accaagaaca gcctgatgca ggatagggat    720
gctgcctctg ccagggcctg gcccaagatg cacactgtga atggctatgt gaacaggtct    780
ctgcctggcc tgattggctg ccacaggaag tctgtgtact ggcatgtgat tggcatgggc    840
accacccctg aggtgcatag cattttcctg gagggccaca ccttcctggt gaggaaccac    900
aggcaggcta gcctggagat cagccccatc actttcctga ctgcccagac cctgctgatg    960
```

gacctgggcc agttcctgct gttctgccac atctctagcc accagcatga tggcatggag 1020
gcctatgtga aggtggactc ttgtcctgag gagccccagc tgaggatgaa gaacaatgag 1080
gaggctgagg attatgatga tgatctgact gattctgaga tggatgtggt gaggtttgat 1140
gatgacaaca gcccctcttt catccagatc aggtctgtgg ccaagaagca ccccaagacc 1200
tgggtgcact acattgctgc tgaggaggag gattgggatt atgcccccct ggtgctggcc 1260
cctgatgaca ggagctataa gtctcagtac ctgaacaatg gcccccagag aattggcagg 1320
aagtacaaga aggtgaggtt catggcctat actgatgaga ccttcaaaac cagggaggcc 1380
attcagcatg agtctggcat cctggggccc ctgctgtatg gggaggtggg ggacaccctg 1440
ctgatcatct tcaagaacca ggctagcagg ccttacaaca tctaccccca tgggatcact 1500
gatgtgaggc ccctgtacag caggaggctg cctaaggggg tgaagcacct gaaggacttt 1560
cccattctgc ctggggagat cttcaagtat aagtggactg tgactgtgga ggatgggccc 1620
accaagtctg accccaggtg cctgactagg tactactcta gctttgtgaa catggagagg 1680
gacctggcct ctgggctgat tggccccctg ctgatctgtt acaaggagtc tgtggaccag 1740
aggggcaacc agatcatgtc tgataagagg aatgtgatcc tgttctctgt gtttgatgag 1800
aacaggagct ggtacctgac tgagaacatc cagagattcc tgcccaaccc tgctggggtg 1860
cagctggagg atcctgagtt ccaggccagc aacatcatgc attctatcaa tgggtatgtg 1920
tttgatagcc tgcagctgtc tgtgtgtctg catgaggtgg cctactggta cattctgagc 1980
attggggccc agactgactt cctgtctgtg ttcttctctg gctacacttt caaacacaag 2040
atggtgtatg aggacaccct gaccctgttc cccttctctg ggagactgt gtttatgagc 2100 atggagaacc ctgggctgtg gattctgggc tgccacaact ctgacttcag aaacaggggc 2160
atgactgccc tgctgaaggt gtcttcttgt gataagaaca ctggggacta ttatgaagac 2220
agctatgagg acatctctgc ctacctgctg agcaagaata atgctattga gcccaggtct 2280
ttctctcaga acccccctgt gctgaagagg caccagaggg agatcaccag gaccaccctg 2340
cagtctgatc aggaggagat tgactatgat gacactattt ctgtggagat gaagaaggaa 2400
gactttgata tctatgatga ggatgagaac cagagcccta ggagcttcca gaagaagact 2460
aggcattact tcattgctgc tgtggagagg ctgtgggact atggcatgag cagcagcccc 2520
catgtgctga ggaatagggc tcagtctggc tctgtgcctc agttcaagaa ggtggtgttc 2580
caggaattca ctgatggcag cttcactcag cccctgtaca ggggggagct gaatgagcac 2640
ctggggctgc tgggccctta catcagggct gaggtggagg acaatatcat ggtgaccttt 2700
aggaaccagg cctctaggcc ttacagcttc tactctagcc tgatctctta tgaagaggac 2760
cagaggcagg gggctgagcc caggaagaac tttgtgaagc ccaatgagac taagacttac 2820
ttctggaagg tgcagcacca catggctccc accaaggatg agtttgactg caaggcttgg 2880
gcctacttct ctgatgtgga cctggagaag gatgtgcact ctgggctgat tgggcccctg 2940
ctggtgtgcc acactaacac tctgaatcct gcccatggca gacaggtgac tgtgcaggag 3000
tttgccctgt tttttaccat ctttgatgag actaagtctt ggtacttcac tgagaacatg 3060
gagaggaact gcagggcccc ctgcaacatc cagatggagg atcccacctt caaggagaac 3120
tacaggtttc atgccatcaa tggctacatc atggacaccc tgcctggcct ggtgatggct 3180
caggaccaga ggattaggtg gtatctgctg agcatgggca gcaatgagaa tatccactct 3240
atccacttct ctgggcatgt gttcactgtg aggaagaagg aggagtacaa gatggccctg 3300

```
tataacctgt atcctggggt gtttgagact gtggagatgc tgcccagcaa ggctggcatc   3360

tggagagtgg agtgcctgat tggggagcac ctgcatgctg gcatgagcac tctgtttctg   3420

gtgtatagca acaagtgtca gacccctctg ggcatggcct ctgggcacat tagggacttt   3480

cagatcactg cttctggcca gtatgggcag tgggctccca agctggccag gctgcactat   3540

tctggcagca ttaatgcctg gagcaccaag gagcctttca gctggatcaa ggtggacctg   3600

ctggccccca tgatcatcca tgggatcaag acccaggggg ctaggcagaa gttcagcagc   3660

ctgtacatca gccagtttat catcatgtat tctctggatg gcaagaagtg gcagacctac   3720

aggggcaatt ctactggcac tctgatggtg ttctttggga atgtggatag ctctgggatc   3780

aagcataata tcttcaatcc ccccattatt gctaggtata tcaggctgca ccccacccac   3840

tatagcatca ggagcaccct gaggatggag ctgatggggt gtgacctgaa cagctgcagc   3900

atgcccctgg gcatggagag caaggctatt tctgatgccc agatcactgc cagcagctac   3960

tttactaata tgtttgccac ctggagcccc agcaaggcca gactgcacct gcagggcagg   4020

tctaatgcct ggaggcctca ggtgaataac cccaaggagt ggctgcaggt ggacttccag   4080

aaaaccatga aggtgactgg ggtgactacc caggggggtga agtctctgct gaccagcatg   4140

tatgtgaagg agttcctgat ctcttctagc caggatggcc accagtggac cctgttcttt   4200

cagaatggga aggtgaaggt cttccagggc aaccaggata gcttcacccc tgtggtgaat   4260

agcctggatc ctcctctgct gaccaggtat ctgaggatcc acccccagag ctgggtgcat   4320

cagattgccc tgaggatgga ggtgctgggc tgtgaggctc aggacctgta ctga         4374
```

```
<210> SEQ ID NO 15
<211> LENGTH: 4374
<212> TYPE: DNA
<213> ORGANISM: Artificial Sequence
<220> FEATURE:
<223> OTHER INFORMATION: Description of Artificial Sequence: FVIII
      Nucleic Acid

<400> SEQUENCE: 15

atgcagattg agctgagcac ctgtttcttc ctgtgcctgc tgaggttctg tttctctgcc     60

actaggaggt actacctggg ggctgtggag ctgagctggg actatatgca gtctgacctg    120

ggggagctgc ctgtggatgc caggttcccc cccagggtgc ctaagagctt ccccttcaat    180

acttctgtgg tgtacaagaa gactctgttt gtggagttta ctgaccacct gttcaacatt    240

gctaagccca ggcctccctg gatggggctg ctgggcccca ccatccaggc tgaggtgtat    300

gatactgtgg tgattaccct gaagaacatg gcctctcatc cagtgagcct gcatgctgtg    360

ggggtgagct actggaaggc ctctgaaggg gctgagtatg atgaccagac cagccagagg    420

gagaaggagg atgacaaggt gttccctggg ggcagccaca cctatgtgtg gcaggtgctg    480

aaggagaatg gcccaatggc ctctgacccc ctgtgcctga cttatagcta cctgagccat    540

gtggatctgg tgaaggacct gaattctggc ctgattgggg ccctgctggt gtgcagagag    600

ggctctctgg ctaaggagaa gacccagact ctgcacaagt tcatcctgct gtttgctgtg    660

tttgatgagg gcaagagctg gcactctgag actaagaata gcctgatgca ggacagggat    720

gctgcttctg ccagggcctg gcccaagatg catactgtga atggctatgt gaacaggagc    780

ctgcctggcc tgattggctg tcacaggaaa tctgtctact ggcatgtgat tgggatgggc    840

actacccctg aggtgcactc tatcttcctg gagggccata ccttcctggt gaggaaccac    900

aggcaggcca gcctggagat ctctcccatt accttcctga ctgcccagac cctgctgatg    960
```

-continued

```
gatctgggcc agttcctgct gttctgccac atcagcagcc accagcatga tgggatggag   1020
gcttatgtga aggtggatag ctgccctgag gagccccagc tgaggatgaa gaacaatgag   1080
gaggctgagg actatgatga tgacctgact gactctgaga tggatgtggt gaggtttgat   1140
gatgacaact ctcccagctt tattcagatc aggtctgtgg ctaagaagca ccccaagact   1200
tgggtgcact acattgctgc tgaggaggag gactgggact atgcccctct ggtgctggct   1260
cctgatgaca ggtcttacaa gtctcagtac ctgaataatg gccctcagag gattggcagg   1320
aagtacaaga aggtgaggtt catggcctac actgatgaga ccttcaagac cagggaggcc   1380
atccagcatg agtctggcat cctgggcccc ctgctgtatg gggaggtggg ggataccctg   1440
ctgatcatct tcaagaatca ggccagcagg ccctacaaca tctaccccca tggcatcact   1500
gatgtgaggc cactgtacag caggaggctg cccaaggggg tgaagcatct gaaggacttc   1560
cccattctgc ctggggagat cttcaagtac aaatggactg tgactgtgga ggatggccct   1620
accaagtctg accccaggtg tctgaccagg tactacagca gctttgtgaa tatggagagg   1680
gacctggcct ctggcctgat tggcccccctg ctgatctgct acaaggagtc tgtggaccag   1740
aggggcaatc agatcatgtc tgataagagg aatgtgattc tgttctctgt gtttgatgag   1800
aacaggagct ggtacctgac tgagaacatc cagaggttcc tgcccaatcc tgctggggtg   1860
cagctggagg accctgagtt ccaggccagc aatatcatgc acagcatcaa tggctatgtc   1920
tttgacagcc tgcagctgtc tgtgtgcctg catgaggtgg cttactggta tattctgagc   1980
attggggccc agactgattt cctgtctgtg ttcttttctg gctatacctt taagcacaag   2040
atggtgtatg aggacaccct gaccctgttc cccttctctg ggagactgt gttcatgtct   2100
atggagaacc ctgggctgtg gatcctgggc tgccacaact ctgacttcag gaacaggggg   2160
atgactgccc tgctgaaggt gtctagctgt gataagaaca ctggggacta ttatgaggac   2220
agctatgagg acatctctgc ttacctgctg agcaagaaca atgccattga gcccaggtct   2280
ttcagccaga atccccctgt gctgaagagg catcagaggg agatcaccag gaccaccctg   2340
cagtctgatc aggaggagat tgattatgat gacactatct ctgtggaaat gaagaaggag   2400
gactttgaca tctatgatga ggatgagaac cagagcccca ggagcttcca gaagaagacc   2460
aggcactact tcattgctgc tgtggagagg ctgtgggatt atggcatgag cagctctccc   2520
catgtgctga ggaacagagc ccagtctggc tctgtgcctc agttcaagaa ggtggtcttc   2580
caggagttca ctgatggctc tttcacccag cccctgtaca ggggggagct gaatgagcac   2640
ctgggcctgc tggggcccta cattagggct gaggtggagg ataacatcat ggtgactttc   2700
agaaaccagg ccagcaggcc ttacagcttt tactcttctc tgattagcta tgaggaggat   2760
cagaggcagg gggctgagcc taggaagaac tttgtgaagc ccaatgagac caagacctat   2820
ttctggaagg tgcagcacca catggctccc actaaggatg agtttgactg caaggcttgg   2880
gcctacttct ctgatgtgga cctggagaag gatgtgcact ctggcctgat tgggcccctg   2940
ctggtgtgcc acaccaacac cctgaaccct gcccatggca ggcaggtgac tgtgcaggag   3000
tttgccctgt tcttcaccat ctttgatgag actaagagct ggtacttcac tgagaacatg   3060
gagaggaact gcagggcccc ctgcaacatc cagatggagg accccacctt caaggagaat   3120
tacaggttcc atgccatcaa tggctacatt atggacaccc tgcctggcct ggtgatggcc   3180
caggatcaga ggatcaggtg gtatctgctg agcatgggct ctaatgagaa catccacagc   3240
atccacttct ctggccatgt gtttactgtg aggaagaagg aggaatacaa gatggctctg   3300
tataacctgt accctggggt gtttgagact gtggagatgc tgcccagcaa ggctgggatc   3360
```

tggagggtgg agtgcctgat tggggagcac ctgcatgctg ggatgagcac cctgttcctg 3420
gtgtatagca ataagtgcca gaccccctg ggcatggctt ctggccacat cagggatttc 3480
cagatcactg cttctggcca gtatggccag tgggctccca agctggctag gctgcattac 3540
tctgggtcta tcaatgcctg gagcactaag gagcccttca gctggatcaa ggtggacctg 3600
ctggccccca tgatcattca tggcatcaag acccaggggg ctaggcagaa gttcagcagc 3660
ctgtacatca gccagttcat cattatgtac agcctggatg gcaagaagtg gcagacttac 3720
aggggcaata gcactgggac tctgatggtg ttctttggca atgtggactc ttctggcatc 3780
aagcacaaca tcttcaaccc tcccatcatt gccaggtaca ttaggctgca ccctacccac 3840
tactctatca ggagcaccct gaggatggag ctgatggggt gtgatctgaa ctcttgcagc 3900
atgcctctgg gcatggaaag caaagccatc tctgatgccc agatcactgc ctctagctat 3960
ttcaccaata tgtttgccac ctggagccct agcaaggcca ggctgcacct gcagggcaga 4020
tctaatgcct ggaggcccca ggtgaacaat cccaaggagt ggctgcaggt ggacttccag 4080
aagaccatga aggtgactgg ggtgaccact caggggggtga agagcctgct gactagcatg 4140
tatgtgaagg agttcctgat ctcttctagc caggatggcc accagtggac cctgttcttc 4200
cagaatggca aggtgaaagt gttccagggc aaccaggata gcttcactcc tgtggtgaac 4260
tctctggacc ctcccctgct gactaggtac ctgaggattc atccccagag ctgggtgcac 4320
cagattgccc tgaggatgga ggtgctgggc tgtgaggccc aggatctgta ctga 4374

<210> SEQ ID NO 16
<211> LENGTH: 4374
<212> TYPE: DNA
<213> ORGANISM: Artificial Sequence
<220> FEATURE:
<223> OTHER INFORMATION: Description of Artificial Sequence: FVIII
      Nucleic Acid

<400> SEQUENCE: 16
atgcagattg agctgagcac ctgcttcttc ctgtgcctgc tgaggttctg cttctctgcc 60
accaggaggt actacctggg ggctgtggag ctgtcttggg actatatgca gtctgacctg 120
ggggagctgc cagtggatgc caggttcccc cccagggtgc ccaagagctt tcctttcaac 180
acttctgtgg tgtacaagaa gaccctgttt gtggagttca ctgaccacct gttcaatatt 240
gctaagccca ggccaccctg gatgggcctg ctgggcccta ccattcaggc tgaggtgtat 300
gacactgtgg tgattactct gaagaatatg gccagccacc ctgtgagcct gcatgctgtg 360
ggggtgtctt actggaaggc ctctgagggg gctgagtatg atgatcagac ttctcagagg 420
gagaaggagg atgataaggt gttccctggg ggctctcaca cttatgtgtg gcaggtgctg 480
aaggagaatg gccccatggc ttctgatcca ctgtgcctga cctactctta cctgagccat 540
gtggacctgg tgaaggacct gaactctggc ctgattgggg ccctgctggt gtgcagggag 600
ggcagcctgg ccaaggagaa gacccagacc ctgcataagt tcatcctgct gtttgctgtg 660
tttgatgagg ggaagagctg gcactctgag accaagaatt ctctgatgca ggacagggat 720
gctgcctctg ccagggcctg gcctaagatg cacactgtga atggctatgt gaacaggtct 780
ctgcctggcc tgattggctg ccacaggaag tctgtgtact ggcatgtgat tggcatgggc 840
actacccctg aggtgcacag cattttcctg gagggccaca ccttcctggt caggaaccat 900
aggcaggcct ctctggagat cagccccatc actttcctga ctgcccagac cctgctgatg 960
gacctgggcc agttcctgct gttctgccac attagcagcc accagcatga tggcatggag 1020
gcctatgtga aggtggactc ttgccctgag gagccccagc tgaggatgaa gaacaatgag 1080
gaagctgagg attatgatga tgacctgact gactctgaga tggatgtggt gaggtttgat 1140
gatgacaaca gccccagctt catccagatc aggtctgtgg ccaagaagca ccccaagacc 1200
tgggtgcact acattgctgc tgaggaggag gattgggact atgctcccct ggtgctggct 1260
cctgatgata ggagctacaa gtctcagtac ctgaataatg gcccccagag gattggcagg 1320
aagtacaaga aggtgaggtt catggcctac actgatgaga ccttcaagac cagagaggct 1380
atccagcatg agtctgggat cctggggccc ctgctgtatg gggaggtggg ggacaccctg 1440
ctgatcatct tcaagaacca ggccagcaga ccctacaaca tctaccccca tgggatcact 1500
gatgtgaggc ccctgtacag caggaggctg cctaaggggg tgaagcacct gaaggacttc 1560
cccatcctgc ctggggagat cttcaagtat aagtggactg tgactgtgga ggatgggccc 1620
accaagtctg accctaggtg cctgactagg tactactcta gctttgtgaa catggagagg 1680
gacctggcct ctggcctgat tggcccccctg ctgatttgct acaaggagtc tgtggatcag 1740
aggggcaatc agatcatgtc tgacaagagg aatgtgatcc tgttctctgt gtttgatgag 1800
aataggtctt ggtacctgac tgagaacatc cagaggttcc tgcctaatcc tgctggggtg 1860
cagctggagg accctgagtt tcaggccagc aacatcatgc acagcatcaa tggctatgtg 1920
tttgactctc tgcagctgtc tgtgtgcctg catgaggtgg cttactggta tatcctgagc 1980
attggggctc agactgactt cctgtctgtg ttcttttctg gctacacttt taagcacaag 2040
atggtgtatg aggacaccct gaccctgttc cccttttctg gggagactgt gttcatgtct 2100
atggagaacc ctgggctgtg gattctgggc tgtcacaact ctgacttcag aaacaggggc 2160
atgactgccc tgctgaaggt gtctagctgt gacaagaata ctggggacta ctatgaggac 2220
agctatgagg acatttctgc ctatctgctg agcaagaaca atgccattga gcccaggagc 2280
ttttctcaga atccccctgt gctgaagagg caccagagag agatcaccag gaccactctg 2340
cagtctgatc aggaggagat tgattatgat gacactatct ctgtggagat gaagaaagag 2400
gactttgata tctatgatga ggatgagaat cagtctccca ggagcttcca gaagaagact 2460
agacactact tcattgctgc tgtggagagg ctgtgggact atggcatgag ctctagccct 2520
catgtgctga ggaacagggc ccagtctggg tctgtgcccc agttcaagaa ggtggtgttc 2580
caggagttca ctgatggcag ctttacccag cccctgtata ggggggagct gaatgagcat 2640
ctgggcctgc tgggccccta tattagggct gaagtggagg acaacatcat ggtgaccttt 2700
aggaaccagg ccagcaggcc ctacagcttt tacagcagcc tgattagcta tgaggaggat 2760
cagagacagg gggctgagcc caggaagaac tttgtgaagc ccaatgagac caagacctac 2820
ttctggaagg tgcagcacca catggcccct accaaggatg agtttgactg caaggcctgg 2880
gcttacttct ctgatgtgga cctggagaaa gatgtgcact ctggcctgat tgggcccctg 2940
ctggtgtgcc acaccaacac cctgaaccct gcccatggga ggcaggtgac tgtgcaggag 3000
tttgccctgt ttttcaccat ctttgatgag accaagagct ggtacttcac tgagaacatg 3060
gagaggaact gcagggcccc ctgtaacatc cagatggagg atcctacttt caaggagaac 3120
tacaggttcc atgccattaa tgggtacatc atggacaccc tgcctgggct ggtgatggcc 3180
caggatcaga ggattaggtg gtatctgctg tctatgggct ctaatgagaa catccactct 3240
atccacttct ctggccatgt gttcactgtg aggaagaagg aggagtacaa gatggccctg 3300
tacaacctgt accctggggt gtttgaaact gtggagatgc tgccctctaa agctgggatc 3360

```
tggagggtgg agtgcctgat tggggagcac ctgcatgctg gcatgagcac cctgttcctg   3420

gtgtacagca ataagtgcca gactcccctg ggcatggctt ctgggcacat cagggatttc   3480

cagatcactg cctctggcca gtatggccag tgggccccca agctggctag gctgcactac   3540

tctggcagca tcaatgcctg gagcaccaag gagcccttct cttggattaa ggtggacctg   3600

ctggctccca tgatcattca tggcatcaag acccaggggg ccaggcagaa gttttctagc   3660

ctgtatatta gccagttcat catcatgtat agcctggatg ggaagaagtg gcagacctac   3720

aggggggaata gcactggcac cctgatggtg tttttggca atgtggattc ttctggcatc   3780

aagcataaca tcttcaatcc ccctatcatt gccaggtaca ttaggctgca tcccacccat   3840

tactctatca ggagcaccct gaggatggag ctgatggggt gtgatctgaa cagctgtagc   3900

atgcccctgg gcatggagtc caaggctatc tctgatgccc agatcactgc cagcagctac   3960

ttcaccaaca tgtttgccac ctggagcccc agcaaggcca ggctgcacct gcagggcagg   4020

tctaatgcct ggaggcccca ggtgaacaat cccaaggagt ggctgcaggt ggacttccag   4080

aagactatga aggtgactgg ggtgaccact caggggggtga agagcctgct gaccagcatg   4140

tatgtgaagg agttcctgat ctcttctagc caggatgggc atcagtggac cctgtttttt   4200

cagaatggca aagtgaaggt gtttcagggg aatcaggaca gctttacccc tgtggtgaac   4260

agcctggatc ctcctctgct gactagatac ctgaggatcc acccccagag ctgggtccac   4320

cagattgctc tgaggatgga ggtgctgggg tgtgaggctc aggacctgta ctga         4374
```

```
<210> SEQ ID NO 17
<211> LENGTH: 4374
<212> TYPE: DNA
<213> ORGANISM: Artificial Sequence
<220> FEATURE:
<223> OTHER INFORMATION: Description of Artificial Sequence: FVIII
      Nucleic Acid

<400> SEQUENCE: 17
```

```
atgcagattg agctgagcac ctgcttcttt ctgtgcctgc tgaggttctg cttctctgcc     60

accaggaggt actacctggg ggctgtggaa ctgagctggg actatatgca gtctgacctg    120

ggggagctgc ctgtggatgc caggttcccc cccagggtgc ccaagtcttt cccctttaac    180

acttctgtgg tgtacaagaa gaccctgttt gtggagttta ctgaccacct gttcaatatt    240

gccaagccca ggcccccctg gatgggcctg ctgggcccaa ccatccaggc tgaggtgtat    300

gatactgtgg tgatcaccct gaagaacatg gccagccacc ctgtgagcct gcatgctgtg    360

ggggtgagct attggaaggc ttctgagggg gctgagtatg atgaccagac tagccagagg    420

gagaaggagg atgacaaggt gttccctggg gggtctcata cctatgtgtg gcaggtgctg    480

aaggagaatg gccccatggc ctctgacccc ctgtgcctga cctattctta cctgagccat    540

gtggacctgg tcaaggacct gaactctggc ctgattgggg ctctgctggt gtgcagggag    600

ggcagcctgg ccaaggagaa gactcagact ctgcataagt tcatcctgct gtttgctgtg    660

tttgatgagg gcaagagctg gcactctgag accaagaact ctctgatgca ggatagggat    720

gctgcctctg ccagggcctg gcccaagatg cacactgtga atggctatgt gaataggtct    780

ctgcctggcc tgattggctg ccataggaag tctgtgtact ggcatgtgat tggcatgggc    840

actacccctg aggtgcactc tatcttcctg gaggggcaca ccttcctggt gaggaaccac    900

aggcaggcca gcctggagat ctctcccatc accttcctga ctgcccagac tctgctgatg    960

gacctgggcc agttcctgct gttctgccat atcagcagcc accagcatga tggcatggag   1020
```

-continued

```
gcctatgtga aggtggacag ctgcccagag gaaccccagc tgaggatgaa gaacaatgag   1080
gaggctgagg actatgatga tgacctgact gactctgaga tggatgtggt gaggtttgat   1140
gatgacaaca gccccagctt tattcagatc aggtctgtgg ccaagaagca ccccaagacc   1200
tgggtgcact acattgctgc tgaggaggag gactgggatt atgccccccct ggtgctggcc   1260
cctgatgaca ggtcttacaa gtctcagtac ctgaacaatg gcccccagag gattgggagg   1320
aagtacaaga aggtgaggtt catggcctac actgatgaga ccttcaagac cagggaggcc   1380
atccagcatg agtctggcat cctggggccc ctgctgtatg gggaggtggg ggataccctg   1440
ctgattatct tcaagaacca ggctagcagg ccctataaca tctaccccca tggcattact   1500
gatgtgaggc ccctgtactc taggagactg cccaaggggg tgaagcacct gaaagacttc   1560
cccatcctgc ctggggagat cttcaagtat aagtggactg tgactgtgga ggatggcccc   1620
actaagtctg accccaggtg cctgaccagg tattacagca gctttgtgaa tatggagagg   1680
gatctggctt ctggcctgat tggcctctg ctgatttgct acaaggagtc tgtggatcag   1740
agggggaacc agattatgtc tgacaagagg aatgtgattc tgttctctgt gtttgatgag   1800
aacaggagct ggtacctgac tgagaatatc cagaggttcc tgcctaatcc tgctggggtg   1860
cagctggagg accctgagtt ccaggctagc aacattatgc acagcatcaa tggctatgtg   1920
tttgacagcc tgcagctgtc tgtgtgcctg catgaggtgg cttactggta cattctgtct   1980
attggggccc agactgactt cctgtctgtg ttcttctctg gctacacctt caagcacaag   2040
atggtgtatg aggacactct gaccctgttc cccttctctg gggagactgt gttcatgagc   2100
atggagaatc ctgggctgtg gattctgggg tgccacaact ctgatttcag gaacaggggc   2160
atgactgccc tgctgaaggt gagcagctgt gacaagaaca ctggggatta ttatgaggac   2220
agctatgagg acatttctgc ctacctgctg agcaagaaca atgccattga gcctaggagc   2280
ttcagccaga atccccctgt gctgaagaga caccagaggg agatcactag gaccactctg   2340
cagtctgatc aggaggagat tgactatgat gacaccattt ctgtggagat gaagaaggag   2400
gactttgata tttatgatga ggatgagaac cagagcccca gaagcttcca gaagaagacc   2460
aggcactact tcattgctgc tgtggagagg ctgtgggatt atggcatgtc ttctagcccc   2520
catgtgctga ggaacagggc tcagtctggc tctgtgcctc agttcaagaa ggtggtgttc   2580
caggagttca ctgatgggag cttcacccag cctctgtaca ggggggagct gaatgaacat   2640
ctgggcctgc tggggcccta catcagggct gaggtggagg ataatatcat ggtgactttc   2700
aggaatcagg cctctaggcc ctacagcttc tactctagcc tgatcagcta tgaggaggac   2760
cagaggcagg gggctgagcc taggaagaat tttgtgaaac ccaatgagac caagacctac   2820
ttttggaagg tgcagcacca catggcccct accaaggatg agtttgactg taaggcctgg   2880
gcctacttct ctgatgtgga cctggagaag gatgtgcatt ctgggctgat tggcccccctg   2940
ctggtgtgcc acaccaacac cctgaaccct gcccatggca ggcaggtgac tgtgcaggag   3000
tttgccctgt tcttcaccat ctttgatgag actaagagct ggtatttcac tgagaacatg   3060
gagaggaact gtagggctcc ctgcaacatc cagatggagg atccaacttt caaggagaac   3120
tacaggttcc atgccatcaa tggctacatc atggacaccc tgcctggcct ggtgatggcc   3180
caggaccaga ggattaggtg gtacctgctg agcatgggct ctaatgagaa catccactct   3240
atccacttct ctggccatgt gtttactgtg aggaagaagg aggagtacaa gatggctctg   3300
tacaacctgt accctggggt gtttgagact gtggagatgc tgcctagcaa ggctggcatt   3360
tggagagtgg agtgtctgat tggggagcac ctgcatgctg ggatgtctac cctgttcctg   3420
```

gtgtactcta acaagtgcca gaccccccctg gggatggctt ctgggcacat cagagatttt 3480
cagattactg cttctgggca gtatggccag tgggctccca agctggccag actgcattac 3540
tctggctcta ttaatgcttg gagcaccaag gagcctttca gctggatcaa ggtggacctg 3600
ctggctccca tgatcatcca tggcattaag actcaggggg ctaggcagaa gttcagcagc 3660
ctgtatattt ctcagtttat tatcatgtat tctctggatg gcaagaagtg gcagacttac 3720
aggggcaaca gcactggcac cctgatggtg ttctttggca atgtggacag ctctgggatc 3780
aagcataaca tcttcaaccc ccccattatt gccaggtaca tcaggctgca ccccacccac 3840
tattctatca ggagcactct gaggatggag ctgatggggt gtgacctgaa cagctgctct 3900
atgcccctgg gcatggagag caaggccatc tctgatgccc agatcactgc cagctcttat 3960
ttcaccaaca tgtttgccac ctggagcccc agcaaggcca ggctgcacct gcagggcaga 4020
agcaatgcct ggaggcccca ggtgaacaat cctaaggagt ggctgcaggt ggacttccag 4080
aagactatga aggtgactgg ggtgactacc cagggggtga agagcctgct gaccagcatg 4140
tatgtgaagg agttcctgat tagcagcagc caggatgggc atcagtggac cctgttcttc 4200
cagaatggga aggtgaaggt gttccagggc aatcaggaca gcttcacccc tgtggtgaac 4260
agcctggacc cccccctgct gaccaggtac ctgaggatcc atccccagag ctgggtgcac 4320
cagattgctc tgagaatgga ggtgctgggc tgtgaggccc aggacctgta ttga 4374

<210> SEQ ID NO 18
<211> LENGTH: 4374
<212> TYPE: DNA
<213> ORGANISM: Artificial Sequence
<220> FEATURE:
<223> OTHER INFORMATION: Description of Artificial Sequence: FVIII
Nucleic Acid

<400> SEQUENCE: 18
atgcagattg agctgtctac ctgttttttt ctgtgcctgc tgaggttctg cttctctgct 60
accaggaggt attatctggg ggctgtggag ctgagctggg actacatgca gtctgacctg 120
ggggagctgc ctgtggatgc caggtttcct cccagggtgc ctaagagctt ccccttcaac 180
acctctgtgg tgtacaagaa gactctgttt gtggagttca ctgaccacct gttcaacatt 240
gccaagccca ggccccccctg gatggggctg ctgggcccca ctatccaggc tgaggtgtat 300
gatactgtgg tgattaccct gaagaacatg gcctctcacc ctgtgtctct gcatgctgtg 360
ggggtgagct actggaaggc ttctgagggg gctgaatatg atgatcagac ctctcagagg 420
gagaaggagg atgacaaggt gtttcctggg ggcagccaca cctatgtgtg gcaggtgctg 480
aaggagaatg gccccatggc ctctgatccc ctgtgcctga cctacagcta cctgagccat 540
gtggacctgg tgaaggacct gaactctggc ctgattgggg ccctgctggt gtgcagggag 600
ggcagcctgg ccaaggaaaa gacccagacc ctgcataagt tcatcctgct gtttgctgtg 660
tttgatgagg gcaagtcttg gcactctgag accaagaaca gcctgatgca ggacagggat 720
gctgcctctg ctagggcctg gcccaagatg cacactgtga atgggtatgt gaacagatct 780
ctgcctggcc tgattggctg ccacaggaag tctgtgtact ggcatgtgat tggcatgggg 840
accacccctg aggtgcatag catcttcctg gaggggcaca ccttcctggt gagaaatcat 900
aggcaggcca gcctggagat tagccccatc accttcctga ctgcccagac cctgctgatg 960
gacctgggcc agttcctgct gttctgccac atttctagcc accagcatga tggcatggag 1020
gcctatgtga aggtggatag ctgccctgaa gagccccagc tgaggatgaa gaacaatgag 1080

```
gaggctgagg attatgatga tgatctgact gactctgaga tggatgtggt gaggtttgat   1140
gatgacaaca gccccagctt catccagatc aggtctgtgg ccaagaagca ccctaagacc   1200
tgggtgcact acattgctgc tgaagaggag gactgggact atgcccccct ggtgctggcc   1260
ccagatgaca ggtcttacaa gagccagtac ctgaataatg gcccccagag gattgggagg   1320
aagtataaga aagtgaggtt catggcttac actgatgaga cctttaagac tagggaggcc   1380
attcagcatg agtctgggat tctgggccct ctgctgtatg gggaggtggg ggacaccctg   1440
ctgatcattt tcaagaacca ggccagcagg ccctataata tttatcccca tgggattact   1500
gatgtcaggc ccctgtacag caggaggctg cctaaggggg tgaagcacct gaaggacttc   1560
cccattctgc ctggggagat cttcaagtat aagtggactg tgactgtgga ggatggcccc   1620
accaagtctg atcctaggtg cctgaccagg tactatagca gctttgtgaa catggagagg   1680
gacctggctt ctggcctgat tggcccccctg ctgatctgct acaaggaatc tgtggaccag   1740
aggggcaacc agattatgtc tgacaagagg aatgtgatcc tgttttctgt gtttgatgag   1800
aataggagct ggtatctgac tgagaacatc cagaggttcc tgcccaatcc tgctggggtg   1860
cagctggagg accctgagtt ccaggcttct aacatcatgc atagcatcaa tgggtatgtg   1920
tttgactctc tgcagctgtc tgtgtgcctg catgaggtgg cctattggta catcctgagc   1980
attggggccc agactgactt cctgtctgtg ttcttctctg gctacacctt caagcacaag   2040
atggtgtatg aggacaccct gaccctgttc cctttctctg ggagagactgt gttcatgagc   2100
atggagaacc ctggcctgtg gattctgggc tgccataatt ctgacttcag aaacaggggc   2160
atgactgctc tgctgaaggt gagcagctgt gacaagaata ctggggacta ctatgaggac   2220
tcttatgagg atatttctgc ctacctgctg agcaagaaca atgctattga gcccaggagc   2280
ttcagccaga acccccctgt cctgaagagg catcagaggg agatcactag gaccaccctg   2340
cagtctgatc aggaggagat tgactatgat gacactatct ctgtggaaat gaagaaggag   2400
gactttgata tctatgatga ggatgagaac cagagcccca ggtctttcca gaagaagacc   2460
aggcactact tcattgctgc tgtggagagg ctgtgggact atggcatgtc tagcagcccc   2520
catgtgctga ggaacagagc ccagtctggc tctgtgcccc agttcaagaa ggtggtgttt   2580
caggagttca ctgatgggag cttcactcag cccctgtata gggggggagct gaatgagcat   2640
ctgggcctgc tggggcccta catcagggct gaggtggagg ataacatcat ggtgaccttc   2700
aggaaccagg ccagcaggcc ctactctttc tactcttctc tgatcagcta tgaggaggat   2760
cagaggcagg gggctgagcc taggaagaac tttgtcaagc ctaatgagac taagacctac   2820
ttttggaagg tgcagcacca catggctccc actaaggatg agtttgattg caaggcctgg   2880
gcctacttct ctgatgtgga cctggagaag gatgtgcact ctggcctgat tggcccccctg   2940
ctggtgtgtc acaccaatac cctgaaccct gcccatggca ggcaggtcac tgtgcaggag   3000
tttgccctgt ttttcactat ctttgatgag actaagtctt ggtacttcac tgagaacatg   3060
gaaaggaatt gcagggctcc ctgcaacatc cagatggagg accccacctt caaggagaac   3120
tacaggtttc atgccatcaa tggctacatc atggacaccc tgcctggcct ggtgatggct   3180
caggatcaga ggattaggtg gtatctgctg agcatgggca gcaatgagaa catccacagc   3240
atccactttt ctggccatgt gttcactgtg aggaagaagg aggagtacaa gatggctctg   3300
tacaatctgt accctggggt gtttgagact gtggagatgc tgcccagcaa ggctgggatc   3360
tggagggtgg agtgcctgat tggggaacac ctgcatgctg gcatgtctac cctgttcctg   3420
```

```
gtgtactcta acaagtgcca gactcccctg ggcatggcct ctgggcacat cagggacttc   3480

cagatcactg cctctgggca gtatggccag tgggccccta agctggctag gctgcattac   3540

tctggcagca tcaatgcctg gagcaccaag gagcccttca gctggatcaa ggtggacctg   3600

ctggccccta tgatcatcca tggcatcaag acccaggggg ccagacagaa gttctcttct   3660

ctgtacatct ctcagttcat catcatgtac tctctggatg gcaagaagtg gcagacctac   3720

agggggaatt ctactggcac tctgatggtg ttctttggga atgtggatag ctctgggatc   3780

aagcataata ttttcaaccc ccccattatt gctaggtaca tcaggctgca cccaacccac   3840

tactctatta ggtctaccct gaggatggag ctgatgggct gtgacctgaa ctcttgtagc   3900

atgcccctgg gcatggagag caaggctatc tctgatgccc agatcactgc cagcagctac   3960

tttaccaaca tgtttgctac ttggagcccc agcaaggcca ggctgcacct gcagggcagg   4020

agcaatgcct ggaggcccca ggtgaacaac cccaaggagt ggctgcaggt ggattttcag   4080

aagaccatga aggtgactgg ggtgaccact caggggggtga aaagcctgct gactagcatg   4140

tatgtgaagg agtttctgat cagcagctct caggatggcc atcagtggac cctgttcttc   4200

cagaatggca aggtgaaggt gttccagggc aaccaggata gcttcacccc tgtggtgaat   4260

agcctggacc ccccccctgct gaccaggtac ctgaggatcc atccccagag ctgggtgcac   4320

cagattgccc tgaggatgga ggtgctgggc tgtgaagccc aggacctgta ctga         4374
```

<210> SEQ ID NO 19
<211> LENGTH: 4374
<212> TYPE: DNA
<213> ORGANISM: Artificial Sequence
<220> FEATURE:
<223> OTHER INFORMATION: Description of Artificial Sequence: FVIII Nucleic Acid

<400> SEQUENCE: 19

```
atgcaaatag agctctccac ctgcttcttt ctgtgccttt tgcgattctg ctttagtgcc     60

accagaagat actacctggg tgcagtggaa ctgtcatggg actatatgca aagtgatctc    120

ggtgagctgc ctgtggacgc aagatttcct cctagagtgc caaaatcttt tccattcaac    180

acctcagtcg tgtacaaaaa gactctgttt gtagaattca cggatcacct tttcaacatc    240

gctaagccaa ggccaccctg gatgggtctg ctaggtccta ccatccaggc tgaggtttat    300

gatacagtgg tcattacact taagaacatg gcttcccatc ctgtcagtct tcatgctgtt    360

ggtgtatcct actggaaagc ttctgaggga gctgaatatg atgatcagac cagtcaaagg    420

gagaaagaag atgataaagt cttccctggt ggaagccata catatgtctg gcaggtcctg    480

aaagagaatg gtccaatggc ctctgaccca ctgtgcctta cctactcata tctttctcat    540

gtggacctgg taaaagactt gaattcaggc ctcattggag ccctactagt atgtagagaa    600

gggagtctgg ccaaggaaaa gacacagacc ttgcacaaat ttatactact tttgctgta    660

tttgatgaag ggaaaagttg gcactcagaa acaaagaact ccttgatgca ggatagggat    720

gctgcatctg ctcgggcctg gcctaaaatg cacacagtca atggttatgt aaacaggtct    780

ctgccaggtc tgattggatg ccacaggaaa tcagtctatt ggcatgtgat tggaatgggc    840

accactcctg aagtgcactc aatattcctc gaaggtcaca catttcttgt gaggaaccat    900

cgccaggcgt ccttggaaat ctcgccaata actttcctta ctgctcaaac actcttgatg    960

gaccttggac agtttctact gttttgtcat atctcttccc accaacatga tggcatggaa   1020

gcttatgtca aagtagacag ctgtccagag gaaccccaac tacgaatgaa aaataatgaa   1080
```

gaagcggaag actatgatga tgatcttact gattctgaaa tggatgtggt caggtttgat 1140
gatgacaact ctccttcctt tatccaaatt cgctcagttg ccaagaagca tcctaaaact 1200
tgggtacatt acattgctgc tgaagaggag gactgggact atgctccctt agtcctcgcc 1260
cccgatgaca gaagttataa aagtcaatat ttgaacaatg gccctcagcg gattggtagg 1320
aagtacaaaa aagtccgatt tatggcatac acagatgaaa cctttaagac tcgtgaagct 1380
attcagcatg aatcaggaat cttgggacct ttactttatg gggaagttgg agacacactg 1440
ttgattatat ttaagaatca agcaagcaga ccatataaca tctaccctca cggaatcact 1500
gatgtccgtc ctttgtattc aaggagatta ccaaaaggtg taaaacattt gaaggatttt 1560
ccaattctgc caggagaaat attcaaatat aaatggacag tgactgtaga agatgggcca 1620
actaaatcag atcctcggtg cctgacccgc tattactcta gtttcgttaa tatggagaga 1680
gatctagctt caggactcat tggccctctc ctcatctgct acaaagaatc tgtagatcaa 1740
agaggaaacc agataatgtc agacaagagg aatgtcatcc tgttttctgt atttgatgag 1800
aaccgaagct ggtacctcac agagaatata caacgctttc tccccaatcc agctggagtg 1860
cagcttgagg atccagagtt ccaagcctcc aacatcatgc acagcatcaa tggctatgtt 1920
tttgatagtt tgcagttgtc agtttgtttg catgaggtgg catactggta cattctaagc 1980
attggagcac agactgactt cctttctgtc ttcttctctg gatatacctt caaacacaaa 2040
atggtctatg aagacacact caccctattc ccattctcag gagaaactgt cttcatgtcg 2100
atggaaaacc caggtctatg gattctgggg tgccacaact cagactttcg gaacagaggc 2160
atgaccgcct tactgaaggt ttctagttgt gacaagaaca ctggtgatta ttacgaggac 2220
agttatgaag atatttcagc atacttgctg agtaaaaaca atgccattga accaagaagc 2280
ttctcccaaa acccaccagt cttgaaacgc catcaacggg aaataactcg tactactctt 2340
cagtcagatc aagaggaaat tgactatgat gataccatat cagttgaaat gaagaaggaa 2400
gattttgaca tttatgatga ggatgaaaat cagagccccc gcagctttca aaagaaaaca 2460
cgacactatt ttattgctgc agtggagagg ctctgggatt atgggatgag tagctcccca 2520
catgttctaa gaaacagggc tcagagtggc agtgtccctc agttcaagaa agttgttttc 2580
caggaattta ctgatggctc ctttactcag cccttatacc gtggagaact aaatgaacat 2640
ttgggactcc tggggccata tataagagca gaagttgaag ataatatcat ggtaactttc 2700
agaaatcagg cctctcgtcc ctattccttc tattctagcc ttatttctta tgaggaagat 2760
cagaggcaag gagcagaacc tagaaaaaac tttgtcaagc ctaatgaaac caaaacttac 2820
ttttggaaag tgcaacatca tatggcaccc actaaagatg agtttgactg caaagcctgg 2880
gcttatttct ctgatgttga cctggaaaaa gatgtgcact caggcctgat tggacccctt 2940
ctggtctgcc acactaacac actgaaccct gctcatggga gacaagtgac agtacaggaa 3000
tttgctctgt tttcaccat ctttgatgag accaaaagct ggtacttcac tgaaaatatg 3060
gaaagaaact gcagggctcc ctgcaatatc cagatggaag atcccacttt taaagagaat 3120
tatcgcttcc atgcaatcaa tggctacata atggatacac tacctggctt agtaatggct 3180
caggatcaaa ggattcgatg gtatctgctc agcatgggca gcaatgaaaa catccattct 3240
attcatttca gtggacatgt gttcaccgta cgaaaaaaag aggagtataa aatggcactg 3300
tacaatctct atccaggtgt ttttgagaca gtggaaatgt taccatccaa agctggaatt 3360
tggcgggtgg aatgccttat tggcgagcat ctacatgctg ggatgagcac actttttctg 3420
gtgtacagca ataagtgtca gactcccctg ggaatggctt ctggacacat tagagatttt 3480

```
cagattacag cttcaggaca atatggacag tgggccccaa agctggccag acttcattat   3540

tccggatcaa tcaatgcctg gagcaccaag gagccctttt cttggatcaa ggtggatctg   3600

ttggcaccaa tgattattca cggcatcaag acccagggtg cccgtcagaa gttctccagc   3660

ctctacatct ctcagtttat catcatgtat agtcttgatg ggaagaagtg gcagacttat   3720

cgaggaaatt ccactggaac cttaatggtc ttctttggca atgtggattc atctgggata   3780

aaacacaata tttttaaccc tccaattatt gctcgataca tccgtttgca cccaactcat   3840

tatagcattc gcagcactct tcgcatggag ttgatgggct gtgatttaaa tagttgcagc   3900

atgccattgg gaatggagag taaagcaata tcagatgcac agattactgc ttcatcctac   3960

tttaccaata tgtttgccac ctggtctcct tcaaaagctc gacttcacct ccaagggagg   4020

agtaatgcct ggagacctca ggtgaataat ccaaaagagt ggctgcaagt ggacttccag   4080

aagacaatga aagtcacagg agtaactact cagggagtaa aatctctgct taccagcatg   4140

tatgtgaagg agttcctcat ctccagcagt caagatggcc atcagtggac tctcttttt    4200

cagaatggca aagtaaaggt ttttcaggga aatcaagact ccttcacacc tgtggtgaac   4260

tctctagacc caccgttact gactcgctac cttcgaattc acccccagag ttgggtgcac   4320

cagattgccc tgaggatgga ggttctgggc tgcgaggcac aggacctcta ctga         4374
```

<210> SEQ ID NO 20
<211> LENGTH: 4890
<212> TYPE: DNA
<213> ORGANISM: Artificial Sequence
<220> FEATURE:
<223> OTHER INFORMATION: Description of Artificial Sequence: FVIII Nucleic Acid

<400> SEQUENCE: 20

```
atgcagattg agctgagcac ctgcttcttc ctgtgcctgc tgaggttctg cttctctgcc     60

accaggagat actacctggg ggctgtggag ctgagctggg actacatgca gtctgacctg    120

ggggagctgc ctgtggatgc caggttcccc cccagagtgc ccaagagctt ccccttcaac    180

acctctgtgg tgtacaagaa gaccctgttt gtggagttca ctgaccacct gttcaacatt    240

gccaagccca ggccccccctg gatgggcctg ctgggcccca ccatccaggc tgaggtgtat    300

gacactgtgg tgatcaccct gaagaacatg gccagccacc ctgtgagcct gcatgctgtg    360

ggggtgagct actggaaggc ctctgagggg gctgagtatg atgaccagac cagccagagg    420

gagaaggagg atgacaaggt gttccctggg ggcagccaca cctatgtgtg gcaggtgctg    480

aaggagaatg gccccatggc ctctgacccc ctgtgcctga cctacagcta cctgagccat    540

gtggacctgg tgaaggacct gaactctggc ctgattgggg ccctgctggt gtgcagggag    600

ggcagcctgg ccaaggagaa gacccagacc ctgcacaagt tcatcctgct gtttgctgtg    660

tttgatgagg gcaagagctg gcactctgaa accaagaaca gcctgatgca ggacagggat    720

gctgcctctg ccagggcctg gcccaagatg cacactgtga atggctatgt gaacaggagc    780

ctgcctggcc tgattggctg ccacaggaag tctgtgtact ggcatgtgat tggcatgggc    840

accacccctg aggtgcacag catcttcctg gagggccaca ccttcctggt caggaaccac    900

aggcaggcca gcctggagat cagccccatc accttcctga ctgcccagac cctgctgatg    960

gacctgggcc agttcctgct gttctgccac atcagcagcc accagcatga tggcatggag   1020

gcctatgtga aggtggacag ctgccctgag gagccccagc tgaggatgaa gaacaatgag   1080

gaggctgagg actatgatga tgacctgact gactctgaga tggatgtggt gaggtttgat   1140
```

gatgacaaca gccccagctt catccagatc aggtctgtgg ccaagaagca ccccaagacc 1200
tgggtgcact acattgctgc tgaggaggag gactgggact atgccccct ggtgctggcc 1260 cctgatgaca ggagctacaa gagccagtac ctgaacaatg gcccccagag gattggcagg 1320
aagtacaaga aggtcaggtt catggcctac actgatgaaa ccttcaagac cagggaggcc 1380
atccagcatg agtctggcat cctgggcccc ctgctgtatg gggaggtggg ggacaccctg 1440
ctgatcatct tcaagaacca ggccagcagg ccctacaaca tctaccccca tggcatcact 1500
gatgtgaggc ccctgtacag caggaggctg cccaaggggg tgaagcacct gaaggacttc 1560
cccatcctgc ctggggagat cttcaagtac aagtggactg tgactgtgga ggatggcccc 1620
accaagtctg accccaggtg cctgaccaga tactacagca gctttgtgaa catggagagg 1680
gacctggcct ctggcctgat tggcccctg ctgatctgct acaaggagtc tgtggaccag 1740
aggggcaacc agatcatgtc tgacaagagg aatgtgatcc tgttctctgt gtttgatgag 1800
aacaggagct ggtacctgac tgagaacatc cagaggttcc tgcccaaccc tgctggggtg 1860
cagctggagg accctgagtt ccaggccagc aacatcatgc acagcatcaa tggctatgtg 1920
tttgacagcc tgcagctgtc tgtgtgcctg catgaggtgg cctactggta catcctgagc 1980
attggggccc agactgactt cctgtctgtg ttcttctctg gctacacctt caagcacaag 2040
atggtgtatg aggacaccct gaccctgttc cccttctctg ggagactgt gttcatgagc 2100 atggagaacc ctggcctgtg gattctgggc tgccacaact ctgacttcag gaacaggggc 2160
atgactgccc tgctgaaagt ctccagctgt gacaagaaca ctggggacta ctatgaggac 2220
agctatgagg acatctctgc ctacctgctg agcaagaaca atgccattga gcccaggagc 2280
ttcagccaga acagcaggca ccccagcacc aggcagaagc agttcaatgc caccaccatc 2340
cctgagaatg acatagagaa gacagaccca tggtttgccc accggacccc catgcccaag 2400
atccagaatg tgagcagctc tgacctgctg atgctgctga ggcagagccc cacccccat 2460 ggcctgagcc tgtctgacct gcaggaggcc aagtatgaaa ccttctctga tgaccccagc 2520
cctggggcca ttgacagcaa caacagcctg tctgagatga cccacttcag gccccagctg 2580
caccactctg ggacatggt gttcacccct gagtctggcc tgcagctgag gctgaatgag 2640
aagctgggca ccactgctgc cactgagctg aagaagctgg acttcaaagt ctccagcacc 2700
agcaacaacc tgatcagcac catcccctct gacaacctgg ctgctggcac tgacaacacc 2760
agcagcctgg gcccccccag catgcctgtg cactatgaca gccagctgga caccaccctg 2820
tttggcaaga agagcagccc cctgactgag tctgggggcc ccctgagcct gtctgaggag 2880
aacaatgaca gcaagctgct ggagtctggc ctgatgaaca gccaggagag cagctggggc 2940
aagaatgtga gcaccaggag cttccagaag aagaccaggc actacttcat tgctgctgtg 3000
gagaggctgt gggactatgg catgagcagc agcccccatg tgctgaggaa cagggcccag 3060
tctggctctg tgccccagtt caagaaggtg gtgttccagg agttcactga tggcagcttc 3120
acccagcccc tgtacagagg ggagctgaat gagcacctgg gcctgctggg cccctacatc 3180
agggctgagg tggaggacaa catcatggtg accttcagga accaggccag caggccctac 3240
agcttctaca gcagcctgat cagctatgag gaggaccaga ggcagggggc tgagcccagg 3300
aagaactttg tgaagcccaa tgaaaccaag acctacttct ggaaggtgca gcaccacatg 3360
gcccccacca aggatgagtt tgactgcaag gcctgggcct acttctctga tgtggacctg 3420
gagaaggatg tgcactctgg cctgattggc cccctgctgg tgtgccacac caacaccctg 3480
aaccctgccc atggcaggca ggtgactgtg caggagtttg ccctgttctt caccatcttt 3540
gatgaaacca agagctggta cttcactgag aacatggaga ggaactgcag ggccccctgc 3600
aacatccaga tggaggaccc caccttcaag gagaactaca ggttccatgc catcaatggc 3660
tacatcatgg acaccctgcc tggcctggtg atggcccagg accagaggat caggtggtac 3720
ctgctgagca tgggcagcaa tgagaacatc cacagcatcc acttctctgg ccatgtgttc 3780
actgtgagga agaaggagga gtacaagatg gccctgtaca acctgtaccc tggggtgttt 3840
gagactgtgg agatgctgcc cagcaaggct ggcatctgga gggtggagtg cctgattggg 3900
gagcacctgc atgctggcat gagcaccctg ttcctggtgt acagcaacaa gtgccagacc 3960
cccctgggca tggcctctgg ccacatcagg gacttccaga tcactgcctc tggccagtat 4020
ggccagtggg cccccaagct ggccaggctg cactactctg gcagcatcaa tgcctggagc 4080
accaaggagc ccttcagctg gatcaaggtg gacctgctgg cccccatgat catccatggc 4140
atcaagaccc agggggccag gcagaagttc agcagcctgt acatcagcca gttcatcatc 4200
atgtacagcc tggatggcaa gaagtggcag acctacaggg gcaacagcac tggcaccctg 4260
atggtgttct ttggcaatgt ggacagctct ggcatcaagc acaacatctt caaccccccc 4320
atcattgcca gatacatcag gctgcacccc acccactaca gcatcaggag caccctgagg 4380
atggagctga tgggctgtga cctgaacagc tgcagcatgc ccctgggcat ggagagcaag 4440
gccatctctg atgcccagat cactgccagc agctacttca ccaacatgtt tgccacctgg 4500
agccccagca aggccaggct gcacctgcag ggcaggagca atgcctggag gccccaggtc 4560
aacaacccca aggagtggct gcaggtggac ttccagaaga ccatgaaggt gactggggtg 4620
accacccagg gggtgaagag cctgctgacc agcatgtatg tgaaggagtt cctgatcagc 4680
agcagccagg atggccacca gtggaccctg ttcttccaga atggcaaggt gaaggtgttc 4740
cagggcaacc aggacagctt caccccctgtg gtgaacagcc tggacccccc cctgctgacc 4800
agatacctga ggattcaccc ccagagctgg gtgcaccaga ttgccctgag gatggaggtg 4860
ctgggctgtg aggcccagga cctgtactga 4890

<210> SEQ ID NO 21
<211> LENGTH: 4374
<212> TYPE: DNA
<213> ORGANISM: Artificial Sequence
<220> FEATURE:
<223> OTHER INFORMATION: Description of Artificial Sequence: FVIII
Nucleic Acid

<400> SEQUENCE: 21
atgcagattg agctgtcaac ttgctttttc ctgtgcctgc tgagattttg tttttccgct 60
actagaagat actacctggg ggctgtggaa ctgtcttggg attacatgca gagtgacctg 120
ggagagctgc cagtggacgc acgatttcca cctagagtcc ctaaatcatt ccccttcaac 180
accagcgtgg tctataagaa aacactgttc gtggagttta ctgatcacct gttcaacatc 240
gctaagcctc ggccaccctg gatgggactg ctgggaccaa caatccaggc agaggtgtac 300
gacaccgtgg tcattacact gaaaaacatg gcctcacacc ccgtgagcct gcatgctgtg 360
ggcgtcagct actggaaggc ttccgaaggg gcagagtatg acgatcagac ttcccagaga 420
gaaaaagagg acgataaggt gtttcctggc gggtctcata cctatgtgtg gcaggtcctg 480
aaagagaatg gccccatggc ttccgaccct ctgtgcctga cctactctta tctgagtcac 540
gtggacctgg tcaaggatct gaacagcgga ctgatcggag cactgctggt gtgtagggaa 600

-continued gggagcctgg ctaaggagaa aacccagaca ctgcataagt tcattctgct gttcgccgtg 660
tttgacgaag gaaaatcatg gcacagcgag acaaagaata gtctgatgca ggaccgggat 720
gccgcttcag ccagagcttg gcccaaaatg cacactgtga acggctacgt caatcgctca 780
ctgcctggac tgatcggctg ccaccgaaag agcgtgtatt ggcatgtcat cggaatgggc 840
accacacctg aagtgcactc cattttcctg gaggggcata cctttctggt ccgcaaccac 900
cgacaggcct ccctggagat ctctccaatt accttcctga cagctcagac tctgctgatg 960
gatctgggac agttcctgct gttttgccac atcagctccc accagcatga tggcatggag 1020
gcctacgtga aagtggacag ctgtcccgag gaacctcagc tgaggatgaa gaacaatgag 1080
gaagctgaag actatgacga tgacctgacc gactccgaga tggatgtggt ccgattcgat 1140
gacgataaca gcccctcctt tatccagatt agatctgtgg ccaagaaaca ccctaagaca 1200
tgggtccatt acatcgcagc cgaggaagag gactgggatt atgcaccact ggtgctggca 1260
ccagacgatc gatcctacaa atctcagtat ctgaacaatg gaccacagcg gattggcaga 1320
aagtacaaga aagtgaggtt catggcttat accgatgaaa ccttcaagac tcgcgaagca 1380
atccagcacg agagcgggat tctgggacca ctgctgtacg gagaagtggg ggacaccctg 1440
ctgatcattt ttaagaacca ggccagcagg ccttacaata tctatccaca tggaattaca 1500
gatgtgcgcc ctctgtacag ccggagactg ccaaagggcg tcaaacacct gaaggacttc 1560
ccaatcctgc ccggggaaat ttttaagtat aaatggactg tcaccgtcga ggatggcccc 1620
actaagagcg accctaggtg cctgacccgc tactattcta gtttcgtgaa tatggaaagg 1680
gatctggcca gcggactgat cggcccactg ctgatttgtt acaaagagag cgtggatcag 1740
agaggcaacc agatcatgtc cgacaagagg aatgtgattc tgttcagtgt ctttgacgaa 1800
aaccggtcat ggtatctgac cgagaacatc cagagattcc tgcctaatcc agccggagtg 1860
cagctggaag atcctgagtt tcaggcttct aacatcatgc atagtattaa tggctacgtg 1920
ttcgacagtc tgcagctgtc agtgtgtctg cacgaggtcg cttactggta tatcctgagc 1980
attggagcac agacagattt cctgagcgtg ttcttttccg gctacacttt taagcataaa 2040
atggtgtatg aggacacact gactctgttc cccttcagcg gcgaaaccgt gtttatgtcc 2100
atggagaatc ccgggctgtg gatcctggga tgccacaaca gcgatttcag gaatcgcggg 2160
atgactgccc tgctgaaagt gtcaagctgt gacaagaaca ccggagacta ctatgaagat 2220
tcatacgagg acatcagcgc atatctgctg tccaaaaaca atgccattga acccaggtct 2280
tttagtcaga atcctccagt gctgaagagg caccagcgcg agatcacccg cactaccctg 2340
cagagtgatc aggaagagat cgactacgac gatacaattt ctgtggaaat gaagaaagag 2400
gacttcgata tctatgacga agatgagaac cagagtcctc gatcattcca gaagaaaacc 2460
cggcattact ttattgctgc agtggagcgc ctgtgggatt atggcatgtc ctctagtcct 2520
cacgtgctgc gaaatcgggc ccagtcaggg agcgtcccac agttcaagaa agtggtcttc 2580
caggagttta cagacggatc ctttactcag ccactgtacc ggggcgaact gaacgagcac 2640
ctggggctgc tgggacccta tatcagagct gaagtggagg ataacattat ggtcaccttc 2700
agaaatcagg catctaggcc ttacagtttt tattcaagcc tgatctctta cgaagaggac 2760
cagaggcagg gagcagaacc acgaaaaaac ttcgtgaagc ctaatgagac caaaaacatac 2820 ttttggaagg tgcagcacca tatggcccca acaaaagacg aattcgattg caaggcatgg 2880
gcctattttt ctgacgtgga tctggagaag gacgtccaca gtggcctgat cgggccactg 2940
ctggtgtgtc atactaacac cctgaatccc gcacacggca ggcaggtcac tgtccaggaa 3000
ttcgccctgt tctttaccat ctttgatgag acaaaaagct ggtacttcac cgaaaacatg 3060
gagcgaaatt gccgggctcc atgtaatatt cagatggaag accccacatt caaggagaac 3120
taccgctttc atgccatcaa tgggtatatt atggatactc tgcccggact ggtcatggct 3180
caggaccaga gaatcaggtg gtacctgctg agcatggggt ccaacgagaa tatccactca 3240
attcatttca gcggacacgt gtttactgtc cggaagaaag aagagtataa aatggccctg 3300
tacaacctgt atcccggcgt gttcgaaacc gtcgagatgc tgcctagcaa ggcagggatc 3360
tggagagtgg aatgcctgat tggggagcac ctgcatgccg gaatgtctac cctgtttctg 3420
gtgtacagta ataagtgtca gacacccctg ggatggctt ccggacatat ccgggatttc 3480
cagattaccg catctggaca gtacggccag tgggccccta agctggctag actgcactat 3540
tccgggtcta tcaacgcttg gtccacaaaa gagcctttct cttggattaa ggtggacctg 3600
ctggcaccaa tgatcattca tggcatcaaa actcaggggg ccaggcagaa gttctcctct 3660
ctgtacatct cacagtttat catcatgtac agcctggatg gcaagaaatg gcagacatac 3720
cgcggcaata gcacagggac tctgatggtg ttctttggca acgtggacag ttcagggatc 3780
aagcacaaca ttttcaatcc ccctatcatt gctagataca tcaggctgca cccaacccat 3840
tattctattc gaagtacact gcggatggaa ctgatggggt gcgatctgaa cagttgttca 3900
atgcccctgg gaatggagtc caaggcaatc tctgacgccc agattaccgc tagctcctac 3960
ttcactaata tgtttgctac ctggagcccc tccaaagcac gactgcatct gcagggacga 4020
agcaacgcat ggcgaccaca ggtgaacaat cccaaggagt ggctgcaggt cgattttcag 4080
aaaactatga aggtgaccgg agtcacaact cagggcgtga aaagtctgct gacctcaatg 4140
tacgtcaagg agttcctgat ctctagttca caggacggcc accagtggac actgttcttt 4200
cagaacggaa aggtgaaagt cttccagggc aatcaggatt cctttacacc tgtggtcaac 4260
tctctggacc cacccctgct gactcgctac ctgcgaatcc acccacagtc ctgggtgcat 4320
cagattgcac tgagaatgga agtcctgggc tgcgaggccc aggacctgta ttga 4374

<210> SEQ ID NO 22
<211> LENGTH: 222
<212> TYPE: DNA
<213> ORGANISM: Artificial Sequence
<220> FEATURE:
<223> OTHER INFORMATION: Description of Artificial Sequence: TTR Promoter

<400> SEQUENCE: 22
gtctgtctgc acatttcgta gagcgagtgt tccgatactc taatctccct aggcaaggtt 60
catattgact taggttactt attctccttt tgttgactaa gtcaataatc agaatcagca 120
ggtttggagt cagcttggca gggatcagca gcctgggttg gaaggagggg gtataaaagc 180
cccttcacca ggagaagccg tcacacagat ccacaagctc ct 222

<210> SEQ ID NO 23
<211> LENGTH: 5066
<212> TYPE: DNA
<213> ORGANISM: Artificial Sequence
<220> FEATURE:
<223> OTHER INFORMATION: Description of Artificial Sequence: Expression Cassette

<400> SEQUENCE: 23
cctgcaggca gctgcgcgct cgctcgctca ctgaggccgc ccgggcaaag cccgggcgtc 60

-continued

```
gggcgacctt tggtcgcccg gcctcagtga gcgagcgagc gcgcagagag ggagtggcca    120
actccatcac taggggttcc tacgcgtgtc tgtctgcaca tttcgtagag cgagtgttcc    180
gatactctaa tctccctagg caaggttcat attgacttag gttacttatt ctccttttgt    240
tgactaagtc aataatcaga atcagcaggt ttggagtcag cttggcaggg atcagcagcc    300
tgggttggaa ggagggggta taaaagcccc ttcaccagga gaagccgtca cacagatcca    360
caagctcctg ctagcaggta agtgccgtgt gtggttcccg cgggcctggc ctctttacgg    420
gttatggccc ttgcgtgcct tgaattactg acactgacat ccactttttc tttttctcca    480
caggtttaaa cgccaccatg cagattgagc tgagcacctg cttcttcctg tgtctgctga    540
ggttctgctt ctctgccacc aggaggtatt acctgggggc tgtggagctg agctgggact    600
atatgcagtc tgacctgggg gagctgcctg tggatgctag gttccccccc agggtgccca    660
agagcttccc ctttaacact tctgtggtgt acaagaagac cctgtttgtg gagttcactg    720
accacctgtt caacattgcc aagcccaggc ccccctggat ggggctgctg ggcccacca     780
tccaggctga ggtgtatgac actgtggtga tcaccctgaa gaacatggcc agccaccctg    840
tgagcctgca tgctgtgggg gtgagctact ggaaggcttc tgagggggct gagtatgatg    900
accagactag ccagagggag aaggaggatg acaaggtgtt tcctgggggc agccatacct    960
atgtgtggca ggtgctgaag gagaatggcc ccatggcctc tgaccccctg tgcctgacct   1020
acagctacct gtctcatgtg gacctggtga aggacctgaa ctctggcctg attggggctc   1080
tgctggtgtg tagggagggc agcctggcta aggaaaagac ccagaccctg cataagttta   1140
tcctgctgtt tgctgtgttt gatgagggca agagctggca ctctgagacc aagaacagcc   1200
tgatgcagga tagggatgct gcctctgcca gggcttggcc taagatgcac actgtgaatg   1260
ggtatgtgaa taggagcctg cctggcctga ttggctgcca caggaagtct gtgtactggc   1320
atgtgattgg gatgggcacc acccctgagg tccatagcat cttcctggag ggccacactt   1380
tcctggtgag gaaccacaga caggcctctc tggagatctc tcccatcacc ttcctgactg   1440
ctcagactct gctgatggac ctgggccagt tcctgctgtt ttgccatatt agcagccacc   1500
agcatgatgg gatggaggcc tatgtgaagg tggatagctg ccctgaggag cctcagctga   1560
ggatgaagaa caatgaggag gctgaagact atgatgatga cctgactgat tctgagatgg   1620
atgtggtgag gtttgatgat gacaatagcc ccagcttcat tcagatcagg tctgtggcca   1680
agaaacaccc caagacctgg gtgcactaca ttgctgctga ggaagaggac tgggactatg   1740
ctcccctggt gctggcccct gatgataggt cttataagag ccagtacctg aacaatgggc   1800
cccagaggat tggcaggaag tacaagaagg tgaggttcat ggcctacact gatgaaacct   1860
tcaaaaccag ggaggccatt cagcatgagt ctggcatcct gggccctctg ctgtatgggg   1920
aggtgggga caccctgctg atcatcttca agaaccaggc cagcaggccc tacaacatct    1980
atcctcatgg catcactgat gtgaggcccc tgtacagcag gaggctgccc aagggggtga   2040
agcacctgaa agacttcccc atcctgcctg gggagatctt taagtataag tggactgtga   2100
ctgtggagga tggccctacc aagtctgacc ccaggtgtct gaccaggtac tattctagct   2160
ttgtgaacat ggagagggac ctggcctctg gcctgattgg gcccctgctg atctgctaca   2220
aggagtctgt ggaccagagg ggcaaccaga tcatgtctga caagaggaat gtgatcctgt   2280
tttctgtgtt tgatgagaat aggagctggt acctgactga gaacatccag aggtttctgc   2340
ccaatcctgc tggggtgcag ctggaggatc ctgagttcca ggccagcaat atcatgcata   2400
gcatcaatgg ctatgtgttt gacagcctgc agctgtctgt gtgcctgcat gaggtggcct   2460
```

```
actggtacat cctgagcatt ggggcccaga ctgactttct gtctgtgttc ttttctggct   2520
ataccttcaa gcacaagatg gtgtatgagg ataccctgac cctgttcccc ttctctgggg   2580
agactgtgtt catgagcatg gagaatcctg ggctgtggat cctggggtgc cacaactctg   2640
attttaggaa caggggggatg actgccctgc tgaaggtgtc tagctgtgat aagaacactg   2700
gggactacta tgaggacagc tatgaggaca tttctgctta tctgctgtct aagaataatg   2760
ccattgagcc cagaagcttc agccagaatc cccctgtgct gaagagacat cagagggaga   2820
tcaccagaac taccctgcag tctgatcagg aggagattga ctatgatgac actatctctg   2880
tggagatgaa gaaggaggac tttgacatct atgatgagga tgagaatcag tctcccagga   2940
gctttcagaa gaagaccaga cattacttca ttgctgctgt ggagaggctg tgggactatg   3000
gcatgagctc tagccctcat gtgctgagga acagggccca gtctggctct gtgccccagt   3060
tcaagaaggt ggtgttccag gaattcactg atggcagctt cacccagccc ctgtacaggg   3120
gggagctgaa tgagcacctg ggcctgctgg ggccttatat cagggctgag gtggaggata   3180
atattatggt gactttcagg aaccaggcca gcaggcccta ctctttctat agcagcctga   3240
tctcttatga ggaggatcag aggcaggggg ctgagcctag gaagaacttt gtgaagccca   3300
atgagactaa gacctacttc tggaaggtcc agcaccacat ggcccctacc aaggatgagt   3360
ttgactgcaa ggcctgggcc tatttctctg atgtggatct ggagaaggat gtccattctg   3420
ggctgattgg cccccctgctg gtgtgccaca ctaacactct gaatcctgcc catggcaggc   3480
aggtgactgt ccaggagttt gccctgttct tcactatctt tgatgagacc aagagctggt   3540
actttactga gaacatggag aggaactgca gagctccttg caatattcag atggaggacc   3600
ccaccttcaa ggagaattac aggttccatg ccattaatgg gtacatcatg gacaccctgc   3660
ctggcctggt gatggctcag gaccagagga tcaggtggta cctgctgagc atgggctcta   3720
atgagaatat ccacagcatc cacttctctg ggcatgtgtt cactgtgagg aagaaggagg   3780
agtacaagat ggctctgtat aatctgtacc ctggggtgtt tgaaactgtg gagatgctgc   3840
cctctaaggc tggcatctgg agggtggagt gcctgattgg ggagcacctg catgctggca   3900
tgagcaccct gttcctggtg tacagcaaca agtgccagac ccccctgggc atggcctctg   3960
gccacatcag ggacttccag atcactgcct ctggccagta tggccagtgg gcccccaagc   4020
tggccaggct gcactattct ggcagcatca atgcctggag caccaaggag cccttcagct   4080
ggatcaaggt ggacctgctg gcccccatga tcattcatgg catcaagacc caggggggcca   4140
ggcagaagtt cagctctctg tacatctctc agttcatcat catgtactct ctggatggga   4200
agaagtggca gacctacagg ggcaacagca ctggcaccct gatggtgttc tttgggaatg   4260
tggactcttc tggcatcaag cacaacatct tcaatccccc catcattgct aggtatatta   4320
ggctgcatcc cacccactac agcatcaggt ctaccctgag gatggagctg atgggctgtg   4380
acctgaactc ttgcagcatg cccctgggca tggagtctaa ggccatctct gatgcccaga   4440
ttactgccag cagctacttc accaacatgt ttgccacctg gagcccctct aaggccaggc   4500
tgcatctgca ggggaggagc aatgcctgga ggcctcaggt gaacaacccc aaggagtggc   4560
tgcaggtgga tttccagaag accatgaagg tgactggggt gaccacccag gggggtcaaga   4620
gcctgctgac cagcatgtat gtgaaggagt tcctgatcag cagcagccag gatggccacc   4680
agtggactct gttctttcag aatgggaagg tgaaggtgtt tcagggcaat caggactctt   4740
tcacccctgt ggtgaacagc ctggaccccc ccctgctgac cagatacctg aggatccacc   4800
```

-continued

```
cccagtcttg ggtgcatcag attgccctga ggatggaggt gctgggctgt gaggctcagg   4860

atctgtactg agcggccgca ataaaagatc agagctctag agatctgtgt gttggttttt   4920

tgtgtaggaa cccctagtga tggagttggc cactccctct ctgcgcgctc gctcgctcac   4980

tgaggccggg cgaccaaagg tcgcccgacg cccgggcttt gcccgggcgg cctcagtgag   5040

cgagcgagcg cgcagctgcc tgcagg                                        5066
```

```
<210> SEQ ID NO 24
<211> LENGTH: 11976
<212> TYPE: DNA
<213> ORGANISM: Artificial Sequence
<220> FEATURE:
<223> OTHER INFORMATION: Description of Artificial Sequence: Plasmid

<400> SEQUENCE: 24

cctgcaggca gctgcgcgct cgctcgctca ctgaggccgc ccgggcaaag cccgggcgtc     60

gggcgacctt tggtcgcccg gcctcagtga gcgagcgagc gcgcagagag ggagtggcca    120

actccatcac taggggttcc tacgcgtgtc tgtctgcaca tttcgtagag cgagtgttcc    180

gatactctaa tctccctagg caaggttcat attgacttag gttacttatt ctccttttgt    240

tgactaagtc aataatcaga atcagcaggt ttggagtcag cttggcaggg atcagcagcc    300

tgggttggaa ggagggggta taaaagcccc ttcaccagga gaagccgtca cacagatcca    360

caagctcctg ctagcaggta agtgccgtgt gtggttcccg cgggcctggc ctctttacgg    420

gttatggccc ttgcgtgcct tgaattactg acactgacat ccactttttc tttttctcca    480

caggtttaaa cgccaccatg cagattgagc tgagcacctg cttcttcctg tgtctgctga    540

ggttctgctt ctctgccacc aggaggtatt acctgggggc tgtggagctg agctgggact    600

atatgcagtc tgacctgggg gagctgcctg tggatgctag gttccccccc agggtgccca    660

agagcttccc ctttaacact tctgtggtgt acaagaagac cctgtttgtg gagttcactg    720

accacctgtt caacattgcc aagcccaggc ccccctggat ggggctgctg gggcccacca    780

tccaggctga ggtgtatgac actgtggtga tcaccctgaa gaacatggcc agccaccctg    840

tgagcctgca tgctgtgggg gtgagctact ggaaggcttc tgagggggct gagtatgatg    900

accagactag ccagagggag aaggaggatg acaaggtgtt tcctgggggc agccatacct    960

atgtgtggca ggtgctgaag gagaatggcc ccatggcctc tgacccccctg tgcctgacct   1020

acagctacct gtctcatgtg gacctggtga aggacctgaa ctctggcctg attggggctc   1080

tgctggtgtg tagggagggc agcctggcta aggaaaagac ccagaccctg cataagttta   1140

tcctgctgtt tgctgtgttt gatgagggca agagctggca ctctgagacc aagaacagcc   1200

tgatgcagga tagggatgct gcctctgcca gggcttggcc taagatgcac actgtgaatg   1260

ggtatgtgaa taggagcctg cctggcctga ttggctgcca caggaagtct gtgtactggc   1320

atgtgattgg gatgggcacc acccctgagg tccatagcat cttcctggag ggccacactt   1380

tcctggtgag gaaccacaga caggcctctc tggagatctc tcccatcacc ttcctgactg   1440

ctcagactct gctgatggac ctgggccagt tcctgctgtt ttgccatatt agcagccacc   1500

agcatgatgg gatggaggcc tatgtgaagg tggatagctg ccctgaggag cctcagctga   1560

ggatgaagaa caatgaggag gctgaagact atgatgatga cctgactgat tctgagatgg   1620

atgtggtgag gtttgatgat gacaatagcc ccagcttcat tcagatcagg tctgtggcca   1680

agaaacaccc caagacctgg gtgcactaca ttgctgctga ggaagaggac tgggactatg   1740

ctcccctggt gctggcccct gatgataggt cttataagag ccagtacctg aacaatgggc   1800
```

-continued cccagaggat tggcaggaag tacaagaagg tgaggttcat ggcctacact gatgaaacct 1860
tcaaaaccag ggaggccatt cagcatgagt ctggcatcct gggccctctg ctgtatgggg 1920
aggtggggga caccctgctg atcatcttca agaaccaggc cagcaggccc tacaacatct 1980
atcctcatgg catcactgat gtgaggcccc tgtacagcag gaggctgccc aagggggtga 2040
agcacctgaa agacttcccc atcctgcctg ggagatcttt taagtataag tggactgtga 2100
ctgtggagga tggccctacc aagtctgacc ccaggtgtct gaccaggtac tattctagct 2160
ttgtgaacat ggagagggac ctggcctctg gcctgattgg gcccctgctg atctgctaca 2220
aggagtctgt ggaccagagg ggcaaccaga tcatgtctga caagaggaat gtgatcctgt 2280
tttctgtgtt tgatgagaat aggagctggt acctgactga gaacatccag aggtttctgc 2340
ccaatcctgc tggggtgcag ctggaggatc ctgagttcca ggccagcaat atcatgcata 2400
gcatcaatgg ctatgtgttt gacagcctgc agctgtctgt gtgcctgcat gaggtggcct 2460
actggtacat cctgagcatt ggggcccaga ctgactttct gtctgtgttc ttttctggct 2520
ataccttcaa gcacaagatg gtgtatgagg ataccctgac cctgttcccc ttctctgggg 2580
agactgtgtt catgagcatg gagaatcctg ggctgtggat cctggggtgc cacaactctg 2640
attttaggaa cagggggatg actgccctgc tgaaggtgtc tagctgtgat aagaacactg 2700
gggactacta tgaggacagc tatgaggaca tttctgctta tctgctgtct aagaataatg 2760
ccattgagcc cagaagcttc agccagaatc cccctgtgct gaagagacat cagagggaga 2820
tcaccagaac taccctgcag tctgatcagg aggagattga ctatgatgac actatctctg 2880
tggagatgaa gaaggaggac tttgacatct atgatgagga tgagaatcag tctcccagga 2940
gctttcagaa gaagaccaga cattacttca ttgctgctgt ggagaggctg tgggactatg 3000
gcatgagctc tagccctcat gtgctgagga acagggccca gtctggctct gtgccccagt 3060
tcaagaaggt ggtgttccag gaattcactg atggcagctt cacccagccc ctgtacaggg 3120
gggagctgaa tgagcacctg ggcctgctgg ggccttatat cagggctgag gtggaggata 3180
atattatggt gactttcagg aaccaggcca gcaggcccta ctctttctat agcagcctga 3240
tctcttatga ggaggatcag aggcaggggg ctgagcctag gaagaacttt gtgaagccca 3300
atgagactaa gacctacttc tggaaggtcc agcaccacat ggcccctacc aaggatgagt 3360
ttgactgcaa ggcctgggcc tatttctctg atgtggatct ggagaaggat gtccattctg 3420
ggctgattgg cccccctgctg gtgtgccaca ctaacactct gaatcctgcc catggcaggc 3480
aggtgactgt ccaggagttt gccctgttct tcactatctt tgatgagacc aagagctggt 3540
actttactga gaacatggag aggaactgca gagctccttg caatattcag atggaggacc 3600
ccaccttcaa ggagaattac aggttccatg ccattaatgg gtacatcatg gacaccctgc 3660
ctggcctggt gatggctcag gaccagagga tcaggtggta cctgctgagc atgggctcta 3720
atgagaatat ccacagcatc cacttctctg ggcatgtgtt cactgtgagg aagaaggagg 3780
agtacaagat ggctctgtat aatctgtacc ctggggtgtt tgaaactgtg gagatgctgc 3840
cctctaaggc tggcatctgg agggtggagt gcctgattgg ggagcacctg catgctggca 3900
tgagcaccct gttcctggtg tacagcaaca agtgccagac ccccctgggc atggcctctg 3960
gccacatcag ggacttccag atcactgcct ctggccagta tggccagtgg gcccccaagc 4020
tggccaggct gcactattct ggcagcatca atgcctggag caccaaggag cccttcagct 4080
ggatcaaggt ggacctgctg gcccccatga tcattcatgg catcaagacc caggggggcca 4140 ggcagaagtt cagctctctg tacatctctc agttcatcat catgtactct ctggatggga 4200
agaagtggca gacctacagg ggcaacagca ctggcaccct gatggtgttc tttgggaatg 4260
tggactcttc tggcatcaag cacaacatct tcaatccccc catcattgct aggtatatta 4320
ggctgcatcc cacccactac agcatcaggt ctaccctgag gatggagctg atgggctgtg 4380
acctgaactc ttgcagcatg cccctgggca tggagtctaa ggccatctct gatgcccaga 4440
ttactgccag cagctacttc accaacatgt ttgccacctg gagcccctct aaggccaggc 4500
tgcatctgca ggggaggagc aatgcctgga ggcctcaggt gaacaacccc aaggagtggc 4560
tgcaggtgga tttccagaag accatgaagg tgactggggt gaccacccag gggtcaaga 4620
gcctgctgac cagcatgtat gtgaaggagt tcctgatcag cagcagccag gatggccacc 4680
agtggactct gttctttcag aatgggaagg tgaaggtgtt tcagggcaat caggactctt 4740
tcacccctgt ggtgaacagc ctggaccccc ccctgctgac cagatacctg aggatccacc 4800
cccagtcttg ggtgcatcag attgccctga ggatggaggt gctgggctgt gaggctcagg 4860
atctgtactg agcggccgca ataaaagatc agagctctag agatctgtgt gttggttttt 4920
tgtgtaggaa cccctagtga tggagttggc cactccctct ctgcgcgctc gctcgctcac 4980
tgaggccggg cgaccaaagg tcgcccgacg cccgggcttt gcccgggcgg cctcagtgag 5040
cgagcgagcg cgcagctgcc tgcaggggca gcttgaagga aatactaagg caaaggtact 5100
gcaagtgctc gcaacattcg cttatgcgga ttattgccgt agtgccgcga cgccgggggc 5160
aagatgcaga gattgccatg gtacaggccg tgcggttgat attgccaaaa cagagctgtg 5220
ggggagagtt gtcgagaaag agtgcggaag atgcaaaggc gtcggctatt caaggatgcc 5280
agcaagcgca gcatatcgcg ctgtgacgat gctaatccca aaccttaccc aacccacctg 5340
gtcacgcact gttaagccgc tgtatgacgc tctggtggtg caatgccaca aagaagagtc 5400
aatcgcagac aacattttga atgcggtcac acgttagcag catgattgcc acggatggca 5460
acatattaac ggcatgatat tgacttattg aataaaattg ggtaaatttg actcaacgat 5520
gggttaattc gctcgttgtg gtagtgagat gaaaagaggc ggcgcttact accgattccg 5580
cctagttggt cacttcgacg tatcgtctgg aactccaacc atcgcaggca gagaggtctg 5640
caaaatgcaa tcccgaaaca gttcgcaggt aatagttaga gcctgcataa cggtttcggg 5700
attttttata tctgcacaac aggtaagagc attgagtcga taatcgtgaa gagtcggcga 5760
gcctggttag ccagtgctct ttccgttgtg ctgaattaag cgaataccgg aagcagaacc 5820
ggatcaccaa atgcgtacag gcgtcatcgc cgcccagcaa cagcacaacc caaactgagc 5880
cgtagccact gtctgtcctg aattcattag taatagttac gctgcggcct tttacacatg 5940
accttcgtga aagcgggtgg caggaggtcg cgctaacaac ctcctgccgt tttgcccgtg 6000
catatcggtc acgaacaaat ctgattacta aacacagtag cctggatttg ttctatcagt 6060
aatcgacctt attcctaatt aaatagagca aatcccctta ttgggggtaa gacatgaaga 6120
tgccagaaaa acatgacctg ttggccgcca ttctcgcggc aaaggaacaa ggcatcgggg 6180
caatccttgc gtttgcaatg gcgtaccttc gcggcagata taatggcggt gcgtttacaa 6240
aaacagtaat cgacgcaacg atgtgcgcca ttatcgccta gttcattcgt gaccttctcg 6300
acttcgccgg actaagtagc aatctcgctt atataacgag cgtgtttatc ggctacatcg 6360
gtactgactc gattggttcg cttatcaaac gcttcgctgc taaaaaagcc ggagtagaag 6420
atggtagaaa tcaataatca acgtaaggcg ttcctcgata tgctggcgtg gtcggaggga 6480
actgataacg gacgtcagaa aaccagaaat catggttatg acgtcattgt aggcggagag 6540

```
ctatttactg attactccga tcaccctcgc aaacttgtca cgctaaaccc aaaactcaaa   6600
tcaacaggcg ccggacgcta ccagcttctt tcccgttggt gggatgccta ccgcaagcag   6660
cttggcctga aagacttctc tccgaaaagt caggacgctg tggcattgca gcagattaag   6720
gagcgtggcg ctttacctat gattgatcgt ggtgatatcc gtcaggcaat cgaccgttgc   6780
agcaatatct gggcttcact gccgggcgct ggttatggtc agttcgagca taaggctgac   6840
agcctgattg caaaattcaa agaagcgggc ggaacggtca gagagattga tgtatgagca   6900
gagtcaccgc gattatctcc gctctggtta tctgcatcat cgtctgcctg tcatgggctg   6960
ttaatcatta ccgtgataac gccattacct acaaagccca gcgcgacaaa aatgccagag   7020
aactgaagct ggcgaacgcg gcaattactg acatgcagat gcgtcagcgt gatgttgctg   7080
cgctcgatgc aaaatacacg aaggagttag ctgatgctaa agctgaaaat gatgctctgc   7140
gtgatgatgt tgccgctggt cgtcgtcggt tgcacatcaa agcagtctgt cagtcagtgc   7200
gtgaagccac caccgcctcc ggcgtggata atgcagcctc cccccgactg gcagacaccg   7260
ctgaacggga ttatttcacc ctcagagaga ggctgatcac tatgcaaaaa caactggaag   7320
gaacccagaa gtatattaat gagcagtgca gatagagttg cccatatcga tgggcaactc   7380
atgcaattat tgtgagcaat acacacgcgc ttccagcgga gtataaatgc ctaaagtaat   7440
aaaaccgagc aatccattta cgaatgtttg ctgggtttct gttttaacaa cattttctgc   7500
gccgccacaa attttggctg catcgacagt tttcttctgc ccaattccag aaacgaagaa   7560
atgatgggtg atggtttcct ttggtgctac tgctgccggt ttgttttgaa cagtaaacgt   7620
ctgttgagca catcctgtaa taagcagggc cagcgcagta gcgagtagca tttttttcat   7680
ggtgttattc ccgatgcttt ttgaagttcg cagaatcgta tgtgtagaaa attaaacaaa   7740
ccctaaacaa tgagttgaaa tttcatattg ttaatattta ttaatgtatg tcaggtgcga   7800
tgaatcgtca ttgtattccc ggattaacta tgtccacagc cctgacgggg aacttctctg   7860
cgggagtgtc cgggaataat taaaacgatg cacacagggt ttagcgcgta cacgtattgc   7920
attatgccaa cgccccggtg ctgacacgga agaaaccgga cgttatgatt tagcgtggaa   7980
agatttgtgt agtgttctga atgctctcag taaatagtaa tgaattatca aaggtatagt   8040
aatatctttt atgttcatgg atatttgtaa cccatcggaa aactcctgct ttagcaagat   8100
tttccctgta ttgctgaaat gtgatttctc ttgatttcaa cctatcatag gacgtttcta   8160
taagatgcgt gtttcttgag aatttaacat ttacaacctt tttaagtcct tttattaaca   8220
cggtgttatc gttttctaac acgatgtgaa tattatctgt ggctagatag taaatataat   8280
gtgagacgtt gtgacgtttt agttcagaat aaaacaattc acagtctaaa tcttttcgca   8340
cttgatcgaa tatttcttta aaaatggcaa cctgagccat tggtaaaacc ttccatgtga   8400
tacgagggcg cgtagtttgc attatcgttt ttatcgtttc aatctggtct gacctccttg   8460
tgttttgttg atgatttatg tcaaatatta ggaatgtttt cacttaatag tattggttgc   8520
gtaacaaagt gcggtcctgc tggcattctg gagggaaata caaccgacag atgtatgtaa   8580
ggccaacgtg ctcaaatctt catacagaaa gatttgaagt aatattttaa ccgctagatg   8640
aagagcaagc gcatggagcg acaaaatgaa taaagaacaa tctgctgatg atccctccgt   8700
ggatctgatt cgtgtaaaaa atatgcttaa tagcaccatt tctatgagtt accctgatgt   8760
tgtaattgca tgtatagaac ataaggtgtc tctggaagca ttcagagcaa ttgaggcagc   8820
gttggtgaag cacgataata atatgaagga ttattccctg gtggttgact gatcaccata   8880
```

```
actgctaatc attcaaacta tttagtctgt gacagagcca acacgcagtc tgtcactgtc   8940
aggaaagtgg taaaactgca actcaattac tgcaatgccc tcgtaattaa gtgaatttac   9000
aatatcgtcc tgttcggagg gaagaacgcg ggatgttcat tcttcatcac ttttaattga   9060
tgtatatgct ctcttttctg acgttagtct ccgacggcag gcttcaatga cccaggctga   9120
gaaattcccg gacccttttt gctcaagagc gatgttaatt tgttcaatca tttggttagg   9180
aaagcggatg ttgcgggttg ttgttctgcg ggttctgttc ttcgttgaca tgaggttgcc   9240
ccgtattcag tgtcgctgat ttgtattgtc tgaagttgtt tttacgttaa gttgatgcag   9300
atcaattaat acgatacctg cgtcataatt gattatttga cgtggtttga tggcctccac   9360
gcacgttgtg atatgtagat gataatcatt atcactttac gggtcctttc cggtgatccg   9420
acaggttacg gggcggcgac ctgcctgatg cggtattttc tccttacgca tctgtgcggt   9480
atttcacacc gcatacgtca aagcaaccat agtacgcgcc ctgtagcggc gcattaagcg   9540
cggcgggtgt ggtggttacg cgcagcgtga ccgctacact tgccagcgcc ttagcgcccg   9600
ctcctttcgc tttcttccct tcctttctcg ccacgttcgc cggctttccc cgtcaagctc   9660
taaatcgggg gctcccttta gggttccgat ttagtgcttt acggcacctc gaccccaaaa   9720
aacttgattt gggtgatggt tcacgtagtg ggccatcgcc ctgatagacg gtttttcgcc   9780
ctttgacgtt ggagtccacg ttctttaata gtggactctt gttccaaact ggaacaacac   9840
tcaactctat ctcgggctat tcttttgatt tagacctgca ggcatgcaag cttggcactg   9900
gccgtcgttt tacaacgtcg tgactgggaa aaccctggcg ttacccaact taatcgcctt   9960
gcagcacatc ccccttttcgc cagctggcgt aatagcgaag aggcccgcac cgatcgccct  10020
tcccaacagt tgcgcagcct gaatggcgaa tgcgatttat tcaacaaagc cgccgtcccg  10080
tcaagtcagc gtaatgctct gccagtgtta caaccaatta accaattctg attagaaaaa  10140
ctcatcgagc atcaaatgaa actgcaattt attcatatca ggattatcaa taccatattt  10200
ttgaaaaagc cgtttctgta atgaaggaga aaactcaccg aggcagttcc ataggatggc  10260
aagatcctgg tatcggtctg cgattccgac tcgtccaaca tcaatacaac ctattaattt  10320
cccctcgtca aaaataaggt tatcaagtga gaaatcacca tgagtgacga ctgaatccgg  10380
tgagaatggc aaaagcttat gcatttcttt ccagacttgt tcaacaggcc agccattacg  10440
ctcgtcatca aaatcactcg catcaaccaa accgttattc attcgtgatt gcgcctgagc  10500
gagacgaaat acgcgatcgc tgttaaaagg acaattacaa acaggaatcg aatgcaaccg  10560
gcgcaggaac actgccagcg catcaacaat attttcacct gaatcaggat attcttctaa  10620
tacctggaat gctgttttcc cggggatcgc agtggtgagt aaccatgcat catcaggagt  10680
acggataaaa tgcttgatgg tcggaagagg cataaattcc gtcagccagt ttagtctgac  10740
catctcatct gtaacatcat tggcaacgct acctttgcca tgtttcagaa acaactctgg  10800
cgcatcgggc ttcccataca atcgatagat tgtcgcacct gattgcccga cattatcgcg  10860
agcccattta tacccatata aatcagcatc catgttggaa tttaatcgcg gcttcgagca  10920
agacgtttcc cgttgaatat ggctcataac accccttgta ttactgttta tgtaagcaga  10980
cagttttatt gttcatgatg atatattttt atcttgtgca atgtaacatc agagattttg  11040
agacacaacg tggctttgtt gaataaatcg aacttttgct gagttgaagg atcagatcac  11100
gcatcttccc gacaacgcag accgttccgt ggcaaagcaa aagttcaaaa tcaccaactg  11160
gtccacctac aacaaagctc tcatcaaccg tggctccctc actttctggc tggatgatgg  11220
ggcgattcag gcctggtatg agtcagcaac accttcttca cgaggcagac ctctcgacgg  11280
```

```
agttccactg agcgtcagac cccgtagaaa agatcaaagg atcttcttga gatccttttt  11340

ttctgcgcgt aatctgctgc ttgcaaacaa aaaaaccacc gctaccagcg gtggtttgtt  11400

tgccggatca agagctacca actctttttc cgaaggtaac tggcttcagc agagcgcaga  11460

taccaaatac tgttcttcta gtgtagccgt agttaggcca ccacttcaag aactctgtag  11520

caccgcctac atacctcgct ctgctaatcc tgttaccagt ggctgctgcc agtggcgata  11580

agtcgtgtct taccgggttg gactcaagac gatagttacc ggataaggcg cagcggtcgg  11640

gctgaacggg gggttcgtgc acacagccca gcttggagcg aacgacctac accgaactga  11700

gatacctaca gcgtgagcta tgagaaagcg ccacgcttcc cgaagggaga aaggcggaca  11760

ggtatccggt aagcggcagg gtcggaacag gagagcgcac gagggagctt ccagggggaa  11820

acgcctggta tctttatagt cctgtcgggt ttcgccacct ctgacttgag cgtcgatttt  11880

tgtgatgctc gtcagggggg cggagcctat ggaaaaacgc cagcaacgcg gcctttttac  11940

ggttcctggc cttttgctgg ccttttgctc acatgt                            11976
```

```
<210> SEQ ID NO 25
<211> LENGTH: 1457
<212> TYPE: PRT
<213> ORGANISM: Artificial Sequence
<220> FEATURE:
<223> OTHER INFORMATION: Description of Artificial Sequence: FVIII
      Peptide

<400> SEQUENCE: 25

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
```

-continued

```
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655
```

```
Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
        755                 760                 765

Lys Arg His Gln Arg Glu Ile Thr Arg Thr Thr Leu Gln Ser Asp Gln
    770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
                805                 810                 815

Gln Lys Lys Thr Arg His Tyr Phe Ile Ala Ala Val Glu Arg Leu Trp
            820                 825                 830

Asp Tyr Gly Met Ser Ser Ser Pro His Val Leu Arg Asn Arg Ala Gln
        835                 840                 845

Ser Gly Ser Val Pro Gln Phe Lys Lys Val Val Phe Gln Glu Phe Thr
    850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
            900                 905                 910

Ser Leu Ile Ser Tyr Glu Glu Asp Gln Arg Gln Gly Ala Glu Pro Arg
        915                 920                 925

Lys Asn Phe Val Lys Pro Asn Glu Thr Lys Thr Tyr Phe Trp Lys Val
    930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
            980                 985                 990

Gly Arg Gln Val Thr Val Gln Glu  Phe Ala Leu Phe Phe  Thr Ile Phe
        995                 1000                1005

Asp Glu  Thr Lys Ser Trp Tyr  Phe Thr Glu Asn Met  Glu Arg Asn
    1010                1015                1020

Cys Arg  Ala Pro Cys Asn Ile  Gln Met Glu Asp Pro  Thr Phe Lys
    1025                1030                1035

Glu Asn  Tyr Arg Phe His Ala  Ile Asn Gly Tyr Ile  Met Asp Thr
    1040                1045                1050

Leu Pro  Gly Leu Val Met Ala  Gln Asp Gln Arg Ile  Arg Trp Tyr
    1055                1060                1065
```

```
Leu Leu  Ser Met Gly Ser Asn  Glu Asn Ile His Ser  Ile His Phe
    1070                 1075                 1080

Ser Gly  His Val Phe Thr Val  Arg Lys Lys Glu Glu  Tyr Lys Met
    1085                 1090                 1095

Ala Leu  Tyr Asn Leu Tyr Pro  Gly Val Phe Glu Thr  Val Glu Met
    1100                 1105                 1110

Leu Pro  Ser Lys Ala Gly Ile  Trp Arg Val Glu Cys  Leu Ile Gly
    1115                 1120                 1125

Glu His  Leu His Ala Gly Met  Ser Thr Leu Phe Leu  Val Tyr Ser
    1130                 1135                 1140

Asn Lys  Cys Gln Thr Pro Leu  Gly Met Ala Ser Gly  His Ile Arg
    1145                 1150                 1155

Asp Phe  Gln Ile Thr Ala Ser  Gly Gln Tyr Gly Gln  Trp Ala Pro
    1160                 1165                 1170

Lys Leu  Ala Arg Leu His Tyr  Ser Gly Ser Ile Asn  Ala Trp Ser
    1175                 1180                 1185

Thr Lys  Glu Pro Phe Ser Trp  Ile Lys Val Asp Leu  Leu Ala Pro
    1190                 1195                 1200

Met Ile  Ile His Gly Ile Lys  Thr Gln Gly Ala Arg  Gln Lys Phe
    1205                 1210                 1215

Ser Ser  Leu Tyr Ile Ser Gln  Phe Ile Ile Met Tyr  Ser Leu Asp
    1220                 1225                 1230

Gly Lys  Lys Trp Gln Thr Tyr  Arg Gly Asn Ser Thr  Gly Thr Leu
    1235                 1240                 1245

Met Val  Phe Phe Gly Asn Val  Asp Ser Ser Gly Ile  Lys His Asn
    1250                 1255                 1260

Ile Phe  Asn Pro Pro Ile Ile  Ala Arg Tyr Ile Arg  Leu His Pro
    1265                 1270                 1275

Thr His  Tyr Ser Ile Arg Ser  Thr Leu Arg Met Glu  Leu Met Gly
    1280                 1285                 1290

Cys Asp  Leu Asn Ser Cys Ser  Met Pro Leu Gly Met  Glu Ser Lys
    1295                 1300                 1305

Ala Ile  Ser Asp Ala Gln Ile  Thr Ala Ser Ser Tyr  Phe Thr Asn
    1310                 1315                 1320

Met Phe  Ala Thr Trp Ser Pro  Ser Lys Ala Arg Leu  His Leu Gln
    1325                 1330                 1335

Gly Arg  Ser Asn Ala Trp Arg  Pro Gln Val Asn Asn  Pro Lys Glu
    1340                 1345                 1350

Trp Leu  Gln Val Asp Phe Gln  Lys Thr Met Lys Val  Thr Gly Val
    1355                 1360                 1365

Thr Thr  Gln Gly Val Lys Ser  Leu Leu Thr Ser Met  Tyr Val Lys
    1370                 1375                 1380

Glu Phe  Leu Ile Ser Ser Ser  Gln Asp Gly His Gln  Trp Thr Leu
    1385                 1390                 1395

Phe Phe  Gln Asn Gly Lys Val  Lys Val Phe Gln Gly  Asn Gln Asp
    1400                 1405                 1410

Ser Phe  Thr Pro Val Val Asn  Ser Leu Asp Pro Pro  Leu Leu Thr
    1415                 1420                 1425

Arg Tyr  Leu Arg Ile His Pro  Gln Ser Trp Val His  Gln Ile Ala
    1430                 1435                 1440

Leu Arg  Met Glu Val Leu Gly  Cys Glu Ala Gln Asp  Leu Tyr
    1445                 1450                 1455
```

<210> SEQ ID NO 26
<211> LENGTH: 2351
<212> TYPE: PRT
<213> ORGANISM: Artificial Sequence
<220> FEATURE:
<223> OTHER INFORMATION: Description of Artificial Sequence: FVIII
Peptide

<400> SEQUENCE: 26

Met Gln Ile Glu Leu Ser Thr Cys Phe Phe Leu Cys Leu Leu Arg Phe
1 5 10 15

Cys Phe Ser Ala Thr Arg Arg Tyr Tyr Leu Gly Ala Val Glu Leu Ser
20 25 30

Trp Asp Tyr Met Gln Ser Asp Leu Gly Glu Leu Pro Val Asp Ala Arg
35 40 45

Phe Pro Pro Arg Val Pro Lys Ser Phe Pro Phe Asn Thr Ser Val Val
50 55 60

Tyr Lys Lys Thr Leu Phe Val Glu Phe Thr Asp His Leu Phe Asn Ile
65 70 75 80

Ala Lys Pro Arg Pro Pro Trp Met Gly Leu Leu Gly Pro Thr Ile Gln
85 90 95

Ala Glu Val Tyr Asp Thr Val Val Ile Thr Leu Lys Asn Met Ala Ser
100 105 110

His Pro Val Ser Leu His Ala Val Gly Val Ser Tyr Trp Lys Ala Ser
115 120 125

Glu Gly Ala Glu Tyr Asp Asp Gln Thr Ser Gln Arg Glu Lys Glu Asp
130 135 140

Asp Lys Val Phe Pro Gly Gly Ser His Thr Tyr Val Trp Gln Val Leu
145 150 155 160

Lys Glu Asn Gly Pro Met Ala Ser Asp Pro Leu Cys Leu Thr Tyr Ser
165 170 175

Tyr Leu Ser His Val Asp Leu Val Lys Asp Leu Asn Ser Gly Leu Ile
180 185 190

Gly Ala Leu Leu Val Cys Arg Glu Gly Ser Leu Ala Lys Glu Lys Thr
195 200 205

Gln Thr Leu His Lys Phe Ile Leu Leu Phe Ala Val Phe Asp Glu Gly
210 215 220

Lys Ser Trp His Ser Glu Thr Lys Asn Ser Leu Met Gln Asp Arg Asp
225 230 235 240

Ala Ala Ser Ala Arg Ala Trp Pro Lys Met His Thr Val Asn Gly Tyr
245 250 255

Val Asn Arg Ser Leu Pro Gly Leu Ile Gly Cys His Arg Lys Ser Val
260 265 270

Tyr Trp His Val Ile Gly Met Gly Thr Thr Pro Glu Val His Ser Ile
275 280 285

Phe Leu Glu Gly His Thr Phe Leu Val Arg Asn His Arg Gln Ala Ser
290 295 300

Leu Glu Ile Ser Pro Ile Thr Phe Leu Thr Ala Gln Thr Leu Leu Met
305 310 315 320

Asp Leu Gly Gln Phe Leu Leu Phe Cys His Ile Ser Ser His Gln His
325 330 335

Asp Gly Met Glu Ala Tyr Val Lys Val Asp Ser Cys Pro Glu Glu Pro
340 345 350

Gln Leu Arg Met Lys Asn Asn Glu Glu Ala Glu Asp Tyr Asp Asp Asp
355 360 365

```
Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ser Arg His Pro
        755                 760                 765

Ser Thr Arg Gln Lys Gln Phe Asn Ala Thr Thr Ile Pro Glu Asn Asp
    770                 775                 780

Ile Glu Lys Thr Asp Pro Trp Phe Ala His Arg Thr Pro Met Pro Lys
```

```
785                 790                 795                 800

Ile Gln Asn Val Ser Ser Ser Asp Leu Leu Met Leu Leu Arg Gln Ser
                805                 810                 815

Pro Thr Pro His Gly Leu Ser Leu Ser Asp Leu Gln Glu Ala Lys Tyr
            820                 825                 830

Glu Thr Phe Ser Asp Asp Pro Ser Pro Gly Ala Ile Asp Ser Asn Asn
        835                 840                 845

Ser Leu Ser Glu Met Thr His Phe Arg Pro Gln Leu His His Ser Gly
    850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
                885                 890                 895

Val Ser Ser Thr Ser Asn Asn Leu Ile Ser Thr Ile Pro Ser Asp Asn
            900                 905                 910

Leu Ala Ala Gly Thr Asp Asn Thr Ser Ser Leu Gly Pro Pro Ser Met
        915                 920                 925

Pro Val His Tyr Asp Ser Gln Leu Asp Thr Thr Leu Phe Gly Lys Lys
    930                 935                 940

Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
                965                 970                 975

Ser Ser Trp Gly Lys Asn Val Ser Ser Thr Glu Ser Gly Arg Leu Phe
            980                 985                 990

Lys Gly Lys Arg Ala His Gly Pro  Ala Leu Leu Thr Lys  Asp Asn Ala
        995                 1000                1005

Leu Phe  Lys Val Ser Ile Ser  Leu Leu Lys Thr Asn  Lys Thr Ser
    1010                1015                1020

Asn Asn  Ser Ala Thr Asn Arg  Lys Thr His Ile Asp  Gly Pro Ser
    1025                1030                1035

Leu Leu  Ile Glu Asn Ser Pro  Ser Val Trp Gln Asn  Ile Leu Glu
    1040                1045                1050

Ser Asp  Thr Glu Phe Lys Lys  Val Thr Pro Leu Ile  His Asp Arg
    1055                1060                1065

Met Leu  Met Asp Lys Asn Ala  Thr Ala Leu Arg Leu  Asn His Met
    1070                1075                1080

Ser Asn  Lys Thr Thr Ser Ser  Lys Asn Met Glu Met  Val Gln Gln
    1085                1090                1095

Lys Lys  Glu Gly Pro Ile Pro  Pro Asp Ala Gln Asn  Pro Asp Met
    1100                1105                1110

Ser Phe  Phe Lys Met Leu Phe  Leu Pro Glu Ser Ala  Arg Trp Ile
    1115                1120                1125

Gln Arg  Thr His Gly Lys Asn  Ser Leu Asn Ser Gly  Gln Gly Pro
    1130                1135                1140

Ser Pro  Lys Gln Leu Val Ser  Leu Gly Pro Glu Lys  Ser Val Glu
    1145                1150                1155

Gly Gln  Asn Phe Leu Ser Glu  Lys Asn Lys Val Val  Val Gly Lys
    1160                1165                1170

Gly Glu  Phe Thr Lys Asp Val  Gly Leu Lys Glu Met  Val Phe Pro
    1175                1180                1185

Ser Ser  Arg Asn Leu Phe Leu  Thr Asn Leu Asp Asn  Leu His Glu
    1190                1195                1200
```

```
Asn Asn  Thr His Asn Gln Glu  Lys Lys Ile Gln Glu  Glu Ile Glu
    1205                 1210                 1215

Lys Lys  Glu Thr Leu Ile Gln  Glu Asn Val Val Leu  Pro Gln Ile
    1220                 1225                 1230

His Thr  Val Thr Gly Thr Lys  Asn Phe Met Lys Asn  Leu Phe Leu
    1235                 1240                 1245

Leu Ser  Thr Arg Gln Asn Val  Glu Gly Ser Tyr Asp  Gly Ala Tyr
    1250                 1255                 1260

Ala Pro  Val Leu Gln Asp Phe  Arg Ser Leu Asn Asp  Ser Thr Asn
    1265                 1270                 1275

Arg Thr  Lys Lys His Thr Ala  His Phe Ser Lys Lys  Gly Glu Glu
    1280                 1285                 1290

Glu Asn  Leu Glu Gly Leu Gly  Asn Gln Thr Lys Gln  Ile Val Glu
    1295                 1300                 1305

Lys Tyr  Ala Cys Thr Thr Arg  Ile Ser Pro Asn Thr  Ser Gln Gln
    1310                 1315                 1320

Asn Phe  Val Thr Gln Arg Ser  Lys Arg Ala Leu Lys  Gln Phe Arg
    1325                 1330                 1335

Leu Pro  Leu Glu Glu Thr Glu  Leu Glu Lys Arg Ile  Ile Val Asp
    1340                 1345                 1350

Asp Thr  Ser Thr Gln Trp Ser  Lys Asn Met Lys His  Leu Thr Pro
    1355                 1360                 1365

Ser Thr  Leu Thr Gln Ile Asp  Tyr Asn Glu Lys Glu  Lys Gly Ala
    1370                 1375                 1380

Ile Thr  Gln Ser Pro Leu Ser  Asp Cys Leu Thr Arg  Ser His Ser
    1385                 1390                 1395

Ile Pro  Gln Ala Asn Arg Ser  Pro Leu Pro Ile Ala  Lys Val Ser
    1400                 1405                 1410

Ser Phe  Pro Ser Ile Arg Pro  Ile Tyr Leu Thr Arg  Val Leu Phe
    1415                 1420                 1425

Gln Asp  Asn Ser Ser His Leu  Pro Ala Ala Ser Tyr  Arg Lys Lys
    1430                 1435                 1440

Asp Ser  Gly Val Gln Glu Ser  Ser His Phe Leu Gln  Gly Ala Lys
    1445                 1450                 1455

Lys Asn  Asn Leu Ser Leu Ala  Ile Leu Thr Leu Glu  Met Thr Gly
    1460                 1465                 1470

Asp Gln  Arg Glu Val Gly Ser  Leu Gly Thr Ser Ala  Thr Asn Ser
    1475                 1480                 1485

Val Thr  Tyr Lys Lys Val Glu  Asn Thr Val Leu Pro  Lys Pro Asp
    1490                 1495                 1500

Leu Pro  Lys Thr Ser Gly Lys  Val Glu Leu Leu Pro  Lys Val His
    1505                 1510                 1515

Ile Tyr  Gln Lys Asp Leu Phe  Pro Thr Glu Thr Ser  Asn Gly Ser
    1520                 1525                 1530

Pro Gly  His Leu Asp Leu Val  Glu Gly Ser Leu Leu  Gln Gly Thr
    1535                 1540                 1545

Glu Gly  Ala Ile Lys Trp Asn  Glu Ala Asn Arg Pro  Gly Lys Val
    1550                 1555                 1560

Pro Phe  Leu Arg Val Ala Thr  Glu Ser Ser Ala Lys  Thr Pro Ser
    1565                 1570                 1575

Lys Leu  Leu Asp Pro Leu Ala  Trp Asp Asn His Tyr  Gly Thr Gln
    1580                 1585                 1590
```

```
Ile Pro  Lys Glu Glu Trp Lys  Ser Gln Glu Lys Ser  Pro Glu Lys
    1595                 1600                 1605

Thr Ala  Phe Lys Lys Lys Asp  Thr Ile Leu Ser Leu  Asn Ala Cys
    1610                 1615                 1620

Glu Ser  Asn His Ala Ile Ala  Ala Ile Asn Glu Gly  Gln Asn Lys
    1625                 1630                 1635

Pro Glu  Ile Glu Val Thr Trp  Ala Lys Gln Gly Arg  Thr Glu Arg
    1640                 1645                 1650

Leu Cys  Ser Gln Asn Pro Pro  Val Leu Lys Arg His  Gln Arg Glu
    1655                 1660                 1665

Ile Thr  Arg Thr Thr Leu Gln  Ser Asp Gln Glu Glu  Ile Asp Tyr
    1670                 1675                 1680

Asp Asp  Thr Ile Ser Val Glu  Met Lys Lys Glu Asp  Phe Asp Ile
    1685                 1690                 1695

Tyr Asp  Glu Asp Glu Asn Gln  Ser Pro Arg Ser Phe  Gln Lys Lys
    1700                 1705                 1710

Thr Arg  His Tyr Phe Ile Ala  Ala Val Glu Arg Leu  Trp Asp Tyr
    1715                 1720                 1725

Gly Met  Ser Ser Ser Pro His  Val Leu Arg Asn Arg  Ala Gln Ser
    1730                 1735                 1740

Gly Ser  Val Pro Gln Phe Lys  Lys Val Val Phe Gln  Glu Phe Thr
    1745                 1750                 1755

Asp Gly  Ser Phe Thr Gln Pro  Leu Tyr Arg Gly Glu  Leu Asn Glu
    1760                 1765                 1770

His Leu  Gly Leu Leu Gly Pro  Tyr Ile Arg Ala Glu  Val Glu Asp
    1775                 1780                 1785

Asn Ile  Met Val Thr Phe Arg  Asn Gln Ala Ser Arg  Pro Tyr Ser
    1790                 1795                 1800

Phe Tyr  Ser Ser Leu Ile Ser  Tyr Glu Glu Asp Gln  Arg Gln Gly
    1805                 1810                 1815

Ala Glu  Pro Arg Lys Asn Phe  Val Lys Pro Asn Glu  Thr Lys Thr
    1820                 1825                 1830

Tyr Phe  Trp Lys Val Gln His  His Met Ala Pro Thr  Lys Asp Glu
    1835                 1840                 1845

Phe Asp  Cys Lys Ala Trp Ala  Tyr Phe Ser Asp Val  Asp Leu Glu
    1850                 1855                 1860

Lys Asp  Val His Ser Gly Leu  Ile Gly Pro Leu Leu  Val Cys His
    1865                 1870                 1875

Thr Asn  Thr Leu Asn Pro Ala  His Gly Arg Gln Val  Thr Val Gln
    1880                 1885                 1890

Glu Phe  Ala Leu Phe Phe Thr  Ile Phe Asp Glu Thr  Lys Ser Trp
    1895                 1900                 1905

Tyr Phe  Thr Glu Asn Met Glu  Arg Asn Cys Arg Ala  Pro Cys Asn
    1910                 1915                 1920

Ile Gln  Met Glu Asp Pro Thr  Phe Lys Glu Asn Tyr  Arg Phe His
    1925                 1930                 1935

Ala Ile  Asn Gly Tyr Ile Met  Asp Thr Leu Pro Gly  Leu Val Met
    1940                 1945                 1950

Ala Gln  Asp Gln Arg Ile Arg  Trp Tyr Leu Leu Ser  Met Gly Ser
    1955                 1960                 1965

Asn Glu  Asn Ile His Ser Ile  His Phe Ser Gly His  Val Phe Thr
    1970                 1975                 1980

Val Arg  Lys Lys Glu Glu Tyr  Lys Met Ala Leu Tyr  Asn Leu Tyr
```

-continued

```
    1985                1990                1995

Pro Gly  Val Phe Glu Thr Val  Glu Met Leu Pro Ser  Lys Ala Gly
    2000                2005                2010

Ile Trp  Arg Val Glu Cys Leu  Ile Gly Glu His Leu  His Ala Gly
    2015                2020                2025

Met Ser  Thr Leu Phe Leu Val  Tyr Ser Asn Lys Cys  Gln Thr Pro
    2030                2035                2040

Leu Gly  Met Ala Ser Gly His  Ile Arg Asp Phe Gln  Ile Thr Ala
    2045                2050                2055

Ser Gly  Gln Tyr Gly Gln Trp  Ala Pro Lys Leu Ala  Arg Leu His
    2060                2065                2070

Tyr Ser  Gly Ser Ile Asn Ala  Trp Ser Thr Lys Glu  Pro Phe Ser
    2075                2080                2085

Trp Ile  Lys Val Asp Leu Leu  Ala Pro Met Ile Ile  His Gly Ile
    2090                2095                2100

Lys Thr  Gln Gly Ala Arg Gln  Lys Phe Ser Ser Leu  Tyr Ile Ser
    2105                2110                2115

Gln Phe  Ile Ile Met Tyr Ser  Leu Asp Gly Lys Lys  Trp Gln Thr
    2120                2125                2130

Tyr Arg  Gly Asn Ser Thr Gly  Thr Leu Met Val Phe  Phe Gly Asn
    2135                2140                2145

Val Asp  Ser Ser Gly Ile Lys  His Asn Ile Phe Asn  Pro Pro Ile
    2150                2155                2160

Ile Ala  Arg Tyr Ile Arg Leu  His Pro Thr His Tyr  Ser Ile Arg
    2165                2170                2175

Ser Thr  Leu Arg Met Glu Leu  Met Gly Cys Asp Leu  Asn Ser Cys
    2180                2185                2190

Ser Met  Pro Leu Gly Met Glu  Ser Lys Ala Ile Ser  Asp Ala Gln
    2195                2200                2205

Ile Thr  Ala Ser Ser Tyr Phe  Thr Asn Met Phe Ala  Thr Trp Ser
    2210                2215                2220

Pro Ser  Lys Ala Arg Leu His  Leu Gln Gly Arg Ser  Asn Ala Trp
    2225                2230                2235

Arg Pro  Gln Val Asn Asn Pro  Lys Glu Trp Leu Gln  Val Asp Phe
    2240                2245                2250

Gln Lys  Thr Met Lys Val Thr  Gly Val Thr Thr Gln  Gly Val Lys
    2255                2260                2265

Ser Leu  Leu Thr Ser Met Tyr  Val Lys Glu Phe Leu  Ile Ser Ser
    2270                2275                2280

Ser Gln  Asp Gly His Gln Trp  Thr Leu Phe Phe Gln  Asn Gly Lys
    2285                2290                2295

Val Lys  Val Phe Gln Gly Asn  Gln Asp Ser Phe Thr  Pro Val Val
    2300                2305                2310

Asn Ser  Leu Asp Pro Pro Leu  Leu Thr Arg Tyr Leu  Arg Ile His
    2315                2320                2325

Pro Gln  Ser Trp Val His Gln  Ile Ala Leu Arg Met  Glu Val Leu
    2330                2335                2340

Gly Cys  Glu Ala Gln Asp Leu  Tyr
    2345                2350
```

<210> SEQ ID NO 27
<211> LENGTH: 736
<212> TYPE: PRT
<213> ORGANISM: Artificial Sequence
<220> FEATURE:
<223> OTHER INFORMATION: Description of Artificial Sequence: AAV Capsid

<400> SEQUENCE: 27

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Gln Pro Gly Ala Pro Lys Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Lys Leu Ser Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400
```

```
Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
        435                 440                 445

Gln Gly Thr Thr Ser Gly Thr Thr Asn Gln Ser Arg Leu Leu Phe Ser
    450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
        515                 520                 525

Asp Asp Glu Glu Lys Phe Phe Pro Met His Gly Asn Leu Ile Phe Gly
    530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
            580                 585                 590

Thr Arg Thr Val Asn Asp Gln Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Pro Leu
                725                 730                 735
```

<210> SEQ ID NO 28
<211> LENGTH: 738
<212> TYPE: PRT
<213> ORGANISM: Artificial Sequence
<220> FEATURE:
<223> OTHER INFORMATION: Description of Artificial Sequence: AAV Capsid

<400> SEQUENCE: 28

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30
```

```
Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Ser Pro Val Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Asn Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445
```

-continued

Ser Arg Thr Gln Ser Thr Gly Gly Thr Ala Gly Thr Gln Gln Leu Leu
    450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Gln Asn Ala Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 29
<211> LENGTH: 14
<212> TYPE: PRT
<213> ORGANISM: Artificial Sequence
<220> FEATURE:
<223> OTHER INFORMATION: Description of Artificial Sequence: FVIII
      Peptide

<400> SEQUENCE: 29

Ser Phe Ser Gln Asn Pro Pro Val Leu Lys Arg His Gln Arg
1               5                   10

CPG REDUCED FACTOR VIII VARIANTS, COMPOSITIONS AND METHODS AND USES FOR TREATMENT OF HEMOSTASIS DISORDERS

RELATED APPLICATIONS

This patent application is a continuation application of International Application No. PCT/US2016/059793, filed Oct. 31, 2016 and claims the benefit of U.S. patent application No. 62/249,001, filed Oct. 30, 2015, U.S. patent application No. 62/331,872, filed May 4, 2016, U.S. patent application No. 62/349,532, filed Jun. 13, 2016, and U.S. patent application No. 62/357,874, filed Jul. 1, 2016, all of which applications are expressly incorporated herein by reference in their entirety.

SEQUENCE LISTING

The instant application contains a Sequence Listing which has been submitted electronically in ASCII format and is hereby incorporated by reference in its entirety. Said ASCII copy, created on Mar. 9, 2017, is named SPARK0449784SEQLIS.TXT and is 193,519 bytes in size.

FIELD OF THE INVENTION

This invention relates to the fields of recombinant coagulation factor production and the treatment of medical disorders associated with aberrant hemostasis. More particularly, the invention provides nucleic acid variants (sequences) encoding Factor VIII (FVIII) protein, the variants optionally provide increased transcription and/or expression, and/or activity over wild-type FVIII proteins.

INTRODUCTION

Several publications and patent documents are cited throughout the specification in order to describe the state of the art to which this invention pertains. Each of these citations is incorporated herein by reference as though set forth in full.

Hemophilia is an X-linked bleeding disorder present in 1 in 5,000 males worldwide. Therapies aimed at increasing clotting factor levels just above 1% of normal are associated with substantial improvement of the severe disease phenotype. Recent clinical trials for AAV-mediated gene transfer for hemophilia B (HB) have demonstrated sustained long-term expression of therapeutic levels of factor IX (FIX) but established that the AAV vector dose may be limiting due to anti-AAV immune responses to the AAV capsid. While these data relate the hemophilia B, 80% of all hemophilia is due to FVIII deficiency, hemophilia A (HA).

Current treatment for this disease is protein replacement therapy that requires frequent infusion of the Factor VIII protein. There is an immediate need to achieve sustained therapeutic levels of Factor VIII expression so that patients no longer require such frequent protein treatments. Indeed, continuous Factor VIII expression would prevent bleeding episodes and may ensure that immune tolerance to the protein is established.

In summary, gene therapy for HA presents 3 distinct challenges: (1) intrinsic properties of human FVIII (hFVIII) make it difficult to express compared to other proteins of similar size (2) the large size of the FVIII cDNA and sequence specific effects are correlated with rearrangements which hamper AAV production and (3) high rates of anti- FVIII antibody (inhibitors) formation in response to protein therapy that occurs in 25-30% of severe (<1% FVIII) HA patients.

SUMMARY

In accordance with the invention, cytosine-guanine dinucleotide (CpG) reduced nucleic acid variants encoding Factor VIII (FVIII) protein are provided. Such CpG reduced nucleic acid variants are distinct from wild-type nucleic acid encoding FVIII and may encode, for example, human FVIII protein, optionally lacking, in whole or in part, the FVIII B domain. Such CpG reduced nucleic acid variants include variants that exhibit increased expression (e.g., 1-5 fold increased expression) compared to codon-optimized FVIII nucleic acids such as FVIII-CO3 (SEQ ID NO:21), when transferred into cells, leading to increased FVIII protein secretion and therefore increased activity.

In certain embodiments, CpG reduced nucleic acid variants that encode FVIII, with or without deletion of, in whole or in part, the FVIII B domain, can provide for increased expression of FVIII, increased production of FVIII protein in a mammal, as well as provide increased efficacy in the context of gene transfer by increased circulating levels of FVIII protein, and achieving hemostasis for beneficial therapeutic outcomes.

In certain embodiments, a nucleic acid variant encoding FVIII has a reduced CpG content compared to wild-type nucleic acid encoding FVIII. In certain embodiments, a nucleic acid variant has at least 10 fewer CpGs than wild-type nucleic acid encoding FVIII (SEQ ID NO:19). In certain embodiments, a nucleic acid variant has no more than 4 CpGs; has no more than 3 CpGs; has no more than 2 CpGs; or has no more than 1 CpG. In certain embodiments, a nucleic acid variant has at most 4 CpGs; 3 CpGs; 2 CpGs; or 1 CpG. In certain embodiments, a nucleic acid variant has no CpGs.

In certain embodiments, a nucleic acid variant encoding FVIII has a reduced CpG content compared to wild-type nucleic acid encoding FVIII, and such CpG reduced nucleic acid variants have 90% or greater sequence identity to any of SEQ ID NOs:1-18. In certain embodiments, CpG reduced nucleic acid variants have 91%, 92%, 93%, 94%, 95%, 96%, 97%, 98%, 99%, 99.5% or greater sequence identity to any of SEQ ID NOs:1-18. In certain embodiments, CpG reduced nucleic acid variants have 90-95% sequence identity to any of SEQ ID NOs:1-18. In certain embodiments, CpG reduced nucleic acid variants have 95%-100% sequence identity to any of SEQ ID NOs:1-18. In certain embodiments, FVIII encoding CpG reduced nucleic acid variants are set forth in any of SEQ ID NOs:1-18.

In certain embodiments, CpG reduced nucleic acid variants are distinct from FVIII variant V3 (SEQ ID NO:20) and/or are distinct from FVIII variant CO3 (SEQ ID NO:21).

In certain embodiments, a CpG reduced nucleic acid variants encoding FVIII protein provides for greater expression and/or exhibits superior biological activity as compared to wild type FVIII or as compared to wild type FVIII comprising a B domain deletion (e.g., as determined by a plasma levels or a clotting assay or reduced bleeding in a FVIII assay or FVIII deficiency model).

In certain embodiments, CpG reduced nucleic acid variants encoding FVIII protein are at least 75% identical to wild type human FVIII nucleic acid or wild type human FVIII nucleic acid comprising a B domain deletion. In certain embodiments, CpG reduced nucleic acid variants encoding FVIII protein are about 75-95% identical (e.g., about 75%, 76%, 77%, 78%, 79%, 80%, 81%, 82%, 83%, 84%, 85%, 86%, 87%, 88%, 89%, 90%, 91%, 92%, 93%, 94%, 95% identical) to wild type human FVIII nucleic acid or wild type human FVIII nucleic acid comprising a B domain deletion.

In certain embodiments, CpG reduced nucleic acid variants encoding FVIII protein are mammalian, such as human. Such mammalian CpG reduced nucleic acid variants encoding FVIII protein include human forms, which may be based upon human wild type FVIII or human wild type FVIII comprising a B domain deletion.

In accordance with the invention, also provided are vectors and expression vectors that include CpG reduced nucleic acid variants encoding FVIII protein as set forth herein. In particular embodiments, a vector or expression vector comprises an adenovirus-associated virus (AAV) vector, a retroviral vector, an adenoviral vector, a plasmid, or a lentiviral vector. In certain embodiments, an AAV vector comprises an AAV serotype or an AAV pseudotype, such as AAV1, AAV2, AAV3, AAV4, AAV5, AAV6, AAV7, AAV8, AAV9, AAV10, AAV11, Rh10, Rh74 or AAV-2i8 AAV. In certain embodiments, an expression vector includes any of SEQ ID Nos:1-18, or comprises SEQ ID NO: 23 or 24.

In certain embodiments, an expression control element comprises a constitutive or regulatable control element, or a tissue-specific expression control element or promoter. In certain embodiments, an expression control element comprises an element that confers expression in liver. In certain embodiments, an expression control element comprises a TTR promoter or mutant TTR promoter, such as SEQ ID NO:22. In further particular aspects, an expression control element comprises a promoter set forth in PCT publication WO 2016/168728 (U.S. Ser. Nos. 62/148,696; 62/202,133; and 62/212,634), which are incorporated herein by reference in their entirety.

In accordance with the invention, further provided are virus vectors that include a CpG reduced nucleic acid variant encoding FVIII protein, or vectors or expression vectors comprising CpG reduced nucleic acid variant encoding FVIII protein. In particular embodiments, a virus vector comprises an AAV vector, a retroviral vector, an adenoviral vector, a plasmid, or a lentiviral vector.

In certain embodiments, an AAV vector comprises an AAV serotype or an AAV pseudotype comprising an AAV capsid serotype different from an ITR serotype. In additional particular aspects, an AAV vector comprises a VP1, VP2 and/or VP3 capsid sequence having 75% or more sequence identity (e.g., 80%, 85%, 90%, 95%, 96%, 97%, 98%, 99%, 99.1%, 99.2%, 99.3%, 99.4%, 99.5%, 99.6%, 99.7%, 99.8%, etc.) to any of AAV1, AAV2, AAV3, AAV4, AAV5, AAV6, AAV7, AAV8, AAV9, AAV10, AAV11, Rh10, Rh74 or AAV-2i8 AAV serotypes.

Expression vectors can include additional components or elements. In particular embodiments, an expression vector such as AAV vector further includes an intron, an expression control element, one or more AAV inverted terminal repeats (ITRs) (e.g., any of: AAV1, AAV2, AAV3, AAV4, AAV5, AAV6, AAV7, AAV8, AAV9, AAV10, AAV11, Rh10, Rh74 or AAV-2i8 AAV serotypes, or a combination thereof), a filler polynucleotide sequence and/or poly A signal. In certain embodiments, an intron is within or flanks a CpG reduced nucleic acid variant encoding FVIII, and/or an expression control element is operably linked to the CpG reduced nucleic acid variant encoding FVIII, and/or an AAV ITR(s) flanks the 5' or 3' terminus of the CpG reduced nucleic acid variant encoding FVIII, and/or a filler polynucleotide sequence flanks the 5' or 3' terminus of the CpG reduced nucleic acid variant encoding FVIII.

In particular embodiments, an expression control element comprises a constitutive or regulatable control element, or a tissue-specific expression control element or promoter. In certain embodiments, an expression control element comprises an element that confers expression in liver (e.g., a TTR promoter or mutant TTR promoter).

In accordance with the invention, additionally provided are host cells that include CpG reduced nucleic acid variants encoding FVIII protein as set forth herein. In particular embodiments, a host cell includes a CpG reduced nucleic acid variant encoding FVIII protein or an expression vector comprising a CpG reduced nucleic acid variant encoding FVIII protein. In certain embodiments, such host cells produce FVIII protein encoded by the nucleic acid variants and FVIII protein produced is recovered. Such FVIII protein produced by the cells, optionally isolated and/or purified, can be administered to a subject.

In accordance with the invention, yet additionally provided are compositions comprising CpG reduced nucleic acid variant encoding FVIII, vectors and expression vectors set forth herein. In particular embodiments, pharmaceutical compositions include a vector, an expression vector, or a virus or AAV vector, in a biologically compatible carrier or excipient. Such pharmaceutical compositions optionally include empty capsid AAV (e.g., lack vector genome comprising FVIII encoding nucleic acid variant). In additional particular embodiments, CpG reduced nucleic acid variant encoding FVIII protein, vectors, expression vectors, or virus or AAV vectors are encapsulated in a liposome or mixed with phospholipids or micelles.

In accordance with the invention, still further provided are methods for delivering or transferring CpG reduced nucleic acid variant encoding FVIII protein into a mammal or a mammalian cell. In one embodiment, a method includes administering or contacting a CpG reduced nucleic acid variant encoding FVIII, a vector comprising a CpG reduced nucleic acid variant encoding FVIII protein, an expression vector comprising a CpG reduced nucleic acid variant encoding FVIII protein, or a virus or AAV vector comprising a CpG reduced nucleic acid variant encoding FVIII protein to a mammal or mammalian cell, thereby delivering or transferring the nucleic acid sequence into the mammal or mammalian cell. Such methods introduce a CpG reduced nucleic acid variant encoding FVIII protein into a mammalian cell in culture or in a subject (e.g., a patient).

Methods of the invention also include treating mammalian subjects (e.g., patients) such as humans in need of FVIII (the human produces an insufficient amount of FVIII protein, or a defective or aberrant FVIII protein). In one embodiment, a method of treating a mammal in need of FVIII, includes: providing a CpG reduced nucleic acid variant encoding FVIII, or a vector comprising a CpG reduced nucleic acid variant encoding FVIII; or an expression vector comprising CpG reduced nucleic acid variant encoding FVIII, or a virus or AAV vector comprising a CpG reduced nucleic acid variant encoding FVIII; and administering an amount of the CpG reduced nucleic acid variant encoding FVIII, or a vector comprising a CpG reduced nucleic acid variant encoding FVIII, or an expression vector comprising a CpG reduced nucleic acid variant encoding FVIII, or a virus or AAV vector comprising a CpG reduced nucleic acid variant encoding FVIII to the mammalian subject such that FVIII encoded by the nucleic acid variant is expressed in the mammalian subject.

In another embodiment, a method for treatment of a hemostasis related disorder in a patient in need thereof (e.g., the patient produces an insufficient amount of FVIII protein, or a defective or aberrant FVIII protein) includes administration of a therapeutically effective amount of a CpG reduced nucleic acid variant encoding FVIII, or a vector comprising a CpG reduced nucleic acid variant encoding FVIII, or an expression vector comprising a CpG reduced nucleic acid variant encoding FVIII, or a virus or AAV vector comprising a CpG reduced nucleic acid variant encoding FVIII in a biologically acceptable carrier to the patient.

In certain embodiments of the inventive methods, FVIII is expressed at levels having a beneficial or therapeutic effect on the mammal; and/or FVIII is expressed in a cell, tissue or organ of the mammal Such embodiments include introduction of a CpG reduced nucleic acid variant encoding FVIII into a tissue or organ such as liver. Such embodiments also include introduction of a CpG reduced nucleic acid variant encoding FVIII into a secretory cell. Such embodiments further include introduction of a CpG reduced nucleic acid variant encoding FVIII into an endocrine cell or an endothelial cell. Such embodiments additionally include introduction of a CpG reduced nucleic acid variant encoding FVIII into an hepatocyte, a sinusoidal endothelial cell, a megakaryocyte, a platelet or hematopoetic stem cell.

Candidate subjects (e.g., a patient) and mammals (e.g., humans) for administration (e.g., delivery) of a CpG reduced nucleic acid variant encoding FVIII, or a vector comprising a CpG reduced nucleic acid variant encoding FVIII, or an expression vector comprising a CpG reduced nucleic acid variant encoding FVIII, or a virus or AAV vector comprising a CpG reduced nucleic acid variant encoding FVIII include those having or those at risk of having a disorder such as: hemophilia A, von Willebrand diseases and bleeding associated with trauma, injury, thrombosis, thrombocytopenia, stroke, coagulopathy, disseminated intravascular coagulation (DIC) or over-anticoagulation treatment disorder.

Candidate subjects (e.g., a patient) and mammals (e.g., humans) for administration (e.g., delivery) of a CpG reduced nucleic acid variant encoding FVIII, or a vector comprising a CpG reduced nucleic acid variant encoding FVIII, or an expression vector comprising CpG reduced nucleic acid variant encoding FVIII, or a virus or AAV vector comprising a CpG reduced nucleic acid variant encoding FVIII include those or sero-negative for AAV antibodies, as well as those having or those at risk of developing AAV antibodies. Such subjects (e.g., a patient) and mammals (e.g., humans) may be sero-negative or sero-positive for an AAV1, AAV2, AAV3, AAV4, AAV5, AAV6, AAV7, AAV8, AAV9, AAV10, AAV11, AAV-Rh10 or AAV-Rh74 serotype.

Compositions and methods of the invention therefore further include administering empty capsid AAV to said mammal or said patient. In particular embodiments, empty capsid of AAV1, AAV2, AAV3, AAV4, AAV5, AAV6, AAV7, AAV8, AAV9, AAV10, AAV11, AAV-12, AAV-Rh10 and/or AAV-Rh74 serotype is further administered to the mammal or patient.

Methods of administration (e.g., delivery) in accordance with the invention include any mode of contact or delivery, ex vivo or in vivo. In particular embodiments administration (e.g., delivery) is: intravenously, intraarterially, intramuscularly, subcutaneously, intra-cavity, intubation, or via catheter.

The invention also provide methods for testing CpG reduced nucleic acid variants encoding FVIII in small and large animal models that are tolerant to human FVIII in order to assess dosing and monitor immunogenicity of the variants. Use of animal models provide a setting that allows assessment of humans currently receiving protein replacement therapy with hFVIII-BDD without evidence of an anti-hFVIII antibody response who are likely to develop an immune response to such variants.

DESCRIPTION OF DRAWINGS

FIG. 4 shows NHP Study design.

FIG. 5A-5D show hFVIII antigen levels in NHPs following intravenous administration of either $2\times10^{12}$ (A), $5\times10^{12}$ (B) or $1\times10^{13}$ vg/kg (C) of AAV-SPK-8005. Lines represent individual animals. Human FVIII plasma levels were assayed by ELISA and represent repeated measurements, obtained by serial bleeding, on the same group of animals during the course of the study (n=2-3 animals per cohort). Human FVIII levels measured in vehicle-treated animals are shown in open squares in all three graphs.

ε=Development of inhibitors against FVIII.

Figure 6A:
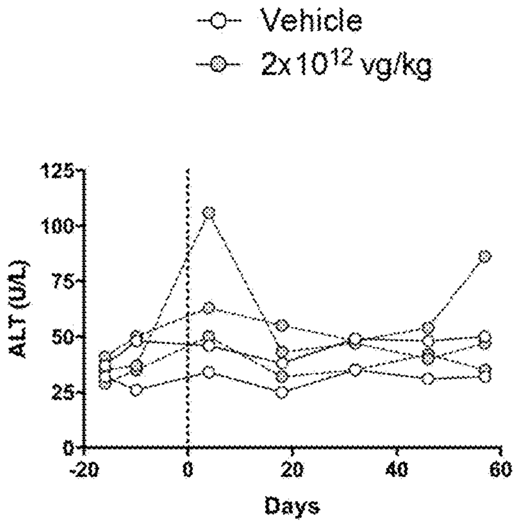
Figure 6C:
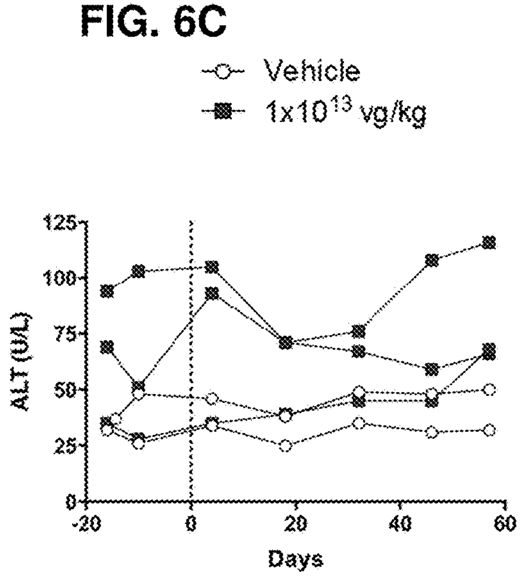
Figure 6B:
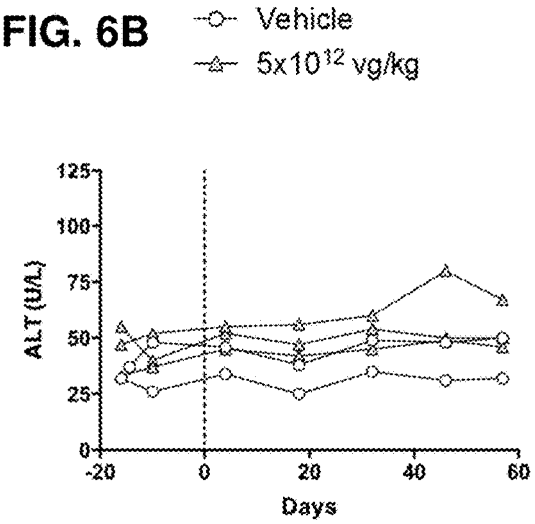

FIG. 6A-6C show ALT levels in NHPs, at $2\times10^{12}$ (A), $5\times10^{12}$ (B) or $1\times10^{13}$ vg/kg (C) of AAV-SPK-8005.

Figure 7A:
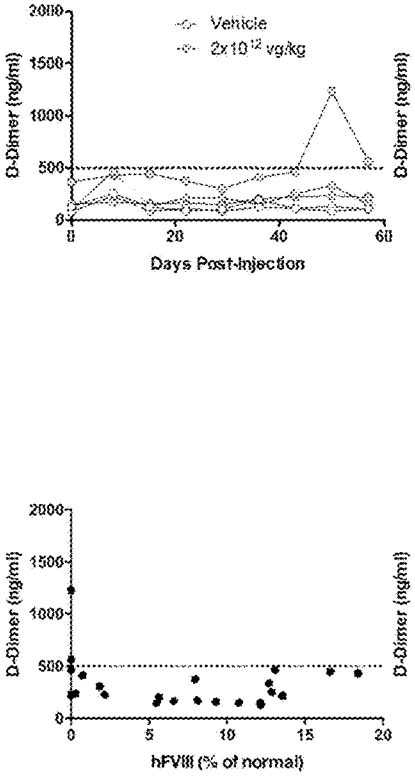
Figure 7B:
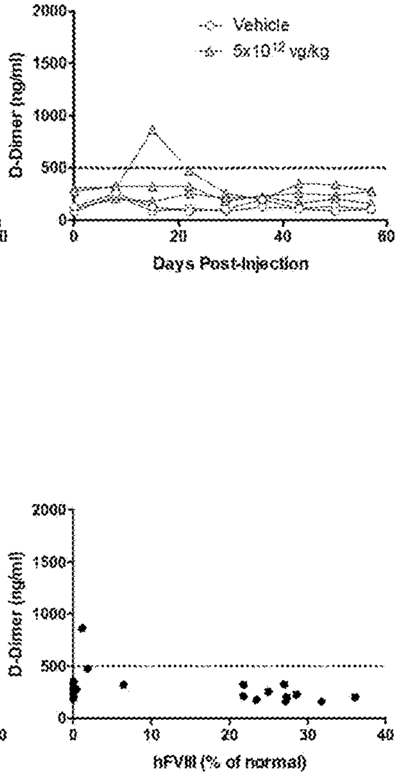
Figure 7C:
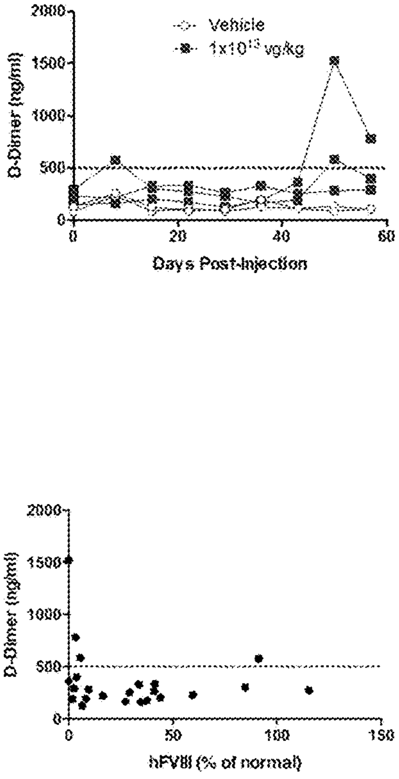

FIG. 7A-7C show D-Dimer levels in NHPs. D-dimer antigen concentration in plasma of NHPs following intravenous administration of either $2\times10^{12}$ (A), $5\times10^{12}$ (B) or $1\times10^{13}$ vg/kg (C) of AAV-SPK-8005. The dotted line indicates 500 ng/ml, the upper limit of normal for D-dimers in humans.

FIG. 8 shows a data summary of FVIII levels in the three doses of AAV-SPK-8005.

FIG. 9A-9D show levels of hFVIII in plasma of cynomolgus macaques following intravenous administration of either $2\times10^{12}$ (A), $6\times10^{12}$ (B) or $2\times10^{13}$ (vg/kg) (C) of AAV-SPK-8011(LK03 capsid)-hFVIII. Lines represent individual animals. hFVIII plasma levels were assayed by ELISA and represent repeated measurements, obtained by serial bleeding, on the same group of animals during the course of the study (n=3 animals per cohort). Human FVIII levels measured in vehicle-treated animals are shown in open squares (n=2). ε=Time when development of inhibitors against FVIII was detected in each individual animal.

Figure 10:
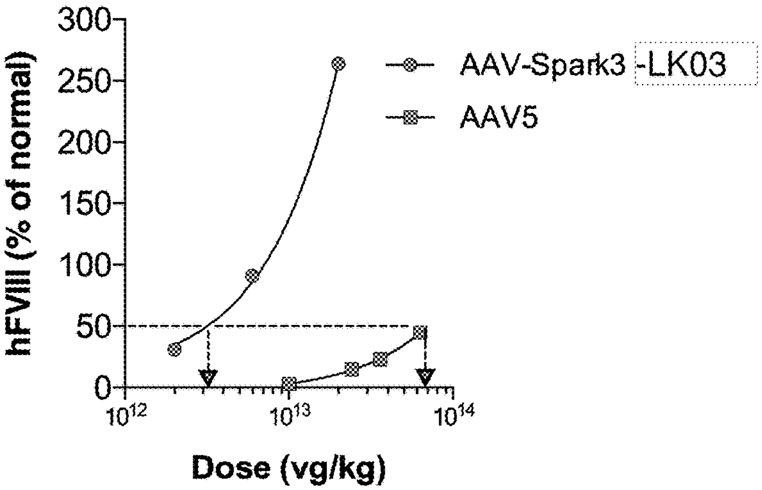

FIG. 10 shows a comparison of FVIII levels achieved with AAV-SPK-8011 (LKO3 capsid)-hFVIII to the reported levels of FVIII delivered by way of AAV vectors with AAV5 and AAV8 capsids. AAV5: www-biomarin-com-pdf-BioMarin R&D Day 4 20 2016.pdf, slide 16. AAV8: McIntosh J et al. Blood 2013; 121(17):3335-44.

Figure 11:
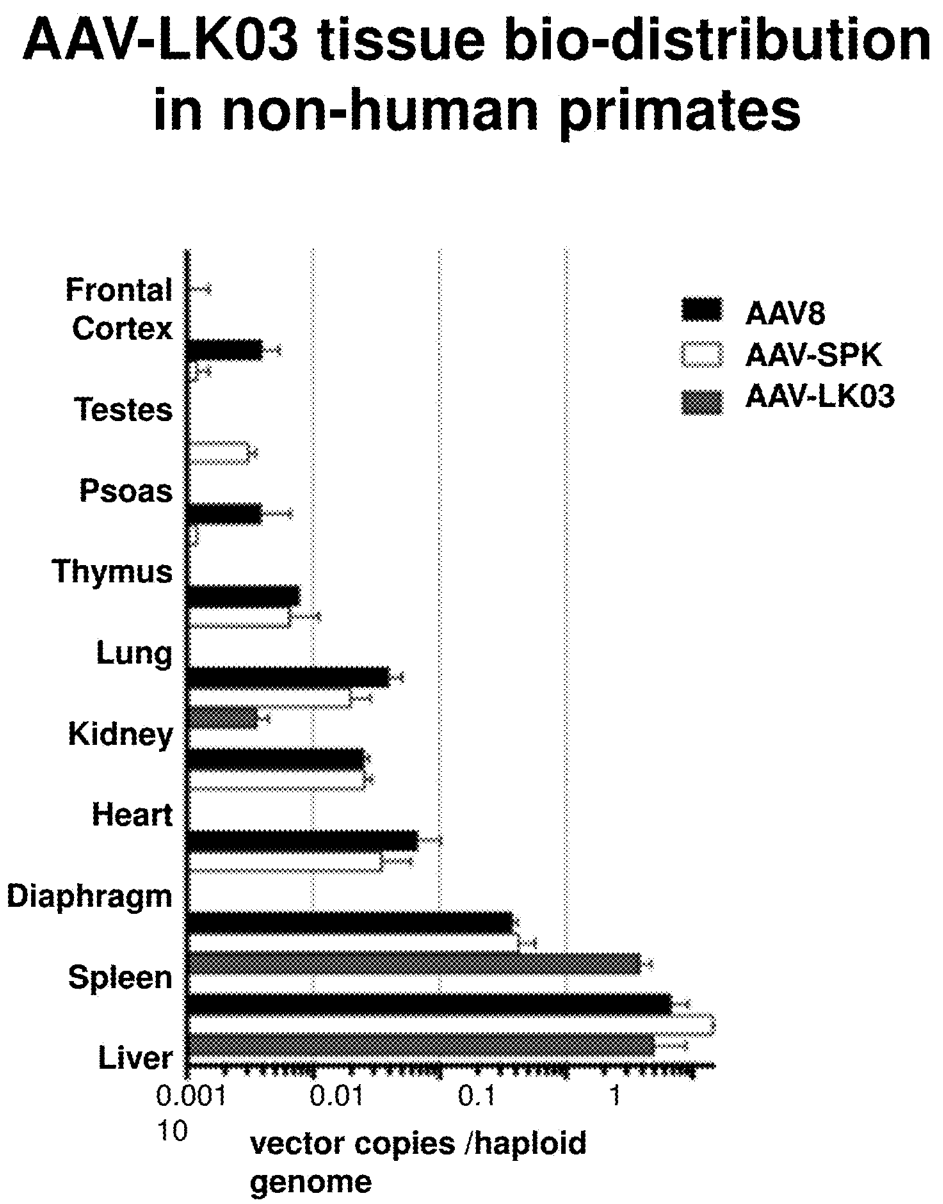

FIG. 11 shows AAV-SPK (SEQ ID NO:28) and AAV-LK03 (SEQ ID NO:27) tissue biodistribution in non-human primates, predominanyl in kidney, spleen and liver ($3^{rd}$ bar for each tissue).

Figure 12:
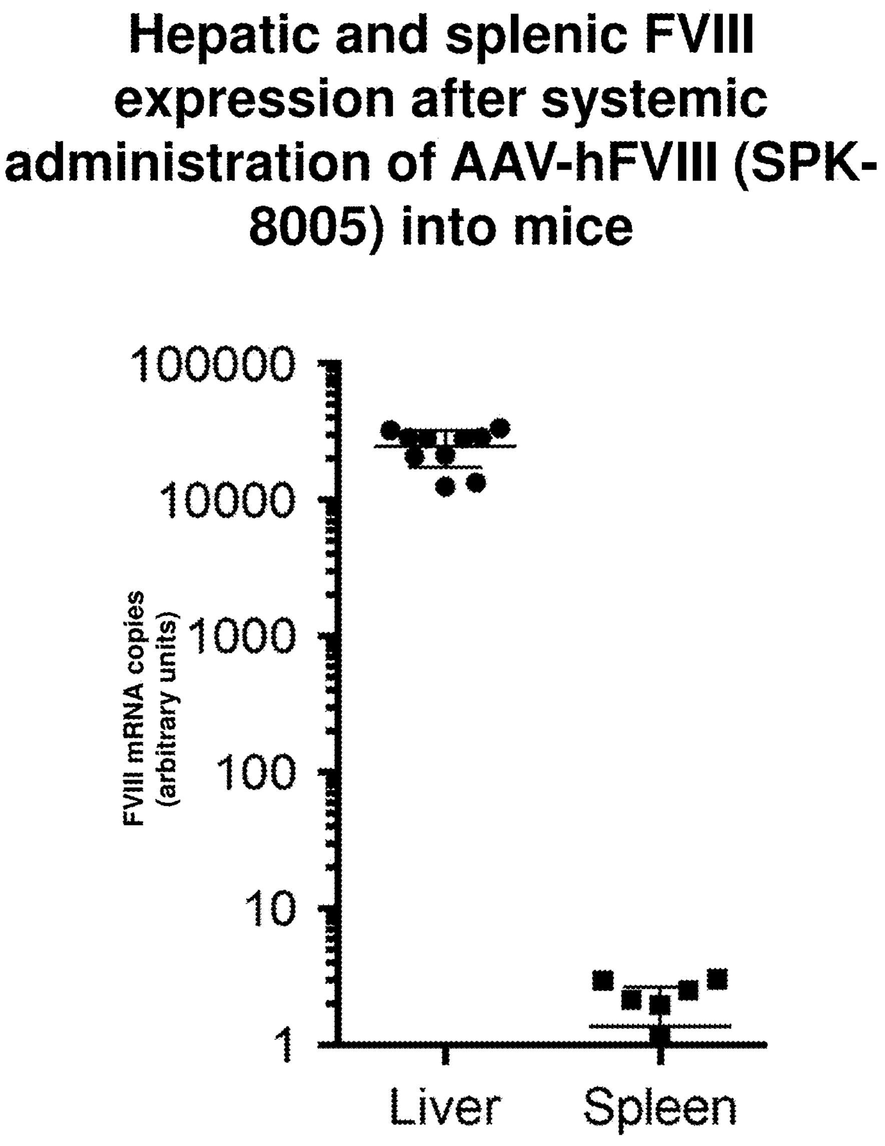

FIG. 12 shows hepatic and splenic FVIII expression after systemic administration of AAV-SPK-8005 into mice.

Figure 13:
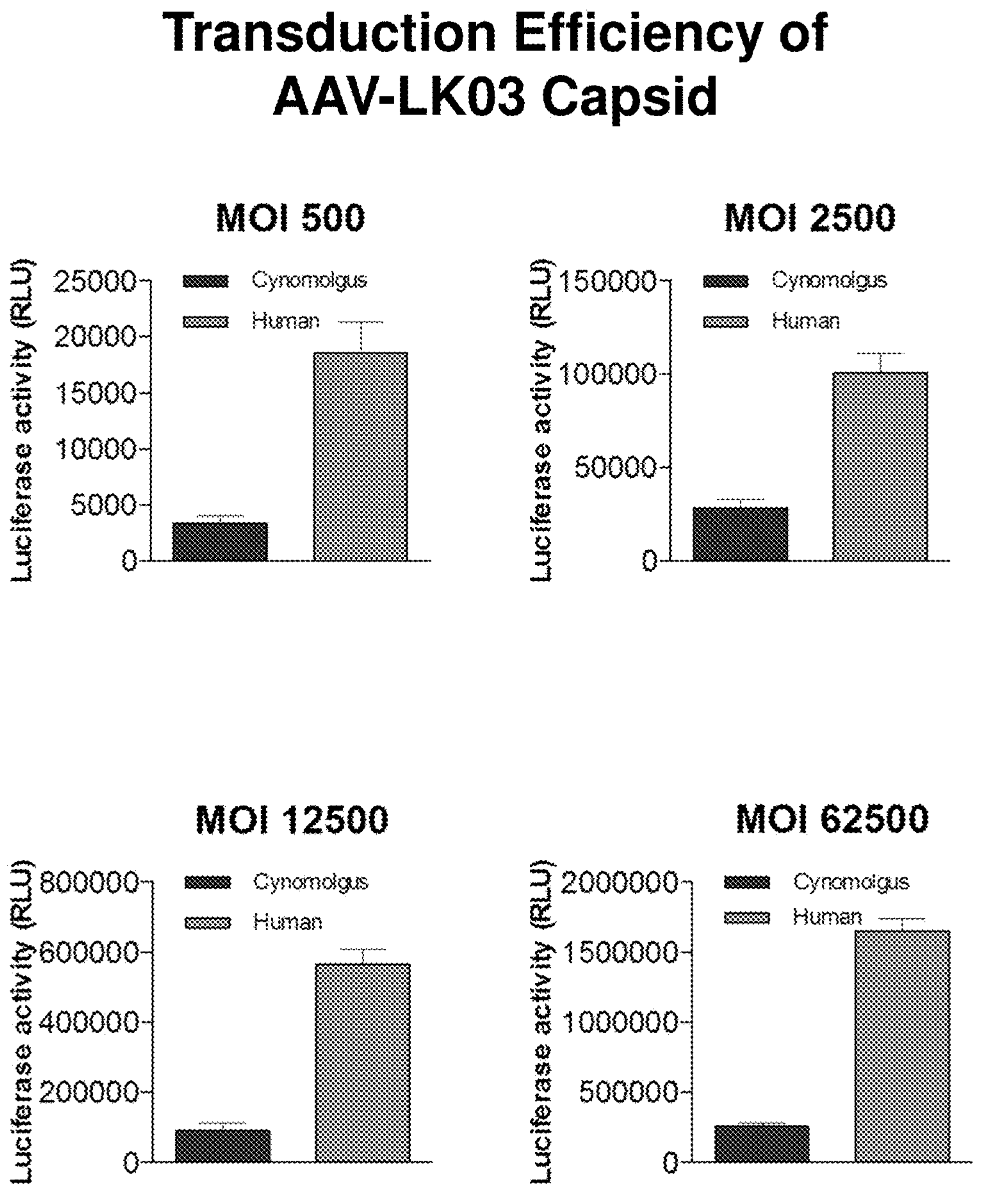

FIG. 13 shows transduction efficiency of the AAV-LK03 capsid analyzed in vitro. X-axis, cynomolgus (left vertical bar), human (right vertical bar).

Figure 14A:
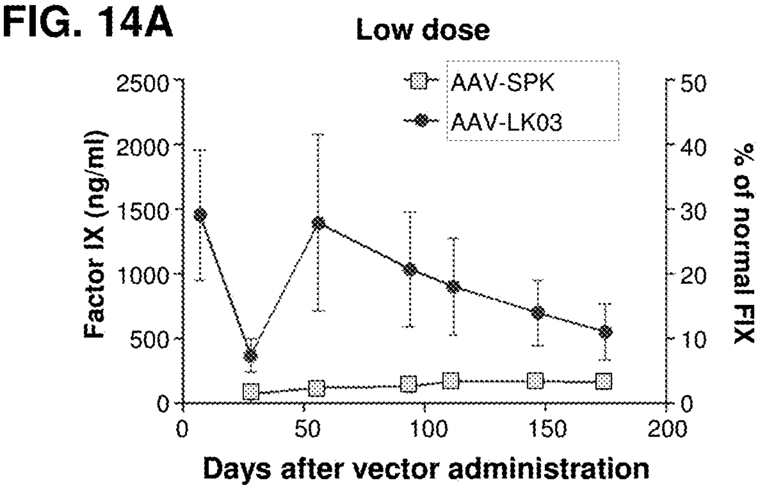
Figure 14B:
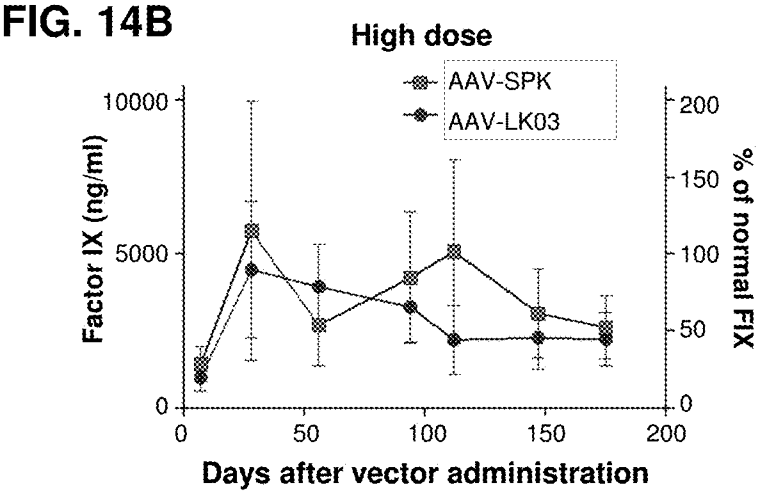

FIG. 14A-14B show plasma concentration of hFIX in rabbits after AAV administration. Rabbits received intravenous injection of hFIX vectors AAV-SPK or AAV-LK03 at doses of (A) $1\times10^{12}$ vg/kg (low dose, n=4) or (B) $1\times10^{13}$ vg/kg (high dose, n=3-5). Human FIX levels between groups were compared using a 2-tailed Mann-Whitney test. No significant differences were observed. Animals 5 and 15 in the low dose cohorts were excluded from the analysis due to misinjection. Animals 9 and 10 were also excluded from the graph as they developed neutralizing antibodies against human FIX.

Figure 15A:
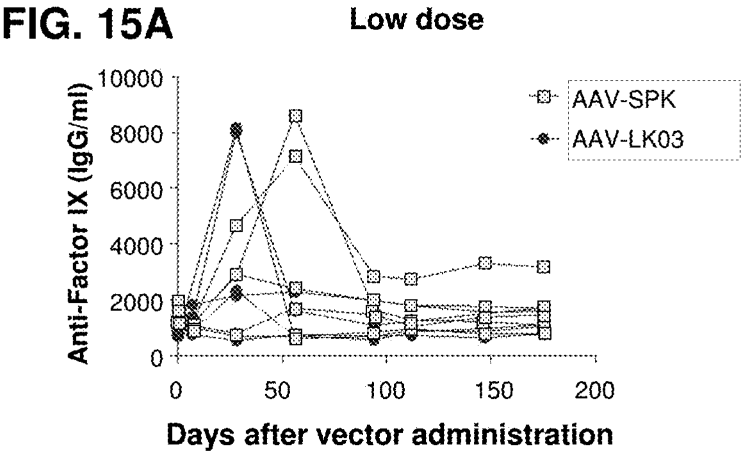
Figure 15B:
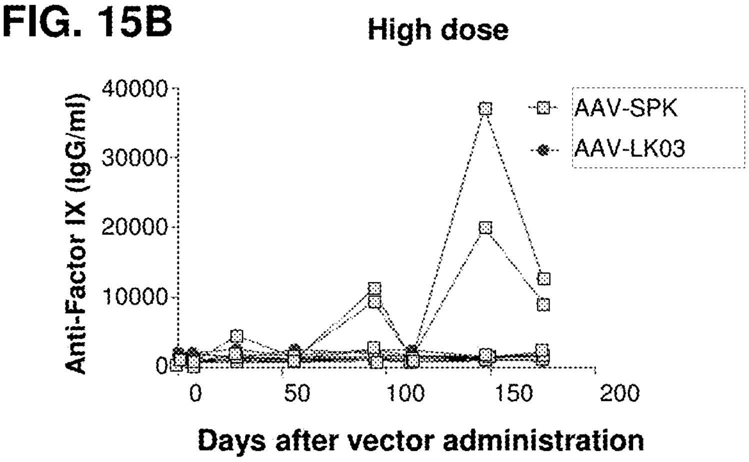

FIG. 15A-15B show a time course of antibody formation to human FIX (anti-FIX). Rabbits received intravenous injection of hFIX vectors AAV-SPK or AAV-LK03 at doses of (A) $1\times10^{12}$ vg/kg (low dose, n=4) or (B) $1\times10^{13}$ vg/kg (high dose, n=3-5). The data are shown for each individual animal.

DETAILED DESCRIPTION

Disclosed herein are CpG reduced nucleic acid variants encoding FVIII, distinct from wild-type nucleic acid that encode FVIII. Such CpG reduced nucleic acid variants encoding FVIII can be expressed at increased levels in cells and/or animals, which in turn can provide increased FVIII protein levels in vivo. Also disclosed are CpG reduced nucleic acid variant encoding FVIII that can provide for greater biological activity in vitro and/or in vivo. Exemplary CpG reduced nucleic acid variant encoding FVIII can exhibit one or more of the following: 1) increased expression in cells and/or animals; 2) increased activity; and 3) a therapeutic effect at lower AAV doses than wild-type hFVIII.

The terms "polynucleotide" and "nucleic acid" are used interchangeably herein to refer to all forms of nucleic acid, oligonucleotides, including deoxyribonucleic acid (DNA) and ribonucleic acid (RNA). Polynucleotides include genomic DNA, cDNA and antisense DNA, and spliced or unspliced mRNA, rRNA tRNA and inhibitory DNA or RNA (RNAi, e.g., small or short hairpin (sh)RNA, microRNA (miRNA), small or short interfering (si)RNA, trans-splicing RNA, or antisense RNA). Polynucleotides include naturally occurring, synthetic, and intentionally modified or altered polynucleotides (e.g., variant nucleic acid). Polynucleotides can be single, double, or triplex, linear or circular, and can be of any length. In discussing polynucleotides, a sequence or structure of a particular polynucleotide may be described herein according to the convention of providing the sequence in the 5' to 3' direction.

As used herein, the terms "modify" or "variant" and grammatical variations thereof, mean that a nucleic acid, polypeptide or subsequence thereof deviates from a reference sequence. Modified and variant sequences may therefore have substantially the same, greater or less expression, activity or function than a reference sequence, but at least retain partial activity or function of the reference sequence. A particular example of a modification or variant is a CpG reduced nucleic acid variant encoding FVIII.

A "nucleic acid" or "polynucleotide" variant refers to a modified sequence which has been genetically altered compared to wild-type. The sequence may be genetically modified without altering the encoded protein sequence. Alternatively, the sequence may be genetically modified to encode a variant protein. A nucleic acid or polynucleotide variant can also refer to a combination sequence which has been codon modified to encode a protein that still retains at least partial sequence identity to a reference sequence, such as wild-type protein sequence, and also has been codon-modified to encode a variant protein. For example, some codons of such a nucleic acid variant will be changed without altering the amino acids of the protein (FVIII) encoded thereby, and some codons of the nucleic acid variant will be changed which in turn changes the amino acids of the protein (FVIII) encoded thereby.

The term "variant Factor VIII (FVIII)" refers to a modified FVIII which has been genetically altered as compared to unmodified wild-type FVIII (e.g., SEQ ID NO:19) or FVIII-BDD. Such a variant can be referred to as a "nucleic acid variant encoding Factor VIII (FVIII)." A particular example of a variant is a CpG reduced nucleic acid encoding FVIII or FVIII-BDD protein. The term "variant" need not appear in each instance of a reference made to CpG reduced nucleic acid encoding FVIII. Likewise, the term "CpG reduced nucleic acid" or the like may omit the term "variant" but it is intended that reference to "CpG reduced nucleic acid" includes variants at the genetic level.

FVIII constructs having reduced CpG content can exhibit improvements compared to wild-type FVIII or FVIII-BDD in which CpG content has not been reduced, and do so without modifications to the nucleic acid that result in amino acid changes to the encoded FVIII or FVIII-BDD protein. When comparing expression, if the CpG reduced nucleic acid encodes a FVIII protein that retains the B-domain, it is appropriate to compare it to wild-type FVIII expression; and if the CpG reduced nucleic acid encodes a FVIII protein without a B-domain, it is compared to expression of wild-type FVIII that also has a B-domain deletion.

A "variant Factor VIII (FVIII)" can also mean a modified FVIII protein such that the modified protein has an amino acid alteration compared to wild-type FVIII. Again, when comparing activity and/or stability, if the encoded variant FVIII protein retains the B-domain, it is appropriate to compare it to wild-type FVIII; and if the encoded variant FVIII protein has a B-domain deletion, it is compared to wild-type FVIII that also has a B-domain deletion.

A variant FVIII can include a portion of the B-domain. Thus, FVIII-BDD includes a portion of the B-domain. Typically, in FVIII-BDD most of the B-domain is deleted.

A variant FVIII can include an "SQ" sequence set forth as SFSQNPPVLKRHQR (SEQ ID NO:29). Typically, such a variant FVIII with an SQ (FVIII/SQ) has a BDD, e.g., at least all or a part of BD is deleted. Variant FVIII, such as FVIII-BDD can have all or a part of the "SQ" sequence, i.e. all or a part of SEQ ID NO:29. Thus, for example, a variant FVIII-BDD with an SQ sequence (SFSQNPPVLKRHQR, SEQ ID NO:29) can have all or just a portion of the amino acid sequence SFSQNPPVLKRHQR. For example, FVIII-BDD can have 1, 2, 3, 4, 5, 6, 7, 8, 9, 10, 11, 12 or 13 amino acid residues of SFSQNPPVLKRHQR included. Thus, SFSQNPPVLKRHQR with 1, 2, 3, 4, 5, 6, 7, 8, 9, 10, 11, 12 or 13 internal deletions as well as 1, 2, 3, 4, 5, 6, 7, 8, 9, 10, 11, 12 or 13 amino- or carboxy terminal deletions are included in the variant FVIII proteins set forth herein.

The "polypeptides," "proteins" and "peptides" encoded by the "nucleic acid" or "polynucleotide" sequences," include full-length native (FVIII) sequences, as with naturally occurring wild-type proteins, as well as functional subsequences, modified forms or sequence variants so long as the subsequence, modified form or variant retain some degree of functionality of the native full-length protein. For example, a CpG reduced nucleic acid encoding FVIII protein can have a B-domain deletion as set forth herein and retain clotting function. In methods and uses of the invention, such polypeptides, proteins and peptides encoded by the nucleic acid sequences can be but are not required to be identical to the endogenous protein that is defective, or whose expression is insufficient, or deficient in the treated mammal.

Non-limiting examples of modifications include one or more nucleotide or amino acid substitutions (e.g., 1-3, 3-5, 5-10, 10-15, 15-20, 20-25, 25-30, 30-40, 40-50, 50-100, 100-150, 150-200, 200-250, 250-500, 500-750, 750-850 or more nucleotides or residues). An example of a nucleic acid modification is CpG reduction. In certain embodiments, a CpG reduced nucleic acid encoding FVIII, such as human FVIII protein, has 10 or fewer CpGs compared to wild-type sequence encoding human Factor FVIII; or has 5 or fewer CpGs compared to wild-type sequence encoding human Factor FVIII; or has no more than 5 CpGs in the CpG reduced nucleic acid encoding FVIII.

An example of an amino acid modification is a conservative amino acid substitution or a deletion (e.g., subsequences or fragments) of a reference sequence, e.g. FVIII, such as FVIII with a B-domain deletion. In particular embodiments, a modified or variant sequence retains at least part of a function or activity of unmodified sequence.

All mammalian and non-mammalian forms of nucleic acid encoding proteins, including other mammalian forms of the CpG reduced nucleic acid encoding FVIII and FVIII proteins disclosed herein are expressly included, either known or unknown. Thus, the invention includes genes and proteins from non-mammals, mammals other than humans, and humans, which genes and proteins function in a substantially similar manner to the FVIII (e.g., human) genes and proteins described herein.

The term "vector" refers to small carrier nucleic acid molecule, a plasmid, virus (e.g., AAV vector), or other vehicle that can be manipulated by insertion or incorporation of a nucleic acid. Such vectors can be used for genetic manipulation (i.e., "cloning vectors"), to introduce/transfer polynucleotides into cells, and to transcribe or translate the inserted polynucleotide in cells. An "expression vector" is a specialized vector that contains a gene or nucleic acid sequence with the necessary regulatory regions needed for expression in a host cell. A vector nucleic acid sequence generally contains at least an origin of replication for propagation in a cell and optionally additional elements, such as a heterologous polynucleotide sequence, expression control element (e.g., a promoter, enhancer), intron, ITR(s), selectable marker (e.g., antibiotic resistance), polyadenylation signal.

A viral vector is derived from or based upon one or more nucleic acid elements that comprise a viral genome. Particular viral vectors include lentivirus, pseudo-typed lentivirus and parvo-virus vectors, such as adeno-associated virus (AAV) vectors. Also provided are vectors comprising a CpG reduced nucleic acid encoding FVIII.

The term "recombinant," as a modifier of vector, such as recombinant viral, e.g., lenti- or parvo-virus (e.g., AAV) vectors, as well as a modifier of sequences such as recombinant polynucleotides and polypeptides, means that the compositions have been manipulated (i.e., engineered) in a fashion that generally does not occur in nature. A particular example of a recombinant vector, such as an AAV vector would be where a polynucleotide that is not normally present in the wild-type viral (e.g., AAV) genome is inserted within the viral genome. An example of a recombinant polynucleotide would be where a CpG reduced nucleic acid encoding a FVIII protein is cloned into a vector, with or without 5', 3' and/or intron regions that the gene is normally associated within the viral (e.g., AAV) genome. Although the term "recombinant" is not always used herein in reference to vectors, such as viral and AAV vectors, as well as sequences such as polynucleotides, recombinant forms including polynucleotides, are expressly included in spite of any such omission.

A recombinant viral "vector" or "AAV vector" is derived from the wild type genome of a virus, such as AAV by using molecular methods to remove the wild type genome from the virus (e.g., AAV), and replacing with a non-native nucleic acid, such as a CpG reduced nucleic acid encoding FVIII. Typically, for AAV one or both inverted terminal repeat (ITR) sequences of AAV genome are retained in the AAV vector. A "recombinant" viral vector (e.g., AAV) is distinguished from a viral (e.g., AAV) genome, since all or a part of the viral genome has been replaced with a non-native sequence with respect to the viral (e.g., AAV) genomic nucleic acid such as a CpG reduced nucleic acid encoding FVIII. Incorporation of a non-native sequence therefore defines the viral vector (e.g., AAV) as a "recombinant" vector, which in the case of AAV can be referred to as a "rAAV vector."

A recombinant vector (e.g., lenti-, parvo-, AAV) sequence can be packaged—referred to herein as a "particle" for subsequent infection (transduction) of a cell, ex vivo, in vitro or in vivo. Where a recombinant vector sequence is encapsidated or packaged into an AAV particle, the particle can also be referred to as a "rAAV." Such particles include proteins that encapsidate or package the vector genome. Particular examples include viral envelope proteins, and in the case of AAV, capsid proteins.

A vector "genome" refers to the portion of the recombinant plasmid sequence that is ultimately packaged or encapsidated to form a viral (e.g., AAV) particle. In cases where recombinant plasmids are used to construct or manufacture recombinant vectors, the vector genome does not include the portion of the "plasmid" that does not correspond to the vector genome sequence of the recombinant plasmid. This non vector genome portion of the recombinant plasmid is referred to as the "plasmid backbone," which is important for cloning and amplification of the plasmid, a process that is needed for propagation and recombinant virus production, but is not itself packaged or encapsidated into virus (e.g., AAV) particles. Thus, a vector "genome" refers to the nucleic acid that is packaged or encapsidated by virus (e.g., AAV).

A "transgene" is used herein to conveniently refer to a nucleic acid that is intended or has been introduced into a cell or organism. Transgenes include any nucleic acid, such as a gene that encodes a polypeptide or protein (e.g., a CpG reduced nucleic acid encoding Factor VIII).

In a cell having a transgene, the transgene has been introduced/transferred by way of vector, such as AAV, "transduction" or "transfection" of the cell. The terms "transduce" and "transfect" refer to introduction of a molecule such as a nucleic acid into a cell or host organism. The transgene may or may not be integrated into genomic nucleic acid of the recipient cell. If an introduced nucleic acid becomes integrated into the nucleic acid (genomic DNA) of the recipient cell or organism it can be stably maintained in that cell or organism and further passed on to or inherited by progeny cells or organisms of the recipient cell or organism. Finally, the introduced nucleic acid may exist in the recipient cell or host organism extrachromosomally, or only transiently.

A "transduced cell" is a cell into which the transgene has been introduced. Accordingly, a "transduced" cell (e.g., in a mammal, such as a cell or tissue or organ cell), means a genetic change in a cell following incorporation of an exogenous molecule, for example, a nucleic acid (e.g., a transgene) into the cell. Thus, a "transduced" cell is a cell into which, or a progeny thereof in which an exogenous nucleic acid has been introduced. The cell(s) can be propagated and the introduced protein expressed, or nucleic acid transcribed. For gene therapy uses and methods, a transduced cell can be in a subject.

An "expression control element" refers to nucleic acid sequence(s) that influence expression of an operably linked nucleic acid. Control elements, including expression control elements as set forth herein such as promoters and enhancers, Vector sequences including AAV vectors can include one or more "expression control elements." Typically, such elements are included to facilitate proper heterologous polynucleotide transcription and if appropriate translation (e.g., a promoter, enhancer, splicing signal for introns, maintenance of the correct reading frame of the gene to permit in-frame translation of mRNA and, stop codons etc.). Such elements typically act in cis, referred to as a "cis acting" element, but may also act in trans.

Expression control can be at the level of transcription, translation, splicing, message stability, etc. Typically, an expression control element that modulates transcription is juxtaposed near the 5' end (i.e., "upstream") of a transcribed nucleic acid. Expression control elements can also be located at the 3' end (i.e., "downstream") of the transcribed sequence or within the transcript (e.g., in an intron). Expression control elements can be located adjacent to or at a distance away from the transcribed sequence (e.g., 1-10, 10-25, 25-50, 50-100, 100 to 500, or more nucleotides from the polynucleotide), even at considerable distances. Nevertheless, owing to the length limitations of certain vectors, such as AAV vectors, expression control elements will typically be within 1 to 1000 nucleotides from the transcribed nucleic acid.

Functionally, expression of operably linked nucleic acid is at least in part controllable by the element (e.g., promoter) such that the element modulates transcription of the nucleic acid and, as appropriate, translation of the transcript. A specific example of an expression control element is a promoter, which is usually located 5' of the transcribed sequence e.g., a CpG reduced nucleic acid encoding FVIII. A promoter typically increases an amount expressed from operably linked nucleic acid as compared to an amount expressed when no promoter exists.

An "enhancer" as used herein can refer to a sequence that is located adjacent to the heterologous polynucleotide. Enhancer elements are typically located upstream of a promoter element but also function and can be located downstream of or within a sequence (e.g., a CpG reduced nucleic acid encoding FVIII). Hence, an enhancer element can be located 100 base pairs, 200 base pairs, or 300 or more base pairs upstream or downstream of a CpG reduced nucleic acid encoding FVIII. Enhancer elements typically increase expressed of an operably linked nucleic acid above expression afforded by a promoter element.

An expression construct may comprise regulatory elements which serve to drive expression in a particular cell or tissue type. Expression control elements (e.g., promoters) include those active in a particular tissue or cell type, referred to herein as a "tissue-specific expression control elements/promoters." Tissue-specific expression control elements are typically active in specific cell or tissue (e.g., liver). Expression control elements are typically active in particular cells, tissues or organs because they are recognized by transcriptional activator proteins, or other regulators of transcription, that are unique to a specific cell, tissue or organ type. Such regulatory elements are known to those of skill in the art (see, e.g., Sambrook et al. (1989) and Ausubel et al. (1992)).

The incorporation of tissue specific regulatory elements in the expression constructs of the invention provides for at least partial tissue tropism for the expression of a CpG reduced nucleic acid encoding FVIII. Examples of promoters that are active in liver are the TTR promoter, human alpha 1-antitrypsin (hAAT) promoter; albumin, Miyatake, et al. *J. Virol.,* 71:5124-32 (1997); hepatitis B virus core promoter, Sandig, et al., *Gene Ther.* 3:1002-9 (1996); alpha-fetoprotein (AFP), Arbuthnot, et al., *Hum. Gene. Ther.,* 7:1503-14 (1996)], among others. An example of an enhancer active in liver is apolipoprotein E (apoE) HCR-1 and HCR-2 (Allan et al., *J. Biol. Chem.,* 272:29113-19 (1997)).

Expression control elements also include ubiquitous or promiscuous promoters/enhancers which are capable of driving expression of a polynucleotide in many different cell types. Such elements include, but are not limited to the cytomegalovirus (CMV) immediate early promoter/enhancer sequences, the Rous sarcoma virus (RSV) promoter/enhancer sequences and the other viral promoters/enhancers active in a variety of mammalian cell types, or synthetic elements that are not present in nature (see, e.g., Boshart et al, Cell, 41:521-530 (1985)), the SV40 promoter, the dihydrofolate reductase promoter, the cytoplasmic β-actin promoter and the phosphoglycerol kinase (PGK) promoter.

Expression control elements also can confer expression in a manner that is regulatable, that is, a signal or stimuli increases or decreases expression of the operably linked heterologous polynucleotide. A regulatable element that increases expression of the operably linked polynucleotide in response to a signal or stimuli is also referred to as an "inducible element" (i.e., is induced by a signal). Particular examples include, but are not limited to, a hormone (e.g., steroid) inducible promoter. Typically, the amount of increase or decrease conferred by such elements is proportional to the amount of signal or stimuli present; the greater the amount of signal or stimuli, the greater the increase or decrease in expression. Particular non-limiting examples include zinc-inducible sheep metallothionine (MT) promoter; the steroid hormone-inducible mouse mammary tumor virus (MMTV) promoter; the T7 polymerase promoter system (WO 98/10088); the tetracycline-repressible system (Gossen, et al., *Proc. Natl. Acad. Sci. USA,* 89:5547-5551 (1992)); the tetracycline-inducible system (Gossen, et al., *Science.* 268:1766-1769 (1995); see also Harvey, et al., *Curr. Opin. Chem. Biol.* 2:512-518 (1998)); the RU486-inducible system (Wang, et al., *Nat. Biotech.* 15:239-243 (1997) and Wang, et al., *Gene Ther.* 4:432-441 (1997)]; and the rapamycin-inducible system (Magari, et al., *J. Clin.*

*Invest.* 100:2865-2872 (1997); Rivera, et al., *Nat. Medicine.* 2:1028-1032 (1996)). Other regulatable control elements which may be useful in this context are those which are regulated by a specific physiological state, e.g., temperature, acute phase, development.

Expression control elements also include the native elements(s) for the heterologous polynucleotide. A native control element (e.g., promoter) may be used when it is desired that expression of the heterologous polynucleotide should mimic the native expression. The native element may be used when expression of the heterologous polynucleotide is to be regulated temporally or developmentally, or in a tissue-specific manner, or in response to specific transcriptional stimuli. Other native expression control elements, such as introns, polyadenylation sites or Kozak consensus sequences may also be used.

The term "operably linked" means that the regulatory sequences necessary for expression of a coding sequence are placed in the appropriate positions relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

In the example of an expression control element in operable linkage with a nucleic acid, the relationship is such that the control element modulates expression of the nucleic acid. More specifically, for example, two DNA sequences operably linked means that the two DNAs are arranged (cis or trans) in such a relationship that at least one of the DNA sequences is able to exert a physiological effect upon the other sequence.

Accordingly, additional elements for vectors include, without limitation, an expression control (e.g., promoter/enhancer) element, a transcription termination signal or stop codon, 5' or 3' untranslated regions (e.g., polyadenylation (polyA) sequences) which flank a sequence, such as one or more copies of an AAV ITR sequence, or an intron.

Further elements include, for example, filler or stuffer polynucleotide sequences, for example to improve packaging and reduce the presence of contaminating nucleic acid. AAV vectors typically accept inserts of DNA having a size range which is generally about 4 kb to about 5.2 kb, or slightly more. Thus, for shorter sequences, inclusion of a stuffer or filler in order to adjust the length to near or at the normal size of the virus genomic sequence acceptable for AAV vector packaging into virus particle. In various embodiments, a filler/stuffer nucleic acid sequence is an untranslated (non-protein encoding) segment of nucleic acid. For a nucleic acid sequence less than 4.7 Kb, the filler or stuffer polynucleotide sequence has a length that when combined (e.g., inserted into a vector) with the sequence has a total length between about 3.0-5.5 Kb, or between about 4.0-5.0 Kb, or between about 4.3-4.8 Kb.

An intron can also function as a filler or stuffer polynucleotide sequence in order to achieve a length for AAV vector packaging into a virus particle. Introns and intron fragments that function as a filler or stuffer polynucleotide sequence also can enhance expression.

The phrase "hemostasis related disorder" refers to bleeding disorders such as hemophilia A, hemophilia A patients with inhibitory antibodies, deficiencies in coagulation Factors, VII, VIII, IX and X, XI, V, XII, II, von Willebrand factor, combined FV/FVIII deficiency, vitamin K epoxide reductase C1 deficiency, gamma-carboxylase deficiency; bleeding associated with trauma, injury, thrombosis, thrombocytopenia, stroke, coagulopathy, disseminated intravascular coagulation (DIC); over-anticoagulation associated with heparin, low molecular weight heparin, pentasaccharide, warfarin, small molecule antithrombotics (i.e. FXa inhibitors); and platelet disorders such as, Bernard Soulier syndrome, Glanzman thromblastemia, and storage pool deficiency.

The term "isolated," when used as a modifier of a composition, means that the compositions are made by the hand of man or are separated, completely or at least in part, from their naturally occurring in vivo environment. Generally, isolated compositions are substantially free of one or more materials with which they normally associate with in nature, for example, one or more protein, nucleic acid, lipid, carbohydrate, cell membrane.

With reference to nucleic acids of the invention, the term "isolated" refers to a nucleic acid molecule that is separated from one or more sequences with which it is immediately contiguous (in the 5' and 3' directions) in the naturally occurring genome (genomic DNA) of the organism from which it originates. For example, the "isolated nucleic acid" may comprise a DNA or cDNA molecule inserted into a vector, such as a plasmid or virus vector, or integrated into the DNA of a prokaryote or eukaryote.

With respect to RNA molecules of the invention, the term "isolated" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to protein, the term "isolated protein" or "isolated and purified protein" is sometimes used herein. This term refers primarily to a protein produced by expression of an isolated nucleic acid molecule. Alternatively, this term may refer to a protein which has been sufficiently separated from other proteins with which it would naturally be associated, so as to exist in "substantially pure" form.

The term "isolated" does not exclude combinations produced by the hand of man, for example, a recombinant vector (e.g., rAAV) sequence, or virus particle that packages or encapsidates a vector genome and a pharmaceutical formulation. The term "isolated" also does not exclude alternative physical forms of the composition, such as hybrids/chimeras, multimers/oligomers, modifications (e.g., phosphorylation, glycosylation, lipidation) or derivatized forms, or forms expressed in host cells produced by the hand of man.

The term "substantially pure" refers to a preparation comprising at least 50-60% by weight the compound of interest (e.g., nucleic acid, oligonucleotide, protein, etc.). The preparation can comprise at least 75% by weight, or about 90-99% by weight, of the compound of interest. Purity is measured by methods appropriate for the compound of interest (e.g. chromatographic methods, agarose or polyacrylamide gel electrophoresis, HPLC analysis, and the like).

The phrase "consisting essentially of" when referring to a particular nucleotide sequence or amino acid sequence means a sequence having the properties of a given SEQ ID NO. For example, when used in reference to an amino acid sequence, the phrase includes the sequence per se and molecular modifications that would not affect the basic and novel characteristics of the sequence.

The term "oligonucleotide," as used herein refers to primers and probes, and is defined as a nucleic acid molecule comprised of two or more ribo- or deoxyribonucleotides, such as more than three. The exact size of the oligonucleotide will depend on various factors and on the particular application for which the oligonucleotide is used.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and method of use. For example, for diagnostic applications, depending on the complexity of the target sequence, the oligonucleotide probe typically contains 15-25 or more nucleotides, although it may contain fewer nucleotides.

The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to act functionally as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product.

The primer may vary in length depending on the particular conditions and requirements of the application. For example, in diagnostic applications, the oligonucleotide primer is typically 15-25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

The term "identity," "homology" and grammatical variations thereof, mean that two or more referenced entities are the same, when they are "aligned" sequences. Thus, by way of example, when two polypeptide sequences are identical, they have the same amino acid sequence, at least within the referenced region or portion. Where two polynucleotide sequences are identical, they have the same polynucleotide sequence, at least within the referenced region or portion. The identity can be over a defined area (region or domain) of the sequence. An "area" or "region" of identity refers to a portion of two or more referenced entities that are the same. Thus, where two protein or nucleic acid sequences are identical over one or more sequence areas or regions they share identity within that region. An "aligned" sequence refers to multiple polynucleotide or protein (amino acid) sequences, often containing corrections for missing or additional bases or amino acids (gaps) as compared to a reference sequence.

The identity can extend over the entire length or a portion of the sequence. In certain embodiments, the length of the sequence sharing the percent identity is 2, 3, 4, 5 or more contiguous nucleic acids or amino acids, e.g., 6, 7, 8, 9, 10, 11, 12, 13, 14, 15, 16, 17, 18, 19, 20, etc. contiguous nucleic acids or amino acids. In additional embodiments, the length of the sequence sharing identity is 21 or more contiguous nucleic acids or amino acids, e.g., 21, 22, 23, 24, 25, 26, 27, 28, 29, 30, 31, 32, 33, 34, 35, 36, 37, 38, 39, 40, etc. contiguous nucleic acids or amino acids. In further embodiments, the length of the sequence sharing identity is 41 or more contiguous nucleic acids or amino acids, e.g. 42, 43, 44, 45, 45, 47, 48, 49, 50, etc., contiguous nucleic acids or amino acids. In yet further embodiments, the length of the sequence sharing identity is 50 or more contiguous nucleic acids or amino acids, e.g., 50-55, 55-60, 60-65, 65-70, 70-75, 75-80, 80-85, 85-90, 90-95, 95-100, 100-150, 150-200, 200-250, 250-300, 300-500, 500-1,000, etc. contiguous nucleic acids or amino acids.

As set forth herein, CpG reduced nucleic acid variants encoding FVIII will be distinct from wild-type but may exhibit sequence identity with wild-type FVIII protein with, or without B-domain. In CpG reduced nucleic acid variants encoding FVIII, at the nucleotide sequence level, a CpG reduced nucleic acid encoding FVIII will typically be at least about 70% identical, more typically about 75% identical, even more typically about 80%-85% identical to wild-type FVIII encoding nucleic acid. Thus, for example, a CpG reduced nucleic acid encoding FVIII may have 75%-85% identity to wild-type FVIII encoding gene, or to each other, i.e., X01 vs. X02, X03 vs. X04, etc. as set forth herein.

At the amino acid sequence level, a variant such as a variant FVIII protein will be at least about 70% identical, more typically about 75% identical, or 80% identical, even more typically about 85 identity, or 90% or more identity. In other embodiments, a variant such as a variant FVIII protein has at least 90%, 91%, 92%, 93%, 94%, 95%, 96%, 97%, 98%, 99% or more identity to a reference sequence, e.g. wild-type FVIII protein with or without B-domain.

To determine identity, if the FVIII (CpG reduced nucleic acid encoding FVIII) retains the B-domain, it is appropriate to compare identity to wild-type FVIII. If the FVIII (CpG reduced nucleic acid encoding FVIII) has a B-domain deletion, it is appropriate to compare identity to wild-type FVIII that also has a B-domain deletion.

The terms "homologous" or "homology" mean that two or more referenced entities share at least partial identity over a given region or portion. "Areas, regions or domains" of homology or identity mean that a portion of two or more referenced entities share homology or are the same. Thus, where two sequences are identical over one or more sequence regions they share identity in these regions. "Substantial homology" means that a molecule is structurally or functionally conserved such that it has or is predicted to have at least partial structure or function of one or more of the structures or functions (e.g., a biological function or activity) of the reference molecule, or relevant/corresponding region or portion of the reference molecule to which it shares homology.

The extent of identity (homology) or "percent identity" between two sequences can be ascertained using a computer program and/or mathematical algorithm. For purposes of this invention comparisons of nucleic acid sequences are performed using the GCG Wisconsin Package version 9.1, available from the Genetics Computer Group in Madison, Wis. For convenience, the default parameters (gap creation penalty=12, gap extension penalty=4) specified by that program are intended for use herein to compare sequence identity. Alternately, the Blastn 2.0 program provided by the National Center for Biotechnology Information (found on the world wide web at ncbi.nlm.nih.gov/blast/; Altschul et al., 1990, J Mol Biol 215:403-410) using a gapped alignment with default parameters, may be used to determine the level of identity and similarity between nucleic acid sequences and amino acid sequences. For polypeptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SEARCH sequence comparison programs are also used to quantitate extent of identity (Pearson et al., *Proc. Natl. Acad. Sci.* USA 85:2444 (1988); Pearson, *Methods Mol Biol.* 132:185 (2000); and Smith et al., *J. Mol. Biol.* 147:195 (1981)). Programs for quantitating protein structural similarity using Delaunay-based topological mapping have also been developed (Bostick et al., *Biochem Biophys Res Commun.* 304:320 (2003)).

Nucleic acid molecules, expression vectors (e.g., vector genomes), plasmids, including CpG reduced nucleic acid variants encoding FVIII of the invention may be prepared by using recombinant DNA technology methods. The availability of nucleotide sequence information enables preparation of isolated nucleic acid molecules of the invention by a variety of means. For example, CpG reduced nucleic acid variants encoding FVIII can be made using various standard cloning, recombinant DNA technology, via cell expression or in vitro translation and chemical synthesis techniques. Purity of polynucleotides can be determined through sequencing, gel electrophoresis and the like. For example, nucleic acids can be isolated using hybridization or computer-based database screening techniques. Such techniques include, but are not limited to: (1) hybridization of genomic DNA or cDNA libraries with probes to detect homologous nucleotide sequences; (2) antibody screening to detect polypeptides having shared structural features, for example, using an expression library; (3) polymerase chain reaction (PCR) on genomic DNA or cDNA using primers capable of annealing to a nucleic acid sequence of interest; (4) computer searches of sequence databases for related sequences; and (5) differential screening of a subtracted nucleic acid library.

Nucleic acids of the invention may be maintained as DNA in any convenient cloning vector. In a one embodiment, clones are maintained in a plasmid cloning/expression vector, such as pBluescript (Stratagene, La Jolla, Calif.), which is propagated in a suitable *E. coli* host cell. Alternatively, nucleic acids may be maintained in vector suitable for expression in mammalian cells. In cases where post-translational modification affects coagulation function, nucleic acid molecule can be expressed in mammalian cells.

CpG reduced nucleic acid variants encoding FVIII of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid of the invention. Such oligonucleotides are useful as probes for detecting FVIII expression.

A B-domain deleted, CpG reduced nucleic acid variant encoding FVIII of the invention, optionally having amino acid substitutions, deletions or additions, may be prepared in a variety of ways, according to known methods. The protein may be purified from appropriate sources, e.g., transformed bacterial or animal cultured cells or tissues which express engineered FVIII by immune-affinity purification.

The availability of CpG reduced nucleic acid variants encoding FVIII enables production of FVIII using in vitro expression methods known in the art. For example, a cDNA or gene may be cloned into an appropriate in vitro transcription vector, such as pSP64 or pSP65 for in vitro transcription, followed by cell-free translation in a suitable cell-free translation system, such as wheat germ or rabbit reticulocyte lysates. In vitro transcription and translation systems are commercially available, e.g., from Promega Biotech, Madison, Wis. or BRL, Rockville, Md.

Alternatively, larger quantities of FVIII may be produced by expression in a suitable prokaryotic or eukaryotic expression system. For example, a CpG reduced nucleic acid variant encoding FVIII, for example, may be inserted into a plasmid vector adapted for expression in a bacterial cell, such as *E. coli* or a mammalian cell line such as baby hamster kidney (BHK), CHO or Hela cells. Alternatively, tagged fusion proteins comprising FVIII can be generated. Such FVIII-tagged fusion proteins are encoded by part or all of a DNA molecule, ligated in the correct codon reading frame to a nucleotide sequence encoding a portion or all of a desired polypeptide tag which is inserted into a plasmid vector adapted for expression in a bacterial cell, such as *E. coli* or a eukaryotic cell, such as, but not limited to, yeast and mammalian cells.

Vectors such as those described herein optionally comprise regulatory elements necessary for expression of the DNA in the host cell positioned in such a manner as to permit expression of the encoded protein in the host cell. Such regulatory elements required for expression include, but are not limited to, promoter sequences, enhancer sequences and transcription initiation sequences as set forth herein and known to the skilled artisan.

A FVIII encoded by a CpG reduced nucleic acid variant, produced by gene expression in a recombinant prokaryotic or eukaryotic system, may be purified according to methods known in the art. In an embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6-8 histidine residues at their N-terminus or C-terminus. Alternative tags may comprise the FLAG epitope, GST or the hemagglutinin epitope. Such methods are commonly used by skilled practitioners.

FVIII proteins, prepared by the aforementioned methods, may be analyzed according to standard procedures. For example, such proteins may be assessed for altered coagulation properties according to known methods.

Accordingly, the invention also provides methods of making a polypeptide (as disclosed), the method including expression from nucleic acid encoding the polypeptide (generally nucleic acid). This may conveniently be achieved by culturing a host cell, containing such a vector, under appropriate conditions which cause or allow production of the polypeptide. Polypeptides may also be produced in in vitro systems.

Methods and uses of the invention of the invention include delivering (transducing) nucleic acid (transgene) into host cells, including dividing and/or non-dividing cells. The nucleic acids, recombinant vector (e.g., rAAV), methods, uses and pharmaceutical formulations of the invention are additionally useful in a method of delivering, administering or providing a protein to a subject in need thereof, as a method of treatment. In this manner, the nucleic acid is transcribed and the protein may be produced in vivo in a subject. The subject may benefit from or be in need of the protein because the subject has a deficiency of the protein, or because production of the protein in the subject may impart some therapeutic effect, as a method of treatment or otherwise.

Vectors including lenti- or parvo-virus vector (e.g., AAV) sequences, recombinant virus particles, methods and uses may be used to deliver a CpG reduced nucleic acid variant encoding FVIII with a biological effect to treat or ameliorate one or more symptoms associated with a FVIII deficiency or abnormality Recombinant lenti- or parvo-virus vector (e.g., AAV) sequences, plasmids, recombinant virus particles, methods and uses may be used to provide therapy for various disease states involving or due to a FVIII deficiency or abnormality.

Invention nucleic acids, vectors, expression vectors (e.g., rAAV), and recombinant virus particles, methods and uses permit the treatment of genetic diseases, e.g., a FVIII deficiency. For deficiency state diseases, gene transfer can be used to bring a normal gene into affected tissues for replacement therapy, as well as to create animal models for the disease using antisense mutations. For unbalanced disease states, gene transfer could be used to create a disease state in a model system, which could then be used in efforts to counteract the disease state. The use of site-specific integration of nucleic acid sequences to correct defects is also possible.

In particular embodiments, CpG reduced nucleic acid variants encoding FVIII may be used, for example, as therapeutic and/or prophylactic agents (protein or nucleic acid) which modulate the blood coagulation cascade or as a transgene in gene. For example, CpG reduced nucleic acid variants encoding FVIII may have similar coagulation activity as wild-type FVIII, or altered coagulation activity compared to wild-type FVII. Cell-based strategies allow continuous expression of CpG reduced nucleic acid variants encoding FVIII in hemophilia A patients. As disclosed herein, certain modifications of FVIII molecules (nucleic acid and protein) result in increased expression at the nucleic acid level, increased coagulation activity thereby effectively improving hemostasis.

CpG reduced nucleic acid variants encoding FVIII may be used for a variety of purposes in accordance with the invention. In one embodiment, a nucleic acid delivery vehicle (i.e., an expression vector) for modulating blood coagulation is provided wherein the expression vector comprises a CpG reduced nucleic acid variants encoding FVIII as described herein. Administration of FVIII-encoding expression vectors to a patient results in the expression of FVIII protein which serves to alter the coagulation cascade. In accordance with the invention, expression of CpG reduced nucleic acid variants encoding FVIII protein as described herein, or a functional fragment, increases hemostasis.

In additional embodiments of the invention, compositions and methods are provided for administration of a viral vector comprising a CpG reduced nucleic acid variant encoding FVIII. In one embodiment, the expression vector comprising CpG reduced nucleic acid variant encoding FVIII is a viral vector.

Expression vectors comprising CpG reduced nucleic acid variants encoding FVIII may be administered alone, or in combination with other molecules useful for modulating hemostasis. According to the invention, vectors, expression vectors or combination of therapeutic agents may be administered to the patient alone or in a pharmaceutically acceptable or biologically compatible compositions.

Viral vectors such as lenti- and parvo-virus vectors, including AAV serotypes and variants thereof provide a means for delivery of nucleic acid into cells ex vivo, in vitro and in vivo, which encode proteins such that the cells express the encoded protein. AAV are viruses useful as gene therapy vectors as they can penetrate cells and introduce nucleic acid/genetic material so that the nucleic acid/genetic material may be stably maintained in cells. In addition, these viruses can introduce nucleic acid/genetic material into specific sites, for example. Because AAV are not associated with pathogenic disease in humans, AAV vectors are able to deliver heterologous polynucleotide sequences (e.g., therapeutic proteins and agents) to human patients without causing substantial AAV pathogenesis or disease.

Viral vectors which may be used in the invention include, but are not limited to, adeno-associated virus (AAV) vectors of multiple serotypes (e.g., AAV-1 to AAV-12, and others) and hybrid/chimeric AAV vectors, lentivirus vectors and pseudo-typed lentivirus vectors (e.g., Ebola virus, vesicular stomatitis virus (VSV), and feline immunodeficiency virus (FIV)), herpes simplex virus vectors, adenoviral vectors (with or without tissue specific promoters/enhancers), vaccinia virus vectors, retroviral vectors, lentiviral vectors, non-viral vectors and others.

AAV and lentiviral particles may be used to advantage as vehicles for effective gene delivery. Such virions possess a number of desirable features for such applications, including tropism for dividing and non-dividing cells. Early clinical experience with these vectors also demonstrated no sustained toxicity and immune responses were minimal or undetectable. AAV are known to infect a wide variety of cell types in vivo and in vitro by receptor-mediated endocytosis or by transcytosis. These vector systems have been tested in humans targeting retinal epithelium, liver, skeletal muscle, airways, brain, joints and hematopoietic stem cells. Non-viral vectors, for example, based on plasmid DNA or mini-circles, are also suitable gene transfer vectors for a large gene as that encoding FVIII.

It may be desirable to introduce a vector that can provide, for example, multiple copies of a desired gene and hence greater amounts of the product of that gene. Improved AAV and lentiviral vectors and methods for producing these vectors have been described in detail in a number of references, patents, and patent applications, including: Wright J. F. (Hum Gene Ther 20:698-706, 2009) a technology used for the production of clinical grade vector at Children's Hospital of Philadelphia. Lentiviral vector can also be produced at CHOP and the other vectors are available through the Lentivirus vector production core laboratory by NHLBI Gene Therapy Resource Program (GTRP)-Lentivirus Vector Production Core Laboratory.

Accordingly, in various embodiments of the invention a vector includes a lenti- or parvo-viral vector, such as an adeno-viral vector. In particular embodiments, a recombinant vector is a parvovirus vector. Parvoviruses are small viruses with a single-stranded DNA genome. "Adeno-associated viruses" (AAV) are in the parvovirus family.

Accordingly, the invention provides viral vectors that include CpG reduced nucleic acid variants encoding FVIII. For example, a recombinant AAV vector can include CpG reduced nucleic acid variants encoding FVIII, where the encoded FVIII protein optionally has B-domain deletion. Vector delivery or administration to a subject (e.g., mammal) therefore provides FVIII to a subject such as a mammal (e.g., human).

Direct delivery of vectors or ex-vivo transduction of human cells followed by infusion into the body will result in FVIII expression thereby exerting a beneficial therapeutic effect on hemostasis. In the context of invention Factor VIII described herein, such administration enhances pro-coagulation activity.

AAV vectors and lentiviral vectors do not typically include viral genes associated with pathogenesis. Such vectors typically have one or more of the wild type AAV genes deleted in whole or in part, for example, rep and/or cap genes, but retain at least one functional flanking ITR sequence, as necessary for the rescue, replication, and packaging of the recombinant vector into an AAV vector particle. For example, only the essential parts of vector e.g., the ITR and LTR elements, respectively are included. An AAV vector genome would therefore include sequences required in cis for replication and packaging (e.g., functional ITR sequences)

Recombinant AAV vector, as well as methods and uses thereof, include any viral strain or serotype. As a non-limiting example, a recombinant AAV vector can be based upon any AAV genome, such as AAV-1, -2, -3, -4, -5, -6, -7, -8, -9, -10, -11, -12, -rh74, -rh10 or AAV-2i8, for example. Such vectors can be based on the same strain or serotype (or subgroup or variant), or be different from each other. As a non-limiting example, a recombinant AAV vector based upon one serotype genome can be identical to one or more of the capsid proteins that package the vector. In addition, a recombinant AAV vector genome can be based upon an AAV (e.g., AAV2) serotype genome distinct from one or more of the AAV capsid proteins that package the vector. For example, the AAV vector genome can be based upon AAV2, whereas at least one of the three capsid proteins could be a AAV1, AAV3, AAV4, AAV5, AAV6, AAV7, AAV8, AAV9, AAV10, AAV11, AAV12, Rh10, Rh74 or AAV-2i8 or variant thereof, for example.

In particular embodiments, adeno-associated virus (AAV) vectors include AAV1, AAV2, AAV3, AAV4, AAV5, AAV6, AAV7, AAV8, AAV9, AAV10, AAV11, AAV12, Rh10, Rh74 and AAV-2i8, as well as variants (e.g., capsid variants, such as amino acid insertions, additions, substitutions and deletions) thereof, for example, as set forth in WO 2013/158879 (International Application PCT/US2013/037170), WO 2015/013313 (International Application PCT/US2014/047670) and US 2013/0059732 (U.S. Pat. No. 9,169,299, discloses LK01, LK02, LK03, etc.).

AAV variants include variants and chimeras of AAV1, AAV2, AAV3, AAV4, AAV5, AAV6, AAV7, AAV8, AAV9, AAV10, AAV11, AAV12, Rh10, Rh74 and AAV-2i8 capsid. Accordingly, AAV vectors and AAV variants (e.g., capsid variants) that include (encapsidate or package) CpG reduced nucleic acid variants encoding FVIII, are provided.

AAV and AAV variants (e.g., capsid variants) serotypes (e.g., VP1, VP2, and/or VP3 sequences) may or may not be distinct from other AAV serotypes, including, for example, AAV1-AAV12, Rh74 or Rh10 (e.g., distinct from VP1, VP2, and/or VP3 sequences of any of AAV1-AAV12, Rh74 or Rh10 serotypes).

As used herein, the term "serotype" is a distinction used to refer to an AAV having a capsid that is serologically distinct from other AAV serotypes. Serologic distinctiveness is determined on the basis of the lack of cross-reactivity between antibodies to one AAV as compared to another AAV. Such cross-reactivity differences are usually due to differences in capsid protein sequences/antigenic determinants (e.g., due to VP1, VP2, and/or VP3 sequence differences of AAV serotypes). Despite the possibility that AAV variants including capsid variants may not be serologically distinct from a reference AAV or other AAV serotype, they differ by at least one nucleotide or amino acid residue compared to the reference or other AAV serotype.

Under the traditional definition, a serotype means that the virus of interest has been tested against serum specific for all existing and characterized serotypes for neutralizing activity and no antibodies have been found that neutralize the virus of interest. As more naturally occurring virus isolates of are discovered and/or capsid mutants generated, there may or may not be serological differences with any of the currently existing serotypes. Thus, in cases where the new virus (e.g., AAV) has no serological difference, this new virus (e.g., AAV) would be a subgroup or variant of the corresponding serotype. In many cases, serology testing for neutralizing activity has yet to be performed on mutant viruses with capsid sequence modifications to determine if they are of another serotype according to the traditional definition of serotype. Accordingly, for the sake of convenience and to avoid repetition, the term "serotype" broadly refers to both serologically distinct viruses (e.g., AAV) as well as viruses (e.g., AAV) that are not serologically distinct that may be within a subgroup or a variant of a given serotype.

AAV vectors therefore include gene/protein sequences identical to gene/protein sequences characteristic for a particular serotype. As used herein, an "AAV vector related to AAV1" refers to one or more AAV proteins (e.g., VP1, VP2, and/or VP3 sequences) that has substantial sequence identity to one or more polynucleotides or polypeptide sequences that comprise AAV1. Analogously, an "AAV vector related to AAV8" refers to one or more AAV proteins (e.g., VP1, VP2, and/or VP3 sequences) that has substantial sequence identity to one or more polynucleotides or polypeptide sequences that comprise AAV8. An "AAV vector related to AAV-Rh74" refers to one or more AAV proteins (e.g., VP1, VP2, and/or VP3 sequences) that has substantial sequence identity to one or more polynucleotides or polypeptide sequences that comprise AAV-Rh74. Such AAV vectors related to another serotype, e.g., AAV1, AAV2, AAV3, AAV4, AAV5, AAV6, AAV7, AAV8, AAV9, AAV10, AAV11, AAV12, Rh10, Rh74 or AAV-2i8, can therefore have one or more distinct sequences from AAV1, AAV2, AAV3, AAV4, AAV5, AAV6, AAV7, AAV8, AAV9, AAV10, AAV11, AAV12, Rh10, Rh74 and AAV-2i8, but can exhibit substantial sequence identity to one or more genes and/or proteins, and/or have one or more functional characteristics of AAV1, AAV2, AAV3, AAV4, AAV5, AAV6, AAV7, AAV8, AAV9, AAV10, AAV11, AAV12, Rh10, Rh74 or AAV-2i8 (e.g., such as cell/tissue tropism). Exemplary non-limiting AAV variants include capsid variants of any of VP1, VP2, and/or VP3.

In various exemplary embodiments, an AAV vector related to a reference serotype has a polynucleotide, polypeptide or subsequence thereof that includes or consists of a sequence at least 80% or more (e.g., 85%, 90%, 95%, 96%, 97%, 98%, 99%, 99.1%, 99.2%, 99.3%, 99.4%, 99.5%, etc.) identical to one or more AAV1, AAV2, AAV3, AAV4, AAV5, AAV6, AAV7, AAV8, AAV9, AAV10, AAV11, AAV12, Rh10, Rh74 or AAV-2i8 (e.g., such as an ITR, or a VP1, VP2, and/or VP3 sequences).

Compositions, methods and uses of the invention include AAV sequences (polypeptides and nucleotides), and subsequences thereof that exhibit less than 100% sequence identity to a reference AAV serotype such as AAV1, AAV2, AAV3, AAV4, AAV5, AAV6, AAV7, AAV8, AAV9, AAV10, AAV11, AAV12, Rh10, or AAV-2i8, but are distinct from and not identical to known AAV genes or proteins, such as AAV1, AAV2, AAV3, AAV4, AAV5, AAV6, AAV7, AAV8, AAV9, AAV10, AAV11, AAV12, Rh10, Rh74 or AAV-2i8, genes or proteins, etc. In one embodiment, an AAV polypeptide or subsequence thereof includes or consists of a sequence at least 75% or more identical, e.g., 80%, 85%, 85%, 87%, 88%, 89%, 90%, 91%, 92%, 93%, 94%, 95%, 96%, 97%, 98%, 99%, 99.1%, 99.2%, 99.3%, 99.4%, 99.5%, etc., up to 100% identical to any reference AAV sequence or subsequence thereof, such as AAV1, AAV2, AAV3, AAV4, AAV5, AAV6, AAV7, AAV8, AAV9, AAV10, AAV11, AAV12, Rh10, Rh74 or AAV-2i8 (e.g., VP1, VP2 and/or VP3 capsid or ITR). In certain embodiments, an AAV variant has 1, 2, 3, 4, 5, 5-10, 10-15, 15-20 or more amino acid substitutions.

Recombinant AAV vectors, including AAV1, AAV2, AAV3, AAV4, AAV5, AAV6, AAV7, AAV8, AAV9, AAV10, AAV11, AAV12, Rh10, Rh74 or AAV-2i8 and variant, related, hybrid and chimeric sequences, can be constructed using recombinant techniques that are known to the skilled artisan, to include one or more nucleic acid sequences (transgenes) flanked with one or more functional AAV ITR sequences.

In one embodiment of the invention, CpG reduced nucleic acid variants encoding FVIII, vector or expression vector, may be administered to a patient via infusion in a biologically compatible carrier, for example, via intravenous injection. The CpG reduced nucleic acid variants encoding FVIII, vectors and expression vectors of the invention may optionally be encapsulated into liposomes or mixed with other phospholipids or micelles to increase stability of the molecule. CpG reduced nucleic acid variants encoding FVIII, vectors and expression vectors of the invention, may be administered alone or in combination with other agents known to modulate hemostasis (e.g., Factor V, Factor Va or derivatives thereof).

An appropriate composition in which to deliver FVIII may be determined by a medical practitioner upon consideration of a variety of physiological variables, including, but not limited to, the patient's condition and hemodynamic state. A variety of compositions well suited for different applications and routes of administration are well known in the art and are described hereinbelow.

A preparation containing purified FVIII protein, produced by expression of CpG reduced nucleic acid variants encoding FVIII, vectors and expression vectors of the invention, contains a physiologically acceptable matrix and may be formulated as a pharmaceutical preparation. The preparation can be formulated using substantially known prior art methods, it can be mixed with a buffer containing salts, such as NaCl, $CaCl_2$, and amino acids, such as glycine and/or lysine, and in a pH range from 6 to 8. Until needed, the purified preparation containing FVIII can be stored in the form of a finished solution or in lyophilized or deep-frozen form.

A preparation can be stored in lyophilized form and is dissolved into a visually clear solution using an appropriate reconstitution solution. Alternatively, the preparation according to the invention can also be made available as a liquid preparation or as a liquid that is deep-frozen. The preparation according to the invention may optionally be especially stable, i.e., it can be allowed to stand in dissolved form for a prolonged time prior to administration or delivery.

The preparation according to the invention can be made available as a pharmaceutical preparation with FVIII activity in the form of a one-component preparation or in combination with other factors in the form of a multi-component preparation. Prior to processing the purified protein into a pharmaceutical preparation, the purified protein is subjected to the conventional quality controls and fashioned into a therapeutic form of presentation. In particular, during the recombinant manufacture, the purified preparation is tested for the absence of cellular nucleic acids as well as nucleic acids that are derived from the expression vector, such as is described in EP 0 714 987.

The pharmaceutical protein preparation may be used at dosages of between 30-100 IU/kg (One I.U is 100 ng/ml) at as single daily injection or up to 3 times/day for several days. Patients may be treated immediately upon presentation at the clinic with a bleed. Alternatively, patients may receive a bolus infusion every eight to twelve hours, or if sufficient improvement is observed, a once daily infusion of the FVIII.

Accordingly, invention nucleic acids, vectors, recombinant vectors (e.g., rAAV), and recombinant virus particles and other compositions, agents, drugs, biologics (proteins) can be incorporated into pharmaceutical compositions. Such pharmaceutical compositions are useful for, among other things, administration and delivery to a subject in vivo or ex vivo.

In particular embodiments, pharmaceutical compositions also contain a pharmaceutically acceptable carrier or excipient. Such excipients include any pharmaceutical agent that does not itself induce an immune response harmful to the individual receiving the composition, and which may be administered without undue toxicity.

As used herein the term "pharmaceutically acceptable" and "physiologically acceptable" mean a biologically acceptable formulation, gaseous, liquid or solid, or mixture thereof, which is suitable for one or more routes of administration, in vivo delivery or contact. A "pharmaceutically acceptable" or "physiologically acceptable" composition is a material that is not biologically or otherwise undesirable, e.g., the material may be administered to a subject without causing substantial undesirable biological effects. Thus, such a pharmaceutical composition may be used, for example in administering a nucleic acid, vector, viral particle or protein to a subject.

Pharmaceutically acceptable excipients include, but are not limited to, liquids such as water, saline, glycerol, sugars and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding, free base forms. In other cases, a preparation may be a lyophilized powder which may contain any or all of the following: 1-50 mM histidine, 0.1%-2% sucrose, and 2-7% mannitol, at a pH range of 4.5 to 5.5, that is combined with buffer prior to use.

Pharmaceutical compositions include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

Pharmaceutical compositions can be formulated to be compatible with a particular route of administration or delivery, as set forth herein or known to one of skill in the art. Thus, pharmaceutical compositions include carriers, diluents, or excipients suitable for administration by various routes.

Compositions suitable for parenteral administration comprise aqueous and non-aqueous solutions, suspensions or emulsions of the active compound, which preparations are typically sterile and can be isotonic with the blood of the intended recipient. Non-limiting illustrative examples include water, buffered saline, Hanks' solution, Ringer's solution, dextrose, fructose, ethanol, animal, vegetable or synthetic oils. Aqueous injection suspensions may contain substances which increase the viscosity of the suspension, such as sodium carboxymethyl cellulose, sorbitol, or dextran.

Additionally, suspensions of the active compounds may be prepared as appropriate oil injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone.

After pharmaceutical compositions have been prepared, they may be placed in an appropriate container and labeled for treatment. For administration of FVIII-containing vectors or polypeptides, such labeling would include amount, frequency, and method of administration.

Pharmaceutical compositions and delivery systems appropriate for the compositions, methods and uses of the invention are known in the art (see, e.g., *Remington: The Science and Practice of Pharmacy* (2003) $20^{th}$ ed., Mack Publishing Co., Easton, Pa.; *Remington's Pharmaceutical Sciences* (1990) $18^{th}$ ed., Mack Publishing Co., Easton, Pa.; *The Merck Index* (1996) $12^{th}$ ed., Merck Publishing Group, Whitehouse, N.J.; *Pharmaceutical Principles of Solid Dosage Forms* (1993), Technonic Publishing Co., Inc., Lancaster, Pa.; Ansel and Stoklosa, *Pharmaceutical Calculations* (2001) $11^{th}$ ed., Lippincott Williams & Wilkins, Baltimore, Md.; and Poznansky et al., *Drug Delivery Systems* (1980), R. L. Juliano, ed., Oxford, N.Y., pp. 253-315).

The invention also provides methods for introducing CpG reduced nucleic acid variants encoding FVIII into a cell or an animal. In a particular embodiment, the invention provides methods for modulating hemostasis. In one embodiment, a method includes contact or administration of an individual (patient or subject such as a mammal) with a nucleic acid delivery vehicle (e.g., an AAV vector) comprising CpG reduced nucleic acid variant encoding FVIII under conditions wherein the FVIII polypeptide is expressed in the individual. In another embodiment, a method includes providing cells of an individual (patient or subject such as a mammal) with a nucleic acid delivery vehicle (e.g., an AAV vector) comprising a CpG reduced nucleic acid variant encoding FVIII under conditions wherein the FVIII polypeptide is expressed in the individual.

From the foregoing, it can be seen that CpG reduced nucleic acid variants encoding FVIII may be used in the treatment of disorders associated with deficient, insufficient or aberrant blood coagulation.

Compositions of CpG reduced nucleic acid variants encoding FVIII, including vectors, recombinant vectors (e.g., rAAV), and recombinant virus particles can be administered, and methods and uses of the invention can be provided, in a sufficient or effective amount to a subject in need thereof. An "effective amount" or "sufficient amount" refers to an amount that provides, in single or multiple doses, alone or in combination, with one or more other compositions (therapeutic or immunosuppressive agents such as a drug), treatments, protocols, or therapeutic regimens agents, a detectable response of any duration of time (long or short term), an expected or desired outcome in or a benefit to a subject of any measurable or detectable degree or for any duration of time (e.g., for minutes, hours, days, months, years, or cured).

Doses can vary and depend upon the type, onset, progression, severity, frequency, duration, or probability of the disease to which treatment is directed, the clinical endpoint desired, previous or simultaneous treatments, the general health, age, gender, race or immunological competency of the subject and other factors that will be appreciated by the skilled artisan. The dose amount, number, frequency or duration may be proportionally increased or reduced, as indicated by any adverse side effects, complications or other risk factors of the treatment or therapy and the status of the subject. The skilled artisan will appreciate the factors that may influence the dosage and timing required to provide an amount sufficient for providing a therapeutic or prophylactic benefit.

The dose to achieve a therapeutic effect, e.g., the dose in vector genomes/per kilogram of body weight (vg/kg), will vary based on several factors including, but not limited to: route of administration, the level of heterologous polynucleotide expression required to achieve a therapeutic effect, the specific disease treated, any host immune response to the viral vector, a host immune response to the heterologous polynucleotide or expression product (protein), and the stability of the protein expressed. One skilled in the art can determine a rAAV/vector genome dose range to treat a patient having a particular disease or disorder based on the aforementioned factors, as well as other factors. Generally, doses will range from at least $1\times10^8$, or more, for example, $1\times10^9$, $1\times10^{10}$, $1\times10^{11}$, $1\times10^{12}$, $1\times10^{13}$ or $1\times10^{14}$, or more, vector genomes per kilogram (vg/kg) of the weight of the subject, to achieve a therapeutic effect. AAV dose in the range of $1\times10^{10}$-$1\times10^{11}$ in mice, and $1\times10^{12}$-$1\times10^{13}$ in dogs have been effective.

Using hemophilia B as an example, generally speaking, it is believed that, in order to achieve a therapeutic effect, a blood coagulation factor concentration that is greater than 1% of factor concentration found in a normal individual is needed to change a severe disease phenotype to a moderate one. A severe phenotype is characterized by joint damage and life-threatening bleeds. To convert a moderate disease phenotype into a mild one, it is believed that a blood coagulation factor concentration greater than 5% of normal is needed. FVIII levels in normal humans are about 150-200 ng/ml plasma, but may be less (e.g., range of about 100-150 ng/ml) or greater (e.g., range of about 200-300 ng/ml) and still considered normal due to functioning clotting as determined, for example, by an activated partial thromboplastin time (aPTT) one-stage clotting assay. Thus, a therapeutic effect can be achieved by expression of FVIII such that the total amount of FVIII in the subject/human is greater than 1% of the FVIII present in normal subjects/humans, e.g., 1% of 100-300 ng/ml.

With respect to treating such a hemophilic subject, a typical dose is at least $1\times10^{10}$ vector genomes (vg) per kilogram (vg/kg) of the weight of the subject, or between about $1\times10^{10}$ to $1\times10^{11}$ of the weight of the subject, or between about $1\times10^{11}$ to $1\times10^{12}$ vg/kg of the weight of the subject, or between about $1\times10^{12}$ to $1\times10^{13}$ vg/kg of the weight of the subject, to achieve a desired therapeutic effect. AAV vector doses can be at a level, typically at the lower end of the dose spectrum, such that there is not a substantial immune response against the FVIII or AAV vector.

The doses of an "effective amount" or "sufficient amount" for treatment (e.g., to ameliorate or to provide a therapeutic benefit or improvement) typically are effective to provide a response to one, multiple or all adverse symptoms, consequences or complications of the disease, one or more adverse symptoms, disorders, illnesses, pathologies, or complications, for example, caused by or associated with the disease, to a measurable extent, although decreasing, reducing, inhibiting, suppressing, limiting or controlling progression or worsening of the disease is a satisfactory outcome.

An effective amount or a sufficient amount can but need not be provided in a single administration, may require multiple administrations, and, can but need not be, administered alone or in combination with another composition (e.g., agent), treatment, protocol or therapeutic regimen. For example, the amount may be proportionally increased as indicated by the need of the subject, type, status and severity of the disease treated or side effects (if any) of treatment. In addition, an effective amount or a sufficient amount need not be effective or sufficient if given in single or multiple doses without a second composition (e.g., another drug or agent), treatment, protocol or therapeutic regimen, since additional doses, amounts or duration above and beyond such doses, or additional compositions (e.g., drugs or agents), treatments, protocols or therapeutic regimens may be included in order to be considered effective or sufficient in a given subject. Amounts considered effective also include amounts that result in a reduction of the use of another treatment, therapeutic regimen or protocol, such as administration of recombinant clotting factor protein (e.g., FVIII) for treatment of a clotting disorder (e.g., hemophilia A).

Accordingly, methods and uses of the invention also include, among other things, methods and uses that result in a reduced need or use of another compound, agent, drug, therapeutic regimen, treatment protocol, process, or remedy. For example, for a blood clotting disease, a method or use of the invention has a therapeutic benefit if in a given subject a less frequent or reduced dose or elimination of administration of a recombinant clotting factor protein to supplement for the deficient or defective (abnormal or mutant) endogenous clotting factor in the subject. Thus, in accordance with the invention, methods and uses of reducing need or use of another treatment or therapy are provided.

An effective amount or a sufficient amount need not be effective in each and every subject treated, nor a majority of treated subjects in a given group or population. An effective amount or a sufficient amount means effectiveness or sufficiency in a particular subject, not a group or the general population. As is typical for such methods, some subjects will exhibit a greater response, or less or no response to a given treatment method or use.

The term "ameliorate" means a detectable or measurable improvement in a subject's disease or symptom thereof, or an underlying cellular response. A detectable or measurable improvement includes a subjective or objective decrease, reduction, inhibition, suppression, limit or control in the occurrence, frequency, severity, progression, or duration of the disease, or complication caused by or associated with the disease, or an improvement in a symptom or an underlying cause or a consequence of the disease, or a reversal of the disease. For HemA, an effective amount would be an amount that reduces frequency or severity of acute bleeding episodes in a subject, for example, or an amount that reduces clotting time as measured by a clotting assay, for example.

Accordingly, pharmaceutical compositions of the invention include compositions wherein the active ingredients are contained in an effective amount to achieve the intended therapeutic purpose. Determining a therapeutically effective dose is well within the capability of a skilled medical practitioner using the techniques and guidance provided in the invention.

Therapeutic doses will depend on, among other factors, the age and general condition of the subject, the severity of the aberrant blood coagulation phenotype, and the strength of the control sequences regulating the expression levels of CpG reduced nucleic acid variants encoding FVIII. Thus, a therapeutically effective amount in humans will fall in a relatively broad range that may be determined by a medical practitioner based on the response of an individual patient to vector-based FVIII treatment. Such doses may be alone or in combination with an immunosuppressive agent or drug.

Compositions such as pharmaceutical compositions may be delivered to a subject, so as to allow production of a biologically active protein (e.g., Factor VIII (FVIII) encoded by CpG reduced nucleic acid variant) or by inducing continuous expression of the FVIII transgene in vivo by gene- and or cell-based therapies or by ex-vivo modification of the patient's or donor's cells. In a particular embodiment, pharmaceutical compositions comprising sufficient genetic material to enable a recipient to produce a therapeutically effective amount of a FVIII polypeptide can influence hemostasis in the subject.

The compositions may be administered alone. In certain embodiments, CpG reduced nucleic acid variant encoding FVIII, vector, expression vector/recombinant vector (e.g., rAAV), or recombinant virus particle provides a therapeutic effect without an immunosuppressive agent. The therapeutic effect of FVIII optionally is sustained for a period of time, e.g., 2-4, 4-6, 6-8, 8-10, 10-14, 14-20, 20-25, 25-30, or 30-50 days or more, for example, 50-75, 75-100, 100-150, 150-200 days or more without administering an immunosuppressive agent. Accordingly, in certain embodiments CpG reduced nucleic acid variant encoding FVIII, vector, expression vector/recombinant vector (e.g., rAAV), or recombinant virus particle provide a therapeutic effect without administering an immunosuppressive agent for a period of time.

The compositions may be administered in combination with at least one other agent. In certain embodiments, CpG reduced nucleic acid variant encoding FVIII, vector, expression vector/recombinant vector (e.g., rAAV), or recombinant virus particle are administered in conjunction with one or more immunosuppressive agents prior to, substantially at the same time or after administering a CpG reduced nucleic acid variant encoding FVIII, vector, expression vector/recombinant vector (e.g., rAAV), or recombinant virus particle. In certain embodiments, CpG reduced nucleic acid variant encoding FVIII, vector, expression vector/recombinant vector (e.g., rAAV), or recombinant virus particle are administered in conjunction with one or more immunosuppressive agents after a period of time following administering a CpG reduced nucleic acid variant encoding FVIII, vector, expression vector/recombinant vector (e.g., rAAV), or recombinant virus particle, e.g., 1-12, 12-24 or 24-48 hours, or 2-4, 4-6, 6-8, 8-10, 10-14, 14-20, 20-25, 25-30, 30-50, or more than 50 days following administering a CpG reduced nucleic acid variant encoding FVIII, vector, expression vector/recombinant vector (e.g., rAAV), or recombinant virus particle. Such administration of immunosuppressive agents after a period of time following administering a CpG reduced nucleic acid variant encoding FVIII, vector, expression vector/recombinant vector (e.g., rAAV), or recombinant virus particle if there is a decrease in FVIII after the initial expression levels for a period of time, e.g., 20-25, 25-30, 30-50, 50-75, 75-100, 100-150, 150-200 or more than 200 days following administering a CpG reduced nucleic acid variant encoding FVIII, vector, expression vector/recombinant vector (e.g., rAAV), or recombinant virus particle.

In certain embodiments, an immunosuppressive agent is an anti-inflammatory agent. In certain embodiments, an immunosuppressive agent is a steroid. In certain embodiments, an immunosuppressive agent is cyclosporine (e.g., cyclosporine A), mycophenolate, Rituximab or a derivative thereof. Additional particular agents include a stabilizing compound.

Compositions may be administered in any sterile, biocompatible pharmaceutical carrier, including, but not limited to, saline, buffered saline, dextrose, and water. The compositions may be administered to a patient alone, or in combination with other agents (e.g., co-factors) which influence hemostasis.

Factor VIII, alone or in combination with other agents may be administered or contacted or directly infused into a patient in an appropriate biological carrier as described herein. Vectors and expression vectors of the invention comprising a CpG reduced nucleic acid variant encoding FVIII, may be administered to a patient by a variety of means to achieve and optionally maintain for a period of time a prophylactically and/or therapeutically effective level of FVIII polypeptide. One of skill in the art could readily determine specific protocols for using the FVIII encoding expression vectors of the invention for the therapeutic treatment of a particular patient.

Protocols for the generation of adenoviral vectors and administration to patients have been described in U.S. Pat. Nos. 5,998,205; 6,228,646; 6,093,699; 6,100,242; and International Patent Application Nos. WO 94/17810 and WO 94/23744, which are incorporated herein by reference in their entirety. In particular, for example, AAV vectors are employed to deliver Factor VIII (FVIII) encoded by CpG reduced nucleic acid variants to a patient in need thereof.

Factor VIII (FVIII) encoded by CpG reduced nucleic acid variants delivered by way of AAV vectors of the invention may be administered to a patient by any means known.

Methods and uses of the invention include delivery and administration systemically, regionally or locally, or by any route, for example, by injection or infusion. Delivery of the pharmaceutical compositions in vivo may generally be accomplished via injection using a conventional syringe, although other delivery methods such as convection-enhanced delivery are envisioned (See e.g., U.S. Pat. No. 5,720,720). For example, compositions may be delivered subcutaneously, epidermally, intradermally, intrathecally, intraorbitally, intramucosally, intraperitoneally, intravenously, intra-pleurally, intraarterially, orally, intrahepatically, via the portal vein, or intramuscularly. Other modes of administration include oral and pulmonary administration, suppositories, and transdermal applications. A clinician specializing in the treatment of patients with blood coagulation disorders may determine the optimal route for administration of the adenoviral-associated vectors comprising CpG reduced nucleic acid variants encoding FVIII based on a number of criteria, including, but not limited to: the condition of the patient and the purpose of the treatment (e.g., enhanced or reduced blood coagulation).

Invention methods and uses can be combined with any compound, agent, drug, treatment or other therapeutic regimen or protocol having a desired therapeutic, beneficial, additive, synergistic or complementary activity or effect. Exemplary combination compositions and treatments include second actives, such as, biologics (proteins), agents (e.g., immunosuppressive agents) and drugs. Such biologics (proteins), agents, drugs, treatments and therapies can be administered or performed prior to, substantially contemporaneously with or following any other method or use of the invention, for example, a therapeutic method of treating a subject for a blood clotting disease such as HemA.

The compound, agent, drug, treatment or other therapeutic regimen or protocol can be administered as a combination composition, or administered separately, such as concurrently or in series or sequentially (prior to or following) delivery or administration of a nucleic acid, vector, recombinant vector (e.g., rAAV), or recombinant virus particle. The invention therefore provides combinations in which a method or use of the invention is in a combination with any compound, agent, drug, therapeutic regimen, treatment protocol, process, remedy or composition, set forth herein or known to one of skill in the art. The compound, agent, drug, therapeutic regimen, treatment protocol, process, remedy or composition can be administered or performed prior to, substantially contemporaneously with or following administration of a nucleic acid, vector, recombinant vector (e.g., rAAV), or recombinant virus particle of the invention, to a subject.

The invention is useful in animals including human and veterinary medical applications. Suitable subjects therefore include mammals, such as humans, as well as non-human mammals. The term "subject" refers to an animal, typically a mammal, such as humans, non-human primates (apes, gibbons, gorillas, chimpanzees, orangutans, macaques), a domestic animal (dogs and cats), a farm animal (poultry such as chickens and ducks, horses, cows, goats, sheep, pigs), and experimental animals (mouse, rat, rabbit, guinea pig). Human subjects include fetal, neonatal, infant, juvenile and adult subjects. Subjects include animal disease models, for example, mouse and other animal models of blood clotting diseases such as HemA and others known to those of skill in the art.

Subjects appropriate for treatment in accordance with the invention include those having or at risk of producing an insufficient amount or having a deficiency in a functional gene product (e.g., FVIII protein), or produce an aberrant, partially functional or non-functional gene product (e.g., FVIII protein), which can lead to disease. Subjects appropriate for treatment in accordance with the invention also include those having or at risk of producing an aberrant, or defective (mutant) gene product (protein) that leads to a disease such that reducing amounts, expression or function of the aberrant, or defective (mutant) gene product (protein) would lead to treatment of the disease, or reduce one or more symptoms or ameliorate the disease. Target subjects therefore include subjects having aberrant, insufficient or absent blood clotting factor production, such as hemophiliacs (e.g., hemophilia A).

Subjects can be tested for an immune response, e.g., antibodies against AAV. *Candidate henophilia* subjects can therefore be screened prior to treatment according to a method of the invention. Subjects also can be tested for antibodies against AAV after treatment, and optionally monitored for a period of time after treatment. Subjects developing antibodies can be treated with an immunosuppressive agent, or can be administered one or more additional amounts of AAV vector.

Subjects appropriate for treatment in accordance with the invention also include those having or at risk of producing antibodies against AAV. AAV vectors can be administered or delivered to such subjects using several techniques. For example, empty capsid AAV (i.e., AAV lacking a FVIII nucleic acid) can be delivered to bind to the AAV antibodies in the subject thereby allowing the AAV vector bearing CpG reduced nucleic acid variant encoding FVIII to transform cells of the subject. Amounts of empty capsid AAV to administer can be calibrated based upon the amount of AAV antibodies produced in a particular subject. Empty capsid can be of any AAV serotype, for example, AAV1, AAV2, AAV3, AAV4, AAV5, AAV6, AAV7, AAV8, AAV9, AAV10, AAV11, AAV12, Rh10, Rh74 or AAV-2i8.

Alternatively or in addition to, AAV vector can be delivered by direct intramuscular injection (e.g., one or more slow-twitch fibers of a muscle). In another alternative, a catheter introduced into the femoral artery can be used to delivery AAV vectors to liver via the hepatic artery. Non-surgical means can also be employed, such as endoscopic retrograde cholangiopancreatography (ERCP), to deliver AAV vectors directly to the liver, thereby bypassing the bloodstream and AAV antibodies. Other ductal systems, such as the ducts of the submandibular gland, can also be used as portals for delivering AAV vectors into a subject that develops or has preexisting anti-AAV antibodies.

Administration or in vivo delivery to a subject can be performed prior to development of an adverse symptom, condition, complication, etc. caused by or associated with the disease. For example, a screen (e.g., genetic) can be used to identify such subjects as candidates for invention compositions, methods and uses. Such subjects therefore include those screened positive for an insufficient amount or a deficiency in a functional gene product (e.g., FVIII protein), or that produce an aberrant, partially functional or non-functional gene product (e.g., FVIII protein).

Administration or in vivo delivery to a subject in accordance with the methods and uses of the invention as disclosed herein can be practiced within 1-2, 2-4, 4-12, 12-24 or 24-72 hours after a subject has been identified as having the disease targeted for treatment, has one or more symptoms of the disease, or has been screened and is identified as positive as set forth herein even though the subject does not have one or more symptoms of the disease. Of course, methods and uses of the invention can be practiced 1-7, 7-14, 14-21, 21-48 or more days, months or years after a subject has been identified as having the disease targeted for treatment, has one or more symptoms of the disease, or has been screened and is identified as positive as set forth herein.

A "unit dosage form" as used herein refers to physically discrete units suited as unitary dosages for the subject to be treated; each unit containing a predetermined quantity optionally in association with a pharmaceutical carrier (excipient, diluent, vehicle or filling agent) which, when administered in one or more doses, is calculated to produce a desired effect (e.g., prophylactic or therapeutic effect). Unit dosage forms may be within, for example, ampules and vials, which may include a liquid composition, or a composition in a freeze-dried or lyophilized state; a sterile liquid carrier, for example, can be added prior to administration or delivery in vivo. Individual unit dosage forms can be included in multi-dose kits or containers. Recombinant vector (e.g., rAAV) sequences, recombinant virus particles, and pharmaceutical compositions thereof can be packaged in single or multiple unit dosage form for ease of administration and uniformity of dosage.

Subjects can be tested for FVIII amounts or FVIII activity to determine if such subjects are appropriate for treatment according to a method of the invention. Candidate hemophilia subjects can be tested for FVIII amounts or activity prior to treatment according to a method of the invention. Subjects also can be tested for amounts of FVIII or FVIII activity after treatment according to a method of the invention. Such treated subjects can be monitored after treatment for FVIII amounts or FVIII activity, periodically, e.g., every 1-4 weeks or 1-6 months.

Subjects can be tested for one or more liver enzymes for an adverse response or to determine if such subjects are appropriate for treatment according to a method of the invention. Candidate hemophilia subjects can therefore be screened for amounts of one or more liver enzymes prior to treatment according to a method of the invention. Subjects also can be tested for amounts of one or more liver enzymes after treatment according to a method of the invention. Such treated subjects can be monitored after treatment for elevated liver enzymes, periodically, e.g., every 1-4 weeks or 1-6 months.

Exemplary liver enzymes include alanine aminotransferase (ALT), aspartate aminotransferase (AST), and lactate dehydrogenase (LDH), but other enzymes indicative of liver damage can also be monitored. A normal level of these enzymes in the circulation is typically defined as a range that has an upper level, above which the enzyme level is considered elevated, and therefore indicative of liver damage. A normal range depends in part on the standards used by the clinical laboratory conducting the assay.

Subjects can be monitored for bleeding episodes to determine if such subjects are eligible for or responding to treatment, and/or the amount or duration of responsiveness. Subjects can be monitored for bleeding episodes to determine if such subjects are in need of an additional treatment, e.g., a subsequent AAV vector administration or administration of an immunosuppressive agent, or more frequent monitoring. Hemophilia subjects can therefore be monitored for bleeding episodes prior to and after treatment according to a method of the invention. Subjects also can be tested for frequency and severity of bleeding episodes during or after treatment according to a method of the invention.

The invention provides kits with packaging material and one or more components therein. A kit typically includes a label or packaging insert including a description of the components or instructions for use in vitro, in vivo, or ex vivo, of the components therein. A kit can contain a collection of such components, e.g., a nucleic acid, recombinant vector, virus (e.g., AAV) vector, or virus particle and optionally a second active, such as another compound, agent, drug or composition.

A kit refers to a physical structure housing one or more components of the kit. Packaging material can maintain the components sterilely, and can be made of material commonly used for such purposes (e.g., paper, corrugated fiber, glass, plastic, foil, ampules, vials, tubes, etc.).

Labels or inserts can include identifying information of one or more components therein, dose amounts, clinical pharmacology of the active ingredient(s) including mechanism of action, pharmacokinetics and pharmacodynamics. Labels or inserts can include information identifying manufacturer, lot numbers, manufacture location and date, expiration dates. Labels or inserts can include information identifying manufacturer information, lot numbers, manufacturer location and date. Labels or inserts can include information on a disease for which a kit component may be used. Labels or inserts can include instructions for the clinician or subject for using one or more of the kit components in a method, use, or treatment protocol or therapeutic regimen. Instructions can include dosage amounts, frequency or duration, and instructions for practicing any of the methods, uses, treatment protocols or prophylactic or therapeutic regimes described herein.

Labels or inserts can include information on any benefit that a component may provide, such as a prophylactic or therapeutic benefit. Labels or inserts can include information on potential adverse side effects, complications or reactions, such as warnings to the subject or clinician regarding situations where it would not be appropriate to use a particular composition. Adverse side effects or complications could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities.

Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a bar-coded printed label, a disk, optical disk such as CD- or DVD-ROM/RAM, DVD, MP3, magnetic tape, or an electrical storage media such as RAM and ROM or hybrids of these such as magnetic/optical storage media, FLASH media or memory type cards.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All patents, patent applications, publications, and other references, GenBank citations and ATCC citations cited herein are incorporated by reference in their entirety. In case of conflict, the specification, including definitions, will control.

Various terms relating to the biological molecules of the invention are used hereinabove and also throughout the specification and claims.

All of the features disclosed herein may be combined in any combination. Each feature disclosed in the specification may be replaced by an alternative feature serving a same, equivalent, or similar purpose. Thus, unless expressly stated otherwise, disclosed features (e.g., CpG reduced nucleic acid variants encoding FVIII, vector, plasmid, expression/recombinant vector (e.g., rAAV) sequence, or recombinant virus particle) are an example of a genus of equivalent or similar features.

As used herein, the singular forms "a", "and," and "the" include plural referents unless the context clearly indicates otherwise. Thus, for example, reference to "a nucleic acid" includes a plurality of such nucleic acids, reference to "a vector" includes a plurality of such vectors, and reference to "a virus" or "particle" includes a plurality of such viruses/particles.

As used herein, all numerical values or numerical ranges include integers within such ranges and fractions of the values or the integers within ranges unless the context clearly indicates otherwise. Thus, to illustrate, reference to 80% or more identity, includes 81%, 82%, 83%, 84%, 85%, 86%, 87%, 88%, 89%, 90%, 91%, 92%, 93%, 94% etc., as well as 81.1%, 81.2%, 81.3%, 81.4%, 81.5%, etc., 82.1%, 82.2%, 82.3%, 82.4%, 82.5%, etc., and so forth.

Reference to an integer with more (greater) or less than includes any number greater or less than the reference number, respectively. Thus, for example, a reference to less than 100, includes 99, 98, 97, etc. all the way down to the number one (1); and less than 10, includes 9, 8, 7, etc. all the way down to the number one (1).

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth.

Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-850, includes ranges of 1-20, 1-30, 1-40, 1-50, 1-60, 10-30, 10-40, 10-50, 10-60, 10-70, 10-80, 20-40, 20-50, 20-60, 20-70, 20-80, 20-90, 50-75, 50-100, 50-150, 50-200, 50-250, 100-200, 100-250, 100-300, 100-350, 100-400, 100-500, 150-250, 150-300, 150-350, 150-400, 150-450, 150-500, etc.

The invention is generally disclosed herein using affirmative language to describe the numerous embodiments and aspects. The invention also specifically includes embodiments in which particular subject matter is excluded, in full or in part, such as substances or materials, method steps and conditions, protocols, or procedures. For example, in certain embodiments or aspects of the invention, materials and/or method steps are excluded. Thus, even though the invention is generally not expressed herein in terms of what the invention does not include aspects that are not expressly excluded in the invention are nevertheless disclosed herein.

A number of embodiments of the invention have been described. Nevertheless, one skilled in the art, without departing from the spirit and scope of the invention, can make various changes and modifications of the invention to adapt it to various usages and conditions. Accordingly, the following examples are intended to illustrate but not limit the scope of the invention claimed in any way.

Example 1

Disclosed herein are gene constructs for use in gene therapy methods to treat hemophilia. In addition, these factor VIII (FVIII) encoding gene constructs may be useful in vitro in the setting of protein expression systems, to produce recombinant FVIII protein for administration. Each gene construct can optionally include one or more of an expression control (e.g., promoter) element, factor VIII gene and other regulatory features required for expression of the gene, such as introns, ITRs, stop codons, poly A signals, etc.

Example 2

CpG Reduced Factor VIII DNA Sequences and Certain Vector Constructs, Plasmid Constructs and AAV Vector Producing Cell Lines.

18 different CpG reduced nucleic acid variants encoding FVIII (SEQ ID NOs:1-18) were produced and assessed in expression assays. CpG reduced human FVIII cDNA constructs were generated with a mutant transthyretin (TTRmut) promoter (SEQ ID NO:22).

AAV-SPK-8011 expression cassette has the CpG reduced FVIII-X07 nucleic acid sequence and the LK03 capsid for packaging. LK03 capsid has substantial homology to AAV3, a non-pathogenic, naturally replication deficient single-stranded DNA virus.

Packaging plasmid pLK03 is a 7,484 bp plasmid construct that carries the AAV2 Rep and AAV-LK03 Cap genes under the control of AAV2 p5 promoter, bacterial origin of replication and gene conferring resistance to Kanamycin in bacterial cells. In this construct, the p5 rep promoter has been moved 3' of the cap gene to reduce the potential for formation of wild-type or pseudo wild type AAV species, and to increase yield of the vector.

The cloned DNA for gene transfer is a gene expression cassette, packaged into the AAV-LK03 capsid as a single-stranded genome, encoding human coagulation factor VIII (hFVIII) under control of a liver-specific promoter. The expression plasmid is referred to as pAAV-TTRmut-hFVIII-X07. It was modified by the introduction of 4 point mutations in the TTR promoter, and the coding region optimized to increase expression of human FVIII. The AAV expression cassette contains the following elements:

AAV2 ITR

Transthyretin (TTR) promoter: A liver-specific transthyretin (TTR) promoter with 4 point mutations that increase gene expression compared with the wild type promoter (Costa et al. 1991)

Synthetic intron: Derived from human elongation factor EF-1 alpha gene

FVIII coding sequence: B-domain deleted, codon-optimized human FVIII coding sequence.

Rabbit beta globin poly A signal sequence (Levitt et al. 1989).

AAV2 ITR

Three DNA plasmid constructs are used to transfect human embryo kidney 293 cells to produce the SPK-8011 vector by a helper virus-free process (Matsushita et al. 1998):

The gene cassette (hFVIII coding sequence and associated regulatory elements) is cloned into a plasmid to give the vector plasmid, pAAV-TTRmut-hFVIII-X07.

The AAV viral genome (rep and cap) lacking the viral ITRs is cloned into a plasmid to give the AAV packaging plasmid, pLK03, providing the required AAV2 rep and AAV-LK03 cap genes in trans for AAV vector packaging. The viral promoter (p5) for the rep gene was relocated in the plasmid in order to prevent formation of replication competent AAV by non-homologous recombination.

Three genes from adenovirus-2 are cloned into a third plasmid (pCCVC-AD2HP) providing the necessary helper virus genes for vector production. Plasmid pCCVC-AD2HPv2 is an 11,832 bp plasmid construct that carries three adenovirus genes, E2A, E4 and the VA RNAs to provide 'helper' functions necessary for replication and encapsidation of AAV vector. Plasmid pCCVC-AD2HPv2 is a derivative of pCCVC-AD2HP in which the DrdI-DrdI 1882 bp restriction fragment containing the $Amp^R$ gene and part of the pUC ori sequence has been removed and replaced with the DrdI-DrdI fragment from plasmid pAAV2-hRPE65v2 containing the entire $Kan^R$ gene and part of the pUC ori sequence.

The cell substrate used for AAV vector production is a derivative of primary human embryonic kidney cells (HEK) 293. The HEK293 cell line is a permanent line transformed by sheared human adenovirus type 5 (Ad5) DNA (Graham et al. 1977). The Working Cell Bank is derived from a characterized HEK293 Master Cell Bank from the Center for Cellular and Molecular Therapeutics (CCMT) at The Children's Hospital of Philadelphia (CHOP).

Example 3

Evaluation of AAV-hFVIII Vectors in Mice.

FVIII transgene constructs (hFVIII) were packaged into adeno-associated viral (AAV) vectors and delivered to mice. In brief, groups of 4 hemophilia A/$CD4^{-/-}$ mice were injected at 8-10 weeks of age with $4\times10^{12}$ vg/kg of AAV-hFVIII vectors. Immunodeficient mice were used to enable quantification of FVIII plasma levels, as the inhibitory antibodies to FVIII that are generated in normal mice prevent long-term analysis of FVIII expression.

Figure 1:
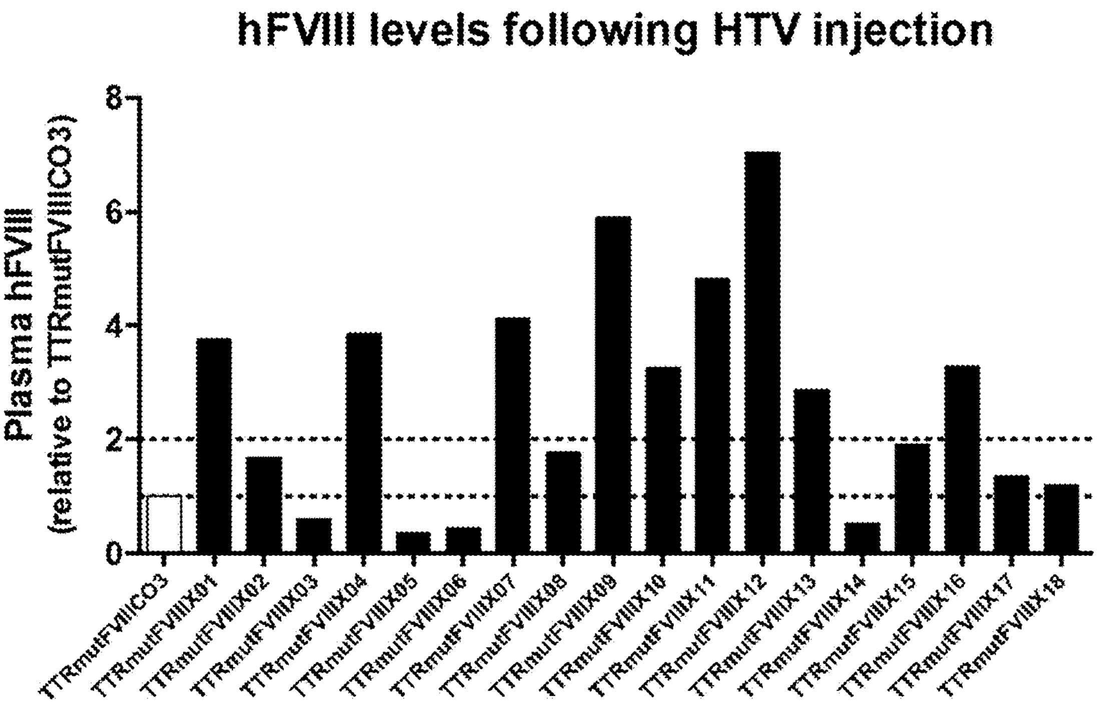
FIG. 1 shows human FVIII (hFVIII) levels 24 hour following hydrodynamic tail vein (HTV) injection of 50 μg of plasmid, for 18 different clones (X01-X18 corresponding to SEQ ID Nos:1-18, respectively) and FVIII-CO3 (SEQ ID NO:21).
Figures 2A, 2B, 2C:
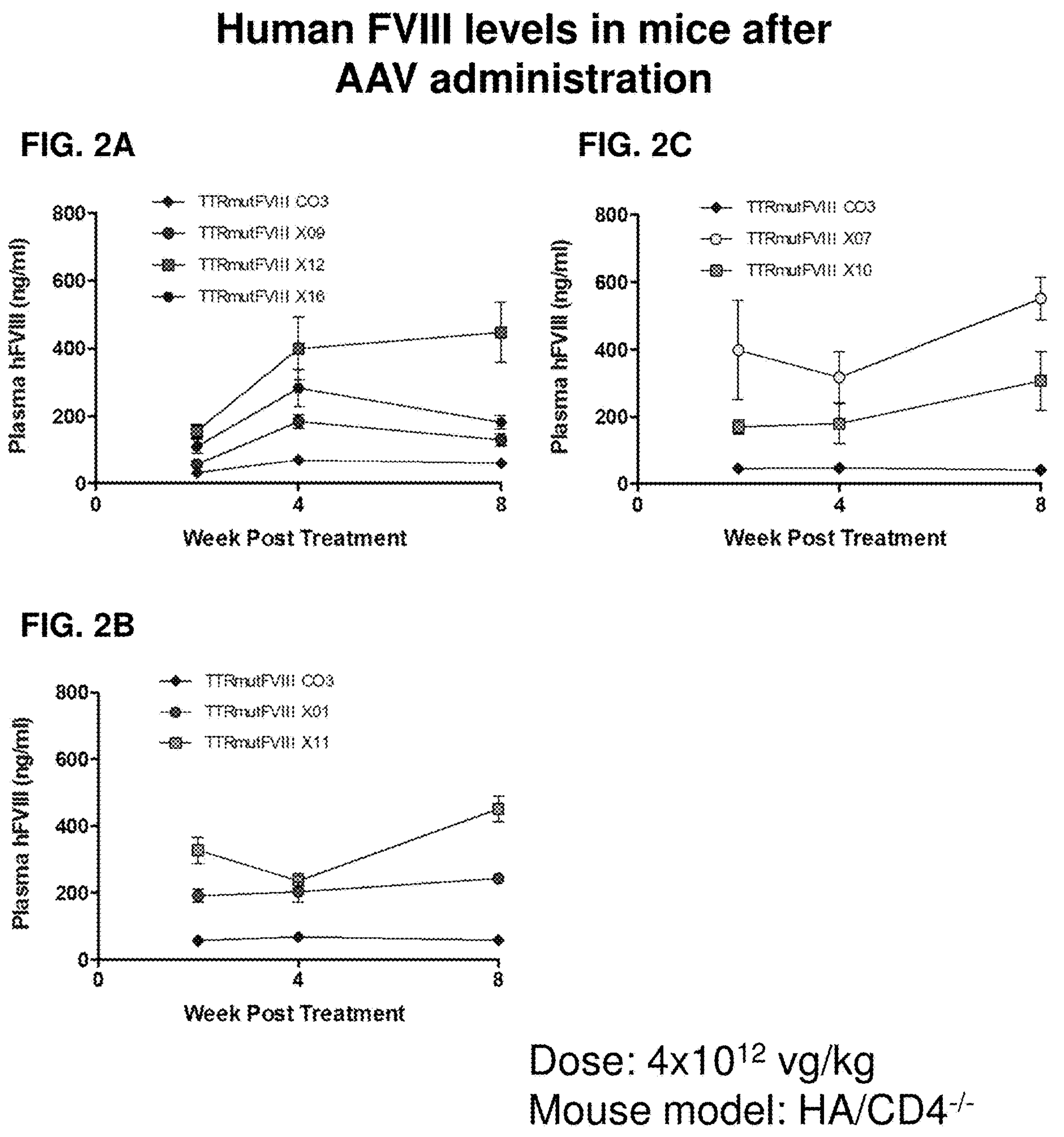
FIG. 2A-2C show FVIII levels in hemophilia A/CD4$^{-/-}$ mice after AAV vector administration of FVIII (A) CO3 (SEQ ID NO:21), X09 (SEQ ID NO:9), X12 (SEQ ID NO:12) and X16 (SEQ ID NO:16); (B) CO3 (SEQ ID NO:21), X01 (SEQ ID NO:1) and X11 (SEQ ID NO:11); or (C) CO3 (SEQ ID NO:21), X07 (SEQ ID NO:7) and X10 (SEQ ID NO:10).

Levels of FVIII expression were determined and in several instances were higher than expression provided by the CO3 sequence (SEQ ID NO:21) encoding hFVIII. As shown in FIG. 2, vectors including AAV-SPK-8005 expressed higher hFVIII levels compared to reference AAV-CO3vector. The data surprisingly reveal that several of the DNA sequences expressed higher levels of FVIII than a codon-optimized sequence (CO3, SEQ ID NO:21) encoding FVIII.

AAV-Spark8005 (also designated SPK-8005), rather than AAV-LK03-hFVIII (also designated AAV-LK03-hFVIII and SPK-8011), was used in this study to ensure efficient transduction (i.e.; hFVIII transgene expression) of mouse hepatocytes. Thus, this study was designed to evaluate the safety of sustained hFVIII expression, and not the safety of the AAV-LK03 capsid.

The three doses of AAV-SPK-8005-hFVIII used ($4\times10^{10}$, $8\times10^{10}$, $1.6\times10^{11}$ vg/mouse; approximately $1.6\times10^{12}$, $3.2\times10^{12}$, $6.4\times10^{12}$ vg/kg, based on mouse weight of 25 g) were chosen to generate approximately 5-25, 25-75, and 50-150% hFVIII antigen levels, respectively. The study involved 350 male NOD/SCID mice (Table 1) and was divided into two sub-studies: Main study (n=270) and Bioanalysis study (n=80). In the Main study, 60 mice were treated with either vehicle or one of the three doses of vector ($4\times10^{10}$, $8\times10^{10}$, $1.6\times10^{11}$ vg/mouse). Ten mice were used for day 29/30 assessments of clinical chemistries, 10 were used for hematology, and coagulation assessments were made on the remaining 10 animals. These 30 mice were sacrificed on day 29 or 30. The other group of 30 mice that were treated with either vehicle or one of the three vector doses was handled similarly at the day 87 timepoint, and they were sacrificed on day 87. Upon termination, gross pathology observations were performed on all animals in the Main study and comprehensive histopathology was performed on 10 animals/cohort per timepoint (hematology subset). Another cohort of 30 naïve mice was used for background control clinical pathology measurements.

In the Bioanalysis study, 20 mice were injected with vehicle or one of the three vector doses. These animals were bled prior to test article injection and serially on days 15, 30, 60, and 87. The intended volume of plasma collected for each sample should have been sufficient for determination of both hFVIII antigen and D-dimer levels. However, due to insufficient plasma volume collections, only a single assay was performed on individual mouse plasma at all timepoints, with the exception of the terminal timepoint. Thus, some mice were evaluated for circulating levels of hFVIII antigen and others for D-dimer levels. Since more plasma is required to perform the hFVIII ELISA (minimum of 50 uL) than the D-dimer ELISA (minimum of 20 uL), the choice of assay was dictated by the volume of plasma collected.

TABLE 1

Mouse study design

| Group No. | Test Material | Dose Level (vg/mouse) | Dose Volume (μL/mouse) | Dose Concentration (vg/mL) | No. of Mice: Main Study: Day 29/30 Subset | No. of Mice: Main Study: Day 87 Subset | No. of Mice: Bioanalysis Study[a] |
|---|---|---|---|---|---|---|---|
| Naïve[b] | None | Na | na | na | na | na | na |
| 1 | Control Article | 0 | 200 | 0 | 30 | 30 | 20 |
| 2 | AAV-SPK-8005[c] | $4\times10^{10}$ | 200 | $2\times10^{11}$ | 30 | 30 | 20 |
| 3 | AAV-SPK-8005[c] | $8\times10^{10}$ | 200 | $4\times10^{11}$ | 30 | 30 | 20 |
| 4 | AAV-SPK-8005[c] | $1.6\times10^{11}$ | 200 | $8\times10^{11}$ | 30 | 30 | 20 |
| Naïve[b] | None | Na | na | na | na | na | na |

[a]Blood was collected from all mice at predose and on Days 15, 30, 60, and 87 of study.

[b]Blood was collected from 30 total mice (10 naïve mice per clinical pathology evaluation) Clinical Pathology-Main Study for background control levels.

[c] AAV-SPK-8005-hFVIII is also designated SPK-8005 na = Not applicable

Figure 3A:
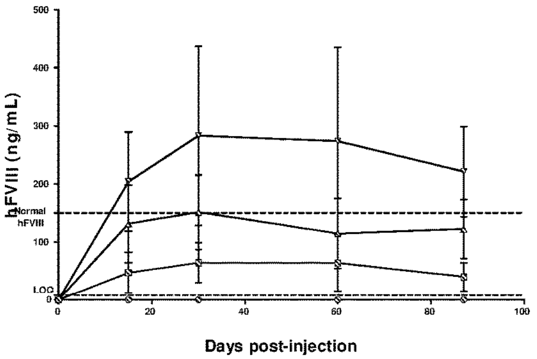
FIG. 3A-3B show levels of hFVIII antigen in ng/ml (B) or % total antigen (C) in plasma of NOD/SCID mice following intravenous administration of either vehicle (circle), $4\times10^{10}$ (square), $8\times10^{10}$ (triangle), or $1.6\times10^{11}$ vg/mouse (inverted triangle) of AAV-SPK-8005-hFVIII over the course of 87 days. Lines represent hFVIII averages±SD in each cohort. Human FVIII plasma levels were assayed by ELISA and ng/ml FVIII was converted to % normal FVIII levels by assuming 150 ng/ml is equivalent to 100% activity.
Figure 3B:
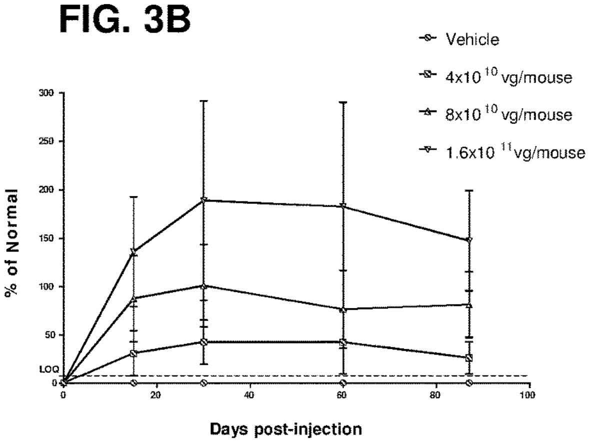

Plasma FVIII Antigen Levels:

As shown in FIG. 3A-3B, a dose-response was observed in the circulating levels of hFVIII antigen over the course of 87 days. At the low dose of vector ($4\times10^{10}$ vg/mouse), average hFVIII levels of 64+/−49 ng/ml were seen at day 60 post-injection, and 115+/−60 ng/ml and 273+/58 ng/ml were seen at the mid and high doses, respectively. These antigen levels represent 43, 77, and 182% of normal hFVIII antigen (150 ng/mL is equivalent to 100%). Therefore, in hemostatically normal NOD/SCID mice, total (mouse+human) FVIII levels of 143%, 177% and 282% would be expected at the three dose levels, respectively. Thus, using AAV-SPK-8005-hFVIII, sustained and supraphysiological levels of hFVIII were observed in the plasma of immunodeficient mice, making this study appropriate for assessing safety of long-term expression of hFVIII.

Figure 3C:
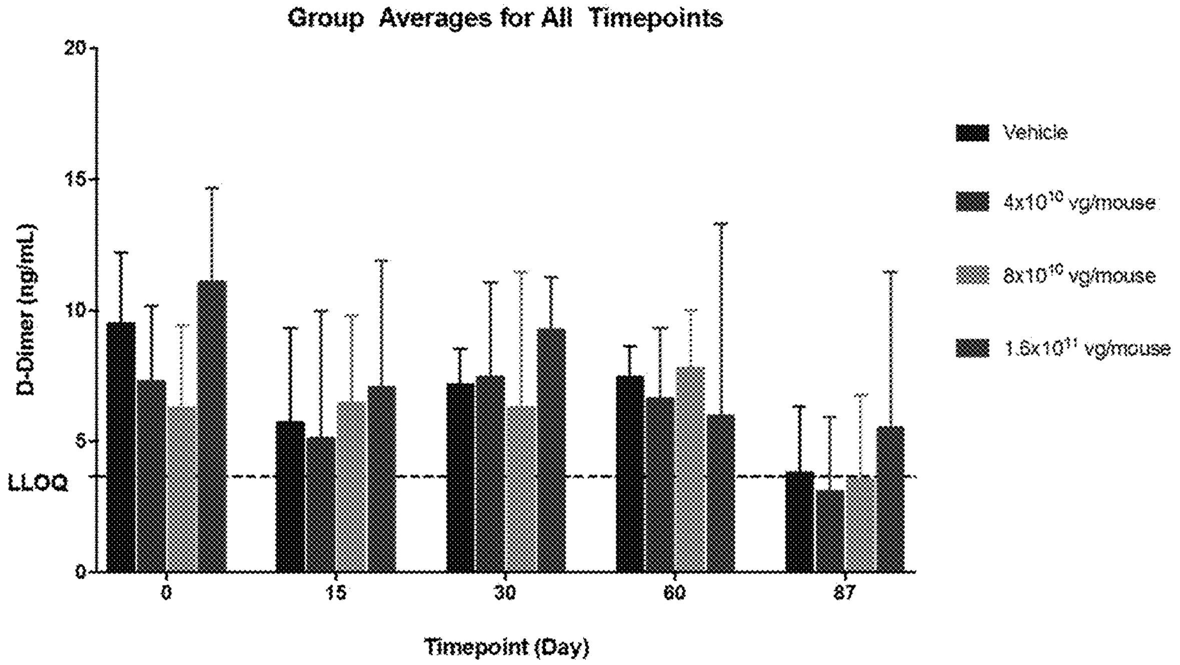
FIG. 3C shows levels of D-dimers in plasma of NOD/SCID mice following intravenous administration of either vehicle, $4\times10^{10}$, $8\times10^{10}$ or $1.6\times10^{11}$ vg/mouse of AAV-SPK-8005-hFVIII as illustrated, left to right at each timepoint, x-axis. Bars represent averages±SD of mice in each cohort. D-dimer levels were assayed by ELISA.

D-Dimer Levels:

In order to assess the potential for thrombogenesis due to sustained expression of hFVIII in hemostatically normal, but immunodeficient mice, D-dimer antigen levels were measured. The average predose level of D-dimers among 50 naïve mice was 8.8+/−2.9 ng/ml. The data in FIG. 3C represent average D-dimer levels in the four dose cohorts. There was no statistical difference in D-dimer levels between cohorts at all five timepoints (1 way ANOVA p=0.46). It was concluded that sustained expression of hFVIII at levels has high as 194% of normal (day 30), and for at least 87 days, is not associated with an elevated level of D-dimers in this strain of mice.

Clinical and Anatomical Pathology:

There were nine animals (6 Main study and 3 Bioanalysis study) either euthanized early or found dead during the course of this study.

The six Main study animals were evaluated histopathologically, and malignant lymphomas were observed in four of these six mice, including one vehicle control-injected mouse. (Group 1 animal 7729, Group 3 animal 7871, Group 3 animal 7880, and Group 3 animal 7874). The biological significance of the neoplastic findings was considered to be equivocal. Statistical significance of individual group comparisons to the control group was considered unlikely. A high spontaneous frequency of thymic lymphomas, as well as neoplastic enlargements of spleens and lymph nodes are known to occur in this strain (Prochazka, Gaskins, Shultz, & Leiter, 1992).

Non-neoplastic findings related to the test article were not present in these six mice. The microscopic findings observed were considered incidental and of the nature commonly observed in this strain and age of mice, and/or were of similar incidence and severity in control and treated animals and, therefore, were considered unrelated to administration of AAV-SPK-8005-hFVIII.

The remaining 234 mice included in the Main study survived to the scheduled timepoints. No adverse or AAV-SPK-8005-hFVIII-related clinical observations occurred in the mice throughout the study. All clinical observations of scab formation, fur loss or thin cover and bent tail were considered unrelated to administration of AAV-SPK-8005-hFVIII, because these observations are common in this mouse species and/or occurred across groups. Body weights and body weight gains were comparable among dose groups and unaffected by administration of AAV-SPK-8005-hFVIII. An apparent significant ($p<0.05$ or $p<0.01$) reduction in Group 4 mean body weights from Day 32 to study completion was attributed to redistribution of the group weights (some heavier animals euthanized in Group 4 as compared to Group 1) after the Day 29/30 euthanasia, and was not related to AAV-SPK-8005-hFVIII administration. Group 4 mice gained weight in a comparable manner to the other groups throughout the study. All other significant ($p<0.05$ or $p<0.01$) differences in mean body weights or body weight gains were not considered related to AAV-SPK-8005-hFVIII, because the increases and decreases were sporadic with no dose-dependence and were considered related to normal fluctuations in mouse body weights.

Clinical pathology was performed on the Main study animals. Clinical chemistry parameters were analyzed on 10 mice/cohort per time point (day 29/30 and day 87). Coagulation assessments were performed on another group of 10 mice/cohort, and hematology measurements were made on the other group of 10 mice/cohort. Gross pathology was performed on all animals and histopathology was performed on the group of 10 mice utilized for hematology assessments. There were no AAV-SPK-8005-hFVIII-related changes in hematology or clinical chemistry parameters in mice from either the Day 29/30 and Day 87 euthanasia timepoints. In general, where significant ($p<0.05$ or $p<0.01$) differences in hematology and clinical chemistry parameters as compared to the control values existed, the differences were not related to AAV-SPK-8005-hFVIII, because corresponding parameters were unaffected and the observations were not dose-dependent. All changes in clinical chemistry and hematology parameters were sporadic, attributed to a single animal, of a magnitude of change commonly observed in laboratory animals and/or within the clinical pathology parameters assessed for the naïve animals.

Changes in coagulation parameters were observed in mice administered AAV-SPK-8005-hFVIII. A dose-dependent reduction in mean aPTT was observed at the Day 29/30 timepoint, with Group 3 and 4 values significantly ($p<0.05$ or $p<0.01$) different from control values. A significant ($p<0.01$) reduction in mean aPTT values was also observed in all AAV-SPK-8005-hFVIII groups as compared to the control group at the Day 87 timepoint. Reduced mean prothrombin time was also observed in the AAV-SPK-8005-hFVIII groups as compared to the control group at Days 29/30 and 87, however the reduction was only statistically significant ($p<0.05$ or $p<0.01$) for Groups 2 and 3 on day 29/30 and Group 4 on Day 87. Mean fibrinogen values were comparable among dose groups throughout the study. These effects are considered related to the pharmacologic effect of AAV-SPK-8005-hFVIII, and not considered adverse. As shown in FIGS. 3A-3C and discussed above, all mice injected with AAV-SPK-8005-hFVIII expressed hFVIII antigen and thus, supraphysiological levels of total FVIII are predicted to circulate in the plasma of these hemostatically normal mice. These levels would be expected to have an effect on coagulation parameters, such as reduced aPTT and prothrombin times.

A group of 120 Main study mice (30/cohort) were sacrificed on day 29 or 30 of the study. No gross pathology observations related to AAV-SPK-8005-hFVIII were made on these mice. Analysis of organ weights revealed that the absolute weights of heart and kidney differed between the 10 control and vector-injected animals sacrificed on day 29; however, this was not observed between the 10 control and vector-injected animals sacrificed on day 30, so the significance of this finding is unclear. There was no microscopic correlate to the statistically significant increase in heart and kidney absolute weights (and these weights as a percent of brain weight) observed on day 29. Furthermore, heart and kidney weight as a percent of body weight were not significantly different from controls. There was a significant increase in mean absolute lung weight in Group 2 animals, but this was considered incidental and unrelated AAV-SPK-8005-hFVIII because there was no dose dependence. No other organ weight changes were noted at Day 29/30.

Upon histopathological analyses on Day 29/30, there were five animals with neoplastic findings. A bronchioloalveolar adenoma was observed in one Group 2 animal (7824). Malignant lymphoma was observed in one Group 2 animal (7838), one Group 3 animal (7885), and one group 4 animal (7941). Adenoma was observed in stomach in one Group 4 animal (7942). No neoplastic findings were observed in Group 1. The biological significance of the neoplastic findings is considered to be equivocal. Statistical significance of individual group comparisons to the control group is unlikely. However, it is noteworthy that neoplastic findings were only observed in treated animals at Day 29/30. In the absence of historical control data for NOD SCID mice at a comparable age, these neoplastic findings are inconclusive.

No test article-related non-neoplastic microscopic findings were noted. The microscopic findings observed were considered incidental, of the nature commonly observed in this strain and age of mice, and/or were of similar incidence and severity in control and treated animals and, therefore, were considered unrelated to administration of AAV-SPK-8005-hFVIII.

Another group of 120 Main study mice (30/cohort) were sacrificed 87 days post-injection and analyzed in a similar manner. Although no gross pathology observations considered related to AAV-SPK-8005-hFVIII were seen, lesions were observed in four mice (one enlarged thymus not analyzed histologically, one enlarged thymus correlated to malignant lymphoma, one enlarged spleen not analyzed histologically, one discolored testis). In contrast to what was observed at day 29/30, decreased heart weights, not increased weights were observed. In addition, decreases in liver weights were seen. The statistically significant changes in heart weight were small and not clearly related to dose. The statistical significant change in absolute liver weight was small and the liver weights to body and brain weight were comparable among groups. Therefore the slight changes were interpreted as incidental and unrelated to administration of AAV-SPK-8005-hFVIII. No other organ weight changes were noted at Day 87.

Histopathology performed on mice on day 87 post-injection identified four animals with neoplastic findings. Malignant lymphoma was observed in one Group 2 animal (7808) and three Group 3 animals (7868, 7869 and 7870). No neoplastic findings were observed in Group 1. The biological significance of the neoplastic findings is considered to be equivocal. Statistical significance of individual group comparisons to the control group is unlikely. However, it is noteworthy that neoplastic findings were only observed in treated animals at Day 87. In the absence of historical control data for NOD SCID mice at a comparable age these neoplastic findings are inconclusive.

With regards to non-neoplastic changes, no test article-related microscopic findings were noted. The microscopic findings observed were considered incidental, of the nature commonly observed in this strain and age of mice, and/or were of similar incidence in control and treated animals and, therefore, were considered unrelated to administration of AAV-SPK-8005-hFVIII.

Conclusions:

A single administration of AAV-SPK-8005-hFVIII at doses of $4\times10^{10}$, $8\times10^{10}$, or $1.6\times10^{11}$ vg/mouse, or control article, by intravenous injection to male NOD/SCID mice was well tolerated. AAV-SPK-8005-hFVIII did not result in any test article-related mortality, adverse clinical observations or changes in body weight. There were no toxicologically important differences in organ weights, hematology or coagulation parameters and no treatment-related gross pathology or histopathology findings in the male mice at Days 29/30 or Day 87. The reductions in mean aPTT and prothrombin time that were observed at both euthanasia timepoints were considered related to the supraphysiologic levels of FVIII that were expressed in these hemostatically normal mice, and were not adverse. Within the Main study (terminal evaluations), malignancies were observed in nine out of 60 vector-injected mice, or 15% of the animals. Seven of these nine mice had lymphomas, which were most commonly seen in lymph nodes. This immunodeficient mouse strain is known to have a high spontaneous frequency of lymphomas (Prochazka et al., 1992), and a life span of just 8.5 months. Thus, the frequency of tumors seen in this study is unlikely related to AAV-SPK-8005-hFVIII administration. The purpose of this study was to evaluate the safety of sustained expression of hFVIII over the course of approximately three months. It was not designed to evaluate the AAV-SPK capsid. AAV-SPK and an immunodeficient mouse strain were used to ensure high level expression of hFVIII. Administration of AAV-SPK-8005-hFVIII to NOD/SCID mice resulted in sustained and high levels of hFVIII. Thus, this study was appropriate for assessing the safety of long-term expression of hFVIII.

Example 4

Evaluation of AAV-SPK-8005 and AAV-SPK-8011(LK03 Capsid, FVIII-X07 (SEQ ID NO: 7)) Vectors in Non-Human Primates (NHPs).

Based on the results in mice, FVIII transgene constructs packaged into adeno-associated viral (AAV) vectors were delivered to non-human primates (NHPs).

In brief, a dose-ranging study in male cynomolgus macaques administered a single intravenous infusion of AAV-SPK-8005 or AAV-SPK-8011 (LK03 capsid). Expression of hFVIII was evaluated over 8 weeks. The animal groups and dose levels of each are shown in FIG. 4.

NHPs received an intravenous infusion via the saphenous vein using a calibrated infusion pump over approximately 30 minutes. Macaques were prescreened for neutralizing antibodies against the AAV capsid. All treated animals were initially determined to have a <1:3 titer before vector administration. This was done to ensure successful hepatic transduction, as even low titers inhibit vector uptake by liver cells after systemic delivery (Jiang et al. 2006). All animals were also negative for the presence of neutralizing antibodies against FVIII before gene transfer.

Plasma levels of hFVIII were measured by a human-specific ELISA that does not detect the cynomolgus endogenous FVIII. All the animals in the study, with the exception of one macaque in the mid dose cohort, express hFVIII following vector delivery. Human factor VIII antigen levels peaked at around 1-2 weeks following vector administration. At one week after gene transfer, NHPs transduced with $2\times10^{12}$ vg/kg of AAV-SPK-8005 expressed hFVIII antigen levels of 13.2±3% (average±standard error of the mean). At one week after gene transfer, average hFVIII levels in two of the three animals in the next treatment cohort ($5\times10^{12}$ vg/kg) were 27±0.2%. Human FVIII could not be detected in the third macaque in that cohort at any time point. Upon re-testing of baseline plasma samples it was determined that this animal was in fact positive for the presence of anti-AAV antibodies and that the initially determined titer of <1:3 was incorrect. Finally, at the highest tested dose of $1\times10^{13}$ vg/kg, peak hFVIII antigen levels of 54.1±15.6% were observed after AAV infusion.

As anticipated by studies in NHPs expressing human FIX, human FVIII expression declined in approximately one third of the animals around week 4, concomitant with the appearance of inhibitor antibodies to hFVIII in these 3 macaques (labeled with a ε symbol in FIG. 5). Development of species-specific antibodies to hFVIII has been previously documented in non-human primates, and is likely due to differences in several amino acid residues between the human transgene product and the endogenous cynomolgus FVIII (McIntosh, J. et al., *Blood* 121:3335-44 (2013)).

To assess potential thrombogenesis due to continuous expression of human FVIII, D-dimer antigen levels were measured in this study. It should be noted that reports on the clinical relevance or even the normal values of D-dimer antigen levels in cynomolgus macaques are scarce; as a reference, the normal range for D-dimers in humans is below 500 ng/ml. Since the animals express endogenous cynomolgus FVIII, production of hFVIII as a result of hepatic gene transfer will result in supraphysiological levels of FVIII activity.

The animal that was dosed at $5\times10^{12}$ vg/kg but did not express human FVIII had a peak of 863 ng/ml two weeks after AAV infusion. The rest of the animals did not show any significant increase in D-dimer antigen levels compared to baseline values. Taken together, these results suggest that expression of human FVIII, at the levels targeted in this study, is not associated with an increased risk of thrombosis.

Four weeks after vector administration, no vector-related changes were apparent. Liver function tests showed normal values, with minor fluctuations that appeared to be unrelated to vector dose, as they were present prior to dosing in most cases (FIG. 6).

D-dimer levels up to week 5 are shown in FIG. 7. One animal in the high dose cohort had a slight (577 ng/ml), transient elevation in D-dimer levels one week after vector administration, when circulating human FVIII peaked at around 100%; the D-dimer levels rapidly returned to normal after this single elevate measurement. Notably, there was no correlation between D-dimer levels and hFVIII antigen levels (FIG. 7, bottom panels).

For AAV-SPK-8011(LK03 capsid) vector, three cohorts of cynomolgus macaques (n=3) were treated with increasing doses of AAV-SPK-8011(LK03 capsid) ($2\times10^{12}$, $6\times10^{12}$ and $2\times10^{13}$ (vg/kg); FIG. 4). Animals were monitored for clinical observations, body weights clinical pathology (clinical chemistry, hematology, coagulation, urinalysis). In addition, hFVIII antigen levels, FVIII inhibitory antibodies and D-dimer levels were assessed throughout the study.

The hFVIII antigen data is shown in FIG. 9. Average hFVIII antigen levels peaked around week 2-3 with 22.3±6.2% hFVIII seen in the low dose cohort and 61.6±15.7% and 153±58.1% observed in the mid and high dose cohorts, respectively, using 150 ng/ml as the 100% normal hFVIII antigen level (FIG. 9A-9D). Thus, the LK03 AAV capsid serotype efficiently transduces NHP hepatocytes in vivo unlike mouse liver.

FVIII expression levels attained with AAV-SPK-8011 (LK03 capsid) were compared to reported levels of FVIII attained with AAV5 and AAV8 capsid based AAV vectors for delivery of FVIII. A comparison revealed levels of FVIII achieved with AAV-SPK-8011(LK03 capsid) were greater than the reported levels of FVIII delivered by way of AAV vectors with AAV5 and AAV8 capsids (FIG. 10).

Humoral response to hFVIII in plasma of cynomolgus macaques was measured following administration of either $2\times10^{12}$, $6\times10^{12}$ or $2\times10^{13}$ vg/kg of AAV-SPK-8011(LK03 capsid). The animals were assessed for anti-hFVIII IgG antibodies by ELISA at baseline and at the indicated time points.

Despite the therapeutic hFVIII levels observed soon after gene transfer, in most animals the levels began to decline around week 4. This was consistent with previous studies using another AAV-hFVIII vector, and correlated with an increase in anti-hFVIII antibodies. Generation of anti-FVIII antibodies has also been observed by others following hepatic AAV-hFVIII gene transfer in NHPs (McIntosh, J. et al., *Blood* 121:3335-44 (2013)).

Example 5

Biodistribution of AAV-LK03 Capsid in Non-Human Primates (NHPs).

Biodistribution of the AAV-LK03 capsid in non-human primates was evaluated in a non-GLP study. Intravenous administration of an AAV-LK03-encapsidated vector encoding human coagulation factor IX (AAV-LK03-hFIX) showed that the two main target tissues are the liver and the spleen (FIG. 11). The splenic tropism is not a unique characteristic of AAV-LK03. For example, the AAV5 capsid, which has been used in several liver-directed gene therapy trials (e.g. NCT02396342, NCT02082860, NCT02576795) with a strong safety record, targets the spleen with the same if not higher efficacy than it targets the liver of non-human primates (Paneda et al. 2013). The SPK-8011 expression cassette uses the mouse transthyretin or TTR promoter, which is considered liver-specific (Costa, 1991). To further support the liver-specific nature of the promoter, a PCR-based expression analysis measured vector-derived FVIII expression in the livers and spleens of mice after administration of a different AAV vector packaging the same expression cassette as SPK-8011 (i.e. AAV-SPK-8005). As shown in FIG. 12, human FVIII expression in the spleen is several orders of magnitude lower compared with that derived from hepatocytes.

This is the first clinical study to use AAV-LK03, although studies have been conducted using other AAV vectors including several for hemophilia B (NCT02396342, NCT01620801 NCT00076557, NCT02484092, NCT02618915, NCT00979238, NCT01687608) and one for hemophilia A (NCT02576795). A study conducted by St. Jude Children's Research Hospital in collaboration with University College London utilized an AAV8 vector carrying a self-complementary genome encoding a codon-optimized human factor IX cDNA, scAAV2/8-LP1-hFIXco. Ten subjects who received the vector have had stable factor IX levels of 1-6% through a median of 3.2 years and all participants have either discontinued or reduced the use of prophylactic factor replacement (Nathwani et al. 2014). A clinical study for hemophilia A used an AAV5 encapsidated vector encoding human FVIII (NCT02576795). Preliminary data presented in 2016 demonstrate increases in FVIII activity after gene transfer in several subjects ranging from 2-60% with follow-up of up to 16 weeks (BioMarin, April 2016).

Example 6

Transduction Efficiency of AAV-LK03 Capsid Analyzed in an In Vitro Setting.

Primary hepatocytes from cynomolgus macaque and human origin were transduced with an AAV-LK03 vector expressing luciferase at four different multiplicities of infection (MOI) ranging from 500 to 62,500 vector genomes per cell. Seventy-two hours after transduction, luciferase expression was analyzed.

The AAV-LK03 capsid uniquely demonstrated significantly higher efficiency in transducing human hepatocytes in culture. In the representative example shown in FIG. 13, LK03 demonstrated approximately 5-fold higher efficiency in transducing human hepatocytes as compared to non-human primate hepatocytes in vitro. Importantly, these results are consistent across multiple MOIs and replicate studies.

Example 7

Assessment of Germline Transmission of Vector-Encoded Sequences.

Assessment of the potential for germline transmission of vector-encoded sequences is critical for clinical translation of gene transfer strategies. This study was designed with the following goals: (1) to evaluate dissemination of AAV-SPK and AAV-LK03 to semen and to determine the kinetics of vector clearance; and (2) to ensure that AAV administration to rabbits was successful, which was confirmed by analysis of human factor IX antigen and anti-FIX antibodies in plasma.

In this study, a rabbit model was used to analyze vector dissemination to the semen of two vector capsids, namely AAV-SPK and AAV-LK03 (Table 2). Dissemination of AAV-SPK to semen showed both dose-dependent and time-dependent kinetics, with the higher dose showing elevated levels of vector sequences in semen for a longer time. The kinetics were very similar to what has been seen previously with AAV8 vectors (Favaro P, et al., *Molecular Therapy* 17:1022-1030 (2009)). In contrast, limited dissemination to semen occurred with the AAV-LK03 vector. This is unlikely due to lower over-all vector exposure in AAV-LK03 injected mice, since the levels of hFIX expressed from AAV-LK03 were similar or higher than those seen with the AAV-SPK vector, and the ability to mediate liver-derived hFIX expression can be used as a surrogate for gene transfer.

TABLE 2

| Study design | | | |
|---|---|---|---|
| Group No. | Test Material | Dose Level (vg/kg) | No. of Animals |
| 1 | AAV-SPK-hFIX.C16 | $1 \times 10^{12}$ | 5 |
| 2A | AAV-SPK-hFIX.C16 | $1 \times 10^{13}$ | 3 |
| 2B* | AAV-SPK-hFIX.C19-PD | $1 \times 10^{13}$ | 2 |
| 3 | AAV-LK03-hFIX.C16 | $1 \times 10^{12}$ | 5 |
| 4 | AAV-LK03-hFIX.C16 | $1 \times 10^{13}$ | 5 |
| 5 | Vehicle | N/A | 2 |

*Two different hFIX coding sequences were used in the AAV-SPK cohorts, i.e. three animals received AAV-SPK-hFIX.C16 and two animals were treated with AAV-SPK-hFIX.C19-Padua (PD). Since the main goal of this study was to assess germline transmission of the two novel AAV capsids, this was considered acceptable. The main differences between the hFIX.C16 and hFIX.C19-Padua transgenes are that the latter is codon-optimized and encodes a high specific activity hFIX variant.

Methods

Animals and Vectors:

New Zealand white rabbits were obtained from Covance Research Products (Denver, Pa.) and treated at 6 months of age with AAV vectors produced at the Children's Hospital of Philadelphia Vector Core. The test and control articles were administered via the marginal ear vein.

Semen Collection:

An artificial vagina (AV), developed by researchers at Argus Research Lab, Inc. (Horsham, Pa.) was used for semen collection. The AV is lined with a condom from which the tip is removed and a collection tube is added, and the AV is filled with warm water (55° C.). Semen samples were obtained from a practiced buck stimulated by a teaser doe. Samples were collected prior to injection and at 1, 2, 4, 6, 8, and 10 weeks and 3-8 months post-injection. Semen samples were shipped to Charles River Laboratories (Reno, Nev.) for analysis of vector copy number using a validated real-time quantitative PCR assay.

Blood Sample Collection:

Blood was collected by medial auricular artery or marginal ear vein puncture prior to AAV administration and at multiple time points (pre, 1 week and 1-6 months post-injection). Each sample was placed on ice following collection, processed to plasma and. stored in an −80° C. freezer until shipment to the Sponsor, where it was also kept in an −80° C. freezer until the assay was performed.

Human Factor IX Levels:

Levels of human FIX (hFIX) protein in rabbit plasma were quantified using a sandwich-style FIX ELISA kit (Affinity Biologicals, FIX:EIA) as follows: first, the wells of a microtiter plate were coated with a capture antibody that recognizes hFIX and that does not cross-react with endogenous rabbit FIX (1:1000 dilution). Reference plasma with a known human hFIX concentration was diluted to generate a standard curve (the highest standard [500 ng/ml] was serially diluted down to 7.8 ng/ml). Sample plasmas were diluted depending on the expected concentration so that the absorbance values fell within the range of the standard curve. After addition of the samples to the wells, the plate was incubated at room temperature for 90 minutes and then washed three times. A horseradish peroxidase (HRP)-conjugated secondary antibody to hFIX was added to the plate to bind to the captured FIX (1:100 dilution). After washing the plate to remove unbound conjugated antibody, the peroxidase activity was measured following incubation with 1-Step Ultra TMB Substrate (Thermo Scientific, catalog number 34028). The reaction was stopped with 1M sulfuric acid and read on a SpectraMax M2e microplate reader at an absorbance setting of 450 nm. The absorbance value obtained is proportional to the concentration of hFIX present in the sample.

Anti-hFIX Antibody Levels:

The anti-hFIX assay is conceptually and methodologically similar to the hFIX ELISA described above. In short, plates were coated with 1 μg/ml of recombinant hFIX (Benefix, Wyeth). After incubation of plasma samples, a goat anti-rabbit IgG HRP-conjugated antibody (SIGMA, A4914) is used for detection. Samples with an IgG level two-fold higher than baseline readings were considered positive.

Results

Vector Dissemination to Semen

New Zealand rabbits were injected with AAV-SPK or AAV-LK03 (n=5 per group) vectors expressing hFIX under the control of the ApoE/hAAT liver-specific promoter at two doses: $1\times10^{12}$ vg/kg (low dose) or $1\times10^{13}$ vg/kg (high dose). Semen samples from all rabbits were obtained prior to injection and at 1, 2, 4, 6, 8, and 10 weeks and 3-8 months post-injection. Genomic DNA was purified from semen samples and analyzed for the presence of hFIX sequences using a quantitative polymerase chain reaction (Q-PCR) assay. The validated assay was developed by Charles River Laboratories (Reno, Nev.). Semen samples were considered to be positive if they had detectable hFIX levels above the lower limit of quantitation (LLOQ) (10 copies/reaction or 50 copies/μg at approximately 200 ng/reaction). Semen samples from rabbits that were negative for hFIX vector sequences on at least three consecutive timepoints were not analyzed further.

Pretreatment semen DNA from all vector and vehicle-injected animals was negative for hFIX sequences. The semen from rabbits injected with the low dose of AAV-SPK-hFIX ($1\times10^{12}$ vg/kg) was in general negative for hFIX sequences, except for three animals that had low levels at weeks 1-4 (maximum 3151 copies/μg DNA or $\sim1\times10^{-2}$ copies/haploid genome). None of the samples collected beyond week 4 were positive for vector sequences (Table 3). At the high dose of AAV-SPK-hFIX ($1\times10^{13}$ vg/kg), higher levels of vector were present (maximum 178,352 copies/μg DNA or 0.59 copies/haploid genome), and it took longer to clear, up to 5 month between the five animals (Table 3). With the exception of one animal (week 1), rabbits treated with the low dose of AAV-LK03-hFIX showed no dissemination of hFIX sequences to semen (Table 3). In addition, very little vector dissemination to semen was observed at a ten-fold higher dose, with three animals lacking any hFIX sequences at all timepoints and two animals showing low levels at week 2 (maximum: 392 copies/ug DNA or $1.3\times10^{-3}$ copies/haploid genome), but not at later timepoints (Table 3). Among the two vehicle-injected animals, one had a spurious finding at week 1 (56 copies/ug DNA) and at month 5 (96 copies/μg DNA). These values are near the LLOQ, and most likely represent contamination at the semen collection or DNA preparation step.

TABLE 3

| Detection of hFIX DNA sequences in rabbit semen following AAV-SPK and AAV-LK03 administration as a function of time. | | | | | | | | | | | | | | |
|---|---|---|---|---|---|---|---|---|---|---|---|---|---|---|
| Vector | Dose | Pre | W 1 | W 2 | W 4 | W 6 | W 8 | W 10 | M 3 | M 4 | M 5 | M 6 | M 7 | M 8 |
| SPK | low | 0/5 | 3/5 | 3/5 | 1/5 | 0/5 | 0/5 | 0/5 | 0/5 | 0/5 | 0/5 | Ndt | Ndt | Ndt |
| SPK | high | 0/5 | 5/5 | 4/5 | 4/5 | 3/5 | 1/5 | 2/5 | 0/5 | 1/5 | 0/5 | 0/5 | 0/5 | 0/5 |
| LK03 | low | 0/5 | 1/5 | 0/5 | 0/5 | 0/5 | 0/5 | 0/5 | 0/5 | 0/5 | 0/5 | Ndt | Ndt | Ndt |
| LK03 | high | 0/5 | 2/5 | 2/5 | 0/5 | 0/5 | 0/5 | 0/5 | 0/5 | 0/5 | 0/5 | Ndt | Ndt | Ndt |

Number of animals out of 5 with positive semen samples.
W = week;
M = month;
Ndt = not determined Plasma Human FIX Antigen Levels Circulating hFIX levels were measured in plasma samples from the animals described above at the indicated timepoints (FIGS. 14A-14B and Table 4).

TABLE 4

| Human FIX expression levels (ng/ml) following vector administration | | | | | | | | | | | |
|---|---|---|---|---|---|---|---|---|---|---|---|
| | | | | Day after injection | | | | | | | |
| Animal | Capsid | Transgene | vg/kg | 0 | 7 | 28 | 56 | 94 | 112 | 147 | 175 |
| 1 | SPK | FIX.C16 | 1E+12 | ND | ND | 49.0 | 39.7 | 70.6 | 126.1 | 147.9 | 102.4 |
| 2 | SPK | FIX.C16 | 1E+12 | ND | ND | 50.0 | 104.9 | 139.5 | 147.0 | 171.8 | 198.4 |
| 3 | SPK | FIX.C16 | 1E+12 | ND | ND | 36.4 | 76.5 | 95.0 | 114.8 | 114.7 | 78.9 |
| 4 | SPK | FIX.C16 | 1E+12 | ND | ND | 148.2 | 254.4 | 214.5 | 291.5 | 236.7 | 274.9 |
| 5 | SPK | FIX.C16 | 1E+12 | ND | ND | ND | ND | 31.3 | 10.5 | 13.4 | ND |
| 6 | SPK | FIX.C16 | 1E+13 | ND | 347.9 | 2341.0 | 1224.5 | 1102.2 | 1031.6 | 959.0 | 830.7 |
| 7 | SPK | FIX.C16 | 1E+13 | ND | 1564.1 | 14174.2 | 5311.2 | 3281.9 | 3300.9 | 2405.9 | 2640.8 |
| 8 | SPK | FIX.C16 | 1E+13 | ND | 2344.8 | 756.5 | 1515.0 | 8305.2 | 10907.0 | 5838.9 | 4352.8 |
| 9 | SPK | FIX.C19-PD | 1E+13 | ND | 103.3 | 234.4 | ND | 40.4 | 83.4 | 316.6 | 381.9 |
| 10 | SPK | FIX.C19-PD | 1E+13 | ND | 642.2 | 2873.5 | ND | 31.6 | 14.1 | 14.1 | ND |
| 11 | LK03 | FIX.C16 | 1E+12 | ND | 333.1 | 604.9 | 1659.2 | 2151.8 | 1914.7 | 1358.4 | 1120.9 |
| 12 | LK03 | FIX.C16 | 1E+12 | ND | 2138.4 | 532.4 | 3199.8 | 1306.6 | 985.3 | 732.0 | 593.4 |
| 13 | LK03 | FIX.C16 | 1E+12 | ND | 2465.9 | 45.3 | 84.9 | 134.4 | 168.6 | 127.0 | 84.9 |
| 14 | LK03 | FIX.C16 | 1E+12 | ND | 886.1 | 289.0 | 636.4 | 551.7 | 547.4 | 582.3 | 410.4 |
| 15 | LK03 | FIX.C16 | 1E+12 | ND | ND | ND | 35.0 | 109.0 | 30.2 | 24.8 | ND |
| 16 | LK03 | FIX.C16 | 1E+13 | ND | 90.7 | 404.6 | 2228.9 | 1265.4 | 899.5 | 715.6 | 693.2 |
| 17 | LK03 | FIX.C16 | 1E+13 | ND | 424.7 | 546.6 | 490.2 | 695.9 | 437.0 | 964.4 | 821.4 |
| 18 | LK03 | FIX.C16 | 1E+13 | ND | 1255.6 | 1787.2 | 6079.2 | 4628.5 | 1874.0 | 1576.0 | 2226.4 |
| 19 | LK03 | FIX.C16 | 1E+13 | ND | 518.4 | 8917.2 | 2772.7 | 2905.7 | 1195.0 | 1877.0 | 1899.3 |
| 20 | LK03 | FIX.C16 | 1E+13 | ND | 2615.0 | 10782.8 | 8075.5 | 6908.0 | 6630.8 | 6226.0 | 5489.2 |
| 21 | Vehicle | FIX.C16 | N/A | ND | ND | ND | 28.9 | 31.1 | 16.1 | ND | ND |
| 22 | Vehicle | FIX.C16 | N/A | ND | ND | ND | 29.2 | 30.6 | 11.9 | ND | ND |

ND = Not detected

In the low dose cohorts, the AAV-LK03 vector appeared to be a more potent vector compared with AAV-SPK, as measured by circulating hFIX levels. Six months after treatment with AAV-LK03 or AAV-SPK, average hFIX levels were 552±217 ng/ml vs. 164±45 ng/ml, respectively (FIG. 14A). However, this difference did not reach statistical significance, likely due to the limited number of animals. Interestingly, no hFIX expression was detected seven days after administration of the AAV-SPK vector, whereas robust expression derived from the AAV-LK03 was observed at the same time point. The low hFIX levels in two of the animals (rabbits #5 and #15), barely detectable above background, might be attributed to failed injections. Eliminating these animals from the analysis did not change the lack of statistical significance.

The two capsids appeared to be equally potent when tested at the high dose. Specifically, six months after treatment with $1\times10^{13}$ vg/kg of AAV-LK03 or AAV-SPK, average hFIX levels were 2226±868 ng/ml vs. 2052±909 ng/ml, respectively (FIG. 14B). Of note, two different hFIX coding sequences were used in the AAV-SPK group, i.e. three animals received AAV-SPK-hFIX.C16 and two animals were treated with AAV-SPK-hFIX.C19-Padua (PD). The main differences between the hFIX.C16 and hFIX.C19-PD transgenes are that the latter is codon-optimized and encodes a high specific activity hFIX variant, which affects the biological activity of the protein, but not antigen levels, as measured by ELISA.

Anti-FIX Antibodies

Based on a report by others, it was anticipated that approximately 20-40% of the animals would develop antibodies against human FIX vectors (Favaro P, et al., *Molecular Therapy* 17:1022-1030 (2009)). FIGS. 15A-15B and Tables 5A and 5B summarize anti-AAV IgG levels in this study. Interestingly, three out of five animals treated with the low dose of AAV-LK03 were positive for human FIX antibodies one month after vector administration, but the IgG levels declined with time and only one animal was barely twice the baseline levels at the end of the study (Table 5B). The kinetics of anti-FIX IgG appearance and ulterior clearance in this group of rabbits correlates well with the sharp decrease in hFIX levels observed at day 28, which was followed by a "rebound" in circulating hFIX (FIG. 14A). Also, the high antibody titers against hFIX in the two animals treated with AAV-SPK-hFIX.C19-Padua may explain the low expression levels in these two rabbits.

TABLE 5A

Summary of antibody formation (IgG, ng/ml) to human FIX in individual AAV-injected rabbits

| | | | | Day after injection | | | | | | | |
|---|---|---|---|---|---|---|---|---|---|---|---|
| Animal | Capsid | Transgene | vg/kg | 0 | 7 | 28 | 56 | 94 | 112 | 147 | 175 |
| 1 | SPK | FIX.C16 | 1.00E+12 | 1390 | 1134 | 2864 | 8627 | 1631 | 1261 | 1210 | 1088 |
| 2 | SPK | FIX.C16 | 1.00E+12 | 1706 | 1143 | 4670 | 7132 | 2834 | 2733 | 3294 | 3180 |
| 3 | SPK | FIX.C16 | 1.00E+12 | 1904 | 1128 | 2919 | 2394 | 1964 | 1792 | 1753 | 1688 |
| 4 | SPK | FIX.C16 | 1.00E+12 | 1256 | 1084 | 789 | 1692 | 1463 | 1034 | 1367 | 1457 |
| 5 | SPK | FIX.C16 | 1.00E+12 | 1086 | 1004 | 701 | 664 | 834 | 956 | 774 | 785 |
| 6 | SPK | FIX.C16 | 1.00E+13 | 565 | 836 | 940 | 814 | 1246 | 721 | 1326 | 1592 |
| 7 | SPK | FIX.C16 | 1.00E+13 | 792 | 721 | 666 | 709 | 960 | 829 | 909 | 1084 |
| 8 | SPK | FIX.C16 | 1.00E+13 | 1016 | 863 | 1729 | 1705 | 2539 | 1619 | 1406 | 2143 |
| 9 | SPK | FIX.C19-PD | 1.00E+13 | 768 | 783 | 1330 | 1076 | 11241 | 893 | 37141 | 12634 |
| 10 | SPK | FIX.C19-PD | 1.00E+13 | 566 | 541 | 4556 | 1398 | 9356 | 1270 | 20050 | 9167 |
| 11 | LK03 | FIX.C16 | 1.00E+12 | 1606 | 1821 | 2150 | 2283 | 1973 | 1788 | 1561 | 1580 |
| 12 | LK03 | FIX.C16 | 1.00E+12 | 813 | 1391 | 7993 | 1603 | 1087 | — | 1505 | 1702 |
| 13 | LK03 | FIX.C16 | 1.00E+12 | 699 | N/A | 8153 | 610 | 680 | 903 | 871 | 1040 |
| 14 | LK03 | FIX.C16 | 1.00E+12 | 776 | 756 | 534 | 760 | 699 | 709 | 636 | 769 |
| 15 | LK03 | FIX.C16 | 1.00E+12 | 890 | 891 | 2320 | 693 | 561 | 843 | 972 | 1102 |
| 16 | LK03 | FIX.C16 | 1.00E+13 | 1479 | 2050 | 2579 | 1501 | 1487 | 1622 | 1526 | 1768 |
| 17 | LK03 | FIX.C16 | 1.00E+13 | 1979 | 1801 | 1506 | 1087 | 1196 | 837 | 1025 | 876 |
| 18 | LK03 | FIX.C16 | 1.00E+13 | 2074 | 1968 | 1368 | 1236 | 1284 | 1247 | 1107 | 1067 |
| 19 | LK03 | FIX.C16 | 1.00E+13 | 1131 | 1270 | 792 | 1237 | 2415 | 2463 | 1529 | 1597 |
| 20 | LK03 | FIX.C16 | 1.00E+13 | 967 | 2065 | 1250 | 2537 | 1927 | 1459 | 1343 | 1603 |
| 21 | Vehicle | FIX.C16 | N/A | 899 | 1074 | 1124 | 844 | 853 | 916 | 1017 | 961 |
| 22 | Vehicle | FIX.C16 | N/A | 477 | 702 | 891 | 471 | 460 | 541 | 536 | 597 |

N/A, not available

TABLE 5B

Number of rabbits per group positive for anti-hFIX antibodies over time

| | $1 \times 10^{12}$ vg/kg | | $1 \times 10^{13}$ vg/kg | |
|---|---|---|---|---|
| | AAV-SPK | AAV-LK03 | AAV-SPK | AAV-LK03 |
| Day 28 | 2/5 | 3/5 | 1/5 | 0/5 |
| Day 175 | 0/5 | 1/5 | 4/5 | 0/5 |

Conclusion

Dissemination of AAV-SPK and AAV-LK03 vectors to semen was quantified using a validated assay over the course of up to eight months. AAV-SPK vector sequences were detected in semen of all five rabbits one week after administration of the high vector dose. The majority of the animals cleared the sequences by week 10 and the last detected positive sample occurred at month 5. This is similar to the time course of an AAV8 vector administered to rabbits at the same dose vectors (Favaro P, et al., *Molecular Therapy* 17:1022-1030 (2009)). In contrast, very limited distribution of AAV-LK03 was observed following a high dose of this vector, with three of five animals showing no vector sequences in semen at any timepoint. The lower dissemination of vector to semen was unlikely due to a lower overall exposure of AAV-LK03 in rabbits. Confirmation that rabbits were successfully injected with each AAV vector was demonstrated by measuring hFIX plasma levels, a surrogate for gene transfer. At the high dose in this study ($1\times10^{13}$ vg/kg), similar circulating levels of hFIX were observed in animals injected with AAV-LK03 and AAV-SPK, demonstrating that the vectors are equally potent in mediating liver gene transfer.

Consistent with studies evaluating germline transmission of AAV2 and AAV8 vectors expressing a hFIX transgene, some of the animals develop anti-hFIX antibodies, likely due to the amino acid differences between rabbit and human factor IX.

These results add to the current body of data on the potential for germline transmission of AAV vectors. AAV-SPK has a similar pattern as the previously investigated serotypes, AAV2 and AAV8 vectors (Favaro P, et al., *Molecular Therapy* 17:1022-1030 (2009)). That is, there is a dose-dependent dissemination of AAV vector sequences to semen, with complete clearance over time. AAV-LK03, however, differs from AAV2, AAV8, and AAV-SPK, in that very little vector distributes to the semen, potentially making this vector capsid safer than the others in terms of genotoxicity.

Example 8

A clinical study will be conducted to determine safety and kinetics of a single IV infusion of AAV-FVIII. The AAV capsid that will be used for the AAV vector will have shown in preclinical studies to have had good safety and efficacy, the ability to achieve clinically relevant FVIII activity levels at dose of about $1\times10^{12}$ vg/kg or greater, optionally after 1-3 months of vector infusion; and cross reacting neutralizing antibodies (Ab) to the AAV capsid approximately 10% less prevalent than AAV8. The design of a representative clinical study can be as shown in Table 6.

TABLE 6

AAV-FVIII Clinical Study Design

| | |
|---|---|
| Safety and Tolerability of AAV-FVIII | Clinically significant in vital signs, lab values and clinical assessments (including number of bleeds and QoL) from baseline |
| Kinetics of AAV-FVIII | Transgene FVIII activity levels and antigen levels at peak and |
| steady-state | |
| Dosing | Starting, Middle and Highest Dose Cohorts will each include 2-5 subjects |
| Design | Open-label, non-randomized, dose escalation |
| Participating countries | USA and potentially Europe, Japan and Canada |
| Sample size | Up to 15 subjects |

TABLE 6-continued

| AAV-FVIII Clinical Study Design | |
|---|---|
| Eligibility | Ages Eligible for Study: 18 Years and older<br>Genders Eligible for Study: Male<br>Accepts Healthy Volunteers: No |
| Inclusion Criteria | Able to provide informed consent and comply with requirements of the study<br>Males ≥ 18 y.o. with confirmed diagnosis of hemophilia A (≤2 IU/dL or ≤2% endogenous factor VIII)<br>Received ≥ 50 exposure days to factor VIII products<br>A minimum of an average of 4 bleeding events per year requiring episodic treatment of factor VIII infusions or prophylactic factor VIII infusions<br>No measurable factor VIII inhibitor as assessed by the central laboratory and have no prior history of inhibitors to factor VIII protein<br>Agree to use reliable barrier contraception until 3 consecutive samples are negative for vector sequences |
| Exclusion Criteria | Evidence of active hepatitis B or C<br>Currently on antiviral therapy for hepatitis B or C<br>Have significant underlying liver disease<br>Have serological evidence* of HIV-1 or HIV-2 with CD4 counts ≤ 200/mm3 (* subjects who are HIV+ and stable with CD4 count > 200/mm3 and undetectable viral load are eligible to enroll)<br>Have detectable antibodies reactive with variant AAV capsid<br>Participated in a gene transfer trial within the last 52 weeks or an investigational drug within the last 12 weeks<br>Unable or unwilling to comply with study assessments |

TABLE 6-continued

| AAV-FVIII Clinical Study Design | |
|---|---|
| Screening Visit | Eligibility evaluation<br>AAV NAb titer is the major screen failure |
| Day 0 Visit | FVIII product incremental recovery then vector infusion |
| Follow-up Visits (~17 visits) | Safety and kinetic evaluations |
| End-of Study Visit (at about week 52) | Final safety evaluation |

Example 9

TTR Promoter

The characterization of the transthyretin (TTR) promoter was originally described in Costa and Grayson 1991, Nucleic Acids Research 19(15):4139-4145. The TTR promoter sequence was a modified sequence, from TATTTGTGTAG to TATTGACTTAG.

```
TTR promoter with 4 nucleotide mutation (TTRmut),
                                       SEQ ID NO: 22
GTCTGTCTGCACATTTCGTAGAGCGAGTGTTCCGATACTCTAATCTCCCT

AGGCAAGGTTCATATTGACTTAGGTTACTTATTCTCCTTTTGTTGACTAA

GTCAATAATCAGAATCAGCAGGTTTGGAGTCAGCTTGGCAGGGATCAGCA

GCCTGGGTTGGAAGGAGGGGGTATAAAAGCCCCTTCACCAGGAGAAGCCG

TCACACAGATCCACAAGCTCCT
```

Example 10

CpG Reduced FVIII Encoding Transgene Constructs and Exemplary AAV Capsids.

```
FVIII encoding CpG reduced nucleic acid variant X01
                                                          (SEQ ID NO: 1)
atgcagattg agctgtctac ctgcttcttc ctgtgcctgc tgaggttctg cttctctgct

accaggaggt actacctggg ggctgtggag ctgagctggg attacatgca gtctgacctg

ggggagctgc ctgtggatgc caggtttccc cccagggtgc ccaagagctt ccccttcaat

acctctgtgg tgtataagaa gaccctgttt gtggagttca ctgatcatct gttcaacatt

gctaaaccca ggccccccctg gatggggctg ctgggcccta ccatccaggc tgaggtgtat

gacactgtgg tgatcactct gaagaacatg gctagccatc ctgtgtctct gcatgctgtg

ggggtgagct actggaaggc ttctgagggg gctgagtatg atgatcagac tagccagagg

gagaaggagg atgacaaggt gttccctggg ggctctcaca cctatgtctg gcaggtgctg

aaggagaatg gccccatggc ctctgatcct ctgtgtctga cctatagcta cctgagccat

gtggacctgg tgaaggacct gaactctggc ctgattgggg ccctgctggt gtgtagggag

gggagcctgg ccaaggagaa gacccagacc ctgcacaagt tcattctgct gtttgctgtg

tttgatgagg gcaagagctg gcattctgaa accaagaaca gcctgatgca ggacagggat

gctgcctctg ctagggcctg gcccaagatg cacactgtga atgggtatgt caataggtct

ctgcctggcc tgattggctg ccacaggaag tctgtgtact ggcatgtgat tgggatgggc

accacccctg aggtgcacag catctttctg gagggccaca ccttcctggt gaggaatcac

agacaggcca gcctggagat cagccccatc accttcctga ctgcccagac cctgctgatg

gacctgggcc agtttctgct gttctgccac atctctagcc accagcatga tggcatggag

gcctatgtga aggtggactc ctgccctgag gagccccagc tgaggatgaa gaataatgag
```

-continued gaggctgagg actatgatga tgacctgact gactctgaga tggatgtggt gagatttgat gatgacaatt ctcccagctt cattcagatc aggtctgtgg ccaagaagca tcccaagacc tgggtgcact acattgctgc tgaggaggag gactgggact atgccccct ggtgctggcc cctgatgaca ggagctataa gagccagtac ctgaataatg gcccccagag gattgggagg aagtataaga aggtgaggtt catggcctat actgatgaaa ccttcaagac cagagaggcc atccagcatg agtctgggat cctggggccc ctgctgtatg gggaggtggg ggacaccctg ctgatcatct tcaagaacca ggccagcagg ccctacaaca tctaccctca tggcatcact gatgtgaggc ctctgtacag cagaaggctg cccaaggggg tgaagcatct gaaggacttc cccattctgc ctggggagat tttcaagtac aagtggactg tgactgtgga ggatggccca accaagtctg accctaggtg cctgactagg tactacagca gctttgtgaa tatggagagg gacctggcct ctggcctgat tggcccctg ctgatctgct acaaggagtc tgtggatcag aggggcaacc agatcatgtc tgacaagagg aatgtgatcc tgttctctgt gtttgatgag aacaggagct ggtacctgac tgagaacatt cagaggtttc tgcccaaccc tgctggggtg cagctggagg accctgaatt ccaggcctct aacatcatgc acagcattaa tggctatgtg tttgacagcc tgcagctgtc tgtgtgcctg catgaggtgg cctactggta cattctgagc attggggccc agactgactt cctgtctgtg ttcttctctg gctacacctt taagcacaag atggtgtatg aggataccct gaccctgttt cctttctctg ggagactgt gttcatgagc atggagaacc ctggcctgtg gatcctgggc tgccacaact ctgacttcag gaacaggggg atgactgctc tgctgaaggt gagcagctgt gataagaaca ctggggacta ctatgaggac agctatgagg acatctctgc ctatctgctg agcaagaata atgctattga gcccaggagc ttctctcaga acccccctgt gctgaagagg caccagaggg agatcaccag aactactctg cagtctgacc aggaggagat tgactatgat gacaccatct ctgtggagat gaagaaggag gattttgata tttatgatga ggatgaaaac cagagcccca ggagctttca gaagaagact aggcactatt tcattgctgc tgtggagagg ctgtgggact atggcatgtc ttctagcccc catgtgctga ggaacagggc ccagtctggc tctgtgcccc agttcaagaa ggtggtgttc caggagttca ctgatggcag cttcactcag cccctgtaca ggggggagct gaatgagcac ctggggctgc tgggccctta tatcagggct gaggtggagg ataacatcat ggtgaccttc aggaaccagg ccagcaggcc ctacagcttc tactctagcc tgatcagcta tgaggaggac cagaggcagg gggctgagcc caggaagaac tttgtgaagc ccaatgagac caagacttat ttctggaagg tgcagcacca tatggccccc accaaggatg agtttgattg caaagcctgg gcctacttct ctgatgtgga cctggagaag gatgtgcact ctgggctgat tggcccctg ctggtgtgcc acaccaacac tctgaaccct gcccatggca ggcaggtgac tgtgcaggag tttgccctgt tcttcaccat ctttgatgag actaagagct ggtacttcac tgagaacatg gagaggaact gcagggcccc ctgcaatatc cagatggagg accccacctt taaggaaaat tataggtttc atgccattaa tggctacatc atggacaccc tgcctggcct ggtgatggcc caggaccaga ggatcaggtg gtacctgctg agcatgggca gcaatgagaa cattcacagc atccacttct ctggccatgt gttcactgtg aggaagaagg aggagtacaa gatggccctg tataatctgt accctggggt gtttgagact gtggagatgc tgcccagcaa ggctggcatc tggagggtgg agtgcctgat tggggagcac ctgcatgctg gcatgagcac cctgttcctg gtgtattcta acaagtgtca gaccccctg ggcatggcct ctggccatat cagggacttc -continued cagatcactg cctctggcca gtatgggcag tgggccccca agctggccag gctgcattac
tctggcagca tcaatgcctg gagcaccaag gagccattca gctggattaa ggtggacctg
ctggctccaa tgattatcca tggcatcaag acccaggggg ccaggcagaa gtttagcagc
ctgtacatct ctcagtttat catcatgtac tctctggatg gcaaaaagtg gcagacctac
aggggcaatt ctactggcac tctgatggtg ttctttggca atgtggacag ctctgggatc
aagcacaaca tctttaaccc ccctatcatt gccaggtaca ttaggctgca ccccacccat
tacagcatca ggagcaccct gaggatggag ctgatgggct gtgatctgaa cagctgcagc
atgcccctgg gcatggagag caaggctatc tctgatgccc agattactgc cagcagctac
ttcaccaata tgtttgccac ctggagcccc agcaaggcca ggctgcacct gcagggcagg
tctaatgcct ggaggcccca ggtgaacaac cccaaggagt ggctgcaggt ggacttccag
aagaccatga aggtgactgg ggtgaccacc cagggggtga agagcctgct gactagcatg
tatgtgaagg agttcctgat cagcagcagc caggatggcc atcagtggac cctgttcttc
cagaatggca aggtgaaggt gttccagggc aatcaggaca gcttcacccc tgtggtgaac
agcctggacc ccccctgct gaccagatac ctgaggatcc acccccagag ctgggtgcat
cagattgccc tgaggatgga ggtgctgggg tgtgaggccc aggacctgta ctga FVIII encoding CpG reduced nucleic acid variant X02
(SEQ ID NO: 2)

atgcagattg agctgtctac ctgctttttc ctgtgtctgc tgaggttctg cttctctgcc
actaggaggt actacctggg ggctgtggag ctgtcttggg attacatgca gtctgatctg
ggggagctgc ctgtggatgc caggtttcct cccagggtgc ccaagtcttt ccccttcaat
acctctgtgg tgtataagaa gaccctgttt gtggagttta ctgatcacct gttcaacatt
gccaagccca ggcccccttg gatgggcctg ctggggccca ccatccaggc tgaggtgtat
gacactgtgg tgatcaccct gaagaacatg gcctctcacc ctgtgagcct gcatgctgtg
ggggtgagct actggaaggc ctctgagggg gctgagtatg atgaccagac cagccagagg
gagaaggagg atgataaggt gttccctggg gggagccaca cttatgtgtg gcaggtgctg
aaggagaatg gcccaatggc ctctgatccc ctgtgcctga cctattctta cctgagccat
gtggacctgg tgaaggacct gaactctggc ctgattgggg ccctgctggt gtgcagggag
ggctctctgg ctaaggagaa gacccagacc ctgcacaagt tcatcctgct gtttgctgtg
tttgatgagg ggaagagctg gcactctgag accaagaaca gcctgatgca ggacagggat
gctgcctctg ccagggcctg gcccaaaatg cacactgtga atggctatgt gaataggagc
ctgcctggcc tgattggctg ccacaggaag tctgtgtatt ggcatgtgat tggcatgggc
accacccctg aggtgcactc tatcttcctg gagggccata ctttcctggt gaggaatcat
aggcaggcca gcctggagat tagccccatt acctttctga ctgcccagac cctgctgatg
gacctgggcc agttcctgct gttttgccac atcagctctc accagcatga tggcatggag
gcctatgtga aggtggatag ctgccctgag gagccccagc tgaggatgaa gaacaatgag
gaggctgagg attatgatga tgatctgact gattctgaaa tggatgtggt gaggtttgat
gatgacaata gcccctcttt catccagatc aggtctgtgg ccaagaagca tcctaagacc
tgggtgcact acattgctgc tgaggaggag gactgggact atgctcccct ggtgctggcc
cctgatgaca ggtcttacaa gagccagtac ctgaacaatg gcccccagag aattgggagg
aagtataaga aggtgagatt catggcttac actgatgaga ccttcaagac tagggaggcc
atccagcatg agtctggcat tctgggcccc ctgctgtatg gggaggtggg ggacaccctg
ctgatcatct tcaagaacca ggcctctagg ccctacaata tttacccccca tgggatcact -continued gatgtgaggc ccctgtacag caggaggctg cctaaggggg tgaagcatct gaaggacttc cccatcctgc ctggggagat cttcaagtat aagtggactg tgactgtgga agatggcccc accaagtctg accctaggtg cctgaccagg tactactctt cttttgtgaa catggagagg gacctggcct ctggcctgat tggcccccctg ctgatctgct acaaggagtc tgtggaccag agggggaacc agattatgtc tgacaagagg aatgtgattc tgttctctgt gtttgatgag aacaggagct ggtatctgac tgagaacatc cagaggttcc tgcccaatcc tgctggggtg cagctggagg accctgagtt ccaggccagc aacatcatgc acagcatcaa tgggtatgtg tttgattctc tgcagctgtc tgtgtgcctg catgaggtgg cctactggta catcctgagc attggggctc agactgattt cctgtctgtg ttcttttctg gctacacctt taagcataag atggtgtatg aggacactct gaccctgttt cccttctctg ggagactgt gtttatgagc atggagaacc ctggcctgtg gatcctgggc tgccacaact ctgatttcag gaacaggggc atgactgctc tgctgaaggt gtcttcttgt gacaagaaca ctggggacta ttatgaggac agctatgagg acatctctgc ctacctgctg agcaagaaca atgctattga gcccagatct ttcagccaga accccccctgt gctgaagagg caccagaggg agatcactag gaccaccctg cagtctgacc aggaggagat tgactatgat gacactatct ctgtggagat gaagaaggag gactttgata tctatgatga ggatgagaac cagtctccca ggagcttcca gaaaaagacc aggcactact tcattgctgc tgtggagagg ctgtgggact atggcatgtc ttctagcccc catgtgctga ggaacagggc ccagtctggg tctgtgcccc agttcaagaa ggtggtgttc caggagttca ctgatgggag cttcacccag cctctgtaca ggggggagct gaatgagcac ctggggctgc tgggccctta tattagggct gaggtggagg acaacatcat ggtgactttc aggaatcagg cctctaggcc ctatagcttc tacagctctc tgatcagcta tgaggaggat cagaggcagg gggctgagcc caggaagaac tttgtgaagc ccaatgagac caagacctac ttctggaagg tgcagcacca catggctcct accaaggatg agtttgactg caaggcctgg gcctactttt ctgatgtgga cctggagaag gatgtgcact ctggcctgat tggcccccctg ctggtgtgtc ataccaacac cctgaaccct gcccatggca ggcaggtgac tgtgcaggag tttgccctgt tcttcaccat ctttgatgag accaagagct ggtactttac tgagaacatg gagaggaatt gcagagcccc ttgcaacatc cagatggagg acccaacctt caaagagaac tacaggttcc atgccatcaa tggtacatc atggacaccc tgcctggcct ggtgatggct caggaccaga ggatcaggtg gtatctgctg agcatgggca gcaatgagaa tatccatagc attcacttct ctggccatgt gttcactgtg aggaagaagg aggagtacaa gatggccctg tataacctgt accctggggt gtttgagact gtggagatgc tgccaagcaa ggctgggatt tggagggtgg agtgcctgat tggggagcac ctgcatgctg gcatgtctac cctgttcctg gtgtactcca ataagtgcca gacccccctg ggcatggcct ctggccacat cagggacttc cagatcactg cctctggcca gtatgggcag tgggccccaa agctggccag gctgcactat tctgggagca tcaatgcttg gagcaccaag gagcctttca gctggattaa ggtggatctg ctggccccca tgatcattca tggcatcaaa acccaggggg ctagacagaa gttttctagc ctgtacatca gccagttcat catcatgtac agcctggatg gcaagaagtg gcagacttac aggggcaata gcactggcac cctgatggtg ttttttggca atgtggacag ctctggcatc aagcacaaca tctttaaccc ccccattatt gccaggtata tcaggctgca tcccacccac tattctatta ggtctactct gagaatggag ctgatgggct gtgacctgaa cagctgtagc -continued atgcccctgg ggatggagag caaggctatc tctgatgccc agatcactgc cagctcttat
ttcaccaata tgtttgccac ctggtctccc tctaaggcca ggctgcacct gcagggcagg
agcaatgctt ggaggcccca ggtgaataac cccaaggagt ggctgcaggt ggacttccag
aagaccatga aggtgactgg ggtgactacc caggggggtga agtctctgct gactagcatg
tatgtgaagg agttcctgat cagcagcagc caggatgggc atcagtggac tctgttcttc
cagaatggca aggtgaaggt cttccagggg aaccaggata gcttcactcc tgtggtgaac
tctctggacc cccccctgct gactaggtat ctgaggatcc acccccagag ctgggtgcac
cagattgccc tgaggatgga ggtgctgggc tgtgaggccc aggacctgta ttga FVIII encoding CpG reduced nucleic acid variant X03

(SEQ ID NO: 3)

atgcagattg aactgtctac ttgtttcttc ctgtgcctgc tgaggttttg cttctctgct
actaggaggt actatctggg ggctgtggag ctgtcttggg actatatgca gtctgacctg
ggggagctgc ctgtggatgc taggtttccc cccagggtgc ccaagagctt cccctttaac
acctctgtgg tgtataagaa gactctgttt gtggagttca ctgaccatct gttcaacatt
gccaagccaa ggccccccctg gatgggcctg ctgggcccca ccatccaggc tgaggtgtat
gacactgtgg tgattactct gaagaacatg gccagccatc ctgtgagcct gcatgctgtg
ggggtgtctt actggaaggc ctctgagggg gctgagtatg atgaccagac ctctcagagg
gagaaggagg atgacaaggt gttccctggg ggctctcata cctatgtgtg gcaggtcctg
aaggagaatg ggcccatggc ctctgacccc ctgtgcctga cctactctta tctgtctcat
gtggacctgg tgaaggacct gaactctggc ctgattgggg ccctgctggt gtgcagggag
ggcagcctgg ctaaggagaa gacccagact ctgcacaagt tcatcctgct gtttgctgtg
tttgatgagg gcaagagctg gcactctgag accaagaaca gcctgatgca ggacagggat
gctgcctctg ctagggcctg gcccaagatg cacactgtga atgggtatgt gaacaggagc
ctgccaggcc tgattggctg ccataggaag tctgtgtatt ggcatgtgat tgggatgggg
actacccctg aggtccacag cattttcctg gaggggcata cctttctggt gaggaaccac
aggcaggcct ctctggagat ctctcccatt actttcctga ctgcccagac cctgctgatg
gacctgggcc agttcctgct gttctgccac atcagcagcc accagcatga tggcatggag
gcctatgtga aggtggatag ctgccctgag gagccccagc tgaggatgaa aaacaatgag
gaggctgagg attatgatga tgacctgact gattctgaga tggatgtggt gaggtttgat
gatgataaca gccccagctt catccagatt aggtctgtgg ccaagaagca tcccaagacc
tgggtgcact acattgctgc tgaggaggag gattgggact atgctcctct ggtgctggcc
cctgatgaca ggagctacaa gagccagtac ctgaataatg gcccccagag gattggcagg
aagtataaga aggtgaggtt catggcctac actgatgaga cctttaagac cagggaggcc
atccagcatg aatctgggat cctgggcccc ctgctgtatg gggaggtggg ggacaccctg
ctgattatct ttaagaacca ggctagcagg ccctacaaca tttacccccca tggcattact
gatgtgaggc ccctgtacag caggaggctg cccaaggggg tgaagcacct gaaggatttc
cccattctgc ctggggagat ctttaagtac aaatggactg tgactgtgga ggatggccct
actaagtctg atcccaggtg tctgaccaga tactacagca gctttgtgaa tatggagagg
gacctggctt ctggcctgat tggcccccctg ctgatctgct acaaggagtc tgtggaccag
aggggcaatc agattatgtc tgacaagagg aatgtgatcc tgttctctgt gtttgatgag
aacagaagct ggtacctgac tgagaacatc cagaggttcc tgcccaaccc tgctggggtg
cagctggagg accctgagtt ccaggctagc aatatcatgc acagcattaa tggctatgtg -continued tttgacagcc tgcagctgtc tgtgtgcctg catgaggtgg cctattggta cattctgagc attggggccc agactgattt cctgtctgtg ttcttttctg gctacacctt caagcacaag atggtgtatg aggatactct gaccctgttt cccttctctg ggagactgt gttcatgagc atggagaacc ctggcctgtg gatcctgggc tgtcacaact ctgacttcag gaacaggggc atgactgccc tgctgaaggt gagctcttgt gataagaaca ctggggacta ctatgaggac tcttatgagg acatctctgc ctacctgctg agcaagaaca atgctattga gcccaggagc ttctctcaga atcccccctgt gctgaagagg catcagaggg agatcactag gactaccctg cagtctgacc aggaagagat tgactatgat gacaccatct ctgtggaaat gaagaaggag gactttgata tctatgatga ggatgaaaac cagagcccca ggagcttcca gaagaagacc aggcattact tcattgctgc tgtggagagg ctgtgggact atgggatgag ctcttctccc catgtgctga ggaatagggc tcagtctggc tctgtcccac agttcaagaa ggtggtgttt caggagttca ctgatggcag cttcactcag cccctgtaca ggggggagct gaatgagcat ctgggcctgc tggggcccta catcagggct gaggtggagg ataacattat ggtgactttc aggaaccagg cctctaggcc ctacagcttc tacagcagcc tgatcagcta tgaggaggac cagaggcagg gggctgagcc caggaagaac tttgtgaagc ccaatgagac taagacctat ttctggaagg tgcagcatca catggctccc actaaagatg agtttgactg caaggcctgg gcctacttct ctgatgtgga tctggagaag gatgtgcatt ctgggctgat tggccctctg ctggtctgcc atactaacac cctgaatcct gcccatggca ggcaggtgac tgtgcaggag tttgccctgt tctttaccat ctttgatgag accaagtctt ggtacttcac tgagaacatg gagaggaact gcagggcccc ctgtaacatc cagatggagg accccacctt taaggagaac tacaggttcc atgccatcaa tggctacatc atggacactc tgcctggcct ggtgatggcc caggaccaga ggatcaggtg gtacctgctg tctatgggct ctaatgagaa cattcattct atccacttct ctggccatgt gtttactgtg aggaagaagg aggagtacaa gatggccctg tacaatctgt accctggggt gtttgaaact gtggagatgc tgccctctaa ggctggcatc tggagggtgg agtgcctgat tggggaacac ctgcatgctg gcatgagcac cctgttcctg gtctatagca ataagtgcca gaccccccctg ggatggcct ctgggcatat cagagacttc cagatcactg cctctggcca gtatggccag tgggccccca agctggccag gctgcactac tctggcagca ttaatgcctg gagcaccaag gagcccttct cttggatcaa ggtggacctg ctggctccca tgatcatcca tgggatcaag acccaggggg ccaggcagaa gttcagcagc ctgtacatct ctcagttcat catcatgtac tctctggatg gcaagaagtg gcagacctac aggggcaata gcactgggac cctgatggtg ttctttggga atgtggacag ctctggcatc aagcacaata tcttcaaccc ccccatcatt gccaggtaca tcagactgca ccccactcat tacagcatca ggagcactct gaggatggag ctgatgggct gtgacctgaa tagctgctct atgcccctgg gcatggagag caaggccatt tctgatgccc agattactgc ctcttcttac ttcactaata tgtttgccac ctggagcccc agcaaggcca ggctgcatct gcaggggagg agcaatgcct ggaggcccca ggtgaacaac cccaaggagt ggctgcaggt ggacttccag aagactatga aggtgactgg ggtgaccact caggggggtga agagcctgct gaccagcatg tatgtgaagg agttcctgat ctcttctagc caggatgggc accagtggac cctgtttttc cagaatggga aggtgaaggt gtttcagggc aatcaggaca gctttactcc tgtggtgaac agcctggacc cccccctgct gactaggtac ctgaggattc acccccagag ctgggtgcac -continued cagattgccc tgaggatgga ggtgctgggc tgtgaggccc aggatctgta ctga FVIII encoding CpG reduced nucleic acid variant X04

(SEQ ID NO: 4)

atgcagattg agctgtctac ctgcttcttt ctgtgcctgc tgaggttctg tttctctgcc actaggaggt attatctggg ggctgtggag ctgtcctggg actacatgca gtctgatctg ggggagctgc ctgtggatgc caggttccct cccagggtgc ccaagtcttt ccctttcaat acctctgtgg tgtacaagaa gactctgttt gtggagttta ctgatcacct gtttaacatt gccaagccca ggccccctg gatggggctg ctgggcccca ccatccaggc tgaggtgtat gacactgtgg tgattactct gaagaatatg gcttctcacc ctgtgagcct gcatgctgtg ggggtgagct actggaaggc ctctgagggg gctgagtatg atgaccagac cagccagagg gagaaggagg atgacaaggt gttccctggg ggcagccaca cttatgtgtg gcaggtgctg aaggagaatg gcccaatggc ctctgacccc ctgtgcctga cctacagcta tctgagccat gtggatctgg tgaaggatct gaactctggc ctgattgggg ccctgctggt gtgcagggag ggctctctgg ccaaggagaa gactcagact ctgcacaagt tcatcctgct gtttgctgtg tttgatgagg gcaagagctg gcactctgag accaagaact ctctgatgca ggatagggat gctgcttctg ccagggcctg gcccaagatg cacactgtga atgggtatgt gaataggagc ctgcctgggc tgattgggtg tcacaggaag tctgtgtact ggcatgtgat tggcatgggc accactcctg aggtgcacag catctttctg gagggccaca cttttctggt gaggaatcac aggcaggcca gcctggagat cagccccatc accttcctga ctgcccagac cctgctgatg gatctgggcc agttcctgct gttttgccat atcagcagcc atcagcatga tgggatggag gcttatgtga aggtggactc ttgccctgag gagcctcagc tgaggatgaa gaataatgaa gaggctgagg actatgatga tgatctgact gactctgaga tggatgtggt gaggtttgat gatgacaaca gccccagctt tatccagatt aggtctgtgg ccaagaagca ccccaagacc tgggtgcatt acattgctgc tgaggaagag gattgggact atgccccccct ggtgctggcc cctgatgaca ggagctacaa gtctcagtac ctgaacaatg gccctcagag gattggcagg aagtacaaga aggtgaggtt catggcttac actgatgaga ccttcaagac cagggaggcc attcagcatg aatctgggat cctgggcccc ctgctgtatg gggaggtggg ggacaccctg ctgattattt tcaagaacca ggccagcagg ccctacaaca tttatcctca tggcattact gatgtgagac ccctgtacag caggaggctg cctaaggggg tgaagcacct gaaggacttc cccatcctgc ctggggagat cttcaagtac aagtggactg tgactgtgga ggatggcccc actaagtctg accccaggtg cctgactagg tactactcca gctttgtgaa catggagagg gacctggcct ctggcctgat tggcccccctg ctgatctgct acaaggagtc tgtggatcag aggggcaacc agatcatgtc tgacaagaga aatgtgatcc tgttctctgt gtttgatgag aataggtctt ggtacctgac tgagaacatc cagaggtttc tgcctaatcc tgctggggtg cagctggagg atcctgagtt ccaggcctct aacattatgc acagcatcaa tgggtatgtg tttgacagcc tgcagctgtc tgtgtgcctg catgaggtgg cctactggta catcctgagc attggggccc agactgactt tctgtctgtg ttcttctctg gctacacctt taagcataag atggtgtatg aggacaccct gactctgttc cccttctctg gggagactgt gttcatgagc atggagaacc caggcctgtg gatcctgggc tgccacaact ctgatttcag gaataggggc atgactgccc tgctgaaggt gagcagctgt gataagaaca ctggggacta ttatgaggat agctatgagg acatctctgc ctacctgctg agcaagaaca atgccattga gcccaggagc ttcagccaga atcctcctgt gctgaagagg caccagaggg agatcaccag gaccaccctg -continued cagtctgatc aggaggagat tgactatgat gacactatct ctgtggagat gaagaaggag gactttgaca tctatgatga ggatgagaat cagagcccca ggagcttcca gaagaagact agacactact ttattgctgc tgtggagagg ctgtgggact atggcatgag ctcttctccc catgtgctga gaaacagggc ccagtctggc tctgtgcccc agttcaagaa ggtggtcttc caggagttca ctgatggctc tttcacccag cctctgtata gaggggagct gaatgagcac ctgggcctgc tgggccctta catcagggct gaggtggagg acaatatcat ggtgaccttc aggaaccagg ctagcaggcc ctactctttc tacagcagcc tgatcagcta tgaggaggac cagaggcagg gggctgagcc taggaagaat tttgtgaagc ccaatgagac caagacctac ttctggaagg tgcagcacca catggctccc actaaggatg agtttgactg caaggcctgg gcctactttt ctgatgtgga cctggagaag gatgtgcatt ctggcctgat tggcccccctg ctggtctgcc acaccaatac tctgaaccct gctcatggga gacaggtgac tgtgcaggag tttgccctgt tcttcaccat ctttgatgag accaagtcct ggtactttac tgagaacatg gagaggaatt gcagggcccc ttgcaacatc cagatggagg accccacctt caaggaaaat tataggttcc atgccatcaa tggctacatc atggacaccc tgcctggcct ggtgatggcc caggaccaga ggatcaggtg gtatctgctg tctatgggct ctaatgagaa catccacagc atccatttct ctggccatgt gttcactgtg aggaagaagg aggagtataa gatggctctg tacaacctgt accctggggt ctttgagact gtggagatgc tgcccagcaa ggctggcatt tggagggtgg agtgcctgat tggggaacac ctgcatgctg ggatgagcac cctgttcctg gtgtactcta acaagtgcca gaccccactg ggcatggctt ctggccacat cagggatttc cagattactg cctctggcca gtatggccag tgggctccca agctggctag gctgcactac tctgggagca tcaatgcctg gtctactaag gagccttttct cttggatcaa agtggacctg ctggccccta tgatcatcca tgggatcaag actcaggggg ccaggcagaa gttcagcagc ctgtacatct ctcagttcat cattatgtac agcctggatg gcaagaagtg gcagacctac aggggcaaca gcactggcac cctgatggtg ttctttggga atgtggacag ctctgggatt aagcacaaca tctttaaccc ccccatcatt gccaggtata tcaggctgca ccctacccac tacagcatta ggagcaccct gaggatggag ctgatgggct gtgacctgaa cagctgcagc atgcccctgg ggatggagag caaggccatt tctgatgctc agatcactgc ttctagctac ttcactaaca tgtttgccac ctggtctccc agcaaggcta gactgcacct gcaggggagg agcaatgcct ggaggcccca ggtgaataat cccaaggagt ggctgcaggt ggatttccag aaaaccatga aggtgactgg ggtgactacc cagggggtga agtctctgct gaccagcatg tatgtgaagg agttcctgat cagcagcagc caggatgggc atcagtggac cctgttcttt cagaatggga aggtgaaggt gtttcagggc aatcaggaca gcttcacccc tgtggtgaac agcctggacc cccccctgct gaccaggtac ctgaggatcc acccccagag ctgggtgcat cagattgccc tgaggatgga ggtgctgggc tgtgaggccc aggacctgta ctga FVIII encoding CpG reduced nucleic acid variant X05

(SEQ ID NO: 5)

atgcagattg agctgtctac ttgcttcttc ctgtgcctgc tgaggttctg cttctctgcc actaggaggt attacctggg ggctgtggag ctgagctggg actatatgca gtctgacctg ggggagctgc ctgtggatgc caggtttcct cccagggtgc ctaagagctt ccccttcaac acctctgtgg tgtacaagaa gactctgttt gtggagttta ctgatcatct gttcaacatt gccaagccca ggcctccttg gatggggctg ctgggcccca ccatccaggc tgaggtgtat -continued gacactgtgg tgattaccct gaagaatatg gccagccatc ctgtgagcct gcatgctgtg ggggtgagct attggaaggc ctctgagggg gctgagtatg atgatcagac tagccagagg gagaaggagg atgacaaggt gttccctggg gggagccata cctatgtgtg gcaggtgctg aaggagaatg gccccatggc ctctgaccct ctgtgcctga cttatagcta cctgagccat gtggatctgg tgaaggacct gaactctggc ctgattgggg ccctgctggt gtgcagggag ggcagcctgg ccaaggagaa gactcagacc ctgcacaagt tcatcctgct gtttgctgtg tttgatgagg ggaagtcctg gcactctgag actaagaaca gcctgatgca ggatagggat gctgcttctg ccagggcctg gcctaagatg cacactgtga atggctatgt gaataggagc ctgcctggcc tgattggctg ccataggaag tctgtgtact ggcatgtgat tgggatgggc accacccctg aggtgcactc tattttcctg gagggccata ctttcctggt gaggaaccat aggcaggcca gcctggagat cagccccatc actttcctga ctgcccagac tctgctgatg gacctgggcc agttcctgct gttctgccac atcagcagcc atcagcatga tggcatggag gcttatgtga aggtggacag ctgccctgag gagcctcagc tgaggatgaa gaataatgag gaggctgagg actatgatga tgacctgact gactctgaga tggatgtggt gaggtttgat gatgacaact ctccctcttt catccagatc aggtctgtgg ccaagaagca ccctaagacc tgggtgcact acattgctgc tgaggaggag gattgggact atgcccccct ggtgctggcc ccagatgaca ggagctacaa gtcccagtac ctgaacaatg gcccccagag gattggcagg aagtacaaga aggtgaggtt catggcttat actgatgaga ctttcaagac cagggaggcc atccagcatg agtctggcat cctgggccct ctgctgtatg gggaggtggg ggacaccctg ctgattatct tcaagaacca ggcttctagg ccctacaata tctaccctca tggcatcact gatgtgaggc ccctgtacag caggaggctg cccaaggggg tgaagcatct gaaggatttc cccatcctgc ctggggagat ctttaagtat aagtggactg tgactgtgga ggatggcccc actaagtctg accccaggtg cctgaccagg tattacagca gctttgtgaa catggagagg gatctggctt ctgggctgat tggcccccctg ctgatctgct acaaggagtc tgtggaccag aggggcaacc agatcatgtc tgacaagagg aatgtgatcc tgttctctgt gtttgatgag aataggagct ggtacctgac tgagaacatc cagaggtttc tgcccaatcc tgctggggtg cagctggagg atcctgagtt tcaggcctct aatatcatgc acagcatcaa tggctatgtg tttgactctc tgcagctgtc tgtgtgcctg catgaggtgg cctattggta catcctgagc attggggccc agactgactt tctgtctgtg tttttttctg gctacacctt caagcacaag atggtgtatg aggatactct gactctgttc cctttttctg ggagactgt gttcatgtct atggagaacc ctgggctgtg gattctgggc tgccacaatt ctgacttcag gaacagaggc atgactgctc tgctgaaggt gagcagctgt gacaagaaca ctggggacta ctatgaggac tcttatgagg acatttctgc ctacctgctg agcaagaaca atgccattga gcccagaagc ttttctcaga accccccctgt gctgaagagg caccagaggg agatcaccag gaccaccctg cagtctgacc aggaggagat tgactatgat gatactattt ctgtggagat gaagaaggag gactttgaca tctatgatga ggatgagaac cagagcccca ggtctttcca gaagaagact aggcactact ttattgctgc tgtggagagg ctgtgggact atgggatgtc tagctctcct catgtgctga ggaacagggc ccagtctggc tctgtgcccc agtttaaaaa ggtggtgttc caggaattca ctgatggcag ctttacccag cctctgtaca ggggggagct gaatgagcac ctggggctgc tggggcctta cattagggct gaggtggagg acaacatcat ggtgaccttc aggaatcagg ccagcaggcc ctactctttc tacagcagcc tgatctctta tgaggaggac -continued cagaggcagg gggctgaacc caggaagaac tttgtgaagc ccaatgagac caagacctac
ttctggaagg tgcagcacca catggctccc accaaggatg agtttgattg caaggcctgg
gcttacttct ctgatgtgga tctggagaag gatgtgcact ctgggctgat tggcccccctg
ctggtgtgcc acaccaacac tctgaaccct gcccatggca gacaggtgac tgtgcaggag
tttgccctgt tcttcactat ctttgatgag actaagagct ggtacttcac tgagaacatg
gagaggaatt gcagggcccc ttgcaacatc cagatggagg accccacctt taaggagaac
tacaggtttc atgccattaa tggctacatc atggacaccc tgcctggcct ggtgatggcc
caggaccaga ggatcaggtg gtacctgctg tctatgggga gcaatgagaa catccacagc
attcacttct ctggccatgt gttcactgtg aggaagaagg aggagtacaa gatggccctg
tacaacctgt accctggggt gtttgagact gtggagatgc tgcccagcaa ggctgggatc
tggagggtgg agtgcctgat tggggagcac ctgcatgctg ggatgagcac cctgttcctg
gtgtatagca acaagtgcca gacccccctg ggcatggcct ctggccacat cagagacttt
cagattactg cctctggcca gtatgggcag tgggccccca agctggccag gctgcactat
tctggctcta ttaatgcctg gagcactaag gagcccttca gctggattaa ggtggacctg
ctggctccca tgatcatcca tggcatcaag actcaggggg ccaggcagaa gttctcttct
ctgtacatca gccagttcat tatcatgtac tccctggatg gcaagaagtg gcagacctat
aggggcaaca gcactggcac cctgatggtg ttctttggga atgtggacag ctctggcatc
aagcataata tcttcaatcc ccccatcatt gctaggtaca tcaggctgca ccccacccac
tactctatta ggtctaccct gaggatggag ctgatgggct gtgacctgaa cagctgcagc
atgcctctgg gcatggagag caaagccatc tctgatgccc agatcactgc cagcagctac
tttaccaaca tgtttgctac ttggagcccc agcaaggcca ggctgcacct gcaggggagg
tctaatgcct ggaggcccca ggtgaacaac cccaaggagt ggctgcaggt ggacttccag
aagactatga aggtgactgg ggtgaccacc caggggggtga agagcctgct gacctctatg
tatgtgaagg agttcctgat tagcagcagc caggatggcc accagtggac cctgtttttc
cagaatggga aggtgaaggt gtttcagggg aaccaggaca gcttcactcc tgtggtgaac
tctctggacc ccccccctgct gaccaggtat ctgaggatcc accctcagag ctgggtgcac
cagattgccc tgaggatgga ggtgctgggc tgtgaggccc aggacctgta ctga FVIII encoding CpG reduced nucleic acid variant X06

(SEQ ID NO: 6)

atgcagattg agctgagcac ctgcttcttc ctgtgcctgc tgaggttttg cttctctgcc
accaggaggt actacctggg ggctgtggag ctgagctggg attacatgca gtctgacctg
ggggagctgc ctgtggatgc caggttccct cccagggtgc ccaagtcttt ccccttcaac
acttctgtgg tgtacaagaa gaccctgttt gtggagttta ctgaccacct gttcaacatt
gccaagccca ggcctccctg gatgggcctg ctgggcccca ccattcaggc tgaggtgtat
gacactgtgg tcatcaccct gaaaaatatg gctagccacc ctgtgtctct gcatgctgtg
ggggtgagct actggaaggc ctctgagggg gctgagtatg atgaccagac tagccagagg
gagaaggagg atgacaaggt gttccctggg ggcagccaca cttatgtgtg gcaggtgctg
aaagagaatg gccccatggc ttctgatccc ctgtgtctga cctatagcta cctgagccat
gtggatctgg tgaaggacct gaactctggc ctgattgggg ccctgctggt gtgcagggag
ggcagcctgg ctaaggagaa gacccagacc ctgcataagt tcatcctgct gtttgctgtg
tttgatgagg gcaagagctg gcactctgag actaagaaca gcctgatgca ggatagggat -continued gctgcttctg ccagggcctg gcccaagatg cacactgtga atgggtatgt gaacaggagc ctgcctggcc tgattggctg ccataggaag tctgtctatt ggcatgtgat tggcatgggc actactcctg aggtgcacag catctttctg gagggccaca ccttcctggt gaggaaccac aggcaggcca gcctggagat ctctcccatc actttcctga ctgctcagac cctgctgatg gacctgggcc agttcctgct gttctgtcac atctctagcc accagcatga tggcatggag gcctatgtga aggtggatag ctgccctgag gaaccccagc tgaggatgaa gaacaatgag gaggctgagg attatgatga tgatctgact gattctgaga tggatgtggt gaggtttgat gatgacaatt ctcctagctt cattcagatc agatctgtgg ccaaaaagca tcctaagact tgggtgcatt atattgctgc tgaggaggag gattgggatt atgccccct ggtgctggct cctgatgata ggagctacaa gtctcagtac ctgaataatg gccccagag gattggcagg aagtacaaga aggtgaggtt catggcctac actgatgaga ccttcaagac cagggaggcc attcagcatg agtctgggat tctggggccc ctgctgtatg ggagaggtggg ggataccctg ctgatcattt tcaagaacca ggccagcagg ccctacaaca tctaccccca tgggattact gatgtgaggc ccctgtactc taggaggctg cctaaggggg tgaagcacct gaaggatttt cctatcctgc ctggggaaat cttcaagtac aagtggactg tgactgtgga ggatggcccc actaagtctg atcccaggtg tctgaccagg tattatagct cttttgtgaa catggagagg gatctggcct ctgggctgat tggccctctg ctgatctgct acaaggagtc tgtggaccag aggggcaacc agatcatgtc tgacaagagg aatgtgatcc tgttctctgt gtttgatgag aacaggagct ggtatctgac tgagaacatc cagaggtttc tgcccaatcc tgctggggtg cagctggagg atcctgagtt ccaggctagc aacatcatgc acagcatcaa tgggtatgtg tttgacagcc tgcagctgtc tgtgtgtctg catgaggtgg cctactggta tatcctgtct attggggccc agactgactt cctgtctgtg ttttttctg ggtatacttt taagcacaag atggtgtatg aggacaccct gactctgttc cccttctctg gggagactgt gtttatgagc atggagaacc ctggcctgtg gatcctgggc tgccacaatt ctgacttcag gaatagggg atgactgccc tgctgaaggt gagcagctgt gataagaata ctggggacta ctatgaggac tcttatgagg acatttctgc ctatctgctg tctaagaaca atgccattga acccaggagc ttctctcaga acccccctgt gctgaagagg caccagaggg aaatcaccag aactactctg cagtctgatc aggaggaaat tgactatgat gacactattt ctgtggagat gaagaaggag gactttgaca tctatgatga ggatgagaac cagagcccaa ggagcttcca gaagaagact aggcactact tcattgctgc tgtggagagg ctgtgggact atggcatgag cagcagcccc catgtgctga gaaacagggc ccagtctggg tctgtgcccc agttcaagaa ggtggtgttc caggagttca ctgatgggag cttcacccag cccctgtata gggggagct gaatgagcac ctgggcctgc tgggccccta tattagggct gaggtggagg acaacatcat ggtgaccttc aggaatcagg cctctaggcc ctacagcttc tacagcagcc tgattagcta tgaggaggat cagaggcagg ggctgaacc caggaagaac tttgtgaagc ccaatgagac caagacctat ttctggaagg tgcagcatca catggcccc accaaggatg agtttgactg caaggcctgg gcctacttct ctgatgtgga tctggagaag gatgtgcact ctggcctgat tggccccctg ctggtgtgcc acaccaacac cctgaaccct gctcatggca ggcaggtgac tgtgcaggag tttgccctgt tcttcaccat ctttgatgag actaagtctt ggtacttcac tgagaatatg gagaggaatt gcagggcccc ctgcaatatt cagatggaag accccacctt caaggagaat tacaggttcc atgccattaa tggctacatc atggataccc tgcctggcct ggtgatggcc -continued caggatcaga ggatcaggtg gtacctgctg agcatgggca gcaatgagaa catccactct
atccacttct ctggccatgt gtttactgtg aggaagaagg aggagtataa gatggccctg
tacaacctgt accctggggt ctttgagact gtggagatgc tgccttctaa ggctggcatt
tggagggtgg agtgcctgat tggggaacac ctgcatgctg gcatgtctac cctgttcctg
gtgtacagca ataagtgcca gaccccccctg ggcatggcct ctgggcatat cagggatttc
cagatcactg cctctggcca gtatggccag tgggccccaa agctggctag gctgcactac
tctgggagca tcaatgcctg gagcactaag gagcccttca gctggatcaa ggtggacctg
ctggccccca tgattatcca tgggattaag actcaggggg ccaggcagaa gttcagcagc
ctgtacatca gccagttcat tatcatgtac agcctggatg gcaagaagtg gcagacctat
aggggcaact ctactgggac cctgatggtg ttctttggga atgtggatag ctctgggatc
aagcacaata tcttcaaccc ccccatcatt gccaggtata tcaggctgca ccccacccac
tacagcatta ggtctaccct gaggatggag ctgatgggct gtgatctgaa cagctgtagc
atgcctctgg gcatggagtc taaggccatt tctgatgccc agattactgc tagcagctac
ttcaccaaca tgtttgccac ctggtctccc agcaaggcca ggctgcatct gcagggcagg
tctaatgctt ggaggcccca ggtgaacaac ccaaaggagt ggctgcaggt ggatttccag
aagactatga aggtgactgg ggtgaccact caggggggtga agtctctgct gacctctatg
tatgtgaagg agttcctgat ctctagcagc caggatggcc atcagtggac cctgttcttc
cagaatggca aggtgaaagt gttccagggc aatcaggata gcttcactcc agtggtgaac
agcctggatc cccctctgct gactaggtac ctgaggatcc acccccagag ctgggtgcac
cagattgccc tgaggatgga ggtgctgggc tgtgaggccc aggacctgta ctga FVIII encoding CpG reduced nucleic acid variant X07
(SEQ ID NO: 7)

atgcagattg agctgagcac ctgcttcttc ctgtgtctgc tgaggttctg cttctctgcc
accaggaggt attacctggg ggctgtggag ctgagctggg actatatgca gtctgacctg
ggggagctgc ctgtggatgc taggttcccc cccagggtgc ccaagagctt cccctttaac
acttctgtgg tgtacaagaa gaccctgttt gtggagttca ctgaccacct gttcaacatt
gccaagccca ggccccccctg gatggggctg ctggggccca ccatccaggc tgaggtgtat
gacactgtgg tgatcaccct gaagaacatg gccagccacc ctgtgagcct gcatgctgtg
ggggtgagct actggaaggc ttctgagggg gctgagtatg atgaccagac tagccagagg
gagaaggagg atgacaaggt gtttcctggg ggcagccata cctatgtgtg gcaggtgctg
aaggagaatg gccccatggc ctctgacccc ctgtgcctga cctacagcta cctgtctcat
gtggacctgg tgaaggacct gaactctggc ctgattgggg ctctgctggt gtgtagggag
ggcagcctgg ctaaggaaaa gacccagacc ctgcataagt ttatcctgct gtttgctgtg
tttgatgagg gcaagagctg gcactctgag accaagaaca gcctgatgca ggatagggat
gctgcctctg ccagggcttg gcctaagatg cacactgtga atgggtatgt gaataggagc
ctgcctggcc tgattggctg ccacaggaag tctgtgtact ggcatgtgat tgggatgggc
accacccctg aggtccatag catcttcctg gagggccaca ctttcctggt gaggaaccac
agacaggcct ctctggagat ctctcccatc accttcctga ctgctcagac tctgctgatg
gacctgggcc agttcctgct gttttgccat attagcagcc accagcatga tgggatggag
gcctatgtga aggtggatag ctgccctgag gagcctcagc tgaggatgaa gaacaatgag
gaggctgaag actatgatga tgacctgact gattctgaga tggatgtggt gaggtttgat -continued gatgacaata gccccagctt cattcagatc aggtctgtgg ccaagaaaca ccccaagacc tgggtgcact acattgctgc tgaggaagag gactgggact atgctcccct ggtgctggcc cctgatgata ggtcttataa gagccagtac ctgaacaatg gccccagag gattggcagg aagtacaaga aggtgaggtt catggcctac actgatgaaa ccttcaaaac cagggaggcc attcagcatg agtctggcat cctgggccct ctgctgtatg gggaggtggg ggacaccctg ctgatcatct tcaagaacca ggccagcagg ccctacaaca tctatcctca tggcatcact gatgtgaggc ccctgtacag caggaggctg cccaaggggg tgaagcacct gaaagacttc cccatcctgc ctggggagat ctttaagtat aagtggactg tgactgtgga ggatggccct accaagtctg accccaggtg tctgaccagg tactattcta gctttgtgaa catggagagg gacctggcct ctggcctgat tgggcccctg ctgatctgct acaaggagtc tgtggaccag aggggcaacc agatcatgtc tgacaagagg aatgtgatcc tgttttctgt gtttgatgag aataggagct ggtacctgac tgagaacatc cagaggtttc tgcccaatcc tgctggggtg cagctggagg atcctgagtt ccaggccagc aatatcatgc atagcatcaa tggctatgtg tttgacagcc tgcagctgtc tgtgtgcctg catgaggtgg cctactggta catcctgagc attggggccc agactgactt tctgtctgtg ttcttttctg gctatacctt caagcacaag atggtgtatg aggataccct gaccctgttc cccttctctg gggagactgt gttcatgagc atggagaatc ctgggctgtg gatcctgggg tgccacaact ctgattttag gaacaggggg atgactgccc tgctgaaggt gtctagctgt gataagaaca ctggggacta ctatgaggac agctatgagg acatttctgc ttatctgctg tctaagaata atgccattga gcccagaagc ttcagccaga atcccccctgt gctgaagaga catcagaggg agatcaccag aactaccctg cagtctgatc aggaggagat tgactatgat gacactatct ctgtggagat gaagaaggag gactttgaca tctatgatga ggatgagaat cagtctccca ggagctttca gaagaagacc agacattact tcattgctgc tgtggagagg ctgtgggact atggcatgag ctctagccct catgtgctga ggaacagggc ccagtctggc tctgtgcccc agttcaagaa ggtggtgttc caggaattca ctgatggcag cttcacccag cccctgtaca gggggggagct gaatgagcac ctgggcctgc tggggcctta tatcagggct gaggtggagg ataatattat ggtgactttc aggaaccagg ccagcaggcc ctactctttc tatagcagcc tgatctctta tgaggaggat cagaggcagg gggctgagcc taggaagaac tttgtgaagc ccaatgagac taagacctac ttctggaagg tccagcacca catggcccct accaaggatg agtttgactg caaggcctgg gcctatttct ctgatgtgga tctggagaag gatgtccatt ctgggctgat tggcccccctg ctggtgtgcc acactaacac tctgaatcct gcccatggca ggcaggtgac tgtccaggag tttgccctgt tcttcactat ctttgatgag accaagagct ggtactttac tgagaacatg gagaggaact gcagagctcc ttgcaatatt cagatggagg accccacctt caaggagaat tacaggttcc atgccattaa tgggtacatc atggacaccc tgcctggcct ggtgatggct caggaccaga ggatcaggtg gtacctgctg agcatgggct ctaatgagaa tatccacagc atccacttct ctgggcatgt gttcactgtg aggaagaagg aggagtacaa gatggctctg tataatctgt accctggggt gtttgaaact gtggagatgc tgccctctaa ggctggcatc tggagggtgg agtgcctgat tggggagcac ctgcatgctg gcatgagcac cctgttcctg gtgtacagca acaagtgcca gacccccctg ggcatggcct ctggccacat cagggacttc cagatcactg cctctggcca gtatggccag tgggccccca agctggccag gctgcactat tctggcagca tcaatgcctg gagcaccaag gagcccttca gctggatcaa ggtggacctg -continued ctggccccca tgatcattca tggcatcaag acccaggggg ccaggcagaa gttcagctct ctgtacatct ctcagttcat catcatgtac tctctggatg ggaagaagtg gcagacctac aggggcaaca gcactggcac cctgatggtg ttctttggga atgtggactc ttctggcatc aagcacaaca tcttcaatcc ccccatcatt gctaggtata ttaggctgca tcccacccac tacagcatca ggtctaccct gaggatggag ctgatgggct gtgacctgaa ctcttgcagc atgcccctgg gcatggagtc taaggccatc tctgatgccc agattactgc cagcagctac ttcaccaaca tgtttgccac ctggagcccc tctaaggcca ggctgcatct gcaggggagg agcaatgcct ggaggcctca ggtgaacaac cccaaggagt ggctgcaggt ggatttccag aagaccatga aggtgactgg ggtgaccacc caggggtca agagcctgct gaccagcatg tatgtgaagg agttcctgat cagcagcagc caggatggcc accagtggac tctgttcttt cagaatggga aggtgaaggt gtttcagggc aatcaggact ctttcacccc tgtggtgaac agcctggacc ccccctgct gaccagatac ctgaggatcc acccccagtc ttgggtgcat cagattgccc tgaggatgga ggtgctgggc tgtgaggctc aggatctgta ctga FVIII encoding CpG reduced nucleic acid variant X08

(SEQ ID NO: 8)

atgcagattg agctgagcac ttgctttttt ctgtgcctgc tgaggttttg tttttctgcc accaggaggt actacctggg ggctgtggag ctgagctggg actatatgca gtctgatctg ggggagctgc ctgtggatgc caggttcccc cccagggtgc ccaagtcttt tcccttcaac acctctgtgg tgtataagaa gaccctgttt gtggagttca ctgaccacct gttcaacatt gctaagccta ggccccctg gatgggcctg ctgggcccta ccattcaggc tgaggtgtat gacactgtgg tgatcaccct gaagaacatg gccagccatc ctgtgagcct gcatgctgtg ggggtctctt actggaaggc ctctgagggg gctgagtatg atgaccagac cagccagaga gagaaggagg atgacaaggt cttccctggg ggctctcaca cctatgtgtg gcaggtgctg aaggaaaatg gccccatggc ctctgacccc ctgtgcctga cctacagcta tctgagccat gtggatctgg tgaaggacct gaattctggc ctgattgggg ccctgctggt gtgcagggag ggcagcctgg ccaaggagaa gacccagacc ctgcacaagt ttatcctgct gtttgctgtg tttgatgagg gcaagtcttg gcactctgag actaagaaca gcctgatgca ggacagggat gctgcctctg ccagggcctg gcccaagatg cacactgtga atggctatgt gaacaggagc ctgcctgggc tgattggctg ccacaggaag tctgtgtact ggcatgtgat tggcatgggc accacccctg aggtgcacag catcttcctg gaaggccaca ctttcctggt gaggaaccat aggcaggcca gcctggagat cagccctatc accttcctga ctgcccagac cctgctgatg gatctggggc agttcctgct gttctgccac atctctagcc accagcatga tgggatggag gcctatgtga aggtggacag ctgcccagag gagcctcagc tgaggatgaa aaacaatgaa gaggctgagg attatgatga tgatctgact gactctgaga tggatgtggt gagatttgat gatgacaata gccctagctt tattcagatc aggtctgtgg ctaagaagca ccccaagacc tgggtgcatt acattgctgc tgaggaggag gactgggatt atgctcctct ggtgctggcc cctgatgata ggagctacaa gagccagtac ctgaataatg gccctcagag gattggcagg aagtacaaga aggtgaggtt catggcttac actgatgaga ccttcaagac tagggaggcc atccagcatg agtctgggat cctggggccc ctgctgtatg gggaggtggg ggacaccctg ctgatcatct tcaagaacca ggctagcagg ccttacaaca tctatcccca tgggatcact gatgtgagac ctctgtacag caggaggctg cccaaggggg tcaagcatct gaaagacttc -continued cccatcctgc ctggggagat ctttaagtat aagtggactg tgactgtgga ggatgggccc accaagtctg accccaggtg cctgaccagg tattacagca gctttgtgaa catggagagg gatctggcct ctgggctgat tggccccctg ctgatctgtt acaaggaatc tgtggatcag aggggcaatc agatcatgtc tgacaagagg aatgtgatcc tgttctctgt gtttgatgag aataggtctt ggtacctgac tgaaaacatc cagaggttcc tgcccaaccc tgctggggtc cagctggagg atcctgagtt ccaggctagc aacatcatgc acagcatcaa tgggtatgtg tttgatagcc tgcagctgtc tgtgtgcctg catgaggtgg cctactggta catcctgtct attggggccc agactgactt cctgtctgtg ttcttttctg gctacacctt caagcacaag atggtgtatg aggacaccct gaccctgttc cccttctctg ggagactgt ctttatgagc atggagaacc ctgggctgtg gatcctgggc tgccacaact ctgatttcag gaataggggc atgactgctc tgctgaaggt gagctcttgt gacaagaaca ctggggatta ctatgaggac agctatgagg acatttctgc ctacctgctg agcaagaaca atgccattga gcctaggagc tttagccaga atcctcctgt cctgaagagg caccagaggg agatcaccag gaccaccctg cagtctgacc aggaggagat tgactatgat gataccatct ctgtggagat gaagaaggag gactttgaca tctatgatga ggatgagaat cagtctccca ggagcttcca gaagaagacc aggcactatt tcattgctgc tgtggagagg ctgtgggact atggcatgag cagctctcct catgtgctga ggaatagggc tcagtctggc tctgtgcccc agttcaagaa agtggtgttt caggagttca ctgatggctc tttcacccag cctctgtata gggggggagct gaatgagcac ctggggctgc tgggccccta tatcagggct gaggtggagg ataacatcat ggtgaccttc aggaaccagg cctctaggcc ctacagcttc tatagcagcc tgatcagcta tgaggaggac cagaggcagg gggctgagcc caggaagaac tttgtgaagc ccaatgagac caagacttac ttctggaagg tgcagcatca catggccccc accaaggatg agtttgactg taaggcctgg gcctacttct ctgatgtgga tctggagaag gatgtgcact ctggcctgat tggccccctg ctggtgtgcc ataccaatac tctgaaccct gctcatggca ggcaggtgac tgtgcaggag tttgctctgt tcttcactat ctttgatgag accaagtctt ggtatttcac tgagaatatg gagaggaact gcagggcccc ctgcaacatc cagatggagg accccacctt taaggagaac tataggtttc atgccatcaa tggctacatc atggacaccc tgcctggcct ggtgatggcc caggatcaga ggatcaggtg gtacctgctg agcatggggt ctaatgagaa catccacagc atccacttct ctggccatgt gtttactgtg agaaagaagg aggagtacaa gatggctctg tacaatctgt accctggggt ctttgagact gtggagatgc tgcctagcaa ggctgggatc tggagggtgg agtgcctgat tggggaacat ctgcatgctg ggatgtctac tctgttcctg gtgtacagca acaagtgcca gaccccccctg ggcatggctt ctggccatat cagggacttt cagattactg cctctgggca gtatggccag tgggccccca agctggctag gctgcattat tctggcagca tcaatgcctg gtctactaag gagcccttca gctggatcaa ggtggatctg ctggccccca tgatcatcca tggcatcaag acccaggggg ccaggcagaa gtttagctct ctgtacatta gccagttcat catcatgtac agcctggatg ggaagaagtg gcagacctac aggggcaatt ctactggcac cctgatggtg ttctttggca atgtggacag ctctggcatc aagcacaaca tctttaaccc ccctatcatt gctaggtaca tcaggctgca tcccacccat tacagcatca ggagcaccct gaggatggag ctgatgggct gtgacctgaa ctcttgcagc atgcccctgg gcatggagag caaggccatt tctgatgccc agattactgc cagcagctac ttcactaaca tgtttgccac ctggtctccc agcaaggcca ggctgcacct gcagggcagg -continued agcaatgcct ggaggcccca ggtgaacaac cccaaggagt ggctgcaggt ggatttccag aagaccatga aggtgactgg ggtgaccacc caggggtga agagcctgct gactagcatg tatgtgaagg agttcctgat cagctctagc caggatggcc accagtggac tctgtttttc cagaatggca aggtgaaggt gttccagggc aaccaggact ctttcactcc tgtggtgaac agcctggacc cccccctgct gaccaggtat ctgaggattc acccccagtc ttgggtgcat cagattgccc tgaggatgga ggtgctgggc tgtgaggccc aggatctgta ctga FVIII encoding CpG reduced nucleic acid variant X09

(SEQ ID NO: 9)

atgcagattg agctgagcac ctgcttcttc ctgtgtctgc tgagattttg cttttctgcc actaggaggt attacctggg ggctgtggag ctgtcttggg actacatgca gtctgatctg ggggagctgc ctgtggatgc caggttccca cctagggtgc ctaagagctt tcccttcaat acctctgtgg tgtacaagaa gaccctgttt gtggagttca ctgaccacct gttcaacatt gccaagccta ggccccccctg gatgggcctg ctgggcccta ccatccaggc tgaagtgtat gacactgtgg tgatcaccct gaagaacatg gccagccacc ctgtgagcct gcatgctgtg ggggtgtctt actggaaggc ctctgagggg gctgagtatg atgatcagac cagccagagg gagaaggaag atgacaaggt gttccctggg ggcagccaca cctatgtctg gcaggtgctg aaggagaatg gccccatggc ctctgatccc ctgtgcctga cctactctta cctgagccat gtggacctgg tgaaggatct gaattctggc ctgattgggg ccctgctggt gtgcagggag ggcagcctgg ccaaggagaa gacccagacc ctgcataagt tcatcctgct gtttgctgtg tttgatgaag ggaagagctg gcactctgag actaagaaca gcctgatgca ggacagggat gctgcttctg ccagggcctg gcccaagatg cacactgtga atggctatgt gaatagaagc ctgcctggcc tgattgggtg ccacaggaag tctgtgtact ggcatgtgat tgggatgggc actacccctg aggtgcatag catcttcctg gaaggccata ccttcctggt gaggaatcat aggcaggctt ctctggaaat ttctcccatc actttcctga ctgctcagac cctgctgatg gacctgggcc agttcctgct gttctgccac atcagctctc accagcatga tgggatggag gcctatgtga aggtggacag ctgtcctgag gagccccagc tgaggatgaa gaacaatgag gaggctgagg actatgatga tgacctgact gactctgaga tggatgtggt caggtttgat gatgacaata gcccctcttt catccagatc aggtctgtgg ccaagaagca ccccaagact tgggtgcact acattgctgc tgaggaggag gattgggatt atgcccctct ggtgctggcc cctgatgaca ggagctataa gtctcagtac ctgaataatg gcccccagag gattgggagg aagtataaga aggtgaggtt tatggcctac actgatgaga ccttcaagac cagggaggcc atccagcatg agtctggcat cctgggcccc ctgctgtatg gggaggtggg ggataccctg ctgatcatct tcaagaacca ggcctctagg ccctacaata tctaccctca tggcatcact gatgtgagac ccctgtatag caggaggctg cctaaggggg tgaagcacct gaaggacttc cccatcctgc ctggggagat cttcaagtat aagtggactg tgactgtgga ggatggcccc accaagtctg accccaggtg cctgaccagg tattacagct cttttgtgaa catggagagg gatctggcct ctgggctgat tggcccactg ctgatctgct acaaggagtc tgtggatcag aggggcaatc agatcatgtc tgacaagagg aatgtgatcc tgttttctgt gtttgatgaa aataggtctt ggtatctgac tgagaacatc cagaggtttc tgcccaatcc tgctggggtg cagctggagg atcctgagtt tcaggcctct aatatcatgc attctatcaa tggctatgtg tttgacagcc tgcagctgtc tgtgtgcctg catgaggtgg cctactggta catcctgagc -continued attggggctc agactgactt cctgtctgtg ttcttttctg gctatacttt caagcacaag
atggtgtatg aggacactct gaccctgttc cccttctctg ggagactgt gttcatgtct
atggaaaatc ctgggctgtg gattctgggc tgccacaatt ctgacttcag gaatagggg
atgactgccc tgctgaaggt gtctagctgt gataagaaca ctggggatta ctatgaggac
tcttatgaag atatctctgc ctatctgctg agcaagaaca atgccattga gcccaggagc
ttcagccaga accccctgt gctgaagagg caccagaggg agatcaccag gaccactctg
cagtctgatc aggaggagat tgactatgat gacactatct ctgtggagat gaagaaggag
gattttgaca tttatgatga ggatgagaac cagtctccca ggagcttcca gaagaagacc
aggcattact ttattgctgc tgtggagagg ctgtgggact atgggatgag cagctctcct
catgtgctga ggaacagggc ccagtctggg tctgtgcccc agttcaagaa ggtggtgttc
caggagttca ctgatgggag cttcacccag cccctgtata gggggagct gaatgagcac
ctgggcctgc tgggccccta catcagggct gaggtggagg ataatatcat ggtgaccttc
aggaaccagg ctagcaggcc ttacagcttt tacagcagcc tgatctctta tgaagaagac
cagaggcagg gggctgagcc caggaagaat tttgtgaagc ctaatgagac caagacttat
ttttggaagg tgcagcatca catggctcct accaaggatg agtttgactg caaggcctgg
gcctactttt ctgatgtgga tctggagaag gatgtgcact ctggcctgat tggccctctg
ctggtgtgcc atactaacac tctgaaccct gcccatggga ggcaggtgac tgtgcaggag
tttgccctgt tcttcactat ttttgatgag accaagtctt ggtatttcac tgagaacatg
gagaggaact gcagggctcc ctgcaacatc cagatggaag accccacctt caaggagaac
tataggttcc atgccatcaa tgggtacatc atggataccc tgcctggcct ggtgatggcc
caggatcaga ggattaggtg gtatctgctg agcatgggct ctaatgagaa catccacagc
atccatttct ctggccatgt gttcactgtg aggaagaagg aggagtacaa gatggctctg
tacaacctgt atcctggggt gtttgagact gtggagatgc tgcccagcaa ggctggcatc
tggagggtgg aatgcctgat tggggagcac ctgcatgctg gcatgagcac tctgttcctg
gtgtatagca acaagtgcca gacccccctg ggcatggcct ctggccatat caggatttc
cagatcactg cttctggcca gtatggccag tgggccccca agctggccag gctgcactat
tctggcagca tcaatgcctg gagcactaag gagccttttt cttggatcaa ggtggacctg
ctggccccta tgattattca tggcatcaag acccaggggg ccaggcagaa gttctctagc
ctgtacatct ctcagttcat cattatgtat agcctggatg gcaagaagtg gcagacctac
aggggcaata gcactggcac cctgatggtg tttttggga atgtggactc ttctgggatc
aagcacaaca tctttaaccc ccccatcatt gccaggtata ttaggctgca ccccacccac
tacagcatca ggagcaccct gaggatggag ctgatgggct gtgatctgaa ttcttgctct
atgcccctgg gcatggagag caaggccatc tctgatgccc agatcactgc cagctcttac
ttcaccaaca tgtttgccac ctggtctcct agcaaggcca ggctgcatct gcagggcagg
agcaatgcct ggaggcccca ggtgaacaac cccaaggagt ggctgcaggt ggacttccag
aagaccatga aggtgactgg ggtgaccact caggggggtga agagcctgct gacctctatg
tatgtgaagg agttcctgat cagcagcagc caggatggcc accagtggac tctgttcttc
cagaatggga aggtgaaggt gttccagggc aaccaggata gctttacccc tgtggtgaac
agcctggacc ctcctctgct gaccagatac ctgaggatcc atcctcagag ctgggtgcac
cagattgccc tgaggatgga ggtgctgggc tgtgaggccc aggatctgta ctga FVIII encoding CpG reduced nucleic acid variant X10

-continued (SEQ ID NO: 10)

```
atgcagattg agctgagcac ttgcttcttc ctgtgcctgc tgaggttctg cttttctgct
actaggaggt actacctggg ggctgtggag ctgagctggg attacatgca gtctgacctg
ggggagctgc cagtggatgc caggttcccc cccagggtgc ccaagtcttt tcctttcaac
acctctgtgg tgtacaagaa gaccctgttt gtggagttca ctgaccacct gttcaacatt
gccaagccca ggccccctg gatggggctg ctggggccca ccatccaggc tgaggtgtat
gacactgtgg tgattaccct gaagaacatg gctagccacc ctgtgagcct gcatgctgtg
ggggtgagct attggaaggc ctctgagggg gctgagtatg atgatcagac cagccagagg
gaaaaggagg atgacaaggt gttccctggg ggcagccata cttatgtgtg gcaggtgctg
aaggagaatg ggcccatggc ctctgacccc ctgtgcctga cttacagcta tctgagccat
gtggacctgg tgaaggatct gaactctggc ctgattgggg ctctgctggt gtgcagggag
ggcagcctgg ctaaggagaa gactcagact ctgcataagt tcatcctgct gtttgctgtg
tttgatgaag gcaagagctg gcactctgag accaagaact ctctgatgca ggatagggat
gctgcctctg ccagggcttg gcccaagatg cacactgtga atggctatgt gaacaggagc
ctgcctggcc tgattgggtg ccacaggaag tctgtgtact ggcatgtgat tggcatgggc
accacccctg aggtgcacag catttcctg gagggccaca ccttcctggt gaggaatcac
aggcaggcca gcctggagat cagccccatc accttcctga ctgcccagac cctgctgatg
gacctggggc agtttctgct gttctgccac atcagcagcc atcagcatga tggcatggag
gcctatgtga aggtggactc ttgccctgag gagccccagc tgaggatgaa gaacaatgag
gaggctgagg attatgatga tgacctgact gactctgaga tggatgtggt gaggtttgat
gatgacaata gccccagctt catccagatt aggtctgtgg ccaagaagca ccctaagacc
tgggtgcact acattgctgc tgaggaggag gattgggatt atgcccccct ggtgctggct
cctgatgaca ggtcttataa gagccagtac ctgaacaatg ggccccagag gattggcagg
aagtacaaga aggtgaggtt catggcttac actgatgaga ccttcaagac tagggaggcc
atccagcatg agtctggcat cctgggcccc ctgctgtatg gggaggtggg ggataccctg
ctgatcatct tcaagaacca ggccagcagg ccctacaaca tttaccctca tggcatcact
gatgtgaggc ccctgtacag caggagactg cccaaggggg tgaagcacct gaaggatttt
cccattctgc ctggggagat cttcaagtac aagtggactg tgactgtgga ggatggcccc
accaagtctg atcccaggtg cctgactagg tactactctt cttttgtgaa tatggagagg
gatctggcct ctggcctgat tggccccctg ctgatctgct acaaggagtc tgtggaccag
aggggcaacc agatcatgtc tgacaagagg aatgtgatcc tgttctctgt gtttgatgag
aataggagct ggtacctgac tgagaatatc cagaggttcc tgcctaatcc tgctggggtc
cagctggagg atcctgagtt ccaggctagc aacattatgc acagcatcaa tggctatgtg
tttgattctc tgcagctgtc tgtgtgcctg catgaggtgg cttactggta catcctgtct
attggggccc agactgattt cctgtctgtg ttcttctctg gctacacttt caagcataag
atggtgtatg aggatacct gaccctgttc cccttctctg gggagactgt gttcatgtct
atggagaacc ctggcctgtg gatcctgggc tgtcataact ctgacttcag aaacaggggc
atgactgccc tgctgaaggt gagcagctgt gacaagaaca ctgggggacta ctatgaggac
agctatgagg atatctctgc ttatctgctg agcaagaata tgccattga gcccaggagc
ttcagccaga acccccctgt gctgaagagg caccagaggg agatcactag gactaccctg
cagtctgatc aggaggagat tgactatgat gacaccatct ctgtggagat gaagaaggag
```

-continued gactttgaca tctatgatga ggatgagaac cagtccccca ggtctttcca gaagaagacc aggcactact tcattgctgc tgtggagagg ctgtgggact atggcatgag ctctagcccc catgtgctga ggaacagggc tcagtctggc tctgtgcccc agttcaagaa ggtggtcttc caggagttca ctgatggctc ttttacccag cctctgtaca gaggggagct gaatgagcac ctgggcctgc tgggccccta catcagggct gaggtggagg ataatatcat ggtgaccttc agaaaccagg cctctaggcc ctacagcttc tacagcagcc tgatctctta tgaggaggat cagaggcagg gggctgagcc caggaagaac tttgtgaagc ccaatgagac caagacctac ttctggaagg tgcagcacca tatggcccct actaaggatg agtttgactg caaggcctgg gcttattttt ctgatgtgga cctggagaag gatgtgcact ctgggctgat tggcccccctg ctggtgtgcc acaccaacac cctgaaccct gcccatggca ggcaggtgac tgtgcaggag tttgccctgt tcttcactat ctttgatgag accaagagct ggtacttcac tgagaacatg gagagaaatt gtagggctcc ctgcaatatc cagatggagg accccacctt caaagaaaat tacagattcc atgccatcaa tgggtacatc atggataccc tgcctgggct ggtgatggct caggaccaga ggatcaggtg gtacctgctg agcatggggt ctaatgagaa catccactct atccatttct ctggccatgt gttcactgtg agaaagaagg aggagtataa gatggctctg tacaacctgt acccaggggt gtttgagact gtggaaatgc tgcccagcaa agctgggatc tggagggtgg agtgcctgat tggggagcac ctgcatgctg gcatgtctac cctgttcctg gtgtacagca acaagtgcca gactcccctg ggcatggcct ctgggcacat cagggatttt cagatcactg cctctggcca gtatggccag tgggccccca agctggccag gctgcactac tctggcagca ttaatgcttg gagcactaag gagcccttca gctggatcaa ggtggatctg ctggccccca tgatcatcca tggcatcaag acccaggggg ccaggcagaa gttctctagc ctgtacattt ctcagttcat catcatgtac agcctggatg ggaagaagtg gcagacctac agggggaaca gcactgggac cctgatggtg ttctttggca atgtggatag ctctggcatc aagcacaata tcttcaatcc ccccattatt gccaggtaca ttaggctgca tcctactcac tactctatta ggagcaccct gaggatggag ctgatggggt gtgacctgaa cagctgttct atgcccctgg gcatggagtc taaggctatc tctgatgccc agatcactgc cagcagctac ttcactaata tgtttgccac ctggagccct agcaaggcca gactgcacct gcagggcagg agcaatgcct ggaggcccca ggtgaacaac cccaaggagt ggctgcaggt ggacttccag aagaccatga aggtgactgg ggtgaccact caggggggtga agagcctgct gaccagcatg tatgtgaagg agttcctgat cagcagcagc caggatggcc accagtggac cctgttcttc cagaatggga aggtgaaggt gttccagggc aaccaggact ctttcacccc tgtggtgaac agcctggatc ctcccctgct gaccaggtac ctgaggatcc acccccagag ctgggtgcac cagattgctc tgaggatgga agtgctgggc tgtgaggccc aggatctgta ctga FVIII encoding CpG reduced nucleic acid variant X11

(SEQ ID NO: 11)

atgcagattg agctgagcac ctgcttcttc ctgtgcctgc tgaggttttg cttctctgct accaggaggt actacctggg ggctgtggag ctgagctggg actatatgca gtctgacctg ggggagctgc ctgtggatgc taggttccct cccagggtgc ccaagagctt cccctttaat acctctgtgg tgtacaagaa aaccctgttt gtggagttca ctgaccatct gttcaacatt gccaagccca ggcccccttg gatgggcctg ctgggcccca ccattcaggc tgaggtgtat gacactgtgg tcattaccct gaagaacatg gcttctcacc ctgtgagcct gcatgctgtg ggggtgagct actggaaggc ctctgagggg gctgagtatg atgaccagac cagccagagg -continued gagaaggagg atgataaggt gttccctggg ggcagccaca cctatgtgtg gcaggtgctg aaggagaatg gccccatggc ctctgatccc ctgtgcctga cctactctta tctgtctcat gtggacctgg tgaaggacct gaactctggc ctgattgggg ctctgctggt gtgcagggag ggctctctgg ccaaggagaa gacccagacc ctgcacaagt ttattctgct gtttgctgtc tttgatgagg gcaagagctg gcattctgag accaagaaca gcctgatgca ggacagggat gctgcctctg ccagggcctg gcccaaaatg cacactgtga atggctatgt gaacaggagc ctgcctggcc tgattggctg ccacaggaag tctgtgtact ggcatgtgat tggcatgggc accacccctg aggtgcacag catcttcctg gagggccaca cctttctggt gaggaatcac aggcaggcca gcctggagat tagccccatc accttcctga ctgcccagac cctgctgatg gacctgggcc agttcctgct gttctgccac atcagcagcc accagcatga tggcatggag gcctatgtga aggtggatag ctgccctgag gagccccagc tgaggatgaa aaacaatgag gaggctgagg attatgatga tgacctgact gactctgaga tggatgtggt gaggtttgat gatgacaata gccccagctt tattcagatt aggtctgtgg ctaagaagca ccccaagact tgggtgcact acattgctgc tgaggaggag gattgggact atgcccctct ggtcctggcc cctgatgata ggtcttacaa gagccagtat ctgaacaatg gcccccagag gattggcagg aagtacaaga aggtgaggtt catggcctac actgatgaga cctttaagac cagggaggcc attcagcatg agtctgggat cctgggcccc ctgctgtatg gggaggtggg ggacactctg ctgatcatct tcaagaacca ggccagcagg ccttataaca tctaccctca tgggatcact gatgtgaggc ccctgtactc tagaaggctg cccaaggggg tcaagcacct gaaggatttt cccatcctgc ctggggagat tttcaagtac aagtggactg tgactgtgga ggatggcccc accaagtctg accctaggtg cctgaccagg tactacagct cttttgtgaa catggagagg gacctggcct ctggcctgat tggccctctg ctgatttgct acaaggagtc tgtggaccag aggggcaacc agatcatgtc tgacaagagg aatgtgatcc tgttttctgt gtttgatgag aacaggtctt ggtacctgac tgagaacatc cagaggttcc tgcctaaccc agctggggtg cagctggagg atcctgagtt ccaggccagc aatattatgc atagcattaa tggctatgtg tttgatagcc tgcagctgtc tgtgtgcctg catgaggtgg cctactggta catcctgagc attggggccc agactgactt tctgtctgtg ttcttctctg gctacacctt caagcataag atggtgtatg aggacaccct gactctgttc cctttttctg ggagactgt gtttatgagc atggagaatc ctggcctgtg gatcctgggc tgccataatt ctgacttcag gaacaggggc atgactgccc tgctgaaagt gagcagctgt gacaagaata ctggggacta ctatgaagac agctatgagg acatctctgc ctacctgctg agcaagaaca atgccattga gcccaggagc ttcagccaga accccccagt gctgaagagg caccagagag agatcaccag gactaccctg cagtctgacc aggaggagat tgactatgat gacaccattt ctgtggagat gaagaaggag gactttgaca tttatgatga ggatgagaat cagagcccca ggagcttcca gaagaagact aggcactatt ttattgctgc tgtggagagg ctgtgggact atggcatgag cagctctccc catgtgctga ggaatagggc ccagtctggc tctgtgcctc agttcaagaa ggtggtgttc caggagttca ctgatggcag ctttacccag cccctgtata ggggggagct gaatgagcac ctgggcctgc tgggccccta tatcagggct gaggtggagg acaatattat ggtgaccttt aggaaccagg ccagcaggcc ctactctttc tatagcagcc tgatcagcta tgaggaggac cagaggcagg gggctgagcc caggaagaat tttgtgaagc ctaatgagac caagacctac -continued ttctggaagg tgcagcatca catggccccc accaaggatg agtttgactg caaggcttgg
gcctatttct ctgatgtgga cctggagaag gatgtgcact ctggcctgat tggcccccctg
ctggtgtgcc acactaacac tctgaatcct gcccatggca ggcaggtgac tgtgcaggag
tttgccctgt tcttcaccat ctttgatgag accaagagct ggtacttcac tgagaacatg
gagaggaact gcagggcccc ctgcaacatc cagatggagg atcccacctt caaggagaac
tacaggtttc atgccatcaa tggctacatc atggacactc tgcctggcct ggtgatggcc
caggatcaga ggatcaggtg gtacctgctg agcatgggct ctaatgagaa tatccatagc
atccacttct ctggccatgt gttcactgtc aggaagaagg aggagtacaa gatggctctg
tataatctgt accctggggt gtttgagact gtggagatgc tgcccagcaa ggctggcatc
tggagggtgg agtgcctgat tggggagcac ctgcatgctg ggatgagcac cctgtttctg
gtgtactcta acaagtgcca gacccccctg ggcatggcct ctgggcacat cagggatttc
cagatcactg cttctggcca gtatggccag tgggccccca agctggccag gctgcactac
tctggcagca tcaatgcctg gtctaccaag gagccctttt cttggattaa ggtggacctg
ctggccccca tgatcatcca tggcatcaag acccaggggg ccaggcagaa gttcagcagc
ctgtacatca gccagttcat catcatgtac agcctggatg gcaaaaagtg gcagacctac
aggggcaata gcactgggac tctgatggtg ttctttggca atgtggacag ctctgggatc
aagcacaata tcttcaaccc tcccatcatt gctaggtaca tcaggctgca ccccacccac
tatagcatca ggtctaccct gaggatggag ctgatgggct gtgacctgaa ctcttgcagc
atgcccctgg gcatggagtc caaagctatc tctgatgccc agattactgc cagcagctac
ttcaccaaca tgtttgccac ctggtctccc tctaaggcca ggctgcacct gcagggcagg
agcaatgcct ggaggcccca ggtgaacaat cccaaggagt ggctgcaggt ggatttccag
aaaactatga aggtgactgg ggtgaccacc caggggggtga agtctctgct gaccagcatg
tatgtgaagg agttcctgat ctcttctagc caggatggcc accagtggac tctgttcttc
cagaatggca aggtgaaggt gttccagggc aaccaggaca gcttcacccc tgtggtgaac
tctctggatc ccccccctgct gaccaggtac ctgaggattc atccccagag ctgggtgcac
cagattgctc tgagaatgga ggtgctgggg tgtgaggctc aggacctgta ttga FVIII encoding CpG reduced nucleic acid variant X12

(SEQ ID NO: 12)

atgcagattg agctgtctac ttgttttttt ctgtgcctgc tgaggttctg cttctctgcc
accaggaggt attacctggg ggctgtggag ctgagctggg attacatgca gtctgatctg
ggggagctgc ctgtggatgc caggttcccc cccagggtgc ccaagagctt ccccttcaac
acctctgtgg tgtataagaa gaccctgttt gtggagttca ctgatcatct gtttaacatt
gccaagccca ggcccccctg gatgggcctg ctgggcccaa ctatccaggc tgaggtgtat
gacactgtgg tcatcaccct gaagaatatg gccagccatc ctgtgagcct gcatgctgtg
ggggtgagct actggaaggc ctctgagggg gctgagtatg atgaccagac cagccagagg
gagaaggagg atgacaaggt gttccctggg ggcagccaca cctatgtgtg gcaggtgctg
aaggagaatg gccccatggc ctctgacccc ctgtgcctga cttatagcta cctgtctcat
gtggacctgg tgaaggacct gaactctggc ctgattgggg ccctgctggt ctgtagggaa
ggcagcctgg ccaaggagaa gacccagacc ctgcacaagt ttattctgct gtttgctgtg
tttgatgaag gcaagagctg gcactctgag accaagaatt ctctgatgca ggatagggat
gctgcctctg ccagggcctg gcccaagatg catactgtga atggctatgt gaacagaagc
ctgcctggcc tgattggctg ccataggaag tctgtgtatt ggcatgtgat tgggatgggc -continued actaccccctg aagtgcacag cattttcctg gagggccaca ctttcctggt gaggaaccac
aggcaggcct ctctggagat cagccccatt actttcctga ctgcccagac cctgctgatg
gatctgggcc agttcctgct gttctgccac atctctagcc accagcatga tggcatggag
gcctatgtga aggtggacag ctgccctgag gagccccagc tgaggatgaa gaataatgag
gaggctgagg attatgatga tgacctgact gactctgaga tggatgtggt gaggtttgat
gatgataata gccccagctt catccagatc aggtctgtgg ccaagaagca tcccaagacc
tgggtgcact atattgctgc tgaagaggag gactgggact atgcccctct ggtgctggct
cctgatgaca ggagctataa gagccagtat ctgaacaatg gccccagag gattgggagg
aagtacaaga aggtgaggtt catggcctac actgatgaga cctttaagac cagggaggcc
atccagcatg agtctggcat tctggggccc ctgctgtatg gggaggtggg ggacactctg
ctgatcattt tcaagaacca ggccagcagg ccctacaata tttaccccca tggcatcact
gatgtgaggc ccctgtacag caggaggctg cccaaggggg tgaagcacct gaaggacttc
cccatcctgc ctggggagat cttcaagtac aagtggactg tgactgtgga ggatggccct
accaagtctg accctaggtg tctgactagg tactacagca gctttgtgaa catggagaga
gacctggctt ctggcctgat tggcccctg ctgatctgct acaaggagtc tgtggatcag
aggggcaacc agattatgtc tgataagagg aatgtcatcc tgttctctgt gtttgatgag
aacaggagct ggtatctgac tgagaacatt cagaggttcc tgcccaaccc tgctggggtg
cagctggagg accctgagtt ccaggccagc aacatcatgc attctattaa tggctatgtg
tttgacagcc tgcagctgtc tgtgtgcctg catgaggtgg cctactggta catcctgagc
attggggccc agactgactt tctgtctgtg tttttctctg ggtacacctt caagcacaag
atggtctatg aggacaccct gaccctgttc ccctttttctg ggaaactgt gtttatgagc
atggagaacc ctgggctgtg gatcctgggc tgccacaact ctgactttag gaataggggc
atgactgccc tgctgaaggt gagcagctgt gacaagaata ctggggatta ctatgaggac
agctatgagg atatctctgc ctacctgctg agcaagaaca atgccattga gcctaggagc
ttcagccaga accccccctgt gctgaagagg caccagaggg agatcaccag gaccaccctg
cagtctgatc aggaggagat tgactatgat gacaccatct ctgtggagat gaagaaggag
gactttgata tttatgatga ggatgagaac cagagcccca ggagcttcca gaagaagacc
aggcactatt tcattgctgc tgtggagagg ctgtgggact atggcatgag ctctagcccc
catgtgctga ggaacagggc ccagtctggc tctgtgcccc agttcaagaa ggtggtgttc
caggaattta ctgatggcag ctttacccag cccctgtaca gaggggagct gaatgagcac
ctgggcctgc tgggccccta catcagggct gaggtggagg ataatatcat ggtgaccttt
aggaaccagg cctctaggcc ctattctttt tacagcagcc tgatcagcta tgaggaggac
cagaggcagg gggctgagcc taggaagaac tttgtgaagc ccaatgagac caagacctac
ttttggaaag tgcagcacca catggccccc actaaggatg agtttgattg caaggcctgg
gcctatttct ctgatgtgga cctggagaag gatgtgcact ctggcctgat tggcccctg
ctggtgtgcc acaccaacac tctgaaccct gcccatggca ggcaggtgac tgtgcaggag
tttgccctgt tctttaccat ctttgatgag actaagagct ggtatttcac tgagaacatg
gagaggaact gcagagcccc ttgcaacatc cagatggagg accctacctt caaggagaac
tataggttcc atgccatcaa tgggtacatc atggataccc tgcctggcct ggtgatggct
caggaccaga ggatcaggtg gtacctgctg agcatgggga gcaatgagaa cattcatagc -continued atccacttct ctgggcatgt gttcactgtg aggaagaagg aggagtataa gatggccctg tacaacctgt accctggggt gtttgagact gtggagatgc tgcccagcaa ggctggcatc tggagggtgg agtgcctgat tggggagcac ctgcatgctg gcatgagcac tctgttcctg gtgtacagca acaagtgcca gacccccctg ggcatggcct ctggccacat cagggacttc cagattactg cctctgggca gtatgggcag tgggccccca agctggccag gctgcactac tctgggtcta tcaatgcttg gagcaccaag gagcctttca gctggatcaa ggtggatctg ctggccccca tgatcattca tgggatcaag acccaggggg ccaggcagaa gttcagcagc ctgtatattt ctcagttcat catcatgtat tctctggatg gcaaaaagtg gcagacctat agagggaaca gcactgggac cctgatggtg ttttttggca atgtggatag ctctggcatc aagcacaata tcttcaaccc ccccattatt gccaggtaca tcaggctgca ccccacccac tactctatca ggagcaccct gaggatggag ctgatgggct gtgatctgaa cagctgctct atgcctctgg ggatggaaag caaggccatc tctgatgccc agatcactgc cagcagctat ttcaccaata tgtttgccac ttggagccct agcaaggcta ggctgcatct gcagggcagg tctaatgcct ggaggcccca ggtgaacaac cccaaggagt ggctgcaggt ggacttccag aagactatga aagtgactgg ggtgaccacc cagggggtga aaagcctgct gaccagcatg tatgtgaagg agttcctgat tagcagcagc caggatggcc accagtggac cctgttcttc cagaatggga aggtgaaggt gtttcagggc aatcaggata gcttcacccc agtggtgaac agcctggacc ccccctgct gaccaggtac ctgaggatcc acccccagag ctgggtgcac cagattgccc tgaggatgga ggtgctgggc tgtgaggccc aggatctgta ctga FVIII encoding CpG reduced nucleic acid variant X13

(SEQ ID NO: 13)

atgcagattg agctgagcac ctgctttttc ctgtgcctgc tgaggttctg cttctctgct accaggaggt actacctggg ggctgtggag ctgtcttggg attacatgca gtctgacctg ggggagctgc ctgtggatgc caggtttccc cccagggtgc ccaagtcttt cccctttaac acctctgtgg tgtataagaa gactctgttt gtggagttca ctgatcacct gttcaatatt gccaagccca ggcccccttg gatgggcctg ctgggcccca ctatccaggc tgaggtgtat gacactgtgg tcatcaccct gaagaacatg gccagccacc ctgtgagcct gcatgctgtg ggggtgagct actggaaggc ctctgagggg gctgagtatg atgaccagac cagccagagg gagaaggagg atgacaaggt gttcccaggg gggtctcaca cttatgtgtg gcaggtgctg aaggagaatg ggcccatggc ctctgaccct ctgtgcctga cttatagcta cctgtctcat gtggatctgg tgaaggacct gaactctggc ctgattgggg ccctgctggt gtgcagggag gggagcctgg ccaaggagaa gacccagacc ctgcacaagt tcatcctgct gtttgctgtg tttgatgagg ggaagagctg gcactctgag accaagaata gcctgatgca ggacagggat gctgcttctg ctagggcctg gcctaagatg cacactgtga atggctatgt gaacaggagc ctgcctggcc tgattgggtg tcacaggaag tctgtgtact ggcatgtgat tggcatgggg actactccag aagtgcacag catcttcctg gaggggcaca ccttcctggt gaggaatcac aggcaggcca gcctggagat ttctcccatc actttcctga ctgcccagac cctgctgatg gatctggggc agttcctgct gttctgccac atcagcagcc atcagcatga tgggatggag gcctatgtga aggtggacag ctgccctgag gagcctcagc tgaggatgaa gaacaatgag gaggctgagg actatgatga tgatctgact gactctgaga tggatgtggt gaggtttgat gatgacaact ctcccagctt catccagatc aggtctgtgg ccaagaagca ccccaagacc tgggtgcact acattgctgc tgaggaggag gattgggatt atgctcccct ggtgctggct -continued cctgatgata ggagctacaa gagccagtat ctgaataatg ggccccagag gattggcagg aagtataaga aggtgaggtt catggcctac actgatgaga cctttaagac cagggaggct attcagcatg agtctggcat cctgggcccc ctgctgtatg gggaggtggg ggacaccctg ctgatcattt tcaagaacca ggccagcagg ccctataaca tctatcccca tgggatcact gatgtgaggc ccctgtactc taggaggctg cccaaggggg tcaagcacct gaaggacttc cccatcctgc ctggggagat cttcaagtac aagtggactg tgactgtgga ggatggcccc actaagtctg accccaggtg cctgactagg tactacagca gctttgtgaa catggagaga gatctggcct ctggcctgat tggcccccctg ctgatctgct acaaagagtc tgtggatcag aggggcaacc agatcatgtc tgacaagagg aatgtgatcc tgttctctgt gtttgatgag aacagaagct ggtacctgac tgagaacatt cagaggtttc tgcccaaccc tgctggggtc cagctggagg accctgagtt tcaggccagc aacatcatgc acagcatcaa tgggtatgtg tttgacagcc tgcagctgtc tgtgtgcctg catgaggtgg cctactggta tatcctgagc attggggccc agactgattt cctgtctgtg ttcttctctg gctacacttt caagcacaag atggtgtatg aggataccct gaccctgttc cctttctctg ggaaactgt gttcatgagc atggagaacc ctgggctgtg gatcctgggg tgccacaatt ctgatttcag gaacagaggc atgactgctc tgctgaaggt gtctagctgt gacaagaaca ctggggacta ctatgaggac agctatgagg acatctctgc ctacctgctg agcaagaaca atgctattga acccaggtct ttcagccaga acccccctgt gctgaagagg caccagaggg agatcactag gaccaccctg cagtctgatc aggaggagat tgactatgat gacaccatct ctgtggagat gaagaaggag gactttgaca tctatgatga ggatgagaat cagtctccca ggagcttcca gaagaagact aggcattact tcattgctgc tgtggagagg ctgtgggact atggcatgag ctctagccct catgtgctga ggaacagggc ccagtctggc tctgtgcccc agttcaagaa ggtggtgttt caggagttca ctgatggcag cttcacccag cccctgtaca gggggggagct gaatgagcat ctgggcctgc tgggccccta catcagggct gaggtggagg acaacatcat ggtgaccttc agaaatcagg ctagcaggcc ctacagcttc tacagcagcc tgatctctta tgaggaggac cagaggcagg gggctgagcc caggaagaac tttgtgaagc ccaatgagac caagacctat ttctggaagg tgcagcacca catggccccc accaaggatg agtttgattg caaggcctgg gcctacttct ctgatgtgga cctggagaag gatgtgcatt ctgggctgat tggccctctg ctggtgtgcc acaccaacac cctgaatcct gcccatggca ggcaggtgac tgtgcaggag tttgccctgt tctttactat ctttgatgag accaagtctt ggtattttac tgagaacatg gagaggaact gcagggcccc ctgcaacatc cagatggagg accccacctt caaggagaac tacagattcc atgccatcaa tggctacatt atggacactc tgcctggcct ggtgatggcc caggaccaga ggatcaggtg gtacctgctg tctatgggca gcaatgagaa cattcactct atccacttct ctgggcatgt gttcactgtg aggaagaagg aggagtacaa gatggccctg tacaacctgt accctggggt gtttgagact gtggagatgc tgcctagcaa ggctgggatc tggagggtgg agtgcctgat tggggagcac ctgcatgctg gcatgtctac cctgttcctg gtgtacagca acaagtgcca gacccccctg ggcatggcct ctggccacat cagagatttt cagatcactg cctctggcca gtatggccag tgggctccta agctggccag gctgcactac tctggcagca tcaatgcctg gagcaccaag gagccctta gctggatcaa ggtggacctg ctggccccca tgatcatcca tggcatcaag actcaggggg ccaggcagaa gttctctagc -continued ctgtacatta gccagttcat catcatgtat agcctggatg gcaagaagtg gcagacctac aggggcaaca gcactgggac cctgatggtg ttctttggga atgtggacag ctctgggatc aagcacaata tcttcaaccc ccccattatt gccaggtata ttaggctgca ccccactcac tacagcatta ggagcaccct gaggatggag ctgatgggct gtgatctgaa cagctgcagc atgcccctgg gcatggagtc taaggccatc tctgatgccc agatcactgc cagctcttac ttcaccaaca tgtttgccac ttggagcccc agcaaggcca ggctgcacct gcagggcagg agcaatgcct ggaggcccca ggtgaacaac cccaaggagt ggctgcaggt ggatttccag aagactatga aggtgactgg ggtgaccact caggggggtga agagcctgct gactagcatg tatgtgaagg agttcctgat cagctctagc caggatggcc accagtggac cctgttcttt cagaatggca aggtgaaggt gttccagggc aaccaggact ctttcacccc tgtggtgaat tctctggacc ctcccctgct gactaggtat ctgaggattc atccccagag ctgggtgcat cagattgccc tgaggatgga ggtgctgggc tgtgaggccc aggacctgta ttga FVIII encoding CpG reduced nucleic acid variant X14

(SEQ ID NO: 14)

atgcagattg agctgagcac ctgcttcttc ctgtgcctgc tgaggttttg cttttctgcc actaggaggt actacctggg ggctgtggag ctgtcttggg attacatgca gtctgacctg ggggagctgc cagtggatgc caggttcccc ccaagggtgc ccaagtcttt tcccttcaat acctctgtgg tgtacaagaa gaccctgttt gtggagttta ctgatcatct gtttaacatt gccaagccca ggccccctg gatggggctg ctgggcccca ccatccaggc tgaggtgtat gatactgtgg tgattaccct gaagaatatg gccagccatc ctgtgtctct gcatgctgtg ggggtgtctt attggaaggc ctctgagggg gctgagtatg atgatcagac cagccagagg gagaaggagg atgataaggt gttccctggg ggctctcaca cctatgtgtg gcaggtgctg aaggagaatg ggcctatggc ctctgaccca ctgtgcctga cttacagcta tctgagccat gtggacctgg tgaaggacct gaactctggg ctgattgggg ccctgctggt gtgcagggag ggcagcctgg ccaaggagaa gactcagacc ctgcacaagt tcatcctgct gtttgctgtg tttgatgagg gcaagtcttg gcactctgag accaagaaca gcctgatgca ggatagggat gctgcctctg ccagggcctg gcccaagatg cacactgtga atggctatgt gaacaggtct ctgcctggcc tgattggctg ccacaggaag tctgtgtact ggcatgtgat tggcatgggc accacccctg aggtgcatag cattttcctg gagggccaca ccttcctggt gaggaaccac aggcaggcta gcctggagat cagccccatc actttcctga ctgcccagac cctgctgatg gacctgggcc agttcctgct gttctgccac atctctagcc accagcatga tggcatggag gcctatgtga aggtggactc ttgtcctgag gagccccagc tgaggatgaa gaacaatgag gaggctgagg attatgatga tgatctgact gattctgaga tggatgtggt gaggtttgat gatgacaaca gcccctcttt catccagatc aggtctgtgg ccaagaagca ccccaagacc tgggtgcact acattgctgc tgaggaggag gattgggatt atgcccccct ggtgctggcc cctgatgaca ggagctataa gtctcagtac ctgaacaatg gcccccagag aattggcagg aagtacaaga aggtgaggtt catggcctat actgatgaga ccttcaaaac cagggaggcc attcagcatg agtctggcat cctggggccc ctgctgtatg gggaggtggg ggacaccctg ctgatcatct tcaagaacca ggctagcagg ccttacaaca tctaccccca tgggatcact gatgtgaggc ccctgtacag caggaggctg cctaaggggg tgaagcacct gaaggacttt cccattctgc ctggggagat cttcaagtat aagtggactg tgactgtgga ggatgggccc accaagtctg accccaggtg cctgactagg tactactcta gctttgtgaa catggagagg -continued gacctggcct ctgggctgat tggccccctg ctgatctgtt acaaggagtc tgtggaccag aggggcaacc agatcatgtc tgataagagg aatgtgatcc tgttctctgt gtttgatgag aacaggagct ggtacctgac tgagaacatc cagagattcc tgcccaaccc tgctggggtg cagctggagg atcctgagtt ccaggccagc aacatcatgc attctatcaa tgggtatgtg tttgatagcc tgcagctgtc tgtgtgtctg catgaggtgg cctactggta cattctgagc attggggccc agactgactt cctgtctgtg ttcttctctg gctacacttt caaacacaag atggtgtatg aggacaccct gaccctgttc cccttctctg ggagactgt gtttatgagc atggagaacc ctgggctgtg gattctgggc tgccacaact ctgacttcag aaacaggggc atgactgccc tgctgaaggt gtcttcttgt gataagaaca ctggggacta ttatgaagac agctatgagg acatctctgc ctacctgctg agcaagaata atgctattga gcccaggtct ttctctcaga accccctgt gctgaagagg caccagaggg agatcaccag gaccaccctg cagtctgatc aggaggagat tgactatgat gacactattt ctgtggagat gaagaaggaa gactttgata tctatgatga ggatgagaac cagagcccta ggagcttcca gaagaagact aggcattact tcattgctgc tgtggagagg ctgtgggact atggcatgag cagcagcccc catgtgctga ggaatagggc tcagtctggc tctgtgcctc agttcaagaa ggtggtgttc caggaattca ctgatggcag cttcactcag cccctgtaca gggggggagct gaatgagcac ctggggctgc tgggcccctta catcagggct gaggtggagg acaatatcat ggtgaccttt aggaaccagg cctctaggcc ttacagcttc tactctagcc tgatctctta tgaagaggac cagaggcagg gggctgagcc caggaagaac tttgtgaagc ccaatgagac taagacttac ttctggaagg tgcagcacca catggctccc accaaggatg agtttgactg caaggcttgg gcctacttct ctgatgtgga cctggagaag gatgtgcact ctgggctgat tgggccccctg ctggtgtgcc acactaacac tctgaatcct gcccatggca gacaggtgac tgtgcaggag tttgccctgt tttttaccat ctttgatgag actaagtctt ggtacttcac tgagaacatg gagaggaact gcagggcccc ctgcaacatc cagatggagg atcccacctt caaggagaac tacaggtttc atgccatcaa tggctacatc atggacaccc tgcctggcct ggtgatggct caggaccaga ggattaggtg gtatctgctg agcatgggca gcaatgagaa tatccactct atccacttct ctgggcatgt gttcactgtg aggaagaagg aggagtacaa gatggccctg tataacctgt atcctggggt gtttgagact gtggagatgc tgcccagcaa ggctggcatc tggagagtgg agtgcctgat tggggagcac ctgcatgctg gcatgagcac tctgtttctg gtgtatagca acaagtgtca gacccctctg ggcatggcct ctgggcacat tagggacttt cagatcactg cttctggcca gtatgggcag tgggctccca agctggccag gctgcactat tctggcagca ttaatgcctg gagcaccaag gagcctttca gctggatcaa ggtggacctg ctggccccca tgatcatcca tgggatcaag acccaggggg ctaggcagaa gttcagcagc ctgtacatca gccagtttat catcatgtat tctctggatg gcaagaagtg gcagacctac aggggcaatt ctactggcac tctgatggtg ttctttggga atgtggatag ctctgggatc aagcataata tcttcaatcc ccccattatt gctaggtata tcaggctgca ccccacccac tatagcatca ggagcaccct gaggatggag ctgatggggt gtgacctgaa cagctgcagc atgcccctgg gcatggagag caaggctatt tctgatgccc agatcactgc cagcagctac tttactaata tgtttgccac ctggagcccc agcaaggcca gactgcacct gcagggcagg tctaatgcct ggaggcctca ggtgaataac cccaaggagt ggctgcaggt ggacttccag -continued aaaaccatga aggtgactgg ggtgactacc caggggggtga agtctctgct gaccagcatg tatgtgaagg agttcctgat ctcttctagc caggatggcc accagtggac cctgttcttt cagaatggga aggtgaaggt cttccagggc aaccaggata gcttcacccc tgtggtgaat agcctggatc ctcctctgct gaccaggtat ctgaggatcc acccccagag ctgggtgcat cagattgccc tgaggatgga ggtgctgggc tgtgaggctc aggacctgta ctga FVIII encoding CpG reduced nucleic acid variant X15

(SEQ ID NO: 15)

atgcagattg agctgagcac ctgtttcttc ctgtgcctgc tgaggttctg tttctctgcc actaggaggt actacctggg ggctgtggag ctgagctggg actatatgca gtctgacctg ggggagctgc ctgtggatgc caggttcccc cccagggtgc ctaagagctt ccccttcaat acttctgtgg tgtacaagaa gactctgttt gtggagttta ctgaccacct gttcaacatt gctaagccca ggcctccctg gatggggctg ctgggcccca ccatccaggc tgaggtgtat gatactgtgg tgattaccct gaagaacatg gcctctcatc cagtgagcct gcatgctgtg ggggtgagct actggaaggc ctctgaaggg gctgagtatg atgaccagac cagccagagg gagaaggagg atgacaaggt gttccctggg ggcagccaca cctatgtgtg gcaggtgctg aaggagaatg gcccaatggc ctctgacccc ctgtgcctga cttatagcta cctgagccat gtggatctgg tgaaggacct gaattctggc ctgattgggg ccctgctggt gtgcagagag ggctctctgg ctaaggagaa gacccagact ctgcacaagt tcatcctgct gtttgctgtg tttgatgagg gcaagagctg gcactctgag actaagaata gcctgatgca ggacagggat gctgcttctg ccagggcctg gcccaagatg catactgtga atggctatgt gaacaggagc ctgcctggcc tgattggctg tcacaggaaa tctgtctact ggcatgtgat tgggatgggc actacccctg aggtgcactc tatcttcctg gagggccata ccttcctggt gaggaaccac aggcaggcca gcctggagat ctctcccatt accttcctga ctgcccagac cctgctgatg gatctgggcc agttcctgct gttctgccac atcagcagcc accagcatga tgggatggag gcttatgtga aggtggatag ctgccctgag gagccccagc tgaggatgaa gaacaatgag gaggctgagg actatgatga tgacctgact gactctgaga tggatgtggt gaggtttgat gatgacaact ctcccagctt tattcagatc aggtctgtgg ctaagaagca ccccaagact tgggtgcact acattgctgc tgaggaggag gactgggact atgcccctct ggtgctggct cctgatgaca ggtcttacaa gtctcagtac ctgaataatg gccctcagag gattggcagg aagtacaaga aggtgaggtt catggcctac actgatgaga ccttcaagac cagggaggcc atccagcatg agtctggcat cctgggcccc ctgctgtatg gggaggtggg ggataccctg ctgatcatct tcaagaatca ggccagcagg ccctacaaca tctaccccca tggcatcact gatgtgaggc cactgtacag caggaggctg cccaaggggg tgaagcatct gaaggacttc cccattctgc ctggggagat cttcaagtac aaatggactg tgactgtgga ggatggccct accaagtctg accccaggtg tctgaccagg tactacagca gctttgtgaa tatggagagg gacctggcct ctggcctgat tggcccccctg ctgatctgct acaaggagtc tgtggaccag aggggcaatc agatcatgtc tgataagagg aatgtgattc tgttctctgt gtttgatgag aacaggagct ggtacctgac tgagaacatc cagaggttcc tgcccaatcc tgctggggtg cagctggagg accctgagtt ccaggccagc aatatcatgc acagcatcaa tggctatgtc tttgacagcc tgcagctgtc tgtgtgcctg catgaggtgg cttactggta tattctgagc attggggccc agactgattt cctgtctgtg ttcttttctg gctatacctt taagcacaag atggtgtatg aggacaccct gaccctgttc cccttctctg ggagactgt gttcatgtct -continued atggagaacc ctgggctgtg gatcctgggc tgccacaact ctgacttcag gaacaggggg
atgactgccc tgctgaaggt gtctagctgt gataagaaca ctggggacta ttatgaggac
agctatgagg acatctctgc ttacctgctg agcaagaaca atgccattga gcccaggtct
ttcagccaga atccccctgt gctgaagagg catcagaggg agatcaccag gaccaccctg
cagtctgatc aggaggagat tgattatgat gacactatct ctgtggaaat gaagaaggag
gactttgaca tctatgatga ggatgagaac cagagcccca ggagcttcca gaagaagacc
aggcactact tcattgctgc tgtggagagg ctgtgggatt atggcatgag cagctctccc
catgtgctga ggaacagagc ccagtctggc tctgtgcctc agttcaagaa ggtggtcttc
caggagttca ctgatggctc tttcacccag cccctgtaca ggggggagct gaatgagcac
ctgggcctgc tggggcccta cattagggct gaggtggagg ataacatcat ggtgactttc
agaaaccagg ccagcaggcc ttacagcttt tactcttctc tgattagcta tgaggaggat
cagaggcagg gggctgagcc taggaagaac tttgtgaagc ccaatgagac caagacctat
ttctggaagg tgcagcacca catggctccc actaaggatg agtttgactg caaggcttgg
gcctacttct ctgatgtgga cctggagaag gatgtgcact ctggcctgat tgggcccctg
ctggtgtgcc acaccaacac cctgaaccct gcccatggca ggcaggtgac tgtgcaggag
tttgccctgt tcttcaccat ctttgatgag actaagagct ggtacttcac tgagaacatg
gagaggaact gcagggcccc ctgcaacatc cagatggagg accccacctt caaggagaat
tacaggttcc atgccatcaa tggctacatt atggacaccc tgcctggcct ggtgatggcc
caggatcaga ggatcaggtg gtatctgctg agcatgggct ctaatgagaa catccacagc
atccacttct ctggccatgt gtttactgtg aggaagaagg aggaatacaa gatggctctg
tataacctgt accctggggt gtttgagact gtggagatgc tgcccagcaa ggctgggatc
tggagggtgg agtgcctgat tggggagcac ctgcatgctg ggatgagcac cctgttcctg
gtgtatagca ataagtgcca gacccccctg ggcatggctt ctggccacat cagggatttc
cagatcactg cttctggcca gtatggccag tgggctccca agctggctag gctgcattac
tctgggtcta tcaatgcctg gagcactaag gagcccttca gctggatcaa ggtggacctg
ctggccccca tgatcattca tggcatcaag acccaggggg ctaggcagaa gttcagcagc
ctgtacatca gccagttcat cattatgtac agcctggatg gcaagaagtg gcagacttac
aggggcaata gcactgggac tctgatggtg ttctttggca atgtggactc ttctggcatc
aagcacaaca tcttcaaccc tcccatcatt gccaggtaca ttaggctgca ccctacccac
tactctatca ggagcaccct gaggatggag ctgatggggt gtgatctgaa ctcttgcagc
atgcctctgg gcatggaaag caaagccatc tctgatgccc agatcactgc ctctagctat
ttcaccaata tgtttgccac ctggagccct agcaaggcca ggctgcacct gcagggcaga
tctaatgcct ggaggcccca ggtgaacaat cccaaggagt ggctgcaggt ggacttccag
aagaccatga aggtgactgg ggtgaccact caggggggtga agagcctgct gactagcatg
tatgtgaagg agttcctgat ctcttctagc caggatggcc accagtggac cctgttcttc
cagaatggca aggtgaaagt gttccagggc aaccaggata gcttcactcc tgtggtgaac
tctctggacc ctcccctgct gactaggtac ctgaggattc atccccagag ctgggtgcac
cagattgccc tgaggatgga ggtgctgggc tgtgaggccc aggatctgta ctga FVIII encoding CpG reduced nucleic acid variant X16

(SEQ ID NO: 16)

atgcagattg agctgagcac ctgcttcttc ctgtgcctgc tgaggttctg cttctctgcc

-continued accaggaggt actacctggg ggctgtggag ctgtcttggg actatatgca gtctgacctg ggggagctgc cagtggatgc caggttcccc cccagggtgc ccaagagctt tcctttcaac acttctgtgg tgtacaagaa gaccctgttt gtggagttca ctgaccacct gttcaatatt gctaagccca ggccaccctg gatgggcctg ctgggcccta ccattcaggc tgaggtgtat gacactgtgg tgattactct gaagaatatg gccagccacc ctgtgagcct gcatgctgtg ggggtgtctt actggaaggc ctctgagggg gctgagtatg atgatcagac ttctcagagg gagaaggagg atgataaggt gttccctggg ggctctcaca cttatgtgtg gcaggtgctg aaggagaatg gccccatggc ttctgatcca ctgtgcctga cctactctta cctgagccat gtggacctgg tgaaggacct gaactctggc ctgattgggg ccctgctggt gtgcagggag ggcagcctgg ccaaggagaa gacccagacc ctgcataagt tcatcctgct gtttgctgtg tttgatgagg ggaagagctg gcactctgag accaagaatt ctctgatgca ggacagggat gctgcctctg ccagggcctg gcctaagatg cacactgtga atggctatgt gaacaggtct ctgcctggcc tgattggctg ccacaggaag tctgtgtact ggcatgtgat tggcatgggc actacccctg aggtgcacag cattttcctg gagggccaca ccttcctggt caggaaccat aggcaggcct ctctggagat cagccccatc actttcctga ctgcccagac cctgctgatg gacctgggcc agttcctgct gttctgccac attagcagcc accagcatga tggcatggag gcctatgtga aggtggactc ttgccctgag gagccccagc tgaggatgaa gaacaatgag gaagctgagg attatgatga tgacctgact gactctgaga tggatgtggt gaggtttgat gatgacaaca gccccagctt catccagatc aggtctgtgg ccaagaagca ccccaagacc tgggtgcact acattgctgc tgaggaggag gattgggact atgctcccct ggtgctggct cctgatgata ggagctacaa gtctcagtac ctgaataatg gcccccagag gattggcagg aagtacaaga aggtgaggtt catggcctac actgatgaga ccttcaagac cagagaggct atccagcatg agtctgggat cctggggccc ctgctgtatg gggaggtggg ggacaccctg ctgatcatct tcaagaacca ggccagcaga ccctacaaca tctaccccca tgggatcact gatgtgaggc ccctgtacag caggaggctg cctaaggggg tgaagcacct gaaggacttc cccatcctgc ctggggagat cttcaagtat aagtggactg tgactgtgga ggatgggccc accaagtctg accctaggtg cctgactagg tactactcta gctttgtgaa catggagagg gacctggcct ctggcctgat tggcccccctg ctgatttgct acaaggagtc tgtggatcag aggggcaatc agatcatgtc tgacaagagg aatgtgatcc tgttctctgt gtttgatgag aataggtctt ggtacctgac tgagaacatc cagaggttcc tgcctaatcc tgctggggtg cagctggagg accctgagtt tcaggccagc aacatcatgc acagcatcaa tggctatgtg tttgactctc tgcagctgtc tgtgtgcctg catgaggtgg cttactggta tatcctgagc attggggctc agactgactt cctgtctgtg ttcttttctg gctacacttt taagcacaag atggtgtatg aggacaccct gaccctgttc cccttttctg ggagactgt gttcatgtct atggagaacc ctgggctgtg gattctgggc tgtcacaact ctgacttcag aaacaggggc atgactgccc tgctgaaggt gtctagctgt gacaagaata ctggggacta ctatgaggac agctatgagg acatttctgc ctatctgctg agcaagaaca atgccattga gcccaggagc ttttctcaga atccccctgt gctgaagagg caccagagag agatcaccag gaccactctg cagtctgatc aggaggagat tgattatgat gacactatct ctgtggagat gaagaaagag gactttgata tctatgatga ggatgagaat cagtctccca ggagcttcca gaagaagact agacactact tcattgctgc tgtggagagg ctgtgggact atggcatgag ctctagccct -continued catgtgctga ggaacagggc ccagtctggg tctgtgcccc agttcaagaa ggtggtgttc
caggagttca ctgatggcag ctttacccag cccctgtata ggggggagct gaatgagcat
ctgggcctgc tgggccccta tattagggct gaagtggagg acaacatcat ggtgaccttt
aggaaccagg ccagcaggcc ctacagcttt tacagcagcc tgattagcta tgaggaggat
cagagacagg gggctgagcc caggaagaac tttgtgaagc ccaatgagac caagacctac
ttctggaagg tgcagcacca catggcccct accaaggatg agtttgactg caaggcctgg
gcttacttct ctgatgtgga cctggagaaa gatgtgcact ctggcctgat tgggcccctg
ctggtgtgcc acaccaacac cctgaaccct gcccatggga ggcaggtgac tgtgcaggag
tttgccctgt tttcaccat ctttgatgag accaagagct ggtacttcac tgagaacatg
gagaggaact gcagggcccc ctgtaacatc cagatggagg atcctacttt caaggagaac
tacaggttcc atgccattaa tgggtacatc atggacaccc tgcctgggct ggtgatggcc
caggatcaga ggattaggtg gtatctgctg tctatgggct ctaatgagaa catccactct
atccacttct ctggccatgt gttcactgtg aggaagaagg aggagtacaa gatggccctg
tacaacctgt accctggggt gtttgaaact gtggagatgc tgccctctaa agctgggatc
tggagggtgg agtgcctgat tggggagcac ctgcatgctg gcatgagcac cctgttcctg
gtgtacagca ataagtgcca gactcccctg ggcatggctt ctgggcacat caggatttc
cagatcactg cctctggcca gtatggccag tgggccccca agctggctag gctgcactac
tctggcagca tcaatgcctg gagcaccaag gagcccttct cttggattaa ggtggacctg
ctggctccca tgatcattca tggcatcaag acccaggggg ccaggcagaa gttttctagc
ctgtatatta gccagttcat catcatgtat agcctggatg ggaagaagtg gcagacctac
agggggaata gcactggcac cctgatggtg ttttttggca atgtggattc ttctggcatc
aagcataaca tcttcaatcc ccctatcatt gccaggtaca ttaggctgca tcccacccat
tactctatca ggagcaccct gaggatggag ctgatggggt gtgatctgaa cagctgtagc
atgcccctgg gcatggagtc caaggctatc tctgatgccc agatcactgc cagcagctac
ttcaccaaca tgtttgccac ctggagcccc agcaaggcca ggctgcacct gcagggcagg
tctaatgcct ggaggcccca ggtgaacaat cccaaggagt ggctgcaggt ggacttccag
aagactatga aggtgactgg ggtgaccact caggggtga agagcctgct gaccagcatg
tatgtgaagg agttcctgat ctcttctagc caggatgggc atcagtggac cctgtttttt
cagaatggca aagtgaaggt gtttcagggg aatcaggaca gctttacccc tgtggtgaac
agcctggatc ctcctctgct gactagatac ctgaggatcc acccccagag ctgggtccac
cagattgctc tgaggatgga ggtgctgggg tgtgaggctc aggacctgta ctga FVIII encoding CpG reduced nucleic acid variant X17
(SEQ ID NO: 17)

atgcagattg agctgagcac ctgcttcttt ctgtgcctgc tgaggttctg cttctctgcc
accaggaggt actacctggg ggctgtggaa ctgagctggg actatatgca gtctgacctg
ggggagctgc ctgtggatgc caggttcccc cccagggtgc ccaagtcttt cccctttaac
acttctgtgg tgtacaagaa gaccctgttt gtggagttta ctgaccacct gttcaatatt
gccaagccca ggccccctg gatgggcctg ctgggcccaa ccatccaggc tgaggtgtat
gatactgtgg tgatcaccct gaagaacatg gccagccacc ctgtgagcct gcatgctgtg
ggggtgagct attggaaggc ttctgagggg gctgagtatg atgaccagac tagccagagg
gagaaggagg atgacaaggt gttccctggg ggtctcata cctatgtgtg gcaggtgctg -continued aaggagaatg gccccatggc ctctgacccc ctgtgcctga cctattctta cctgagccat gtggacctgg tcaaggacct gaactctggc ctgattgggg ctctgctggt gtgcagggag ggcagcctgg ccaaggagaa gactcagact ctgcataagt tcatcctgct gtttgctgtg tttgatgagg gcaagagctg gcactctgag accaagaact ctctgatgca ggatagggat gctgcctctg ccagggcctg gcccaagatg cacactgtga atggctatgt gaataggtct ctgcctggcc tgattggctg ccataggaag tctgtgtact ggcatgtgat tggcatgggc actacccctg aggtgcactc tatcttcctg gaggggcaca ccttcctggt gaggaaccac aggcaggcca gcctggagat ctctcccatc accttcctga ctgcccagac tctgctgatg gacctgggcc agttcctgct gttctgccat atcagcagcc accagcatga tggcatggag gcctatgtga aggtggacag ctgcccagag gaaccccagc tgaggatgaa gaacaatgag gaggctgagg actatgatga tgacctgact gactctgaga tggatgtggt gaggtttgat gatgacaaca gccccagctt tattcagatc aggtctgtgg ccaagaagca ccccaagacc tgggtgcact acattgctgc tgaggaggag gactgggatt atgccccccct ggtgctggcc cctgatgaca ggtcttacaa gtctcagtac ctgaacaatg gcccccagag gattgggagg aagtacaaga aggtgaggtt catggcctac actgatgaga ccttcaagac cagggaggcc atccagcatg agtctggcat cctggggccc ctgctgtatg gggaggtggg ggataccctg ctgattatct tcaagaacca ggctagcagg ccctataaca tctaccccca tggcattact gatgtgaggc ccctgtactc taggagactg cccaaggggg tgaagcacct gaaagacttc cccatcctgc ctggggagat cttcaagtat aagtggactg tgactgtgga ggatggcccc actaagtctg accccaggtg cctgaccagg tattacagca gctttgtgaa tatggagagg gatctggctt ctggcctgat tgggcctctg ctgatttgct acaaggagtc tgtggatcag agggggaacc agattatgtc tgacaagagg aatgtgattc tgttctctgt gtttgatgag aacaggagct ggtacctgac tgagaatatc cagaggttcc tgcctaatcc tgctggggtg cagctggagg accctgagtt ccaggctagc aacattatgc acagcatcaa tggctatgtg tttgacagcc tgcagctgtc tgtgtgcctg catgaggtgg cttactggta cattctgtct attggggccc agactgactt cctgtctgtg ttcttctctg gctacacctt caagcacaag atggtgtatg aggacactct gaccctgttc cccttctctg gggagactgt gttcatgagc atggagaatc ctgggctgtg gattctgggg tgccacaact ctgatttcag gaacaggggc atgactgccc tgctgaaggt gagcagctgt gacaagaaca ctggggatta ttatgaggac agctatgagg acatttctgc ctacctgctg agcaagaaca atgccattga gcctaggagc ttcagccaga atccccctgt gctgaagaga caccagaggg agatcactag gaccactctg cagtctgatc aggaggagat tgactatgat gacaccattt ctgtggagat gaagaaggag gactttgata tttatgatga ggatgagaac cagagcccca gaagcttcca gaagaagacc aggcactact tcattgctgc tgtggagagg ctgtgggatt atggcatgtc ttctagcccc catgtgctga ggaacagggc tcagtctggc tctgtgcctc agttcaagaa ggtggtgttc caggagttca ctgatgggag cttcacccag cctctgtaca ggggggagct gaatgaacat ctgggcctgc tggggcccta catcagggct gaggtggagg ataatatcat ggtgactttc aggaatcagg cctctaggcc ctacagcttc tactctagcc tgatcagcta tgaggaggac cagaggcagg gggctgagcc taggaagaat tttgtgaaac ccaatgagac caagacctac ttttggaagg tgcagcacca catggcccct accaaggatg agtttgactg taaggcctgg gcctacttct ctgatgtgga cctggagaag gatgtgcatt ctgggctgat tggccccctg -continued ctggtgtgcc acaccaacac cctgaaccct gcccatggca ggcaggtgac tgtgcaggag
tttgccctgt tcttcaccat ctttgatgag actaagagct ggtatttcac tgagaacatg
gagaggaact gtagggctcc ctgcaacatc cagatggagg atccaacttt caaggagaac
tacaggttcc atgccatcaa tggctacatc atggacaccc tgcctggcct ggtgatggcc
caggaccaga ggattaggtg gtacctgctg agcatgggct ctaatgagaa catccactct
atccacttct ctggccatgt gtttactgtg aggaagaagg aggagtacaa gatggctctg
tacaacctgt accctggggt gtttgagact gtggagatgc tgcctagcaa ggctggcatt
tggagagtgg agtgtctgat tggggagcac ctgcatgctg ggatgtctac cctgttcctg
gtgtactcta acaagtgcca gacccccctg ggatggcttc ctgggcacat cagagatttt
cagattactg cttctgggca gtatggccag tgggctccca agctggccag actgcattac
tctggctcta ttaatgcttg gagcaccaag gagcctttca gctggatcaa ggtggacctg
ctggctccca tgatcatcca tggcattaag actcaggggg ctaggcagaa gttcagcagc
ctgtatattt ctcagtttat tatcatgtat tctctggatg gcaagaagtg gcagacttac
aggggcaaca gcactggcac cctgatggtg ttctttggca atgtggacag ctctgggatc
aagcataaca tcttcaaccc ccccattatt gccaggtaca tcaggctgca ccccacccac
tattctatca ggagcactct gaggatggag ctgatggggt gtgacctgaa cagctgctct
atgcccctgg gcatggagag caaggccatc tctgatgccc agatcactgc cagctcttat
ttcaccaaca tgtttgccac ctggagcccc agcaaggcca ggctgcacct gcagggcaga
agcaatgcct ggaggcccca ggtgaacaat cctaaggagt ggctgcaggt ggacttccag
aagactatga aggtgactgg ggtgactacc caggggggtga agagcctgct gaccagcatg
tatgtgaagg agttcctgat tagcagcagc caggatgggc atcagtggac cctgttcttc
cagaatggga aggtgaaggt gttccagggc aatcaggaca gcttcacccc tgtggtgaac
agcctggacc ccccccctgct gaccaggtac ctgaggatcc atccccagag ctgggtgcac
cagattgctc tgagaatgga ggtgctgggc tgtgaggccc aggacctgta ttga FVIII encoding CpG reduced nucleic acid variant X18
(SEQ ID NO: 18)

atgcagattg agctgtctac ctgttttttt ctgtgcctgc tgaggttctg cttctctgct
accaggaggt attatctggg ggctgtggag ctgagctggg actacatgca gtctgacctg
ggggagctgc ctgtggatgc caggtttcct cccagggtgc ctaagagctt ccccttcaac
acctctgtgg tgtacaagaa gactctgttt gtggagttca ctgaccacct gttcaacatt
gccaagccca ggccccccctg gatggggctg ctgggcccca ctatccaggc tgaggtgtat
gatactgtgg tgattaccct gaagaacatg gcctctcacc ctgtgtctct gcatgctgtg
ggggtgagct actggaaggc ttctgagggg gctgaatatg atgatcagac ctctcagagg
gagaaggagg atgacaaggt gtttcctggg ggcagccaca cctatgtgtg gcaggtgctg
aaggagaatg ggcccatggc ctctgatccc ctgtgcctga cctacagcta cctgagccat
gtggacctgg tgaaggacct gaactctggc ctgattgggg ccctgctggt gtgcagggag
ggcagcctgg ccaaggaaaa gacccagacc ctgcataagt tcatcctgct gtttgctgtg
tttgatgagg gcaagtcttg gcactctgag accaagaaca gcctgatgca ggacagggat
gctgcctctg ctagggcctg gcccaagatg cacactgtga atgggtatgt gaacagatct
ctgcctggcc tgattggctg ccacaggaag tctgtgtact ggcatgtgat tggcatgggg
accacccctg aggtgcatag catcttcctg gaggggcaca ccttcctggt gagaaatcat -continued aggcaggcca gcctggagat tagccccatc accttcctga ctgcccagac cctgctgatg gacctgggcc agttcctgct gttctgccac atttctagcc accagcatga tggcatggag gcctatgtga aggtggatag ctgccctgaa gagccccagc tgaggatgaa gaacaatgag gaggctgagg attatgatga tgatctgact gactctgaga tggatgtggt gaggtttgat gatgacaaca gccccagctt catccagatc aggtctgtgg ccaagaagca ccctaagacc tgggtgcact acattgctgc tgaagaggag gactgggact atgcccccct ggtgctggcc ccagatgaca ggtcttacaa gagccagtac ctgaataatg gcccccagag gattgggagg aagtataaga aagtgaggtt catggcttac actgatgaga cctttaagac tagggaggcc attcagcatg agtctgggat tctgggccct ctgctgtatg gggaggtggg ggacaccctg ctgatcattt tcaagaacca ggccagcagg ccctataata tttatcccca tgggattact gatgtcaggc ccctgtacag caggaggctg cctaaggggg tgaagcacct gaaggacttc cccattctgc ctggggagat cttcaagtat aagtggactg tgactgtgga ggatggcccc accaagtctg atcctaggtg cctgaccagg tactatagca gctttgtgaa catggagagg gacctggctt ctggcctgat tggcccccctg ctgatctgct acaaggaatc tgtggaccag aggggcaacc agattatgtc tgacaagagg aatgtgatcc tgttttctgt gtttgatgag aataggagct ggtatctgac tgagaacatc cagaggttcc tgcccaatcc tgctggggtg cagctggagg accctgagtt ccaggcttct aacatcatgc atagcatcaa tgggtatgtg tttgactctc tgcagctgtc tgtgtgcctg catgaggtgg cctattggta catcctgagc attggggccc agactgactt cctgtctgtg ttcttctctg gctacacctt caagcacaag atggtgtatg aggacaccct gaccctgttc cctttctctg ggagactgt gttcatgagc atggagaacc ctggcctgtg gattctgggc tgccataatt ctgacttcag aaacaggggc atgactgctc tgctgaaggt gagcagctgt gacaagaata ctggggacta ctatgaggac tcttatgagg atatttctgc ctacctgctg agcaagaaca atgctattga gcccaggagc ttcagccaga acccccctgt cctgaagagg catcagaggg agatcactag gaccaccctg cagtctgatc aggaggagat tgactatgat gacactatct ctgtggaaat gaagaaggag gactttgata tctatgatga ggatgagaac cagagcccca ggtctttcca gaagaagacc aggcactact tcattgctgc tgtggagagg ctgtgggact atggcatgtc tagcagcccc catgtgctga ggaacagagc ccagtctggc tctgtgcccc agttcaagaa ggtggtgttt caggagttca ctgatgggag cttcactcag cccctgtata ggggggagct gaatgagcat ctgggcctgc tggggcccta catcagggct gaggtggagg ataacatcat ggtgaccttc aggaaccagg ccagcaggcc ctactctttc tactcttctc tgatcagcta tgaggaggat cagaggcagg gggctgagcc taggaagaac tttgtcaagc ctaatgagac taagacctac ttttggaagg tgcagcacca catggctccc actaaggatg agtttgattg caaggcctgg gcctacttct ctgatgtgga cctggagaag gatgtgcact ctggcctgat tggcccccctg ctggtgtgtc acaccaatac cctgaaccct gcccatggca ggcaggtcac tgtgcaggag tttgccctgt ttttcactat ctttgatgag actaagtctt ggtacttcac tgagaacatg gaaaggaatt gcagggctcc ctgcaacatc cagatggagg accccacctt caaggagaac tacaggtttc atgccatcaa tggctacatc atggacaccc tgcctggcct ggtgatggct caggatcaga ggattaggtg gtatctgctg agcatgggca gcaatgagaa catccacagc atccactttt ctggccatgt gttcactgtg aggaagaagg aggagtacaa gatggctctg tacaatctgt accctggggt gtttgagact gtggagatgc tgcccagcaa ggctgggatc -continued tggagggtgg agtgcctgat tggggaacac ctgcatgctg gcatgtctac cctgttcctg
gtgtactcta acaagtgcca gactcccctg ggcatggcct ctgggcacat cagggacttc
cagatcactg cctctgggca gtatggccag tgggccccta agctggctag gctgcattac
tctggcagca tcaatgcctg gagcaccaag gagcccttca gctggatcaa ggtggacctg
ctggccccta tgatcatcca tggcatcaag acccaggggg ccagacagaa gttctcttct
ctgtacatct ctcagttcat catcatgtac tctctggatg gcaagaagtg gcagacctac
agggggaatt ctactggcac tctgatggtg ttctttggga atgtggatag ctctgggatc
aagcataata ttttcaaccc ccccattatt gctaggtaca tcaggctgca cccaacccac
tactctatta ggtctaccct gaggatggag ctgatgggct gtgacctgaa ctcttgtagc
atgcccctgg gcatggagag caaggctatc tctgatgccc agatcactgc cagcagctac
tttaccaaca tgtttgctac ttggagcccc agcaaggcca ggctgcacct gcagggcagg
agcaatgcct ggaggcccca ggtgaacaac cccaaggagt ggctgcaggt ggattttcag
aagaccatga aggtgactgg ggtgaccact caggggggtga aaagcctgct gactagcatg
tatgtgaagg agtttctgat cagcagctct caggatggcc atcagtggac cctgttcttc
cagaatggca aggtgaaggt gttccagggc aaccaggata gcttcacccc tgtggtgaat
agcctggacc cccccctgct gaccaggtac ctgaggatcc atccccagag ctgggtgcac
cagattgccc tgaggatgga ggtgctgggc tgtgaagccc aggacctgta ctga Wild-type factor VIII-BDD cDNA (SEQ ID NO: 19)

ATGCAAATAG AGCTCTCCAC CTGCTTCTTT CTGTGCCTTT TGCGATTCTG CTTTAGTGCC
ACCAGAAGAT ACTACCTGGG TGCAGTGGAA CTGTCATGGG ACTATATGCA AAGTGATCTC
GGTGAGCTGC CTGTGGACGC AAGATTTCCT CCTAGAGTGC CAAAATCTTT TCCATTCAAC
ACCTCAGTCG TGTACAAAAA GACTCTGTTT GTAGAATTCA CGGATCACCT TTTCAACATC
GCTAAGCCAA GGCCACCCTG GATGGGTCTG CTAGGTCCTA CCATCCAGGC TGAGGTTTAT
GATACAGTGG TCATTACACT TAAGAACATG GCTTCCCATC CTGTCAGTCT TCATGCTGTT
GGTGTATCCT ACTGGAAAGC TTCTGAGGGA GCTGAATATG ATGATCAGAC CAGTCAAAGG
GAGAAAGAAG ATGATAAAGT CTTCCCTGGT GGAAGCCATA CATATGTCTG GCAGGTCCTG
AAAGAGAATG GTCCAATGGC CTCTGACCCA CTGTGCCTTA CCTACTCATA TCTTTCTCAT
GTGGACCTGG TAAAAGACTT GAATTCAGGC CTCATTGGAG CCCTACTAGT ATGTAGAGAA
GGGAGTCTGG CCAAGGAAAA GACACAGACC TTGCACAAAT TTATACTACT TTTTGCTGTA
TTTGATGAAG GGAAAAGTTG GCACTCAGAA ACAAAGAACT CCTTGATGCA GGATAGGGAT
GCTGCATCTG CTCGGGCCTG GCCTAAAATG CACACAGTCA ATGGTTATGT AAACAGGTCT
CTGCCAGGTC TGATTGGATG CCACAGGAAA TCAGTCTATT GGCATGTGAT TGGAATGGGC
ACCACTCCTG AAGTGCACTC AATATTCCTC GAAGGTCACA CATTTCTTGT GAGGAACCAT
CGCCAGGCGT CCTTGGAAAT CTCGCCAATA ACTTTCCTTA CTGCTCAAAC ACTCTTGATG
GACCTTGGAC AGTTTCTACT GTTTTGTCAT ATCTCTTCCC ACCAACATGA TGGCATGGAA
GCTTATGTCA AAGTAGACAG CTGTCCAGAG GAACCCCAAC TACGAATGAA AAATAATGAA
GAAGCGGAAG ACTATGATGA TGATCTTACT GATTCTGAAA TGGATGTGGT CAGGTTTGAT
GATGACAACT CTCCTTCCTT TATCCAAATT CGCTCAGTTG CCAAGAAGCA TCCTAAAACT
TGGGTACATT ACATTGCTGC TGAAGAGGAG GACTGGGACT ATGCTCCCTT AGTCCTCGCC
CCCGATGACA GAAGTTATAA AAGTCAATAT TTGAACAATG GCCCTCAGCG GATTGGTAGG

-continued

AAGTACAAAA AAGTCCGATT TATGGCATAC ACAGATGAAA CCTTTAAGAC TCGTGAAGCT

ATTCAGCATG AATCAGGAAT CTTGGGACCT TTACTTTATG GGGAAGTTGG AGACACACTG

TTGATTATAT TTAAGAATCA AGCAAGCAGA CCATATAACA TCTACCCTCA CGGAATCACT

GATGTCCGTC CTTTGTATTC AAGGAGATTA CCAAAAGGTG TAAAACATTT GAAGGATTTT

CCAATTCTGC CAGGAGAAAT ATTCAAATAT AAATGGACAG TGACTGTAGA AGATGGGCCA

ACTAAATCAG ATCCTCGGTG CCTGACCCGC TATTACTCTA GTTTCGTTAA TATGGAGAGA

GATCTAGCTT CAGGACTCAT TGGCCCTCTC CTCATCTGCT ACAAAGAATC TGTAGATCAA

AGAGGAAACC AGATAATGTC AGACAAGAGG AATGTCATCC TGTTTTCTGT ATTTGATGAG

AACCGAAGCT GGTACCTCAC AGAGAATATA CAACGCTTTC TCCCCAATCC AGCTGGAGTG

CAGCTTGAGG ATCCAGAGTT CCAAGCCTCC AACATCATGC ACAGCATCAA TGGCTATGTT

TTTGATAGTT TGCAGTTGTC AGTTTGTTTG CATGAGGTGG CATACTGGTA CATTCTAAGC

ATTGGAGCAC AGACTGACTT CCTTTCTGTC TTCTTCTCTG GATATACCTT CAAACACAAA

ATGGTCTATG AAGACACACT CACCCTATTC CCATTCTCAG GAGAAACTGT CTTCATGTCG

ATGGAAAACC CAGGTCTATG GATTCTGGGG TGCCACAACT CAGACTTTCG GAACAGAGGC

ATGACCGCCT TACTGAAGGT TTCTAGTTGT GACAAGAACA CTGGTGATTA TTACGAGGAC

AGTTATGAAG ATATTTCAGC ATACTTGCTG AGTAAAAACA ATGCCATTGA ACCAAGAAGC

TTCTCCCAAA ACCCACCAGT CTTGAAACGC CATCAACGGG AAATAACTCG TACTACTCTT

CAGTCAGATC AAGAGGAAAT TGACTATGAT GATACCATAT CAGTTGAAAT GAAGAAGGAA

GATTTTGACA TTTATGATGA GGATGAAAAT CAGAGCCCCC GCAGCTTTCA AAAGAAAACA

CGACACTATT TTATTGCTGC AGTGGAGAGG CTCTGGGATT ATGGGATGAG TAGCTCCCCA

CATGTTCTAA GAAACAGGGC TCAGAGTGGC AGTGTCCCTC AGTTCAAGAA AGTTGTTTTC

CAGGAATTTA CTGATGGCTC CTTTACTCAG CCCTTATACC GTGGAGAACT AAATGAACAT

TTGGGACTCC TGGGGCCATA TATAAGAGCA GAAGTTGAAG ATAATATCAT GGTAACTTTC

AGAAATCAGG CCTCTCGTCC CTATTCCTTC TATTCTAGCC TTATTTCTTA TGAGGAAGAT

CAGAGGCAAG GAGCAGAACC TAGAAAAAAC TTTGTCAAGC CTAATGAAAC CAAAACTTAC

TTTTGGAAAG TGCAACATCA TATGGCACCC ACTAAAGATG AGTTTGACTG CAAAGCCTGG

GCTTATTTCT CTGATGTTGA CCTGGAAAAA GATGTGCACT CAGGCCTGAT TGGACCCCTT

CTGGTCTGCC ACACTAACAC ACTGAACCCT GCTCATGGGA GACAAGTGAC AGTACAGGAA

TTTGCTCTGT TTTTCACCAT CTTTGATGAG ACCAAAAGCT GGTACTTCAC TGAAAATATG

GAAAGAAACT GCAGGGCTCC CTGCAATATC CAGATGGAAG ATCCCACTTT TAAAGAGAAT

TATCGCTTCC ATGCAATCAA TGGCTACATA ATGGATACAC TACCTGGCTT AGTAATGGCT

CAGGATCAAA GGATTCGATG GTATCTGCTC AGCATGGGCA GCAATGAAAA CATCCATTCT

ATTCATTTCA GTGGACATGT GTTCACCGTA CGAAAAAAAG AGGAGTATAA AATGGCACTG

TACAATCTCT ATCCAGGTGT TTTTGAGACA GTGGAAATGT TACCATCCAA AGCTGGAATT

TGGCGGGTGG AATGCCTTAT TGGCGAGCAT CTACATGCTG GGATGAGCAC ACTTTTTCTG

GTGTACAGCA ATAAGTGTCA GACTCCCCTG GGAATGGCTT CTGGACACAT TAGAGATTTT

CAGATTACAG CTTCAGGACA ATATGGACAG TGGGCCCCAA AGCTGGCCAG ACTTCATTAT

TCCGGATCAA TCAATGCCTG GAGCACCAAG GAGCCCTTTT CTTGGATCAA GGTGGATCTG

TTGGCACCAA TGATTATTCA CGGCATCAAG ACCCAGGGTG CCCGTCAGAA GTTCTCCAGC

CTCTACATCT CTCAGTTTAT CATCATGTAT AGTCTTGATG GGAAGAAGTG GCAGACTTAT

CGAGGAAATT CCACTGGAAC CTTAATGGTC TTCTTTGGCA ATGTGGATTC ATCTGGGATA

-continued

AAACACAATA TTTTTAACCC TCCAATTATT GCTCGATACA TCCGTTTGCA CCCAACTCAT

TATAGCATTC GCAGCACTCT TCGCATGGAG TTGATGGGCT GTGATTTAAA TAGTTGCAGC

ATGCCATTGG GAATGGAGAG TAAAGCAATA TCAGATGCAC AGATTACTGC TTCATCCTAC

TTTACCAATA TGTTTGCCAC CTGGTCTCCT TCAAAAGCTC GACTTCACCT CCAAGGGAGG

AGTAATGCCT GGAGACCTCA GGTGAATAAT CCAAAAGAGT GGCTGCAAGT GGACTTCCAG

AAGACAATGA AAGTCACAGG AGTAACTACT CAGGGAGTAA AATCTCTGCT TACCAGCATG

TATGTGAAGG AGTTCCTCAT CTCCAGCAGT CAAGATGGCC ATCAGTGGAC TCTCTTTTTT

CAGAATGGCA AAGTAAAGGT TTTTCAGGGA AATCAAGACT CCTTCACACC TGTGGTGAAC

TCTCTAGACC CACCGTTACT GACTCGCTAC CTTCGAATTC ACCCCCAGAG TTGGGTGCAC

CAGATTGCCC TGAGGATGGA GGTTCTGGGC TGCGAGGCAC AGGACCTCTA CTGA

V3 factor VIII cDNA (SEQ ID NO: 20)

ATGCAGATTGAGCTGAGCACCTGCTTCTTCCTGTGCCTGCTGAGGTTCTGCTTCTCTGCCACCAGGAG

ATACTACCTGGGGGCTGTGGAGCTGAGCTGGGACTACATGCAGTCTGACCTGGGGGAGCTGCCTGTGG

ATGCCAGGTTCCCCCCCAGAGTGCCCAAGAGCTTCCCCTTCAACACCTCTGTGGTGTACAAGAAGACC

CTGTTTGTGGAGTTCACTGACCACCTGTTCAACATTGCCAAGCCCAGGCCCCCCTGGATGGGCCTGCT

GGGCCCCACCATCCAGGCTGAGGTGTATGACACTGTGGTGATCACCCTGAAGAACATGGCCAGCCACC

CTGTGAGCCTGCATGCTGTGGGGGTGAGCTACTGGAAGGCCTCTGAGGGGGCTGAGTATGATGACCAG

ACCAGCCAGAGGGAGAAGGAGGATGACAAGGTGTTCCCTGGGGGCAGCCACACCTATGTGTGGCAGGT

GCTGAAGGAGAATGGCCCCATGGCCTCTGACCCCCTGTGCCTGACCTACAGCTACCTGAGCCATGTGG

ACCTGGTGAAGGACCTGAACTCTGGCCTGATTGGGGCCCTGCTGGTGTGCAGGGAGGGCAGCCTGGCC

AAGGAGAAGACCCAGACCCTGCACAAGTTCATCCTGCTGTTTGCTGTGTTTGATGAGGGCAAGAGCTG

GCACTCTGAAACCAAGAACAGCCTGATGCAGGACAGGGATGCTGCCTCTGCCAGGGCCTGGCCCAAGA

TGCACACTGTGAATGGCTATGTGAACAGGAGCCTGCCTGGCCTGATTGGCTGCCACAGGAAGTCTGTG

TACTGGCATGTGATTGGCATGGGCACCACCCCTGAGGTGCACAGCATCTTCCTGGAGGGCCACACCTT

CCTGGTCAGGAACCACAGGCAGGCCAGCCTGGAGATCAGCCCCATCACCTTCCTGACTGCCCAGACCC

TGCTGATGGACCTGGGCCAGTTCCTGCTGTTCTGCCACATCAGCAGCCACCAGCATGATGGCATGGAG

GCCTATGTGAAGGTGGACAGCTGCCCTGAGGAGCCCCAGCTGAGGATGAAGAACAATGAGGAGGCTGA

GGACTATGATGATGACCTGACTGACTCTGAGATGGATGTGGTGAGGTTTGATGATGACAACAGCCCCA

GCTTCATCCAGATCAGGTCTGTGGCCAAGAAGCACCCCAAGACCTGGGTGCACTACATTGCTGCTGAG

GAGGAGGACTGGGACTATGCCCCCCTGGTGCTGGCCCCTGATGACAGGAGCTACAAGAGCCAGTACCT

GAACAATGGCCCCCAGAGGATTGGCAGGAAGTACAAGAAGGTCAGGTTCATGGCCTACACTGATGAAA

CCTTCAAGACCAGGGAGGCCATCCAGCATGAGTCTGGCATCCTGGGCCCCCTGCTGTATGGGGAGGTG

GGGGACACCCTGCTGATCATCTTCAAGAACCAGGCCAGCAGGCCCTACAACATCTACCCCCATGGCAT

CACTGATGTGAGGCCCCTGTACAGCAGGAGGCTGCCCAAGGGGGTGAAGCACCTGAAGGACTTCCCCA

TCCTGCCTGGGGAGATCTTCAAGTACAAGTGGACTGTGACTGTGGAGGATGGCCCCACCAAGTCTGAC

CCCAGGTGCCTGACCAGATACTACAGCAGCTTTGTGAACATGGAGAGGGACCTGGCCTCTGGCCTGAT

TGGCCCCCTGCTGATCTGCTACAAGGAGTCTGTGGACCAGAGGGGCAACCAGATCATGTCTGACAAGA

GGAATGTGATCCTGTTCTCTGTGTTTGATGAGAACAGGAGCTGGTACCTGACTGAGAACATCCAGAGG

TTCCTGCCCAACCCTGCTGGGGTGCAGCTGGAGGACCCTGAGTTCCAGGCCAGCAACATCATGCACAG

CATCAATGGCTATGTGTTTGACAGCCTGCAGCTGTCTGTGTGCCTGCATGAGGTGGCCTACTGGTACA

-continued

TCCTGAGCATTGGGGCCCAGACTGACTTCCTGTCTGTGTTCTTCTCTGGCTACACCTTCAAGCACAAG

ATGGTGTATGAGGACACCCTGACCCTGTTCCCCTTCTCTGGGGAGACTGTGTTCATGAGCATGGAGAA

CCCTGGCCTGTGGATTCTGGGCTGCCACAACTCTGACTTCAGGAACAGGGGCATGACTGCCCTGCTGA

AAGTCTCCAGCTGTGACAAGAACACTGGGGACTACTATGAGGACAGCTATGAGGACATCTCTGCCTAC

CTGCTGAGCAAGAACAATGCCATTGAGCCCAGGAGCTTCAGCCAGAACAGCAGGCACCCCAGCACCAG

GCAGAAGCAGTTCAATGCCACCACCATCCCTGAGAATGACATAGAGAAGACAGACCCATGGTTTGCCC

ACCGGACCCCCATGCCCAAGATCCAGAATGTGAGCAGCTCTGACCTGCTGATGCTGCTGAGGCAGAGC

CCCACCCCCCATGGCCTGAGCCTGTCTGACCTGCAGGAGGCCAAGTATGAAACCTTCTCTGATGACCC

CAGCCCTGGGGCCATTGACAGCAACAACAGCCTGTCTGAGATGACCCACTTCAGGCCCCAGCTGCACC

ACTCTGGGGACATGGTGTTCACCCCTGAGTCTGGCCTGCAGCTGAGGCTGAATGAGAAGCTGGGCACC

ACTGCTGCCACTGAGCTGAAGAAGCTGGACTTCAAAGTCTCCAGCACCAGCAACAACCTGATCAGCAC

CATCCCCTCTGACAACCTGGCTGCTGGCACTGACAACACCAGCAGCCTGGGCCCCCCCAGCATGCCTG

TGCACTATGACAGCCAGCTGGACACCACCCTGTTTGGCAAGAAGAGCAGCCCCCTGACTGAGTCTGGG

GGCCCCCTGAGCCTGTCTGAGGAGAACAATGACAGCAAGCTGCTGGAGTCTGGCCTGATGAACAGCCA

GGAGAGCAGCTGGGGCAAGAATGTGAGCACCAGGAGCTTCCAGAAGAAGACCAGGCACTACTTCATTG

CTGCTGTGGAGAGGCTGTGGGACTATGGCATGAGCAGCAGCCCCCATGTGCTGAGGAACAGGGCCCAG

TCTGGCTCTGTGCCCCAGTTCAAGAAGGTGGTGTTCCAGGAGTTCACTGATGGCAGCTTCACCCAGCC

CCTGTACAGAGGGGAGCTGAATGAGCACCTGGGCCTGCTGGGCCCCTACATCAGGGCTGAGGTGGAGG

ACAACATCATGGTGACCTTCAGGAACCAGGCCAGCAGGCCCTACAGCTTCTACAGCAGCCTGATCAGC

TATGAGGAGGACCAGAGGCAGGGGGCTGAGCCCAGGAAGAACTTTGTGAAGCCCAATGAAACCAAGAC

CTACTTCTGGAAGGTGCAGCACCACATGGCCCCCACCAAGGATGAGTTTGACTGCAAGGCCTGGGCCT

ACTTCTCTGATGTGGACCTGGAGAAGGATGTGCACTCTGGCCTGATTGGCCCCCTGCTGGTGTGCCAC

ACCAACACCCTGAACCCTGCCCATGGCAGGCAGGTGACTGTGCAGGAGTTTGCCCTGTTCTTCACCAT

CTTTGATGAAACCAAGAGCTGGTACTTCACTGAGAACATGGAGAGGAACTGCAGGGCCCCCTGCAACA

TCCAGATGGAGGACCCCACCTTCAAGGAGAACTACAGGTTCCATGCCATCAATGGCTACATCATGGAC

ACCCTGCCTGGCCTGGTGATGGCCCAGGACCAGAGGATCAGGTGGTACCTGCTGAGCATGGGCAGCAA

TGAGAACATCCACAGCATCCACTTCTCTGGCCATGTGTTCACTGTGAGGAAGAAGGAGGAGTACAAGA

TGGCCCTGTACAACCTGTACCCTGGGGTGTTTGAGACTGTGGAGATGCTGCCCAGCAAGGCTGGCATC

TGGAGGGTGGAGTGCCTGATTGGGGAGCACCTGCATGCTGGCATGAGCACCCTGTTCCTGGTGTACAG

CAACAAGTGCCAGACCCCCCTGGGCATGGCCTCTGGCCACATCAGGGACTTCCAGATCACTGCCTCTG

GCCAGTATGGCCAGTGGGCCCCCAAGCTGGCCAGGCTGCACTACTCTGGCAGCATCAATGCCTGGAGC

ACCAAGGAGCCCTTCAGCTGGATCAAGGTGGACCTGCTGGCCCCCATGATCATCCATGGCATCAAGAC

CCAGGGGGCCAGGCAGAAGTTCAGCAGCCTGTACATCAGCCAGTTCATCATCATGTACAGCCTGGATG

GCAAGAAGTGGCAGACCTACAGGGGCAACAGCACTGGCACCCTGATGGTGTTCTTTGGCAATGTGGAC

AGCTCTGGCATCAAGCACAACATCTTCAACCCCCCCATCATTGCCAGATACATCAGGCTGCACCCCAC

CCACTACAGCATCAGGAGCACCCTGAGGATGGAGCTGATGGGCTGTGACCTGAACAGCTGCAGCATGC

CCCTGGGCATGGAGAGCAAGGCCATCTCTGATGCCCAGATCACTGCCAGCAGCTACTTCACCAACATG

TTTGCCACCTGGAGCCCCAGCAAGGCCAGGCTGCACCTGCAGGGCAGGAGCAATGCCTGGAGGCCCCA

GGTCAACAACCCCAAGGAGTGGCTGCAGGTGGACTTCCAGAAGACCATGAAGGTGACTGGGGTGACCA

CCCAGGGGGTGAAGAGCCTGCTGACCAGCATGTATGTGAAGGAGTTCCTGATCAGCAGCAGCCAGGAT

GGCCACCAGTGGACCCTGTTCTTCCAGAATGGCAAGGTGAAGGTGTTCCAGGGCAACCAGGACAGCTT

-continued

CACCCCTGTGGTGAACAGCCTGGACCCCCCCCTGCTGACCAGATACCTGAGGATTCACCCCCAGAGCT

GGGTGCACCAGATTGCCCTGAGGATGGAGGTGCTGGGCTGTGAGGCCCAGGACCTGTACTGA

CO3 factor VIII cDNA (SEQ ID NO: 21)

atgcagattg agctgtcaac ttgctttttc ctgtgcctgc tgagattttg tttttccgct actagaagat actacctggg ggctgtggaa ctgtcttggg attacatgca gagtgacctg ggagagctgc cagtggacgc acgatttcca cctagagtcc ctaaatcatt ccccttcaac accagcgtgg tctataagaa aacactgttc gtggagttta ctgatcacct gttcaacatc gctaagcctc ggccaccctg gatgggactg ctgggaccaa caatccaggc agaggtgtac gacaccgtgg tcattacact gaaaaacatg gcctcacacc ccgtgagcct gcatgctgtg ggcgtcagct actggaaggc ttccgaaggg gcagagtatg acgatcagac ttcccagaga gaaaaagagg acgataaggt gtttcctggc gggtctcata cctatgtgtg gcaggtcctg aaagagaatg gccccatggc ttccgaccct ctgtgcctga cctactctta tctgagtcac gtggacctgg tcaaggatct gaacagcgga ctgatcggag cactgctggt gtgtagggaa gggagcctgg ctaaggagaa aacccagaca ctgcataagt tcattctgct gttcgccgtg tttgacgaag gaaaatcatg gcacagcgag acaaagaata gtctgatgca ggaccgggat gccgcttcag ccagagcttg gcccaaaatg cacactgtga acggctacgt caatcgctca ctgcctggac tgatcggctg ccaccgaaag agcgtgtatt ggcatgtcat cggaatgggc accacacctg aagtgcactc cattttcctg gaggggcata cctttctggt ccgcaaccac cgacaggcct ccctggagat ctctccaatt accttcctga cagctcagac tctgctgatg gatctgggac agttcctgct gttttgccac atcagctccc accagcatga tggcatggag gcctacgtga aagtggacag ctgtcccgag gaacctcagc tgaggatgaa gaacaatgag gaagctgaag actatgacga tgacctgacc gactccgaga tggatgtggt ccgattcgat gacgataaca gcccctcctt tatccagatt agatctgtgg ccaagaaaca ccctaagaca tgggtccatt acatcgcagc cgaggaagag gactgggatt atgcaccact ggtgctggca ccagacgatc gatcctacaa atctcagtat ctgaacaatg gaccacagcg gattggcaga aagtacaaga aagtgaggtt catggcttat accgatgaaa ccttcaagac tcgcgaagca atccagcacg agagcgggat tctgggacca ctgctgtacg gagaagtggg ggacaccctg ctgatcattt ttaagaacca ggccagcagg ccttacaata tctatccaca tggaattaca gatgtgcgcc ctctgtacag ccggagactg ccaaagggcg tcaaacacct gaaggacttc ccaatcctgc ccggggaaat ttttaagtat aaatggactg tcaccgtcga ggatggcccc actaagagcg accctaggtg cctgacccgc tactattcta gtttcgtgaa tatggaaagg gatctggcca gcggactgat cggcccactg ctgatttgtt acaaagagag cgtggatcag agaggcaacc agatcatgtc cgacaagagg aatgtgattc tgttcagtgt ctttgacgaa aaccggtcat ggtatctgac cgagaacatc cagagattcc tgcctaatcc agccggagtg cagctggaag atcctgagtt tcaggcttct aacatcatgc atagtattaa tggctacgtg ttcgacagtc tgcagctgtc agtgtgtctg cacgaggtcg cttactggta tatcctgagc attggagcac agacagattt cctgagcgtg ttcttttccg gctacacttt taagcataaa atggtgtatg aggacacact gactctgttc cccttcagcg gcgaaaccgt gtttatgtcc atggagaatc ccgggctgtg gatcctggga tgccacaaca gcgatttcag gaatcgcggg atgactgccc tgctgaaagt gtcaagctgt gacaagaaca ccggagacta ctatgaagat -continued

```
tcatacgagg acatcagcgc atatctgctg tccaaaaaca atgccattga acccaggtct
tttagtcaga atcctccagt gctgaagagg caccagcgcg agatcacccg cactaccctg
cagagtgatc aggaagagat cgactacgac gatacaattt ctgtggaaat gaagaaagag
gacttcgata tctatgacga agatgagaac cagagtcctc gatcattcca gaagaaaacc
cggcattact ttattgctgc agtggagcgc ctgtgggatt atggcatgtc ctctagtcct
cacgtgctgc gaaatcgggc ccagtcaggg agcgtcccac agttcaagaa agtggtcttc
caggagttta cagacggatc ctttactcag ccactgtacc ggggcgaact gaacgagcac
ctggggctgc tgggacccta tatcagagct gaagtggagg ataacattat ggtcaccttc
agaaatcagg catctaggcc ttacagtttt tattcaagcc tgatctctta cgaagaggac
cagaggcagg gagcagaacc acgaaaaaac ttcgtgaagc ctaatgagac caaaacatac
ttttggaagg tgcagcacca tatggcccca acaaaagacg aattcgattg caaggcatgg
gcctattttt ctgacgtgga tctggagaag gacgtccaca gtggcctgat cgggccactg
ctggtgtgtc atactaacac cctgaatccc gcacacggca ggcaggtcac tgtccaggaa
ttcgccctgt tctttaccat ctttgatgag acaaaaagct ggtacttcac cgaaaacatg
gagcgaaatt gccgggctcc atgtaatatt cagatggaag accccacatt caaggagaac
taccgctttc atgccatcaa tgggtatatt atggatactc tgcccggact ggtcatggct
caggaccaga gaatcaggtg gtacctgctg agcatggggt ccaacgagaa tatccactca
attcatttca gcggacacgt gtttactgtc cggaagaaag aagagtataa aatggccctg
tacaacctgt atcccggcgt gttcgaaacc gtcgagatgc tgcctagcaa ggcagggatc
tggagagtgg aatgcctgat tggggagcac ctgcatgccg gaatgtctac cctgtttctg
gtgtacagta ataagtgtca gacacccctg ggatggctt ccggacatat ccgggatttc
cagattaccg catctggaca gtacggccag tgggccccta agctggctag actgcactat
tccgggtcta tcaacgcttg gtccacaaaa gagcctttct cttggattaa ggtggacctg
ctggcaccaa tgatcattca tggcatcaaa actcaggggg ccaggcagaa gttctcctct
ctgtacatct cacagtttat catcatgtac agcctggatg gcaagaaatg gcagacatac
cgcggcaata gcacagggac tctgatggtg ttctttggca acgtggacag ttcagggatc
aagcacaaca ttttcaatcc ccctatcatt gctagataca tcaggctgca cccaacccat
tattctattc gaagtacact gcggatggaa ctgatggggt gcgatctgaa cagttgttca
atgcccctgg gaatggagtc caaggcaatc tctgacgccc agattaccgc tagctcctac
ttcactaata tgtttgctac ctggagcccc tccaaagcac gactgcatct gcagggacga
agcaacgcat ggcgaccaca ggtgaacaat cccaaggagt ggctgcaggt cgattttcag
aaaactatga aggtgaccgg agtcacaact cagggcgtga aaagtctgct gacctcaatg
tacgtcaagg agttcctgat ctctagttca caggacggcc accagtggac actgttcttt
cagaacggaa aggtgaaagt cttccagggc aatcaggatt cctttacacc tgtggtcaac
tctctggacc caccctgct gactcgctac ctgcgaatcc acccacagtc ctgggtgcat
cagattgcac tgagaatgga agtcctgggc tgcgaggccc aggacctgta ttga
```

Full length cassette including mutated TTR promoter (TTRmut), synthetic intron, CpG reduced factor VIII cDNA, poly A and ITRs (SEQ ID NO: 23)

```
cctgcaggca gctgcgcgct cgctcgctca ctgaggccgc ccgggcaaag cccgggcgtc
gggcgacctt tggtcgcccg gcctcagtga gcgagcgagc gcgcagagag ggagtggcca
actccatcac taggggttcc tacgcgtgtc tgtctgcaca tttcgtagag cgagtgttcc
```

-continued gatactctaa tctccctagg caaggttcat attgacttag gttacttatt ctccttttgt
tgactaagtc aataatcaga atcagcaggt ttggagtcag cttggcaggg atcagcagcc
tgggttggaa ggagggggta taaaagcccc ttcaccagga gaagccgtca cacagatcca
caagctcctg ctagcaggta agtgccgtgt gtggttcccg cgggcctggc ctctttacgg
gttatggccc ttgcgtgcct tgaattactg acactgacat ccactttttc tttttctcca
caggtttaaa cgccaccatg cagattgagc tgagcacctg cttcttcctg tgtctgctga
ggttctgctt ctctgccacc aggaggtatt acctgggggc tgtggagctg agctgggact
atatgcagtc tgacctgggg gagctgcctg tggatgctag gttccccccc agggtgccca
agagcttccc ctttaacact tctgtggtgt acaagaagac cctgtttgtg gagttcactg
accacctgtt caacattgcc aagcccaggc ccccctggat ggggctgctg ggccccacca
tccaggctga ggtgtatgac actgtggtga tcaccctgaa gaacatggcc agccaccctg
tgagcctgca tgctgtgggg gtgagctact ggaaggcttc tgaggggggct gagtatgatg
accagactag ccagagggag aaggaggatg acaaggtgtt tcctgggggc agccatacct
atgtgtggca ggtgctgaag gagaatggcc ccatggcctc tgaccccctg tgcctgacct
acagctacct gtctcatgtg gacctggtga aggacctgaa ctctggcctg attggggctc
tgctggtgtg tagggagggc agcctggcta aggaaaagac ccagaccctg cataagttta
tcctgctgtt tgctgtgttt gatgagggca agagctggca ctctgagacc aagaacagcc
tgatgcagga tagggatgct gcctctgcca gggcttggcc taagatgcac actgtgaatg
ggtatgtgaa taggagcctg cctggcctga ttggctgcca caggaagtct gtgtactggc
atgtgattgg gatgggcacc acccctgagg tccatagcat cttcctggag ggccacactt
tcctggtgag gaaccacaga caggcctctc tggagatctc tcccatcacc ttcctgactg
ctcagactct gctgatggac ctgggccagt tcctgctgtt ttgccatatt agcagccacc
agcatgatgg gatggaggcc tatgtgaagg tggatagctg ccctgaggag cctcagctga
ggatgaagaa caatgaggag gctgaagact atgatgatga cctgactgat tctgagatgg
atgtggtgag gtttgatgat gacaatagcc ccagcttcat tcagatcagg tctgtggcca
agaaacaccc caagacctgg gtgcactaca ttgctgctga ggaagaggac tgggactatg
ctcccctggt gctggcccct gatgataggt cttataagag ccagtacctg aacaatgggc
cccagaggat tggcaggaag tacaagaagg tgaggttcat ggcctacact gatgaaacct
tcaaaaccag ggaggccatt cagcatgagt ctggcatcct gggccctctg ctgtatgggg
aggtgggggga caccctgctg atcatcttca agaaccaggc cagcaggccc tacaacatct
atcctcatgg catcactgat gtgaggcccc tgtacagcag gaggctgccc aagggggtga
agcacctgaa agacttcccc atcctgcctg ggagatcttt taagtataag tggactgtga
ctgtggagga tggccctacc aagtctgacc ccaggtgtct gaccaggtac tattctagct
ttgtgaacat ggagagggac ctggcctctg gcctgattgg gcccctgctg atctgctaca
aggagtctgt ggaccagagg ggcaaccaga tcatgtctga caagaggaat gtgatcctgt
tttctgtgtt tgatgagaat aggagctggt acctgactga gaacatccag aggtttctgc
ccaatcctgc tggggtgcag ctggaggatc ctgagttcca ggccagcaat atcatgcata
gcatcaatgg ctatgtgttt gacagcctgc agctgtctgt gtgcctgcat gaggtggcct
actggtacat cctgagcatt ggggcccaga ctgactttct gtctgtgttc ttttctggct
ataccttcaa gcacaagatg gtgtatgagg ataccctgac cctgttcccc ttctctgggg -continued agactgtgtt catgagcatg gagaatcctg ggctgtggat cctggggtgc cacaactctg
attttaggaa cagggggatg actgccctgc tgaaggtgtc tagctgtgat aagaacactg
gggactacta tgaggacagc tatgaggaca tttctgctta tctgctgtct aagaataatg
ccattgagcc cagaagcttc agccagaatc cccctgtgct gaagagacat cagagggaga
tcaccagaac taccctgcag tctgatcagg aggagattga ctatgatgac actatctctg
tggagatgaa gaaggaggac tttgacatct atgatgagga tgagaatcag tctcccagga
gctttcagaa gaagaccaga cattacttca ttgctgctgt ggagaggctg tgggactatg
gcatgagctc tagccctcat gtgctgagga acagggccca gtctggctct gtgccccagt
tcaagaaggt ggtgttccag gaattcactg atggcagctt cacccagccc ctgtacaggg
gggagctgaa tgagcacctg ggcctgctgg ggccttatat cagggctgag gtggaggata
atattatggt gactttcagg aaccaggcca gcaggcccta ctctttctat agcagcctga
tctcttatga ggaggatcag aggcaggggg ctgagcctag gaagaacttt gtgaagccca
atgagactaa gacctacttc tggaaggtcc agcaccacat ggcccctacc aaggatgagt
ttgactgcaa ggcctgggcc tatttctctg atgtggatct ggagaaggat gtccattctg
ggctgattgg cccccctgctg gtgtgccaca ctaacactct gaatcctgcc catggcaggc
aggtgactgt ccaggagttt gccctgttct tcactatctt tgatgagacc aagagctggt
actttactga gaacatggag aggaactgca gagctccttg caatattcag atggaggacc
ccaccttcaa ggagaattac aggttccatg ccattaatgg gtacatcatg gacaccctgc
ctggcctggt gatggctcag gaccagagga tcaggtggta cctgctgagc atgggctcta
atgagaatat ccacagcatc cacttctctg ggcatgtgtt cactgtgagg aagaaggagg
agtacaagat ggctctgtat aatctgtacc ctggggtgtt tgaaactgtg gagatgctgc
cctctaaggc tggcatctgg agggtggagt gcctgattgg ggagcacctg catgctggca
tgagcaccct gttcctggtg tacagcaaca agtgccagac ccccctgggc atggcctctg
gccacatcag ggacttccag atcactgcct ctggccagta tggccagtgg gcccccaagc
tggccaggct gcactattct ggcagcatca atgcctggag caccaaggag cccttcagct
ggatcaaggt ggacctgctg gcccccatga tcattcatgg catcaagacc caggggggcca
ggcagaagtt cagctctctg tacatctctc agttcatcat catgtactct ctggatggga
agaagtggca gacctacagg ggcaacagca ctggcaccct gatggtgttc tttgggaatg
tggactcttc tggcatcaag cacaacatct tcaatccccc catcattgct aggtatatta
ggctgcatcc cacccactac agcatcaggt ctaccctgag gatggagctg atgggctgtg
acctgaactc ttgcagcatg cccctgggca tggagtctaa ggccatctct gatgcccaga
ttactgccag cagctacttc accaacatgt ttgccacctg gagcccctct aaggccaggc
tgcatctgca ggggaggagc aatgcctgga ggcctcaggt gaacaacccc aaggagtggc
tgcaggtgga tttccagaag accatgaagg tgactggggt gaccacccag gggggtcaaga
gcctgctgac cagcatgtat gtgaaggagt tcctgatcag cagcagccag gatggccacc
agtggactct gttctttcag aatgggaagg tgaaggtgtt tcagggcaat caggactctt
tcacccctgt ggtgaacagc ctggaccccc ccctgctgac cagatacctg aggatccacc
cccagtcttg ggtgcatcag attgccctga ggatggaggt gctgggctgt gaggctcagg
atctgtactg agcggccgca ataaaagatc agagctctag agatctgtgt gttggttttt
tgtgtaggaa cccctagtga tggagttggc cactccctct ctgcgcgctc gctcgctcac
tgaggccggg cgaccaaagg tcgcccgacg cccgggcttt gcccgggcgg cctcagtgag -continued cgagcgagcg cgcagctgcc tgcagg Full length plasmid including mutated TTR promoter (TTRmut), synthetic intron, CpG reduced factor VIII cDNA, poly A and ITRs (SEQ ID NO: 24)

cctgcaggca gctgcgcgct cgctcgctca ctgaggccgc ccgggcaaag cccgggcgtc gggcgacctt tggtcgcccg gcctcagtga gcgagcgagc gcgcagagag ggagtggcca actccatcac taggggttcc tacgcgtgtc tgtctgcaca tttcgtagag cgagtgttcc gatactctaa tctccctagg caaggttcat attgacttag gttacttatt ctccttttgt tgactaagtc aataatcaga atcagcaggt ttggagtcag cttggcaggg atcagcagcc tgggttggaa ggagggggta taaaagcccc ttcaccagga gaagccgtca cacagatcca caagctcctg ctagcaggta agtgccgtgt gtggttcccg cgggcctggc ctctttacgg gttatggccc ttgcgtgcct tgaattactg acactgacat ccactttttc tttttctcca caggtttaaa cgccaccatg cagattgagc tgagcacctg cttcttcctg tgtctgctga ggttctgctt ctctgccacc aggaggtatt acctgggggc tgtggagctg agctgggact atatgcagtc tgacctgggg gagctgcctg tggatgctag gttccccccc agggtgccca agagcttccc ctttaacact tctgtggtgt acaagaagac cctgtttgtg gagttcactg accacctgtt caacattgcc aagcccaggc ccccctggat ggggctgctg ggccccacca tccaggctga ggtgtatgac actgtggtga tcaccctgaa gaacatggcc agccaccctg tgagcctgca tgctgtgggg gtgagctact ggaaggcttc tgagggggct gagtatgatg accagactag ccagagggag aaggaggatg acaaggtgtt tcctgggggc agccatacct atgtgtggca ggtgctgaag gagaatggcc ccatggcctc tgacccccctg tgcctgacct acagctacct gtctcatgtg gacctggtga aggacctgaa ctctggcctg attggggctc tgctggtgtg tagggagggc agcctggcta aggaaaagac ccagaccctg cataagttta tcctgctgtt tgctgtgttt gatgagggca agagctggca ctctgagacc aagaacagcc tgatgcagga tagggatgct gcctctgcca gggcttggcc taagatgcac actgtgaatg ggtatgtgaa taggagcctg cctggcctga ttggctgcca caggaagtct gtgtactggc atgtgattgg gatgggcacc acccctgagg tccatagcat cttcctggag ggccacactt tcctggtgag gaaccacaga caggcctctc tggagatctc tcccatcacc ttcctgactg ctcagactct gctgatggac ctgggccagt tcctgctgtt ttgccatatt agcagccacc agcatgatgg gatggaggcc tatgtgaagg tggatagctg ccctgaggag cctcagctga ggatgaagaa caatgaggag gctgaagact atgatgatga cctgactgat tctgagatgg atgtggtgag gtttgatgat gacaatagcc ccagcttcat tcagatcagg tctgtggcca agaaacaccc caagacctgg gtgcactaca ttgctgctga ggaagaggac tgggactatg ctcccctggt gctggcccct gatgataggt cttataagag ccagtacctg aacaatgggc cccagaggat tggcaggaag tacaagaagg tgaggttcat ggcctacact gatgaaacct tcaaaaccag ggaggccatt cagcatgagt ctggcatcct gggccctctg ctgtatgggg aggtggggga caccctgctg atcatcttca agaaccaggc cagcaggccc tacaacatct atcctcatgg catcactgat gtgaggcccc tgtacagcag gaggctgccc aagggggtga agcacctgaa agacttcccc atcctgcctg ggagatcttt taagtataag tggactgtga ctgtggagga tggccctacc aagtctgacc ccaggtgtct gaccaggtac tattctagct ttgtgaacat ggagagggac ctggcctctg gcctgattgg gcccctgctg atctgctaca -continued aggagtctgt ggaccagagg ggcaaccaga tcatgtctga caagaggaat gtgatcctgt tttctgtgtt tgatgagaat aggagctggt acctgactga gaacatccag aggtttctgc ccaatcctgc tggggtgcag ctggaggatc ctgagttcca ggccagcaat atcatgcata gcatcaatgg ctatgtgttt gacagcctgc agctgtctgt gtgcctgcat gaggtggcct actggtacat cctgagcatt ggggcccaga ctgactttct gtctgtgttc ttttctggct ataccttcaa gcacaagatg gtgtatgagg ataccctgac cctgttcccc ttctctgggg agactgtgtt catgagcatg gagaatcctg ggctgtggat cctggggtgc cacaactctg attttaggaa caggggggatg actgccctgc tgaaggtgtc tagctgtgat aagaacactg gggactacta tgaggacagc tatgaggaca tttctgctta tctgctgtct aagaataatg ccattgagcc cagaagcttc agccagaatc cccctgtgct gaagagacat cagagggaga tcaccagaac taccctgcag tctgatcagg aggagattga ctatgatgac actatctctg tggagatgaa gaaggaggac tttgacatct atgatgagga tgagaatcag tctcccagga gctttcagaa gaagaccaga cattacttca ttgctgctgt ggagaggctg tgggactatg gcatgagctc tagccctcat gtgctgagga acagggccca gtctggctct gtgccccagt tcaagaaggt ggtgttccag gaattcactg atggcagctt cacccagccc ctgtacaggg gggagctgaa tgagcacctg ggcctgctgg ggccttatat cagggctgag gtggaggata atattatggt gactttcagg aaccaggcca gcaggcccta ctctttctat agcagcctga tctcttatga ggaggatcag aggcaggggg ctgagcctag gaagaacttt gtgaagccca atgagactaa gacctacttc tggaaggtcc agcaccacat ggcccctacc aaggatgagt ttgactgcaa ggcctgggcc tatttctctg atgtggatct ggagaaggat gtccattctg ggctgattgg cccccctgctg gtgtgccaca ctaacactct gaatcctgcc catggcaggc aggtgactgt ccaggagttt gccctgttct tcactatctt tgatgagacc aagagctggt actttactga gaacatggag aggaactgca gagctccttg caatattcag atggaggacc ccaccttcaa ggagaattac aggttccatg ccattaatgg gtacatcatg gacaccctgc ctggcctggt gatggctcag gaccagagga tcaggtggta cctgctgagc atgggctcta atgagaatat ccacagcatc cacttctctg ggcatgtgtt cactgtgagg aagaaggagg agtacaagat ggctctgtat aatctgtacc ctggggtgtt tgaaactgtg gagatgctgc cctctaaggc tggcatctgg agggtggagt gcctgattgg ggagcacctg catgctggca tgagcaccct gttcctggtg tacagcaaca agtgccagac cccccctgggc atggcctctg gccacatcag ggacttccag atcactgcct ctggccagta tggccagtgg gcccccaagc tggccaggct gcactattct ggcagcatca atgcctggag caccaaggag cccttcagct ggatcaaggt ggacctgctg gcccccatga tcattcatgg catcaagacc caggggggcca ggcagaagtt cagctctctg tacatctctc agttcatcat catgtactct ctggatggga agaagtggca gacctacagg ggcaacagca ctggcaccct gatggtgttc tttgggaatg tggactcttc tggcatcaag cacaacatct tcaatccccc catcattgct aggtatatta ggctgcatcc cacccactac agcatcaggt ctaccctgag gatggagctg atgggctgtg acctgaactc ttgcagcatg cccctgggca tggagtctaa ggccatctct gatgcccaga ttactgccag cagctacttc accaacatgt ttgccacctg gagcccctct aaggccaggc tgcatctgca ggggaggagc aatgcctgga ggcctcaggt gaacaacccc aaggagtggc tgcaggtgga tttccagaag accatgaagg tgactggggt gaccacccag ggggtcaaga gcctgctgac cagcatgtat gtgaaggagt tcctgatcag cagcagccag gatggccacc agtggactct gttctttcag aatgggaagg tgaaggtgtt tcagggcaat caggactctt
tcacccctgt ggtgaacagc ctggaccccc ccctgctgac cagatacctg aggatccacc
cccagtcttg ggtgcatcag attgccctga ggatggaggt gctgggctgt gaggctcagg
atctgtactg agcggccgca ataaaagatc agagctctag agatctgtgt gttggttttt
tgtgtaggaa cccctagtga tggagttggc cactccctct ctgcgcgctc gctcgctcac
tgaggccggg cgaccaaagg tcgcccgacg cccgggcttt gcccgggcgg cctcagtgag
cgagcgagcg cgcagctgcc tgcaggggca gcttgaagga aatactaagg caaaggtact
gcaagtgctc gcaacattcg cttatgcgga ttattgccgt agtgccgcga cgccgggggc
aagatgcaga gattgccatg gtacaggccg tgcggttgat attgccaaaa cagagctgtg
ggggagagtt gtcgagaaag agtgcggaag atgcaaaggc gtcggctatt caaggatgcc
agcaagcgca gcatatcgcg ctgtgacgat gctaatccca aaccttaccc aacccacctg
gtcacgcact gttaagccgc tgtatgacgc tctggtggtg caatgccaca aagaagagtc
aatcgcagac aacattttga atgcggtcac acgttagcag catgattgcc acggatggca
acatattaac ggcatgatat tgacttattg aataaaattg ggtaaatttg actcaacgat
gggttaattc gctcgttgtg gtagtgagat gaaaagaggc ggcgcttact accgattccg
cctagttggt cacttcgacg tatcgtctgg aactccaacc atcgcaggca gagaggtctg
caaaatgcaa tcccgaaaca gttcgcaggt aatagttaga gcctgcataa cggtttcggg
atttttata tctgcacaac aggtaagagc attgagtcga taatcgtgaa gagtcggcga
gcctggttag ccagtgctct ttccgttgtg ctgaattaag cgaataccgg aagcagaacc
ggatcaccaa atgcgtacag gcgtcatcgc cgcccagcaa cagcacaacc caaactgagc
cgtagccact gtctgtcctg aattcattag taatagttac gctgcggcct tttacacatg
accttcgtga aagcgggtgg caggaggtcg cgctaacaac ctcctgccgt tttgcccgtg
catatcggtc acgaacaaat ctgattacta aacacagtag cctggatttg ttctatcagt
aatcgacctt attcctaatt aaatagagca aatcccctta ttgggggtaa gacatgaaga
tgccagaaaa acatgacctg ttggccgcca ttctcgcggc aaaggaacaa ggcatcgggg
caatccttgc gtttgcaatg gcgtaccttc gcggcagata taatggcggt gcgtttacaa
aaacagtaat cgacgcaacg atgtgcgcca ttatcgccta gttcattcgt gaccttctcg
acttcgccgg actaagtagc aatctcgctt atataacgag cgtgtttatc ggctacatcg
gtactgactc gattggttcg cttatcaaac gcttcgctgc taaaaaagcc ggagtagaag
atggtagaaa tcaataatca acgtaaggcg ttcctcgata tgctggcgtg gtcggaggga
actgataacg gacgtcagaa aaccagaaat catggttatg acgtcattgt aggcggagag
ctatttactg attactccga tcaccctcgc aaacttgtca cgctaaaccc aaaactcaaa
tcaacaggcg ccggacgcta ccagcttctt tcccgttggt gggatgccta ccgcaagcag
cttggcctga aagacttctc tccgaaaagt caggacgctg tggcattgca gcagattaag
gagcgtggcg ctttacctat gattgatcgt ggtgatatcc gtcaggcaat cgaccgttgc
agcaatatct gggcttcact gccgggcgct ggttatggtc agttcgagca taaggctgac
agcctgattg caaaattcaa agaagcgggc ggaacggtca gagagattga tgtatgagca
gagtcaccgc gattatctcc gctctggtta tctgcatcat cgtctgcctg tcatgggctg
ttaatcatta ccgtgataac gccattacct acaaagccca gcgcgacaaa aatgccagag
aactgaagct ggcgaacgcg gcaattactg acatgcagat gcgtcagcgt gatgttgctg -continued

```
cgctcgatgc aaaatacacg aaggagttag ctgatgctaa agctgaaaat gatgctctgc
gtgatgatgt tgccgctggt cgtcgtcggt tgcacatcaa agcagtctgt cagtcagtgc
gtgaagccac caccgcctcc ggcgtggata atgcagcctc cccccgactg gcagacaccg
ctgaacggga ttatttcacc ctcagagaga ggctgatcac tatgcaaaaa caactggaag
gaacccagaa gtatattaat gagcagtgca gatagagttg cccatatcga tgggcaactc
atgcaattat tgtgagcaat acacacgcgc ttccagcgga gtataaatgc ctaaagtaat
aaaaccgagc aatccattta cgaatgtttg ctgggtttct gttttaacaa cattttctgc
gccgccacaa attttggctg catcgacagt tttcttctgc ccaattccag aaacgaagaa
atgatgggtg atggtttcct ttggtgctac tgctgccggt ttgttttgaa cagtaaacgt
ctgttgagca catcctgtaa taagcagggc cagcgcagta gcgagtagca tttttttcat
ggtgttattc ccgatgcttt ttgaagttcg cagaatcgta tgtgtagaaa attaaacaaa
ccctaaacaa tgagttgaaa tttcatattg ttaatattta ttaatgtatg tcaggtgcga
tgaatcgtca ttgtattccc ggattaacta tgtccacagc cctgacgggg aacttctctg
cgggagtgtc cgggaataat taaaacgatg cacacagggt ttagcgcgta cacgtattgc
attatgccaa cgccccggtg ctgacacgga agaaaccgga cgttatgatt tagcgtggaa
agatttgtgt agtgttctga atgctctcag taaatagtaa tgaattatca aaggtatagt
aatatctttt atgttcatgg atatttgtaa cccatcggaa aactcctgct ttagcaagat
tttccctgta ttgctgaaat gtgatttctc ttgatttcaa cctatcatag gacgtttcta
taagatgcgt gtttcttgag aatttaacat ttacaacctt tttaagtcct tttattaaca
cggtgttatc gttttctaac acgatgtgaa tattatctgt ggctagatag taaatataat
gtgagacgtt gtgacgtttt agttcagaat aaaacaattc acagtctaaa tcttttcgca
cttgatcgaa tatttcttta aaaatggcaa cctgagccat tggtaaaacc ttccatgtga
tacgagggcg cgtagtttgc attatcgttt ttatcgtttc aatctggtct gacctccttg
tgttttgttg atgatttatg tcaaatatta ggaatgtttt cacttaatag tattggttgc
gtaacaaagt gcggtcctgc tggcattctg gagggaaata caaccgacag atgtatgtaa
ggccaacgtg ctcaaatctt catacagaaa gatttgaagt aatattttaa ccgctagatg
aagagcaagc gcatggagcg acaaaatgaa taaagaacaa tctgctgatg atccctccgt
ggatctgatt cgtgtaaaaa atatgcttaa tagcaccatt tctatgagtt accctgatgt
tgtaattgca tgtatagaac ataaggtgtc tctggaagca ttcagagcaa ttgaggcagc
gttggtgaag cacgataata atatgaagga ttattccctg gtggttgact gatcaccata
actgctaatc attcaaacta tttagtctgt gacagagcca acacgcagtc tgtcactgtc
aggaaagtgg taaaactgca actcaattac tgcaatgccc tcgtaattaa gtgaatttac
aatatcgtcc tgttcggagg gaagaacgcg ggatgttcat tcttcatcac ttttaattga
tgtatatgct ctcttttctg acgttagtct ccgacggcag gcttcaatga cccaggctga
gaaattcccg gacccttttt gctcaagagc gatgttaatt tgttcaatca tttggttagg
aaagcggatg ttgcgggttg ttgttctgcg ggttctgttc ttcgttgaca tgaggttgcc
ccgtattcag tgtcgctgat ttgtattgtc tgaagttgtt tttacgttaa gttgatgcag
atcaattaat acgatacctg cgtcataatt gattatttga cgtggtttga tggcctccac
gcacgttgtg atatgtagat gataatcatt atcactttac gggtcctttc cggtgatccg
acaggttacg gggcggcgac ctgcctgatg cggtattttc tccttacgca tctgtgcggt
atttcacacc gcatacgtca aagcaaccat agtacgcgcc ctgtagcggc gcattaagcg
```

-continued cggcgggtgt ggtggttacg cgcagcgtga ccgctacact tgccagcgcc ttagcgcccg
ctcctttcgc tttcttccct tcctttctcg ccacgttcgc cggctttccc cgtcaagctc
taaatcgggg gctcccttta gggttccgat ttagtgcttt acggcacctc gaccccaaaa
aacttgattt gggtgatggt tcacgtagtg ggccatcgcc ctgatagacg gtttttcgcc
ctttgacgtt ggagtccacg ttctttaata gtggactctt gttccaaact ggaacaacac
tcaactctat ctcgggctat tcttttgatt tagacctgca ggcatgcaag cttggcactg
gccgtcgttt tacaacgtcg tgactgggaa aaccctggcg ttacccaact taatcgcctt
gcagcacatc cccctttcgc cagctggcgt aatagcgaag aggcccgcac cgatcgccct
tcccaacagt tgcgcagcct gaatggcgaa tgcgatttat tcaacaaagc cgccgtcccg
tcaagtcagc gtaatgctct gccagtgtta caaccaatta accaattctg attagaaaaa
ctcatcgagc atcaaatgaa actgcaattt attcatatca ggattatcaa taccatattt
ttgaaaaagc cgtttctgta atgaaggaga aaactcaccg aggcagttcc ataggatggc
aagatcctgg tatcggtctg cgattccgac tcgtccaaca tcaatacaac ctattaattt
cccctcgtca aaaataaggt tatcaagtga gaaatcacca tgagtgacga ctgaatccgg
tgagaatggc aaaagcttat gcatttcttt ccagacttgt tcaacaggcc agccattacg
ctcgtcatca aaatcactcg catcaaccaa accgttattc attcgtgatt gcgcctgagc
gagacgaaat acgcgatcgc tgttaaaagg acaattacaa acaggaatcg aatgcaaccg
gcgcaggaac actgccagcg catcaacaat attttcacct gaatcaggat attcttctaa
tacctggaat gctgttttcc cggggatcgc agtggtgagt aaccatgcat catcaggagt
acggataaaa tgcttgatgg tcggaagagg cataaattcc gtcagccagt ttagtctgac
catctcatct gtaacatcat tggcaacgct acctttgcca tgtttcagaa acaactctgg
cgcatcgggc ttcccataca atcgatagat tgtcgcacct gattgcccga cattatcgcg
agcccattta tacccatata aatcagcatc catgttggaa tttaatcgcg gcttcgagca
agacgtttcc cgttgaatat ggctcataac accccttgta ttactgttta tgtaagcaga
cagttttatt gttcatgatg atatattttt atcttgtgca atgtaacatc agagattttg
agacacaacg tggctttgtt gaataaatcg aacttttgct gagttgaagg atcagatcac
gcatcttccc gacaacgcag accgttccgt ggcaaagcaa aagttcaaaa tcaccaactg
gtccacctac aacaaagctc tcatcaaccg tggctccctc actttctggc tggatgatgg
ggcgattcag gcctggtatg agtcagcaac accttcttca cgaggcagac ctctcgacgg
agttccactg agcgtcagac cccgtagaaa agatcaaagg atcttcttga gatccttttt
ttctgcgcgt aatctgctgc ttgcaaacaa aaaaaccacc gctaccagcg gtggtttgtt
tgccggatca agagctacca actctttttc cgaaggtaac tggcttcagc agagcgcaga
taccaaatac tgttcttcta gtgtagccgt agttaggcca ccacttcaag aactctgtag
caccgcctac atacctcgct ctgctaatcc tgttaccagt ggctgctgcc agtggcgata
agtcgtgtct taccgggttg gactcaagac gatagttacc ggataaggcg cagcggtcgg
gctgaacggg gggttcgtgc acacagccca gcttggagcg aacgacctac accgaactga
gatacctaca gcgtgagcta tgagaaagcg ccacgcttcc cgaagggaga aaggcggaca
ggtatccggt aagcggcagg gtcggaacag gagagcgcac gagggagctt ccagggggaa
acgcctggta tctttatagt cctgtcgggt ttcgccacct ctgacttgag cgtcgatttt
tgtgatgctc gtcagggggg cggagcctat ggaaaaacgc cagcaacgcg gcctttttac -continued ggttcctggc cttttgctgg ccttttgctc acatgt FVIII-BDD encoded by X01-X18 nucleic acid sequences. SQ sequence bold/underlined (SEQ ID NO: 25)

MQIELSTCFFLCLLRFCFSATRRYYLGAVELSWDYMQSDLGELPVDARFPPRVPKSFPFNTSVVYKKT

LFVEFTDHLFNIAKPRPPWMGLLGPTIQAEVYDTVVITLKNMASHPVSLHAVGVSYWKASEGAEYDDQ

TSQREKEDDKVFPGGSHTYVWQVLKENGPMASDPLCLTYSYLSHVDLVKDLNSGLIGALLVCREGSLA

KEKTQTLHKFILLFAVFDEGKSWHSETKNSLMQDRDAASARAWPKMHTVNGYVNRSLPGLIGCHRKSV

YWHVIGMGTTPEVHSIFLEGHTFLVRNHRQASLEISPITFLTAQTLLMDLGQFLLFCHISSHQHDGME

AYVKVDSCPEEPQLRMKNNEEAEDYDDDLTDSEMDVVRFDDDNSPSFIQIRSVAKKHPKTWVHYIAAE

EEDWDYAPLVLAPDDRSYKSQYLNNGPQRIGRKYKKVRFMAYTDETFKTREAIQHESGILGPLLYGEV

GDTLLIIFKNQASRPYNIYPHGITDVRPLYSRRLPKGVKHLKDFPILPGEIFKYKWTVTVEDGPTKSD

PRCLTRYYSSFVNMERDLASGLIGPLLICYKESVDQRGNQIMSDKRNVILFSVFDENRSWYLTENIQR

FLPNPAGVQLEDPEFQASNIMHSINGYVFDSLQLSVCLHEVAYWYILSIGAQTDFLSVFFSGYTFKHK

MVYEDTLTLFPFSGETVFMSMENPGLWILGCHNSDFRNRGMTALLKVSSCDKNTGDYYEDSYEDISAY

LLSKNNAIEPR<u>SFSQNPPVLKRHQR</u>EITRTTLQSDQEEIDYDDTISVEMKKEDFDIYDEDENQSPRSF

QKKTRHYFIAAVERLWDYGMSSSPHVLRNRAQSGSVPQFKKVVFQEFTDGSFTQPLYRGELNEHLGLL

GPYIRAEVEDNIMVTFRNQASRPYSFYSSLISYEEDQRQGAEPRKNFVKPNETKTYFWKVQHHMAPTK

DEFDCKAWAYFSDVDLEKDVHSGLIGPLLVCHTNTLNPAHGRQVTVQEFALFFTIFDETKSWYFTENM

ERNCRAPCNIQMEDPTFKENYRFHAINGYIMDTLPGLVMAQDQRIRWYLLSMGSNENIHSIHFSGHVF

TVRKKEEYKMALYNLYPGVFETVEMLPSKAGIWRVECLIGEHLHAGMSTLFLVYSNKCQTPLGMASGH

IRDFQITASGQYGQWAPKLARLHYSGSINAWSTKEPFSWIKVDLLAPMIIHGIKTQGARQKFSSLYIS

QFIIMYSLDGKKWQTYRGNSTGTLMVFFGNVDSSGIKHNIFNPPIIARYIRLHPTHYSIRSTLRMELM

GCDLNSCSMPLGMESKAISDAQITASSYFTNMFATWSPSKARLHLQGRSNAWRPQVNNPKEWLQVDFQ

KTMKVTGVTTQGVKSLLTSMYVKEFLISSSQDGHQWTLFFQNGKVKVFQGNQDSFTPVVNSLDPPLLT

RYLRIHPQSWVHQIALRMEVLGCEAQDLY

Wild-type FVIII with BDD (SEQ ID NO: 26)

MQIELSTCFFLCLLRFCFSATRRYYLGAVELSWDYMQSDLGELPVDARFPPRVPKSFPFNTSVVYKKT

LFVEFTDHLFNIAKPRPPWMGLLGPTIQAEVYDTVVITLKNMASHPVSLHAVGVSYWKASEGAEYDDQ

TSQREKEDDKVFPGGSHTYVWQVLKENGPMASDPLCLTYSYLSHVDLVKDLNSGLIGALLVCREGSLA

KEKTQTLHKFILLFAVFDEGKSWHSETKNSLMQDRDAASARAWPKMHTVNGYVNRSLPGLIGCHRKSV

YWHVIGMGTTPEVHSIFLEGHTFLVRNHRQASLEISPITFLTAQTLLMDLGQFLLFCHISSHQHDGME

AYVKVDSCPEEPQLRMKNNEEAEDYDDDLTDSEMDVVRFDDDNSPSFIQIRSVAKKHPKTWVHYIAAE

EEDWDYAPLVLAPDDRSYKSQYLNNGPQRIGRKYKKVRFMAYTDETFKTREAIQHESGILGPLLYGEV

GDTLLIIFKNQASRPYNIYPHGITDVRPLYSRRLPKGVKHLKDFPILPGEIFKYKWTVTVEDGPTKSD

PRCLTRYYSSFVNMERDLASGLIGPLLICYKESVDQRGNQIMSDKRNVILFSVFDENRSWYLTENIQR

FLPNPAGVQLEDPEFQASNIMHSINGYVFDSLQLSVCLHEVAYWYILSIGAQTDFLSVFFSGYTFKHK

MVYEDTLTLFPFSGETVFMSMENPGLWILGCHNSDFRNRGMTALLKVSSCDKNTGDYYEDSYEDISAY

LLSKNNAIEPRSFSQNSRHPSTRQKQFNATTIPENDIEKTDPWFAHRTPMPKIQNVSSSDLLMLLRQS

PTPHGLSLSDLQEAKYETFSDDPSPGAIDSNNSLSEMTHFRPQLHHSGDMVFTPESGLQLRLNEKLGT

TAATELKKLDFKVSSTSNNLISTIPSDNLAAGTDNTSSLGPPSMPVHYDSQLDTTLFGKKSSPLTESG

GPLSLSEENNDSKLLESGLMNSQESSWGKNVSSTESGRLFKGKRAHGPALLTKDNALFKVSISLLKTN

-continued

KTSNNSATNRKTHIDGPSLLIENSPSVWQNILESDTEFKKVTPLIHDRMLMDKNATALRLNHMSNKTT

SSKNMEMVQQKKEGPIPPDAQNPDMSFFKMLFLPESARWIQRTHGKNSLNSGQGPSPKQLVSLGPEKS

VEGQNFLSEKNKVVVGKGEFTKDVGLKEMVFPSSRNLFLTNLDNLHENNTHNQEKKIQEEIEKKETLI

QENVVLPQIHTVTGTKNFMKNLFLLSTRQNVEGSYDGAYAPVLQDFRSLNDSTNRTKKHTAHFSKKGE

EENLEGLGNQTKQIVEKYACTTRISPNTSQQNFVTQRSKRALKQFRLPLEETELEKRIIVDDTSTQWS

KNMKHLTPSTLTQIDYNEKEKGAITQSPLSDCLTRSHSIPQANRSPLPIAKVSSFPSIRPIYLTRVLF

QDNSSHLPAASYRKKDSGVQESSHFLQGAKKNNLSLAILTLEMTGDQREVGSLGTSATNSVTYKKVEN

TVLPKPDLPKTSGKVELLPKVHIYQKDLFPTETSNGSPGHLDLVEGSLLQGTEGAIKWNEANRPGKVP

FLRVATESSAKTPSKLLDPLAWDNHYGTQIPKEEWKSQEKSPEKTAFKKKDTILSLNACESNHAIAAI

NEGQNKPEIEVTWAKQGRTERLCSQNPPVLKRHQREITRTTLQSDQEEIDYDDTISVEMKKEDFDIYD

EDENQSPRSFQKKTRHYFIAAVERLWDYGMSSSPHVLRNRAQSGSVPQFKKVVFQEFTDGSFTQPLYR

GELNEHLGLLGPYIRAEVEDNIMVTFRNQASRPYSFYSSLISYEEDQRQGAEPRKNFVKPNETKTYFW

KVQHHMAPTKDEFDCKAWAYFSDVDLEKDVHSGLIGPLLVCHTNTLNPAHGRQVTVQEFALFFTIFDE

TKSWYFTENMERNCRAPCNIQMEDPTFKENYRFHAINGYIMDTLPGLVMAQDQRIRWYLLSMGSNENI

HSIHFSGHVFTVRKKEEYKMALYNLYPGVFETVEMLPSKAGIWRVECLIGEHLHAGMSTLFLVYSNKC

QTPLGMASGHIRDFQITASGQYGQWAPKLARLHYSGSINAWSTKEPFSWIKVDLLAPMIIHGIKTQGA

RQKFSSLYISQFIIMYSLDGKKWQTYRGNSTGTLMVFFGNVDSSGIKHNIFNPPIIARYIRLHPTHYS

IRSTLRMELMGCDLNSCSMPLGMESKAISDAQITASSYFTNMFATWSPSKARLHLQGRSNAWRPQVNN

PKEWLQVDFQKTMKVTGVTTQGVKSLLTSMYVKEFLISSSQDGHQWTLFFQNGKVKVFQGNQDSFTPV

VNSLDPPLLTRYLRIHPQSWVHQIALRMEVLGCEAQDLY

AAV-LK03 VP1 Capsid (SEQ ID NO: 27)

MAADGYLPDWLEDNLSEGIREWWALQPGAPKPKANQQHQDNARGLVLPGYKYLGPGNGLDKGEPVNAA

DAAALEHDKAYDQQLKAGDNPYLKYNHADAEFQERLKEDTSFGGNLGRAVFQAKKRLLEPLGLVEEAA

KTAPGKKRPVDQSPQEPDSSSGVGKSGKQPARKRLNFGQTGDSESVPDPQPLGEPPAAPTSLGSNTMA

SGGGAPMADNNEGADGVGNSSGNWHCDSQWLGDRVITTSTRTWALPTYNNHLYKQISSQSGASNDNHY

FGYSTPWGYFDFNRFHCHFSPRDWQRLINNNWGFRPKKLSFKLFNIQVKEVTQNDGTTTIANNLTSTV

QVFTDSEYQLPYVLGSAHQGCLPPFPADVFMVPQYGYLTLNNGSQAVGRSSFYCLEYFPSQMLRTGNN

FQFSYTFEDVPFHSSYAHSQSLDRLMNPLIDQYLYYLNRTQGTTSGTTNQSRLLFSQAGPQSMSLQAR

NWLPGPCYRQQRLSKTANDNNNSNFPWTAASKYHLNGRDSLVNPGPAMASHKDDEEKFFPMHGNLIFG

KEGTTASNAELDNVMITDEEEIRTTNPVATEQYGTVANNLQSSNTAPTTRTVNDQGALPGMVWQDRDV

YLQGPIWAKIPHTDGHFHPSPLMGGFGLKHPPPQIMIKNTPVPANPPTTFSPAKFASFITQYSTGQVS

VEIEWELQKENSKRWNPEIQYTSNYNKSVNVDFTVDTNGVYSEPRPIGTRYLTRPL

AAV-SPK VP1 Capsid used in AAV-SPK-8005 and AAV-SPK-hFIX (SEQ ID NO: 28)

MAADGYLPDWLEDNLSEGIREWWDLKPGAPKPKANQQKQDNGRGLVLPGYKYLGPFNGLDKGEPVNAA

DAAALEHDKAYDQQLQAGDNPYLRYNHADAEFQERLQEDTSFGGNLGRAVFQAKKRVLEPLGLVESPV

KTAPGKKRPVEPSPQRSPDSSTGIGKKGQQPAKKRLNFGQTGDSESVPDPQPIGEPPA<u>A</u>PSG<u>V</u>G<u>PN</u>TM

AAGGGAPMADNNEGADGVGSSSGNWHCDSTWLGDRVITTSTRTWALPTYNNHLYKQISNGTSGGSTND

NTYFGYSTPWGYFDFNRFHCHFSPRDWQRLINNNWGFRPKRLNFKLFNIQVKEVTQNEGTKTIANNLT

STIQVFTDSEYQLPYVLGSAHQGCLPPFPADVFMIPQYGYLTLNNGSQAV

GRSSFYCLEYFPSQMLRTGNNFEFSYNFEDVPFHSSYAHSQSLDRLMNPLIDQYLYYLSRTQSTGGTA

GTQQLLFSQAGPNNMSAQAKNWLPGPCYRQQRVSTTLSQNNNSNFAWTGATKYHLNGRDSLVNPGVAM

-continued

ATHKDDEERFFPSSGVLMFGKQGAGKDNVDYSSVMLTSEEEIKTTNPVATEQYGVVADNLQQQNAAPI

VGAVNSQGALPGMVWQNRDVYLQGPIWAKIPHTDGNFHPSPLMGGFGLKHPPPQILIKNTPVPADPPT

TFNQAKLASFITQYSTGQVSVEIEWELQKENSKRWNPEIQYTSNYYKSTNVDFAVNTEGTYSEPRPIG

TRYLTRNL

Percent Identity Matrix of hFVIII Vectors (WT, CO3, x09, X02, X06, X08, X15, X05, X18, X14, X01, X12, X04, X11, X07, X03, X16, X13, X17 and X10)

| | hFVIII WT | hFVIII CO3 | hFVIII X09 | hFVIII X02 | hFVIII X06 | hFVIII X08 | hFVIII X15 | hFVIII X05 | hFVIII X18 | hFVIII X14 |
|---|---|---|---|---|---|---|---|---|---|---|
| hFVIII WT | | 77.2 | 79.5 | 79.1 | 79.3 | 79.2 | 79.3 | 79.1 | 79 | 79.6 |
| hFVIII CO3 | 77.2 | | 81.9 | 81.9 | 81.5 | 81.3 | 81.6 | 81.6 | 81.2 | 81.4 |
| hFVIII X09 | 79.5 | 81.9 | | 91.5 | 91.4 | 91.8 | 92 | 91.8 | 91 | 91.4 |
| hFVIII X02 | 79.1 | 81.9 | 91.5 | | 91.4 | 91.3 | 92 | 92.1 | 92.2 | 91.7 |
| hFVIII X06 | 79.3 | 81.5 | 91.4 | 91.4 | | 91.8 | 91.9 | 91.8 | 91.5 | 91.8 |
| hFVIII X08 | 79.2 | 81.3 | 91.8 | 91.3 | 91.8 | | 91.8 | 91.5 | 91.5 | 91.8 |
| hFVIII X15 | 79.3 | 81.6 | 92 | 92 | 91.9 | 91.8 | | 92.2 | 91.6 | 91.7 |
| hFVIII X05 | 79.1 | 81.6 | 91.8 | 92.1 | 91.8 | 91.5 | 92.2 | | 92.5 | 91.9 |
| hFVIII X18 | 79 | 81.2 | 91 | 92.2 | 91.5 | 91.5 | 91.6 | 92.5 | | 91.6 |
| hFVIII X14 | 79.6 | 81.4 | 91.4 | 91.7 | 91.8 | 91.8 | 91.7 | 91.9 | 91.6 | |
| hFVIII X01 | 79.6 | 81.1 | 91.5 | 92 | 92.3 | 92.2 | 92.3 | 92.7 | 93 | 93 |
| hFVIII X12 | 79.4 | 81.1 | 91.5 | 91.9 | 91.7 | 91.5 | 92.1 | 92.4 | 92.1 | 92 |
| hFVIII X04 | 79.4 | 81.3 | 91.7 | 91.9 | 91.8 | 92.3 | 92.2 | 92.1 | 91.5 | 91.6 |
| hFVIII X11 | 79.4 | 81.7 | 91.7 | 92 | 92 | 92.5 | 92.5 | 91.5 | 91.8 | 91.8 |
| hFVIII X07 | 79.2 | 81.8 | 92.2 | 91.5 | 91.5 | 92 | 92 | 92.1 | 91.7 | 91.3 |
| hFVIII X03 | 79.4 | 81.6 | 91.5 | 91 | 91.4 | 91.7 | 92.1 | 91.6 | 91.4 | 91.8 |
| hFVIII X16 | 79.1 | 81.9 | 92.1 | 91.5 | 91.7 | 91.4 | 92.2 | 91.7 | 91.1 | 92.3 |
| hFVIII X13 | 79 | 81.8 | 91.8 | 92.3 | 92.4 | 92.3 | 92.3 | 92.3 | 91.8 | 92.2 |
| hFVIII X17 | 79.6 | 82.1 | 91.1 | 91.9 | 91.6 | 91.6 | 92.5 | 91.9 | 91.8 | 91.8 |
| hFVIII X10 | 79.3 | 82.2 | 91.6 | 92.1 | 91.8 | 91.9 | 92 | 92 | 92 | 92 |

| | hFVIII X01 | hFVIII X12 | hFVIII X04 | hFVIII X11 | hFVIII X07 | hFVIII X03 | hFVIII X16 | hFVIII X13 | hFVIII X17 | hFVIII X10 |
|---|---|---|---|---|---|---|---|---|---|---|
| hFVIII WT | 79.6 | 79.4 | 79.4 | 79.4 | 79.2 | 79.4 | 79.1 | 79 | 79.6 | 79.3 |
| hFVIII CO3 | 81.1 | 81.1 | 81.3 | 81.7 | 81.8 | 81.6 | 81.9 | 81.8 | 82.1 | 82.2 |
| hFVIII X09 | 91.5 | 91.5 | 91.7 | 91.7 | 92.2 | 91.5 | 92.1 | 91.8 | 91.1 | 91.6 |
| hFVIII X02 | 92 | 91.9 | 91.9 | 92 | 91.5 | 91 | 91.5 | 92.3 | 91.9 | 92.1 |
| hFVIII X06 | 92.3 | 91.7 | 91.8 | 92 | 91.5 | 91.4 | 91.7 | 92.4 | 91.6 | 91.8 |
| hFVIII X08 | 92.2 | 91.5 | 92.3 | 92.5 | 92 | 91.7 | 91.4 | 92.3 | 91.6 | 91.9 |
| hFVIII X15 | 92.3 | 92.1 | 92.2 | 92.5 | 92 | 92.1 | 92.2 | 92.3 | 92.5 | 92 |
| hFVIII X05 | 92.7 | 92.4 | 92.1 | 91.5 | 92.1 | 91.6 | 91.7 | 92.3 | 91.9 | 92 |
| hFVIII X18 | 93 | 92.1 | 91.5 | 91.8 | 91.7 | 91.4 | 91.1 | 91.8 | 91.8 | 92 |

-continued

Percent Identity Matrix of hFVIII Vectors (WT, CO3, x09, X02, X06, X08, X15, X05, X18, X14, X01, X12, X04, X11, X07, X03, X16, X13, X17 and X10)

| | | | | | | | | | | |
|---|---|---|---|---|---|---|---|---|---|---|
| hFVIII X14 | 93 | 92 | 91.6 | 91.8 | 91.3 | 91.8 | 92.3 | 92.2 | 91.8 | 92 |
| hFVIII X01 | | 93.4 | 92.3 | 92.5 | 92.6 | 92.5 | 92.2 | 92.6 | 92.4 | 92.1 |
| hFVIII X12 | 93.4 | | 92 | 92 | 92.4 | 92.4 | 91.7 | 92.4 | 92.6 | 92.6 |
| hFVIII X04 | 92.3 | 92 | | 92.6 | 92 | 91.5 | 91.5 | 92 | 91.9 | 92.5 |
| hFVIII X11 | 92.5 | 92 | 92.6 | | 92.6 | 92 | 91.9 | 92.3 | 91.8 | 91.9 |
| hFVIII X07 | 92.6 | 92.4 | 92 | 92.6 | | 92.1 | 92 | 92.4 | 91.9 | 92.7 |
| hFVIII X03 | 92.5 | 92.4 | 91.5 | 92 | 92.1 | | 92 | 92.7 | 92.1 | 91.6 |
| hFVIII X16 | 92.2 | 91.7 | 91.5 | 91.9 | 92 | 92 | | 92.4 | 92 | 92.8 |
| hFVIII X13 | 92.6 | 92.4 | 92 | 92.3 | 92.4 | 92.7 | 92.4 | | 92.4 | 92.8 |
| hFVIII X17 | 92.4 | 92.6 | 91.9 | 91.8 | 91.9 | 92.1 | 92 | 92.4 | | 92.9 |
| hFVIII X10 | 92.1 | 92.6 | 92.5 | 91.9 | 92.7 | 91.6 | 92.8 | 92.8 | 92.9 | |

Certain Definitions/Abbreviations Used
BDD: all or at least part of B domain (BD) deleted
FVIII-BDD: FVIII with B domain deletion
SQ: SFSQNPPVLKRHQR (SEQ ID NO: 29)
FVIII/SQ: FVIII with SQ
FVIIIX01-X18: CpG reduced FVIII encoding nucleic acid variants, set forth as SEQ ID Nos: 1-18, respectively.
TTRmut: TTR promoter with 4 mutations, from TAmGTGTAG to TATTGACTTAG
CO3: codon optimized FVIII nucleic acid variant, set forth as SEQ ID NO: 21
NHP: Non human primate
ALT: Alanine aminotransferase
D-dimer: A protein fragment from the break down of a blood clot
SPK-8005: AAV capsid (SEQ ID NO: 28) + TTRmut-hFVIII-X07; also referred to as AAV-SPK-8005
SPK-8011: AAV LK03 capsid (SEQ ID NO: 27) + TTRmut-hFVIII-X07; also referred to as AAV-SPK-8011

While certain of the embodiments of the invention have been described and specifically exemplified above, it is not intended that the invention be limited to such embodiments. Various modifications may be made thereto without departing from the scope and spirit of the invention, as set forth in the following claims.

What is claimed is:

1. A nucleic acid variant encoding Factor VIII (FVIII) having a B domain deletion (FVIII-BDD), wherein said nucleic acid variant has 95% or greater sequence identity to the sequence of SEQ ID NO:7.

2. The nucleic acid variant of claim 1, wherein said nucleic acid variant has 96% or greater sequence identity to the sequence of SEQ ID NO:7.

3. The nucleic acid variant of claim 1, wherein said nucleic acid variant has 20 or fewer cytosine-guanine dinucleotides (CpGs).

4. The nucleic acid variant of claim 1, wherein said nucleic acid variant encodes FVIII-BDD having the sequence of SEQ ID NO:25, or encodes FVIII-BDD having the sequence of SEQ ID NO:25 having a deletion of one, a part or all amino acids of the sequence of SEQ ID NO:29.

5. The nucleic acid variant of claim 1, wherein said FVIII-BDD is human.

6. The nucleic acid variant of claim 1, wherein said FVIII-BDD comprises the sequence of SEQ ID NO:19.

7. The nucleic acid variant of claim 1, wherein said nucleic acid variant has no more than 2 CpGs.

8. The nucleic acid variant of claim 1, wherein said nucleic acid variant has 1 CpG.

9. The nucleic acid variant of claim 1, wherein said nucleic acid variant has no CpGs.

10. The nucleic acid variant of claim 1, wherein said nucleic acid variant has no more than 20 CpGs.

11. An adeno-associated virus (AAV) vector comprising said nucleic acid variant of claim 1.

12. The AAV vector of claim 11, wherein said AAV vector further comprises at least one of:

a) an AAV capsid serotype;

b) an intron;

c) an expression control element operably linked to said nucleic acid variant; and d) one or more AAV inverted terminal repeats (ITRs), wherein said one or more ITR(s) flanks the 5' or 3' terminus of said nucleic acid variant.

13. The AAV vector of claim 12, wherein at least one of said intron, expression control element, and one or more ITRs has been modified to have reduced CpGs.

14. The AAV vector of claim 12, wherein said intron, expression control element, or one or more ITRs has 20 or fewer CpGs.

15. The AAV vector of claim 12, wherein said expression control element comprises an element that confers expression in liver.

16. The AAV vector of claim 12, wherein said expression control element comprises a TTR promoter or a mutant TTR promoter.

17. The AAV vector of claim 12, wherein said ITRs comprise one or more ITRs of any of: AAV1, AAV2, AAV3, AAV4, AAVS, AAV6, AAV7, AAV8, AAV9, AAV10, AAV11, Rh10, Rh74 and AAV-2i8 AAV serotypes, or a combination thereof.

18. The AAV vector of claim 12, wherein said AAV vector further comprises at least one of an ITR, a promoter, a polyA signal and an intron sequence as set forth in the sequence of SEQ ID NO:23.

19. The AAV vector of claim 12, wherein said AAV capsid serotype comprises a modified or variant AAV VP1, VP2 or VP3 capsid having 95% or more sequence identity to at least one of AAV1, AAV2, AAV3, AAV4, AAVS, AAV6, AAV7, AAV8, AAV9, AAV10, AAV11, Rh10, Rh74 or AAV-2i8 VP1, VP2 and VP3 sequences.

20. The AAV vector of claim 12, wherein said AAV vector comprises a capsid having 95% or more sequence identity to the sequence of SEQ ID NO:27 or a capsid having 95% or more sequence identity to the sequence of SEQ ID NO:28.

21. A pharmaceutical composition comprising a plurality of AAV vectors of claim 12 in a biologically compatible carrier or excipient.

22. The pharmaceutical composition of claim 21, further comprising AAV empty capsids.

23. The pharmaceutical composition of claim 21, wherein the ratio of said AAV empty capsids to said AAV vector is about 2:1, 3:1, 4:1, 5:1, 6:1, 7:1, 8:1, 9:1, or 10:1.

24. The pharmaceutical composition of claim 21, further comprising a surfactant.

25. The AAV vector of claim 12, wherein said expression control element flanks the 5' terminus of said nucleic acid variant.

26. An adeno-associated virus (AAV) vector comprising said nucleic acid variant of claim 1, wherein said AAV vector comprises an expression control element that confers expression in liver, and wherein said AAV vector comprises an AAV capsid serotype having the sequence of SEQ ID NO:27.

27. The AAV vector of claim 26, wherein said nucleic acid variant has 96% or greater sequence identity to the sequence of SEQ ID NO:7.

28. The AAV vector of claim 26, wherein said nucleic acid variant has 97% or greater sequence identity to the sequence of SEQ ID NO:7.

29. The AAV vector of claim 26, wherein said nucleic acid variant has 98% or greater sequence identity to the sequence of SEQ ID NO:7.

30. The AAV vector of claim 26, wherein said nucleic acid variant has 99% or greater sequence identity to the sequence of SEQ ID NO:7.

31. The AAV vector of claim 26, wherein said nucleic acid variant has the sequence of SEQ ID NO:7.

32. A method of treating a human in need of FVIII, comprising:

(a) providing a pharmaceutical composition comprising an adeno-associated virus (AAV) vector, wherein said AAV vector comprises (i) a nucleic acid variant encoding Factor VIII (FVIII) having a B domain deletion (FVIII-BDD), wherein said nucleic acid variant has the sequence of SEQ ID NO:7, (ii) an expression control element operably linked to said nucleic acid variant, wherein said expression control element comprises an element that confers expression in liver; and (iii) an AAV capsid serotype having the sequence of SEQ ID NO:27; and (b) intravenously administering an amount of said pharmaceutical composition to said human, wherein said FVIII is expressed in hepatocytes of said human, and wherein said method reduces bleeding episodes in said human and results in reduced need to administer recombinant FVIII to said human.

33. The method of claim 32, wherein said expression control element flanks the 5' terminus of said nucleic acid variant.

34. The method of claim 32, wherein said expression control element has the sequence of SEQ ID NO:22.

35. The method of claim 32, wherein said AAV vector further comprises a polyA signal and an intron sequence as set forth in the sequence of SEQ ID NO:23.

36. The method of claim 32, wherein said AAV vector comprises an expression cassette consisting of the sequence of SEQ ID NO:23.

37. The method of claim 32, wherein said human has hemophilia A.

38. The method of claim 32, wherein said pharmaceutical composition is administered to said human in a range from about $1\times10^8$ to about 1X10" vector genomes per kilogram (vg/kg) of the weight of said human.

39. The method of any of claims 32-38, further comprising administering to said human an immunosuppressive agent.

40. The method of any of claims 32-38, wherein said AAV vector comprises AAV2 inverted terminal repeats (ITRs).

41. The method of any of claims 32-38, wherein said pharmaceutical composition further comprises AAV empty capsids.

* * * * *